(12) United States Patent
Koenig et al.

(10) Patent No.: US 12,121,586 B2
(45) Date of Patent: Oct. 22, 2024

(54) OPTIMIZED VARIANTS OF ANTI-VEGF ANTIBODIES

(71) Applicant: Genentech, Inc., South San Francisco, CA (US)

(72) Inventors: Patrick Koenig, San Francisco, CA (US); Chingwei Vivian Lee, Foster City, CA (US); Karthikan Rajagopal, South San Francisco, CA (US); Amin Famili, South San Francisco, CA (US); Germaine Fuh, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 497 days.

(21) Appl. No.: 17/129,251

(22) Filed: Dec. 21, 2020

(65) Prior Publication Data

US 2021/0115124 A1    Apr. 22, 2021

Related U.S. Application Data

(62) Division of application No. 16/033,353, filed on Jul. 12, 2018, now Pat. No. 10,906,968, which is a
(Continued)

(51) Int. Cl.
*C40B 30/04* (2006.01)
*A61K 39/395* (2006.01)
(Continued)

(52) U.S. Cl.
CPC .......... *A61K 47/61* (2017.08); *A61K 39/3955* (2013.01); *A61K 47/34* (2013.01);
(Continued)

(58) Field of Classification Search
None
See application file for complete search history.

(56) References Cited

U.S. PATENT DOCUMENTS

| | | |
|---|---|---|
| 4,774,378 A | 9/1988 | Faure et al. |
| 4,816,567 A | 3/1989 | Cabilly et al. |

(Continued)

FOREIGN PATENT DOCUMENTS

| | | |
|---|---|---|
| CA | 2019559 C | 12/1990 |
| CN | 1259962 A | 7/2000 |

(Continued)

OTHER PUBLICATIONS

Ravn et al. (Mar. 14, 2013) Methods vol. 60 pp. 99 to 110.*

(Continued)

*Primary Examiner* — Christian C Boesen
(74) *Attorney, Agent, or Firm* — Clark & Elbing LLP; Karen L. Elbing

(57) ABSTRACT

The present invention provides anti-VEGF antibodies and compositions that include anti-VEGF antibodies (e.g., antibody conjugates, fusion proteins, and polymeric formulations), and uses thereof, for example for treatment of disorders associated with pathological angiogenesis. The present invention also provides methods of identifying antibody variants with improved properties, for example, enhanced binding affinity, stability, pharmacokinetics, and/or expression.

20 Claims, 34 Drawing Sheets
(34 of 34 Drawing Sheet(s) Filed in Color)
Specification includes a Sequence Listing.

Related U.S. Application Data division of application No. 15/274,612, filed on Sep. 23, 2016, now Pat. No. 10,072,075.

(60) Provisional application No. 62/271,913, filed on Dec. 28, 2015, provisional application No. 62/222,698, filed on Sep. 23, 2015.

(51) Int. Cl.

| | | |
|---|---|---|
| *A61K 47/34* | (2017.01) | |
| *A61K 47/60* | (2017.01) | |
| *A61K 47/61* | (2017.01) | |
| *C07K 14/475* | (2006.01) | |
| *C07K 16/22* | (2006.01) | |
| *C07K 16/44* | (2006.01) | |
| *C07K 16/46* | (2006.01) | |
| *C12N 15/10* | (2006.01) | |
| *C12N 15/115* | (2010.01) | |
| *A61K 39/00* | (2006.01) | |

(52) U.S. Cl.
CPC ............ *A61K 47/60* (2017.08); *C07K 14/475* (2013.01); *C07K 16/22* (2013.01); *C07K 16/44* (2013.01); *C07K 16/468* (2013.01); *C12N 15/1037* (2013.01); *C12N 15/115* (2013.01); *C40B 30/04* (2013.01); *A61K 2039/505* (2013.01); *A61K 2039/54* (2013.01); *C07K 2317/14* (2013.01); *C07K 2317/21* (2013.01); *C07K 2317/24* (2013.01); *C07K 2317/31* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/90* (2013.01); *C07K 2317/92* (2013.01); *C07K 2317/94* (2013.01); *C07K 2318/20* (2013.01); *C07K 2319/30* (2013.01); *C07K 2319/31* (2013.01); *C12N 2310/16* (2013.01)

(56) References Cited

U.S. PATENT DOCUMENTS

| | | | |
|---|---|---|---|
| 5,427,908 A | 6/1995 | Dower et al. | |
| 5,432,018 A | 7/1995 | Dower et al. | |
| 5,498,530 A | 3/1996 | Schatz et al. | |
| 5,580,717 A | 12/1996 | Dower et al. | |
| 5,658,727 A | 8/1997 | Barbas et al. | |
| 5,688,666 A | 11/1997 | Bass et al. | |
| 5,723,286 A | 3/1998 | Dower et al. | |
| 5,733,743 A | 3/1998 | Johnson et al. | |
| 5,750,373 A | 5/1998 | Garrard et al. | |
| 5,821,337 A | 10/1998 | Carter et al. | |
| 5,837,242 A | 11/1998 | Holliger et al. | |
| 5,928,641 A | 7/1999 | Seon | |
| 5,969,108 A | 10/1999 | McCafferty et al. | |
| 6,054,297 A | 4/2000 | Carter et al. | |
| 6,172,197 B1 | 1/2001 | McCafferty et al. | |
| 6,342,219 B1 | 1/2002 | Thorpe et al. | |
| 6,416,758 B1 | 7/2002 | Thorpe et al. | |
| 6,884,879 B1 | 4/2005 | Baca et al. | |
| 7,208,582 B2 | 4/2007 | Rosen et al. | |
| 7,365,166 B2 | 4/2008 | Baca et al. | |
| 7,622,115 B2 | 11/2009 | Fyfe et al. | |
| 7,691,977 B2 | 4/2010 | Fuh et al. | |
| 7,758,859 B2 | 7/2010 | Fuh et al. | |
| 7,811,785 B2 | 10/2010 | Fuh et al. | |
| 8,092,797 B2 | 1/2012 | Fuh et al. | |
| 8,093,365 B2 | 1/2012 | Wisniewski et al. | |
| 8,101,177 B2 | 1/2012 | Fuh et al. | |
| 8,492,527 B2 | 7/2013 | Fuh et al. | |
| 8,512,699 B2 | 8/2013 | Fuh et al. | |
| 8,975,381 B2 | 3/2015 | Fuh et al. | |
| 9,018,357 B2 | 4/2015 | Fuh et al. | |
| 9,353,177 B2 | 5/2016 | Fuh et al. | |
| 10,047,357 B2* | 8/2018 | Short | C40B 50/06 |
| 10,072,075 B2 | 9/2018 | Koenig et al. | |
| 2006/0280747 A1 | 12/2006 | Fuh et al. | |
| 2007/0020267 A1 | 1/2007 | Fuh et al. | |
| 2007/0141065 A1 | 6/2007 | Fuh et al. | |
| 2009/0142343 A1 | 6/2009 | Fuh et al. | |
| 2009/0232811 A1 | 9/2009 | Klein et al. | |
| 2010/0015158 A1 | 1/2010 | Robinson et al. | |
| 2010/0189719 A1 | 7/2010 | Fuh et al. | |
| 2010/0322946 A1 | 12/2010 | Bostrom et al. | |
| 2011/0014198 A1 | 1/2011 | Fuh et al. | |
| 2011/0020346 A1 | 1/2011 | Fuh et al. | |
| 2011/0092372 A1 | 4/2011 | Almagro et al. | |
| 2012/0165201 A1* | 6/2012 | Short | C12N 15/1058 506/1 |
| 2012/0322982 A1 | 12/2012 | Fuh et al. | |
| 2013/0058955 A1 | 3/2013 | Kelley et al. | |
| 2013/0266581 A1 | 10/2013 | Fuh et al. | |
| 2013/0315918 A1 | 11/2013 | Fuh et al. | |
| 2014/0296475 A1 | 10/2014 | Kim et al. | |
| 2015/0125468 A1 | 5/2015 | Schmidt et al. | |
| 2015/0175689 A1 | 6/2015 | Fuh et al. | |
| 2015/0232549 A1 | 8/2015 | Fuh et al. | |
| 2016/0168242 A1 | 6/2016 | Hass et al. | |
| 2017/0073405 A1 | 3/2017 | Fuh et al. | |
| 2017/0112899 A1 | 4/2017 | Healy et al. | |

FOREIGN PATENT DOCUMENTS

| | | |
|---|---|---|
| CN | 1299833 A | 6/2001 |
| CN | 1420987 A | 5/2003 |
| CN | 1445242 A | 10/2003 |
| CN | 103204933 A | 7/2013 |
| CN | 104761643 A | 7/2015 |
| CN | 104903348 A | 9/2015 |
| EP | 0368684 A1 | 5/1990 |
| EP | 2146727 B1 | 4/2012 |
| EP | 2446890 B1 | 9/2013 |
| EP | 2606899 B1 | 4/2015 |
| WO | WO-93/11161 A1 | 6/1993 |
| WO | WO-95/27062 A1 | 10/1995 |
| WO | WO-97/45450 A1 | 12/1997 |
| WO | WO-98/45331 A2 | 10/1998 |
| WO | WO-00/34337 A1 | 6/2000 |
| WO | WO-01/36972 A2 | 5/2001 |
| WO | WO-02/083849 A2 | 10/2002 |
| WO | WO-03/099999 A2 | 12/2003 |
| WO | WO-03/102157 A2 | 12/2003 |
| WO | WO-2004/056312 A2 | 7/2004 |
| WO | WO-2004/065416 A2 | 8/2004 |
| WO | WO-2005/012359 A2 | 2/2005 |
| WO | WO-2005/012531 A2 | 2/2005 |
| WO | WO-2005/044853 A2 | 5/2005 |
| WO | WO-2005/110374 A1 | 11/2005 |
| WO | WO-2005/110436 A2 | 11/2005 |
| WO | WO-2007/064919 A2 | 6/2007 |
| WO | WO-2007/083984 A1 | 7/2007 |
| WO | WO-2009/120893 A2 | 10/2009 |
| WO | WO-2011/019827 A2 | 2/2011 |
| WO | WO-2011/047442 A1 | 4/2011 |
| WO | WO-2011/066417 A2 | 6/2011 |
| WO | WO-2012/016227 A2 | 2/2012 |
| WO | WO-2013/066106 A2 | 5/2013 |
| WO | WO-2014/074905 A1 | 5/2014 |
| WO | WO-2014/085654 A1 | 6/2014 |
| WO | WO-2014/165513 A2 | 10/2014 |
| WO | WO-2016/073157 A1 | 5/2016 |
| WO | WO-2016/077381 A1 | 5/2016 |
| WO | WO-2016/081639 A1 | 5/2016 |
| WO | WO-2016/168159 A1 | 10/2016 |
| WO | WO-2017/100470 A1 | 6/2017 |

OTHER PUBLICATIONS

Jung et al. (1999) Journal of Molecular Biology vol. 294 pp. 163 to 180.*

(56) References Cited

OTHER PUBLICATIONS

Tao et al., "Characterization of a novel vascular endothelial growth factor receptor—immunoglobulin fusion protein variant," Modern Immunology. 30(5):361-4 (2010).
"Dissociation constant—Wikipedia, the free encyclopedia," retrieved on Jul. 13, 2016, from <https://en.wikipedia.org/wiki/Dissociation_constant> (6 pages).
Adamis et al., "Inhibition of vascular endothelial growth factor prevents retinal ischemia-associated iris neovascularization in a nonhuman primate," Arch Opthalmol. 114(1):66-71 (1996).
Agenda for Cambridge Healthtech Institute's Sixth Annual Phage Display Technologies Engineering Protein Therapeutics, Royal Sonesta Hotel, Cambridge, Massachusetts, Apr. 26-27, 2004 (3 pages).
Aiello et al., "Vascular endothelial growth factor in ocular fluid of patients with diabetic retinopathy and other retinal disorders," N Engl J Med. 331(22):1480-7 (1994).
Altiok et al., "Multivalent hyaluronic acid bioconjugates improve sFlt-1 activity in vitro," Biomaterials. 93:95-105 (2016).
Altiok et al., "sFlt Multivalent Conjugates Inhibit Angiogenesis and Improve Half-Life In Vivo," PLoS One. 11(6):e0155990 (2016) (14 pages).
American College of Rheumatology Subcommittee on Rheumatoid Arthritis Guidelines, "Guidelines for the management of rheumatoid arthritis: 2002 update," Arthritis & Rheum. 46(2):328-346 (2002).
Baca et al., "Antibody humanization using monovalent phage display," J Biol Chem. 272(16):10678-84 (1997).
Baeva et al., "Bacterial endotoxin detection in hyaluronic acid-based medical devices," J Biomed Mater Res B Appl Biomater. 105(5):1210-1215 (2017).
Barbas et al., "In vitro evolution of a neutralizing human antibody to human immunodeficiency virus type 1 to enhance affinity and broaden strain cross-reactivity," Proc Natl Acad Sci U S A. 91(9):3809-13 (1994).
Barbas et al., "Selection and evolution of high-affinity human anti-viral antibodies," Trends Biotechnol. 14(7):230-4 (1996).
Barrios et al., "Length of the antibody heavy chain complementarity determining region 3 as a specificity-determining factor," J Mol Recognit. 17(4):332-8 (2004).
Bass et al., "Hormone phage: An enrichment method for variant proteins with altered binding properties," Proteins. 8(4):309-14 (1990).
Bates et al., "Regulation of microvascular permeability by vascular endothelial growth factors," J Anat. 200(6):581-97 (2002).
Beiboer et al., "Guided selection of a pan carcinoma specific antibody reveals similar binding characteristics yet structural divergence between the original murine antibody and its human equivalent," J Mol Biol. 296(3):833-49 (2000).
Bendig, "Humanization of rodent monoclonal antibodies by CDR grafting," Methods: A Companion to Methods in Enzymology. 8:83-93 (1995).
Berkman et al., "Expression of the vascular permeability factor/vascular endothelial growth factor gene in central nervous system neoplasms," J Clin Invest. 91(1):153-9 (1993).
Boder et al., "Directed evolution of antibody fragments with monovalent femtomolar antigen-binding affinity," Proc Natl Acad Sci U S A. 97(20):10701-5 (2000).
Borgström et al., "Complete inhibition of angiogenesis and growth of microtumors by anti-vascular endothelial growth factor neutralizing antibody: Novel concepts of angiostatic therapy from intravital videomicroscopy," Cancer Res. 56(17):4032-9 (1996).
Brekken et al., "Vascular endothelial growth factor and vascular targeting of solid tumors," Anticancer Res. 21(6B):4221-9 (2001).
Brekken et al., "Vascular endothelial growth factor as a marker of tumor endothelium," Cancer Res. 58(9):1952-9 (1998).
Brezski et al., "Cleavage of IgGs by proteases associated with invasive diseases: an evasion tactic against host immunity?" MAbs. 2(3):212-20 (2010).

Brezski et al., "Human anti-IgG1 hinge autoantibodies reconstitute the effector functions of proteolytically inactivated IgGs," J Immunol. 181(5):3183-92 (2008).
Brown et al., "Expression of vascular permeability factor (vascular endothelial growth factor) and its receptors in adenocarcinomas of the gastrointestinal tract," Cancer Res. 53(19):4727-35 (1993).
Brown et al., "Expression of vascular permeability factor (vascular endothelial growth factor) and its receptors in breast cancer," Hum Pathol. 26(1):86-91 (1995).
Carmeliet et al., "Abnormal blood vessel development and lethality in embryos lacking a single VEGF allele," Nature. 380(6573):435-9 (1996).
Carmeliet et al., "Angiogenesis in cancer and other diseases," Nature. 407(6801):249-57 (2000).
Carter et al., "High level *Escherichia coli* expression and production of a bivalent humanized antibody fragment," Biotechnology (N Y). 10(2):163-7 (1992).
Carter et al., "Humanization of an anti-p185HER2 antibody for human cancer therapy," Proc Natl Acad Sci U S A. 89(10):4285-9 (1992).
Chang et al., "Loop-sequence features and stability determinants in antibody variable domains by high-throughput experiments," Structure. 22(1):9-21 (2014).
Chen et al., "Selection and analysis of an optimized anti-VEGF antibody: crystal structure of an affinity-matured Fab in complex with antigen," J Mol Biol. 293(4):865-81 (1999).
Chothia et al., "Canonical structures for the hypervariable regions of immunoglobulins," J Mol Biol. 196(4):901-17 (1987).
Christinger et al., "Crystallization of the receptor binding domain of vascular endothelial growth factor," Proteins. 26(3):353-7 (1996).
Clackson et al., "Making antibody fragments using phage display libraries," Nature. 352(6336):624-8 (1991).
Colman, "Effects of amino acid sequence changes on antibody-antigen interactions," Res Immunol. 145(1):33-6 (1994).
Cooke et al., "A strategy for antitumor vascular therapy by targeting the vascular endothelial growth factor:receptor complex," Cancer Res. 61(9):3653-9 (2001).
Cunningham et al., "High-resolution epitope mapping of hGH-receptor interactions by alanine-scanning mutagenesis," Science. 244(4908):1081-5 (1989).
De Wildt et al., "Antibody arrays for high-throughput screening of antibody-antigen interactions," Nat Biotechnol. 18(9):989-94 (2000).
Declaration of Germaine Fuh dated Oct. 3, 2012 (4 pages).
Deng et al., "Selection of antibody single-chain variable fragments with improved carbohydrate binding by phage display," J Biol Chem. 269(13):9533-8 (1994).
Deshayes et al., "Rapid identification of small binding motifs with high-throughput phage display: Discovery of peptidic antagonists of IGF-1 function," Chem Biol. 9(4):495-505 (2002).
Drescher, "Characterization of biological interactions with Biacore," GE Healthcare, dated Jun. 27, 2011 (25 pages).
Dvorak et al., "Vascular permeability factor/vascular endothelial growth factor, microvascular hyperpermeability, and angiogenesis," Am J Pathol. 146(5):1029-39 (1995).
E-mail from Cambridge Healthtech Institute, "Germaine Fuh at Phage Display Technologies—Apr. 26-27, 2004," dated Jul. 15, 2016 (2 pages).
Famili et al., "Hyaluronic Acid-Antibody Fragment Bioconjugates for Extended Ocular Pharmacokinetics," Bioconjug Chem. 30(11):2782-9 (2019).
Ferrara et al., "Clinical applications of angiogenic growth factors and their inhibitors," Nat Med. 5(12):1359-1364 (1999).
Ferrara et al., "Heterozygous embryonic lethality induced by targeted inactivation of the VEGF gene," Nature. 380(6573):439-42 (1996).
Ferrara et al., "Molecular and biological properties of the vascular endothelial growth factor family of proteins," Endo Rev. 13(1):18-32 (1992).
Ferrara et al., "Ten years of anti-vascular endothelial growth factor therapy," Nat Rev Drug Discov. 15(6):385-403 (2016).
Ferrara et al., "The biology of vascular endothelial growth factor," Endocr Rev. 18(1):4-25 (1997).

(56) References Cited

OTHER PUBLICATIONS

Ferrara et al., "Vascular endothelial growth factor is essential for corpus luteum angiogenesis," Nat Med. 4(3):336-340 (1998).
Ferrara, "Molecular and biological properties of vascular endothelial growth factor," J Mol Med (Berl). 77(7):527-43 (1999).
Folkman et al., "Angiogenic factors," Science. 235(4787):442-7 (1987).
Fuh et al., "Requirements for binding and signaling of the kinase domain receptor for vascular endothelial growth factor," J Biol Chem. 273(18):11197-204 (1998).
Fuh et al., "Structure-function studies of two synthetic anti-vascular endothelial growth factor Fabs and comparison with the Avastin Fab," J Biol Chem. 281(10):6625-31 (2006).
Fuh, "Antibodies with ligand-like epitope from phage libraries," Department of Protein Engineering, Genentech, Inc., Apr. 2004 (21 pages).
Garrard et al., "Selection of an anti-IGF-1 Fab from a Fab phage library created by mutagenesis of multiple CDR loops," Gene. 128(1):103-9 (1993).
Gerber et al., "Mice expressing a humanized form of VEGF-A may provide insights into the safety and efficacy of anti-VEGF antibodies," Proc Natl Acad Sci U S A. 104(9):3478-83 (2007).
Gerber et al., "VEGF couples hypertrophic cartilage remodeling, ossification and angiogenesis during endochondral bone formation," Nat Med. 5(6):623-8 (1999).
Gerber et al., *Report: Binding of 10 Fab fragments to human VEGF mutants*. Life Sciences and Facility Management, Zurich University of Applied Sciences. Aug. 2, 2016 (14 pages).
Gerber et al., *Report: Expression, purification and VEGF binding of 10 Fab fragments*. Life Sciences and Facility Management, Zurich University of Applied Sciences. Jun. 27, 2016 (18 pages).
Gerber et al., *Report: Inhibition of binding of VEGF to VEGF receptors by 10 Fab fragments*. Life Sciences and Facility Management, Zurich University of Applied Sciences. Sep. 8, 2016 (7 pages).
Gershoni et al., "Epitope mapping: the first step in developing epitope-based vaccines," BioDrugs. 21(3):145-56 (2007).
Gong et al., "Releasable Conjugation of Polymers to Proteins," Bioconjug Chem. 26(7):1172-81 (2015) (10 pages).
Griffiths et al., "Isolation of high affinity human antibodies directly from large synthetic repertoires," EMBO J. 13(14):3245-60 (1994).
Guerrin et al., "Vasculotropin/vascular endothelial growth factor is an autocrine growth factor for human retinal pigment epithelial cells cultured in vitro," J Cell Physiol. 164(2):385-94 (1995).
Hawkins et al., "Selection of phage antibodies by binding affinity. Mimicking affinity maturation," J Mol Biol. 226(3):889-96 (1992).
Hecht et al., "A randomized phase IIIB trial of chemotherapy, bevacizumab, and panitumumab compared with chemotherapy and bevacizumab alone for metastatic colorectal cancer," J Clin Oncol. 27(5):672-80 (2009).
Holash et al., "VEGF-trap: a VEGF blocker with potent antitumor effects," Proc Natl Acad Sci U S A. 99(17):11393-8 (2002).
Holliger et al., "Diabodies: Small bivalent and bispecific antibody fragments," Proc Natl Acad Sci U S A. 90(14):6444-8 (1993).
Hoogenboom et al., "Antibody phage display technology and its applications," Immunotechnology. 4(1):1-20 (1998).
Houck et al., "The vascular endothelial growth factor family: identification of a fourth molecular species and characterization of alternative splicing of RNA," Mol Endocrinol. 5(12):1806-14 (1991).
Hsu et al., "Antibody variable domain interface and framework sequence requirements for stability and function by high-throughput experiments," Structure. 22(1):22-34 (2014) (13 pages).
Jackson et al., "In vitro antibody maturation: Improvement of a high affinity, neutralizing antibody against IL-1 Beta," J Immunol. 154(7):3310-9 (1995).
Jones et al., "Replacing the complementarity-determining regions in a human antibody with those from a mouse," Nature. 321(6069):522-5 (1986).

Kim et al., "Inhibition of vascular endothelial growth factor-induced angiogenesis suppresses tumour growth in vivo," Nature. 362(6423):841-4 (1993).
Kim et al., "The vascular endothelial growth factor proteins: identification of biologically relevant regions by neutralizing monoclonal antibodies," Growth Factors. 7(1):53-64 (1992).
Kitzman et al., "Massively parallel single-amino-acid mutagenesis," Nat Methods. 12(3):203-6 (2015) (8 pages).
Klagsbrun et al., "Regulators of angiogenesis," Annu Rev Physiol. 53:217-39 (1991).
Klohs et al., "Antiangiogenic agents," Curr Opin Biotechnol. 10(6):544-9 (1999).
Knappik et al., "Fully synthetic human combinatorial antibody libraries (HuCAL) based on modular consensus frameworks and CDRs randomized with trinucleotides," J Mol Biol. 296(1):57-86 (2000).
Kobrin et al., "A V region mutation in a phosphocholine-binding monoclonal antibody results in loss of antigen binding," J Immunol. 146(6):2017-20 (1991).
Koenig et al., "Mutational landscape of antibody variable domains reveals a switch modulating the interdomain conformational dynamics and antigen binding," Proc Natl Acad Sci U S A. 114(4):E486-E495 (2017).
Lambrechts et al., "Markers of response for the antiangiogenic agent bevacizumab," J Clin Oncol. 31(9):1219-30 (2013).
Lamdan et al., "Affinity maturation and fine functional mapping of an antibody fragment against a novel neutralizing epitope on human vascular endothelial growth factor," Mol Biosyst. 9(8):2097-106 (2013).
Lee et al., "High-affinity human antibodies from phage-displayed synthetic Fab libraries with a single framework scaffold," J Mol Biol. 340(5):1073-93 (2004).
Leung et al., "Vascular endothelial growth factor is a secreted angiogenic mitogen," Science. 246(4935):1306-9 (1989).
Li et al., "Receptor-selective variants of human vascular endothelial growth factor. Generation and characterization," J Biol Chem. 275(38):29823-8 (2000).
Liang et al., "Cross-species vascular endothelial growth factor (VEGF)-blocking antibodies completely inhibit the growth of human tumor xenografts and measure the contribution of stromal VEGF," J Biol Chem. 281(2):951-61 (2006).
Lowman et al., "Monovalent phage display: A method for selecting variant proteins from random libraries," Methods: A Companion to Methods in Enzymology. 3(3):205-216 (1991).
Lowman et al., "Selecting high-affinity binding proteins by monovalent phage display," Biochemistry. 30(45):10832-8 (1991).
Lowman, "Optimization of therapeutic antibodies using monovalent phage display," Presentation for Bio 2002 Conference, Jun. 12, 2002 (22 pages).
MacCallum et al., "Antibody-antigen interactions: contact analysis and binding site topography," J Mol Biol. 262(5):732-45 (1996).
Marks et al., "By-passing immunization. Human antibodies from V-gene libraries displayed on phage," J Mol Biol. 222(3):581-97 (1991).
Mattern et al., "Association of vascular endothelial growth factor expression with intratumoral microvessel density and tumour cell proliferation in human epidermoid lung carcinoma," Br J Cancer. 73(7):931-4 (1996).
Melnyk et al., "Vascular endothelial growth factor promotes tumor dissemination by a mechanism distinct from its effect on primary tumor growth," Cancer Res. 56(4):921-4 (1996).
Mian et al., "Structure, function, and properties of antibody binding sites," J Mol Biol. 217(1):133-51 (1991).
Morrison et al., "Chimeric human antibody molecules: Mouse antigen-binding domains with human constant region domains," Proc Natl Acad Sci U S A. 81(21):6851-5 (1984).
Morrison et al., "Combinatorial alanine-scanning," Curr Opin Chem Biol. 5(3):302-7 (2001).
Muller et al., "Vascular endothelial growth factor: crystal structure and functional mapping of the kinase domain receptor binding site," Proc Natl Acad Sci U S A. 94(14):7192-7 (1997).

(56) References Cited

OTHER PUBLICATIONS

Muller et al., "VEGF and the Fab fragment of a humanized neutralizing antibody: Crystal structure of the complex at 2.4 A resolution and mutational analysis of the interface," Structure. 6(9):1153-67 (1998).
Oberg-Welsh et al., "Effects of vascular endothelial growth factor on pancreatic duct cell replication and the insulin production of fetal islet-like cell clusters in vitro," Mol Cell Encodrinol. 126(2):125-32 (1997).
Pan et al., "Solution structure of a phage-derived peptide antagonist in complex with vascular endothelial growth factor," J Mol Biol. 316(3):769-87 (2002).
Papadopoulos et al., "Binding and neutralization of vascular endothelial growth factor (VEGF) and related ligands by VEGF Trap, ranibizumab and bevacizumab," Angiogenesis. 15(2):171-85 (2012).
Paul, Chapter 9: Structure and Function of Immunoglobulins, *Fundamental Immunology, Third Edition*. Raven Press Ltd., 292-295 (1993) (6 pages).
Pelegri-O'Day et al., "Therapeutic protein-polymer conjugates: advancing beyond PEGylation," J Am Chem Soc. 136(41):14323-32 (2014).
Pini et al., "Design and use of a phage display library: Human antibodies with subnanomolar affinity against a marker of angiogenesis eluted from a two-dimensional gel," J Biol Chem. 273(34):21769-76 (1998).
Pluckthun, Antibodies from *Escherichia coli*. *The Pharmacology of Monoclonal Antibodies*. Rosenberg & Moore, 269-315 (1994).
Popkov et al., "Human/mouse cross-reactive anti-VEGF receptor 2 recombinant antibodies selected from an immune b9 allotype rabbit antibody library," J Immunol Methods. 288(1-2):149-64 (2004).
Popkov et al., "Rabbit immune repertoires as sources for therapeutic monoclonal antibodies: The impact of kappa allotype-correlated variation in cysteine content on antibody libraries selected by phage display," J Mol Biol. 325(2):325-35 (2003).
Presta et al., "Humanization of an anti-vascular endothelial growth factor monoclonal antibody for the therapy of solid tumors and other disorders," Cancer Res. 57(20):4593-9 (1997).
Presta, "Antibody engineering," Curr Op Struct Biol. 2(4):593-6 (1992).
Rai et al., Chronic Lymphocytic Leukemia. *Hematology: Basic Principles and Practice*. Hoffman, 1350-1363 (2000).
Riechmann et al., "Reshaping human antibodies for therapy," Nature. 332(6162):323-7 (1988).
Rudikoff et al., "Single amino acid substitution altering antigen-binding specificity," Proc Natl Acad Sci U S A. 79(6):1979-83 (1982).
Sato, "Molecular diagnosis of tumor angiogenesis and anti-angiogenic cancer therapy," Int J Clin Oncol. 8(4):200-6 (2003).
Schlaeppi et al., "Characterization of a new potent, in vivo neutralizing monoclonal antibody to human vascular endothelial growth factor," J Cancer Res Clin Oncol. 125(6):336-42 (1999).
Shima et al., "The mouse gene for vascular endothelial growth factor. Genomic structure, definition of the transcriptional unit, and characterization of transcriptional and post-transcriptional regulatory sequences," J Biol Chem. 271(7):3877-83 (1996).
Sidhu et al., "Phage display for selection of novel binding peptides," Methods Enzymol. 328:333-63 (2000).
Sidhu et al., "Phage-displayed antibody libraries of synthetic heavy chain complementarity determining regions," J Mol Biol. 338(2):299-310 (2004).
Siemeister et al., "The alpha-helical domain near the amino terminus is essential for dimerization of vascular endothelial growth factor," J Biol Chem. 273(18):11115-20 (1998).
Siemeister et al., "The pivotal role of VEGF in tumor angiogenesis: Molecular facts and therapeutic opportunities," Cancer Metastasis Rev. 17(2):241-8 (1998).
Sone et al., "Neutralization of vascular endothelial growth factor prevents collagen-induced arthritis and ameliorates established disease in mice," Biochem Biophys Res Commun. 281(2):562-8 (2001).
Stella et al., Prodrugs: A Chemical Approach to Targeted Drug Delivery. *Directed Drug Delivery: A Multidisciplinary Problem*. Borchardt, Repta, Stella, 247-267 (1985).
Streit et al., "Angiogenesis, lymphangiogenesis, and melanoma metastasis," Oncogene. 22(20):3172-9 (2003).
Sugihara et al., "A novel alternatively spliced form of murine vascular endothelial growth factor, VEGF 115," J Biol Chem. 273(5):3033-8 (1998).
Sun et al., "Biological activities of cytokine-neutralizing hyaluronic acid-antibody conjugates," Wound Repair Regen. 18(3):302-10 (2010).
Sun et al., "Cytokine binding by polysaccharide-antibody conjugates," available in PMC Mar. 1, 2012, published in final edited form as: Mol Pharm. 7(5):1769-77 (2010) (20 pages).
Tol et al., "Chemotherapy, bevacizumab, and cetuximab in metastatic colorectal cancer," N Engl J Med. 360(6):563-72 (2009).
Tonini et al., "Molecular basis of angiogenesis and cancer," Oncogene. 22(42):6549-56 (2003).
Van Besien et al., Clinical Manifestations, Staging, and Treatment of Non-Hodgkin Lymphoma. *Hematology: Basic Principles and Practice*. Hoffman, 1293-1339 (2000).
Vaughan et al., "Human antibodies with sub-nanomolar affinities isolated from a large non-immunized phage display library," Nat Biotechnol. 14(3):309-14 (1996).
Verhoeyen et al., "Reshaping human antibodies: Grafting an antilysozyme activity," Science. 239(4847):1534-6 (1988).
Viloria-Petit et al., "Contrasting effects of VEGF gene disruption in embryonic stem cell-derived versus oncogene-induced tumors," EMBO J. 22(16):4091-102 (2003).
Wang et al., "Inhibition of Expression Mouse Fibrosarcoma Growth by a Monoclonal Antibody to Human Vascular Endothelial Growth Factor," Zhongguo Kouqiang Hemian Waike Zashi. 1(1):35-9 (2003).
Warren et al., "Regulation by vascular endothelial growth factor of human colon cancer tumorigenesis in a mouse model of experimental liver metastasis," J Clin Invest. 95(4):1789-97 (1995).
Wells et al., "Rapid evolution of peptide and protein binding properties in vitro," Curr Opin Biotechnol. 3(4):355-62 (1992).
Welti et al. "Recent molecular discoveries in angiogenesis and antiangiogenic therapies in cancer," J Clin Invest. 123(8):3190-200 (2013).
Werther et al., "Humanization of an anti-lymphocyte function-associated antigen (LFA)-1 monoclonal antibody and reengineering of the humanized antibody for binding to rhesus LFA-1," J Immunol. 157(11):4986-4995 (1996).
Wiesmann et al., "Crystal structure at 1.7 A resolution of VEGF in complex with domain 2 of the Flt-1 receptor," Cell. 91(5):695-704 (1997).
Wilman, "Prodrugs in cancer chemotherapy," Biochem Soc Trans. 14(2):375-82 (1986).
Wu et al., "Humanization of a murine monoclonal antibody by simultaneous optimization of framework and CDR residues," J Mol Biol. 294(1):151-62 (1999).
Wu, "Simultaneous humanization and affinity optimization of monoclonal antibodies," Methods Mol Biol. 207:197-212 (2003).
Yang et al., "Comparison of binding characteristics and in vitro activities of three inhibitors of vascular endothelial growth factor A," Mol Pharm. 11(10):3421-30 (2014).
Yelton et al., "Affinity maturation of the BR96 anti-carcinoma antibody by codon-based mutagenesis," J Immunol. 155(4):1994-2004 (1995).
Yu et al., "A humanized anti-VEGF rabbit monoclonal antibody inhibits angiogenesis and blocks tumor growth in xenograft models," PLoS One. 5(2):e9072 (2010) (12 pages).
Yu et al., "Interactions between bevacizumab and murine VEGF-A: A reassessment," Invest Ophthalmol Vis Sci. 49(2):522-7 (2008).
Zapata et al., "Engineering linear F(ab')2 fragments for efficient production in *Escherichia coli* and enhanced antiproliferative activity," Protein Eng. 8(10):1057-62 (1995).
Zemlin et al., "Expressed murine and human CDR-H3 intervals of equal length exhibit distinct repertoires that differ in their amino acid composition and predicted range of structures," J Mol Biol. 334(4):733-49 (2003).

(56) References Cited

OTHER PUBLICATIONS

Zola, Using monoclonal antibodies: Soluble antigens. *Monoclonal antibodies: A manual of techniques*. CRC Press, Inc., 147-181 (2000).
English Translation of Examination Report for Pakistan Patent Application No. 582/2016, (1 page).
English translation of First Office Action for Chinese Patent Application No. 201680054735.X, dated May 8, 2021 (14 pages).
English Translation of Office Action for Colombian Patent Application No. NC2018/0003863, mailed Jan. 8, 2021 (3 pages).
Examination Report for Gulf Cooperation Council Patent Application No. 2016-32068, dated Jun. 17, 2019 (5 pages).
International Preliminary Report on Patentability for International Patent Application No. PCT/US2004/024662, issued Feb. 6, 2006 (12 pages).
International Preliminary Report on Patentability for International Patent Application No. PCT/US2004/029332, issued Jul. 3, 2006 (12 pages).
International Preliminary Report on Patentability for International Patent Application No. PCT/US2016/053454, issued Mar. 27, 2018 (17 pages).
International Search Report and Written Opinion for International Patent Application No. PCT/US2016/053454, mailed Apr. 28, 2017 (31 pages).
International Search Report for International Patent Application No. PCT/US2004/024662, mailed Oct. 14, 2005 (6 pages).
International Search Report for International Patent Application No. PCT/US2004/029332, mailed Oct. 14, 2005 (6 pages).
Invitation to Pay Additional Fees for International Patent Application No. PCT/US2016/053454, mailed Jan. 27, 2017 (10 pages).
Office Action for U.S. Appl. No. 16/033,353, dated Jan. 27, 2020 (5 pages).
Office Action for U.S. Appl. No. 16/033,353, dated Oct. 9, 2019 (10 pages).
Office Action for U.S. Appl. No. 16/033,499, dated Oct. 9, 2019 (11 pages).
Office Action with Search Report for Taiwanese Patent Application No. 105130888, dated Jan. 22, 2021 (15 pages).
Protest Against Norwegian Application No. 20061014, dated Jan. 25, 2017 (13 pages).
Substantive Examination Result Stage II for Indonesian Patent Application No. PID201802295, dated Feb. 15, 2021 (6 pages).
Summons to Attend Oral Proceedings for European Patent Application No. 04779660.2, dated Apr. 26, 2017 (20 pages).
Third Party Observations for European Patent Application No. 04779660.2, submitted Sep. 19, 2016 (26 pages).
Third Party Observations for European Patent Application No. 10009691.6, dated Jan. 22, 2016 (10 pages).
Written Opinion for Singaporean Patent Application No. 11201802379R, dated Mar. 4, 2019 (9 pages).
Konenkov et al., "Angiogenesis in proliferative diabetic retinopathy: rerspectives of anti-VEGF therapy (Review of literature)," Ophthalmosurgery. 4:111-15 (2013) (English abstract included).
English Translation of Decision of Grant for Russian Patent Application No. 2018114723, dated Oct. 21, 2021 (17 pages).
Igawa et al., "Reduced elimination of IgG antibodies by engineering the variable region," Protein Eng Des Sel. 23(5):385-392 (2010).

* cited by examiner

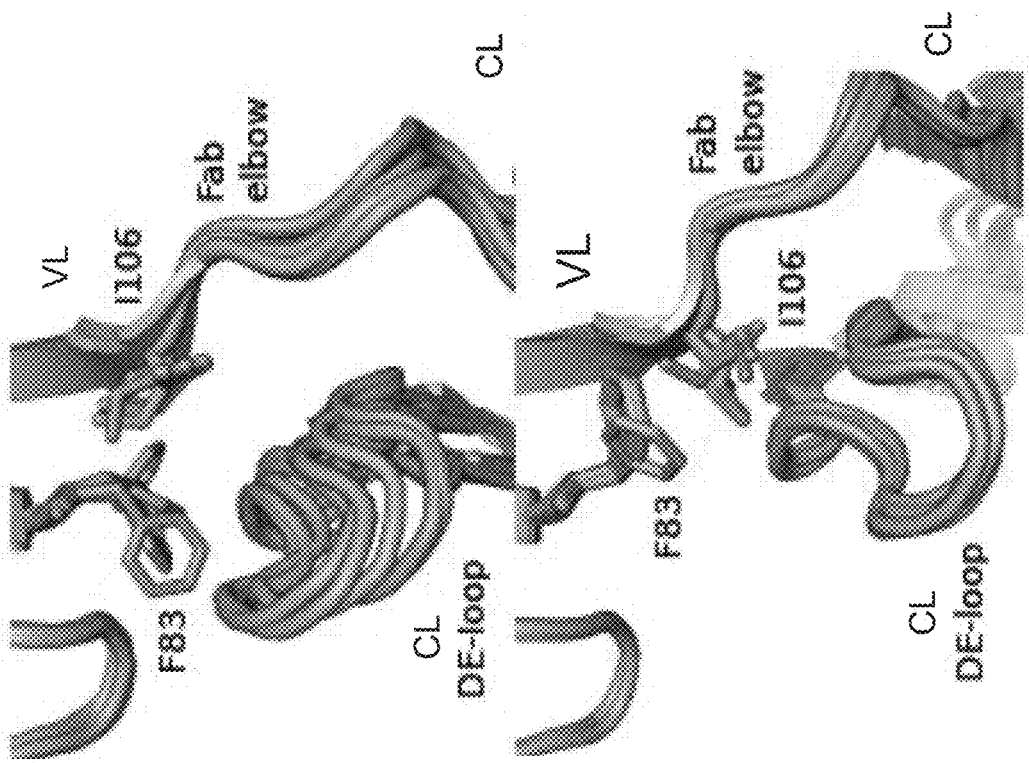
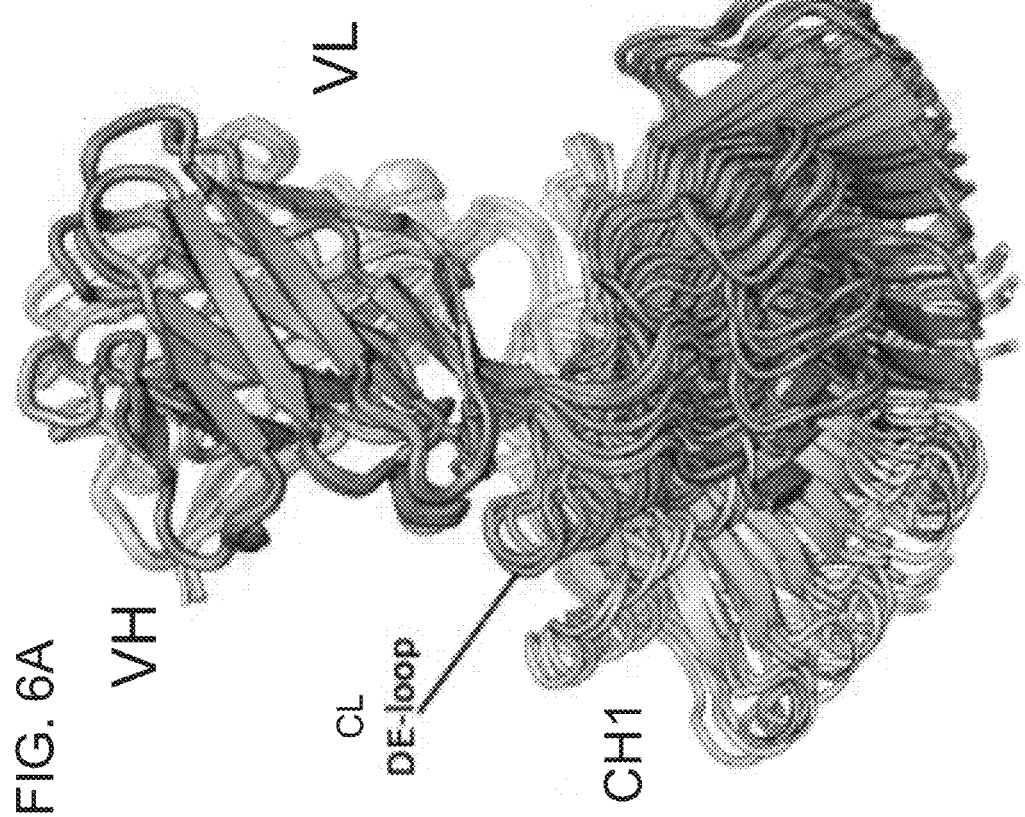

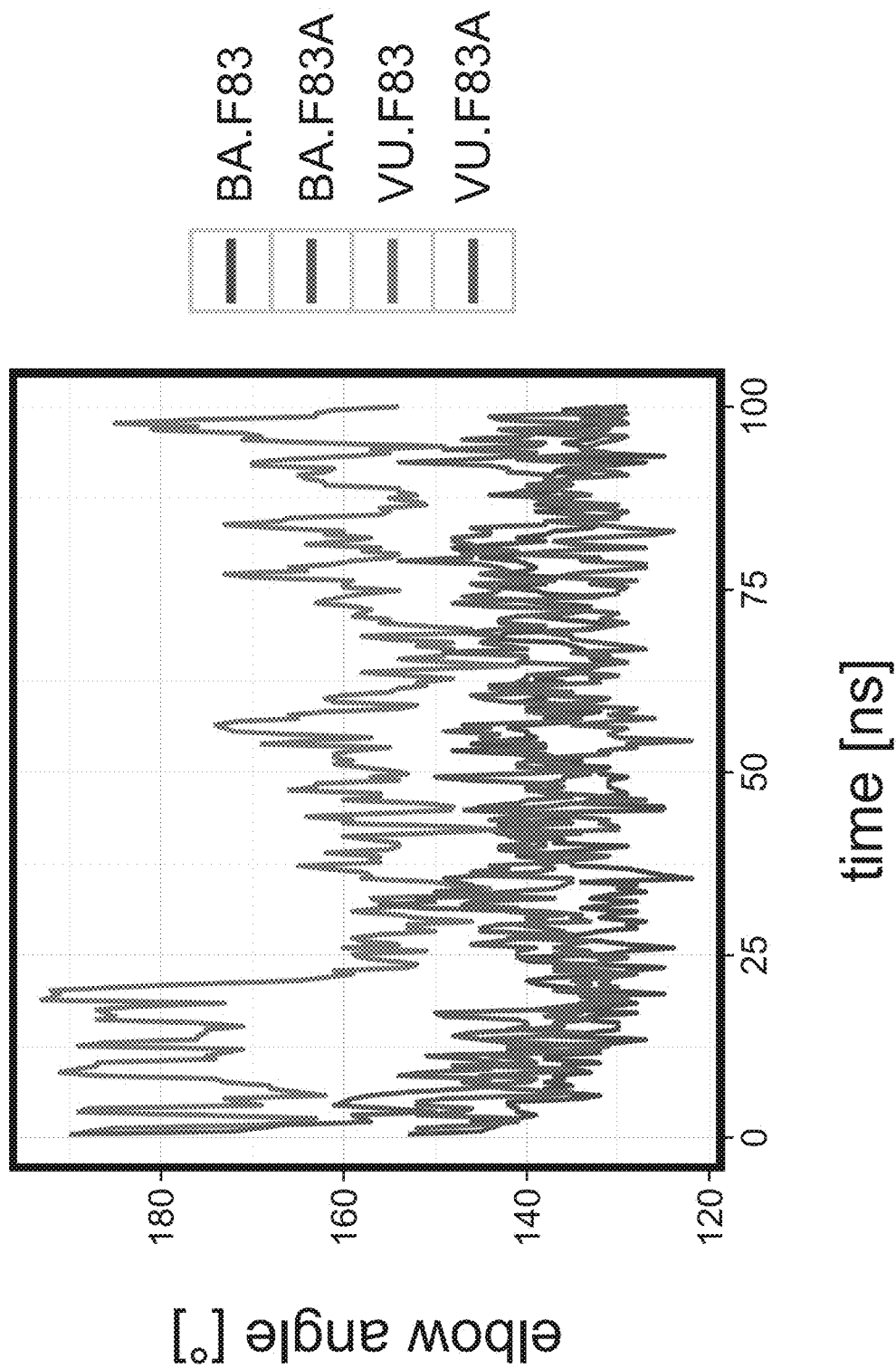

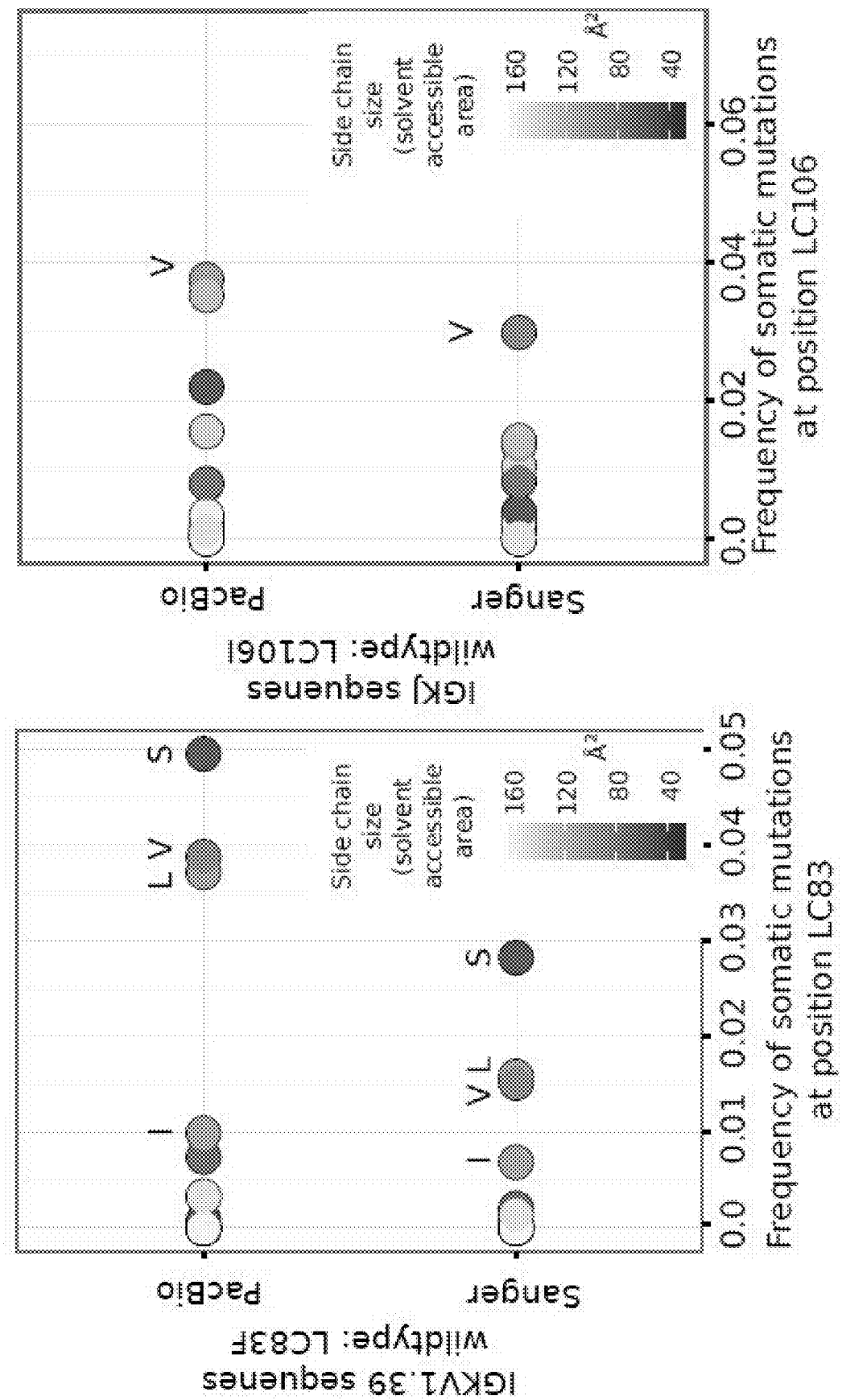

FIG. 12

| Name | 0 weeks | | | 4 weeks | | | 12 weeks | | | 24 weeks | | |
|---|---|---|---|---|---|---|---|---|---|---|---|---|
| | %LMW | %Monomer | %HMW | %LMW | %Monomer | %HMW | %LMW | %Monomer | %HMW | %LMW | %Monomer | %HMW |
| HCLC5 | 1.11 | 97.42 | 1.46 | 5.88 | 93.36 | 0.76 | 11.18 | 81.95 | 6.88 | 18.08 | 80.25 | 1.67 |
| N94A.F83A.Y58R.N82aR | 0.93 | 97.62 | 1.45 | 3.53 | 95.37 | 1.10 | 8.65 | 89.09 | 2.26 | 14.25 | 83.81 | 1.93 |
| N94A.F83A.A40E.T57E | 1.34 | 95.91 | 2.75 | 3.66 | 94.06 | 2.29 | 8.73 | 87.80 | 3.46 | 14.01 | 83.55 | 2.44 |
| N94A.F83A | 1.43 | 95.41 | 3.16 | 3.64 | 93.35 | 3.01 | 8.67 | 86.85 | 4.49 | 14.00 | 82.26 | 3.74 |
| HCLC2 | 3.29 | 91.73 | 4.99 | 5.13 | 90.98 | 3.89 | 9.19 | 84.91 | 5.90 | 14.98 | 81.70 | 3.33 |
| N94A | 1.05 | 97.17 | 1.78 | 4.84 | 93.74 | 1.42 | 10.53 | 87.99 | 1.48 | 16.08 | 81.58 | 2.34 |
| Wild Type G6.31 | 1.35 | 97.38 | 1.27 | 7.37 | 90.86 | 1.77 | 15.68 | 82.63 | 1.69 | 25.08 | 73.00 | 1.92 |
| Ranibizumab | 0.72 | 98.99 | 0.29 | 4.38 | 95.18 | 0.44 | 10.46 | 88.75 | 0.78 | 17.99 | 81.04 | 0.97 |

1

OPTIMIZED VARIANTS OF ANTI-VEGF ANTIBODIES

SEQUENCE LISTING

The instant application contains a Sequence Listing which has been submitted electronically in ASCII format and is hereby incorporated by reference in its entirety. Said ASCII copy, created on Dec. 18, 2020, is named 50474-110006_Sequence_Listing_12_18_20_ST25 and is 41,843 bytes in size.

FIELD OF THE INVENTION

The invention relates generally to anti-VEGF antibodies, as well as compositions that include anti-VEGF antibodies (e.g., antibody conjugates, fusion proteins, and polymeric formulations), with beneficial properties for research, therapeutic, and diagnostic purposes. The invention also relates to methods of identifying antibody variants with improved properties, for example, enhanced binding affinity, stability, and/or expression.

BACKGROUND OF THE INVENTION

Angiogenesis is a tightly-regulated process through which new blood vessels form from pre-existing blood vessels. Although angiogenesis is important during development to ensure adequate blood circulation, many disorders are associated with pathological angiogenesis, such as ocular disorders (e.g., age-related macular degeneration, AMD) and cell proliferative disorders (e.g., cancer). Vascular endothelial growth factor (VEGF) is a clinically-validated driver of angiogenesis and neutralization of VEGF, for example, using an anti-VEGF blocking antibody, can be used to treat disorders associated with pathological angiogenesis.

There remains a need for antibodies, such as anti-VEGF antibodies, with enhanced binding affinity, stability, pharmacokinetics, and/or expression, for example, for use in treating disorders associated with pathological angiogenesis. In particular, there is a need for antibody compositions for long-acting delivery for treatment of ocular disorders (e.g., AMD (e.g., wet AMD), diabetic macular edema (DME), diabetic retinopathy (DR), and retinal vein occlusion (RVO)). In addition, there is an unmet need for improved methods of identifying such antibodies with improved properties (e.g., enhanced binding affinity, stability, pharmacokinetics, and/or expression).

SUMMARY OF THE INVENTION

The present invention provides anti-VEGF antibodies, compositions that include anti-VEGF antibodies (e.g., antibody conjugates, fusion proteins, and polymeric formulations), and methods of use thereof, for example, for treatment of disorders associated with pathological angiogenesis (e.g., ocular disorders and cell proliferative disorders). The present invention also provides methods of identifying antibody variants with improved properties, for example, enhanced binding affinity, stability, pharmacokinetics, and/ or expression.

In one aspect, the invention features an isolated antibody that specifically binds vascular endothelial growth factor (VEGF), wherein the antibody comprises the following six hypervariable regions (HVRs): (a) an HVR-H1 comprising the amino acid sequence of DYWIH (SEQ ID NO: 1); (b) an HVR-H2 comprising the amino acid sequence of GX$_1$TPX$_2$GGX$_3$X$_4$X$_5$YX$_6$DSVX$_7$X$_8$ (SEQ ID NO: 2), wherein X$_1$ is Ile or His, X$_2$ is Ala or Arg, X$_3$ is Tyr or Lys, X$_4$ is Thr or Glu, X$_5$ is Arg, Tyr, Gln, or Glu, X$_6$ is Ala or Glu, X$_7$ is Lys or Glu, and X$_8$ is Gly or Glu; (c) an HVR-H3 comprising the amino acid sequence of FVFFLPYAMDY (SEQ ID NO: 3); (d) an HVR-L1 comprising the amino acid sequence of RASQX$_1$VSTAVA (SEQ ID NO: 4), wherein X$_1$ is Asp or Arg; (e) an HVR-L2 comprising the amino acid sequence of X$_1$ASFLYS (SEQ ID NO: 5), wherein X$_1$ is Ser or Met; and (f) an HVR-L3 comprising the amino acid sequence of X$_1$QGYGX$_2$PFT (SEQ ID NO: 6), wherein X$_1$ is Gln, Asn, or Thr and X$_2$ is Ala, Asn, Gln, or Arg. In some embodiments, the antibody comprises the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7), GITPAGGYEYYADSVKG (SEQ ID NO: 21), or GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10) or QQGYGNPFT (SEQ ID NO: 23).

In some embodiments of the above aspect, the antibody comprises the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some embodiments, the antibody further comprises the following heavy chain variable (VH) domain framework regions (FRs): (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16). In some embodiments, the antibody further comprises the following light chain variable (VL) domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20).

In some embodiments of the above aspect, the antibody comprises the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO:

23). In some embodiments, the antibody further comprises the following VL domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFATYYC (SEQ ID NO: 24); and (d) an FR-L4 comprising the amino acid sequence of FGQGTKVEIK (SEQ ID NO: 20).

In some embodiments of the above aspect, the antibody comprises the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some embodiments, the antibody further comprises the following VL domain FRs: (a) an FR-L1 comprising the amino acid sequence of DIQMTQSPSSLSASVGDRVTITC (SEQ ID NO: 17), DIQMTQSPESLSASVGDEVTITC (SEQ ID NO: 25), or DIQMTQSPSSLSASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19) or GVPSRFSGSGSGTDFTLTIESLQPEDAATYYC (SEQ ID NO: 28); and (d) an FR-L4 comprising the amino acid sequence of FGQGTKVEIK (SEQ ID NO: 20). In some embodiments, the antibody further comprises the following VH domain FRs: (a) an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32).

In another aspect, the invention features an isolated antibody that specifically binds VEGF, wherein the antibody comprises (a) a VH domain comprising an amino acid sequence having at least 95% sequence identity to the amino acid sequence of SEQ ID NO: 11, 40, or 42; (b) a VL domain comprising an amino acid sequence having at least 95% sequence identity to the amino acid sequence of SEQ ID NO: 12, 41, or 46; or (c) a VH domain as in (a) and a VL domain as in (b). In some embodiments, the VH domain further comprises the following FRs: (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14) or WVRQEPGKGLEWVA (SEQ ID NO: 39); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16). In some embodiments, the VH domain comprises the amino acid sequence of SEQ ID NO: 11. In some embodiments, the VL domain further comprises the following FRs: (a) an FR-L1 comprising the amino acid sequence of DIQMTQSPSSLSASVGDRVTITC (SEQ ID NO: 17) or DIQMTQSPSSLSASVGDRVTIDC (SEQ ID NO: 45); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19), GVPSRFSGSGSGTDFTLTISSLQPEDSATYYC (SEQ ID NO: 44), or GVPSRFSGSGSGTDFTLTISSLQPEDVATYYC (SEQ ID NO: 54); and (d) an FR-L4 comprising the amino acid sequence of FGQGTKVEIK (SEQ ID NO: 20) or FGQGTKVEVK (SEQ ID NO: 55). In some embodiments, the VL domain comprises the amino acid sequence of SEQ ID NO:12.

In another aspect, the invention features an isolated antibody that specifically binds VEGF, wherein the antibody comprises (a) a VH domain comprising the amino acid sequence of SEQ ID NO: 11 and (b) a VL domain comprising the amino acid sequence of SEQ ID NO: 12.

In another aspect, the invention features an isolated antibody that specifically binds VEGF, wherein the antibody comprises (a) a VH domain comprising the amino acid sequence of SEQ ID NO: 40 and (b) a VL domain comprising the amino acid sequence of SEQ ID NO: 12.

In another aspect, the invention features an isolated antibody that specifically binds VEGF, wherein the antibody comprises (a) a VH domain comprising the amino acid sequence of SEQ ID NO: 42 and (b) a VL domain comprising the amino acid sequence of SEQ ID NO: 12.

In another aspect, the invention features an isolated antibody that specifically binds VEGF, wherein the antibody comprises (a) a VH domain comprising the amino acid sequence of SEQ ID NO: 42 and (b) a VL domain comprising the amino acid sequence of SEQ ID NO: 41.

In another aspect, the invention features an isolated antibody that specifically binds VEGF, wherein the antibody comprises (a) a VH domain comprising an amino acid sequence having at least 95% sequence identity to the amino acid sequence of SEQ ID NO: 33 or 51; (b) a VL domain comprising an amino acid sequence having at least 95% sequence identity to the amino acid sequence of SEQ ID NO: 12, 34, 35, 36, 37, or 38; or (c) a VH domain as in (a) and a VL domain as in (b). In some embodiments, the antibody further comprises the following FRs: (a) an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 52); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In some embodiments, the VH domain comprises the amino acid sequence of SEQ ID NO: 33. In some embodiments, the VH domain comprises the amino acid sequence of SEQ ID NO: 51. In some embodiments, the antibody further comprises the following FRs: (a) an FR-L1 comprising the amino acid sequence of DIQMTQSPSSLSASVGDRVTITC (SEQ ID NO: 17), DIQMTQSPESLSASVGDEVTITC (SEQ ID NO: 25), or DIQMTQSPSSLSASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19), GVPSRFSGSGSGTDFTLTISSLQPEDFATYYC (SEQ ID NO: 24), or GVPSRFSGSGSGTDFTLTIES- LQPEDAATYYC (SEQ ID NO: 28); and (d) an FR-L4 comprising the amino acid sequence of FGQGTKVEIK (SEQ ID NO: 20). In some embodiments, the VL domain comprises the amino acid sequence of SEQ ID NO: 34. In some embodiments, the VL domain comprises the amino acid sequence of SEQ ID NO: 35. In some embodiments, the VL domain comprises the amino acid sequence of SEQ ID NO: 36. In some embodiments, the VL domain comprises the amino acid sequence of SEQ ID NO: 37. In some embodiments, the VL domain comprises the amino acid sequence of SEQ ID NO: 12. In some embodiments, the VL domain comprises the amino acid sequence of SEQ ID NO: 38.

In another aspect, the invention features an isolated antibody that specifically binds VEGF, wherein the antibody comprises (a) a VH domain comprising the amino acid sequence of SEQ ID NO: 33 and (b) a VL domain comprising the amino acid sequence of SEQ ID NO: 38.

In another aspect, the invention features an isolated antibody that specifically binds VEGF, wherein the antibody comprises (a) a VH domain comprising the amino acid sequence of SEQ ID NO: 33 and (b) a VL domain comprising the amino acid sequence of SEQ ID NO: 34.

In another aspect, the invention features an isolated antibody that specifically binds VEGF, wherein the antibody comprises (a) a VH domain comprising the amino acid sequence of SEQ ID NO: 33 and (b) a VL domain comprising the amino acid sequence of SEQ ID NO: 35.

In another aspect, the invention features an isolated antibody that specifically binds VEGF, wherein the antibody comprises (a) a VH domain comprising the amino acid sequence of SEQ ID NO: 33 and (b) a VL domain comprising the amino acid sequence of SEQ ID NO: 36.

In another aspect, the invention features an isolated antibody that specifically binds VEGF, wherein the antibody comprises (a) a VH domain comprising the amino acid sequence of SEQ ID NO: 33 and (b) a VL domain comprising the amino acid sequence of SEQ ID NO: 37.

In another aspect, the invention features an isolated antibody that specifically binds VEGF, wherein the antibody comprises (a) a VH domain comprising the amino acid sequence of SEQ ID NO: 33 and (b) a VL domain comprising the amino acid sequence of SEQ ID NO: 12.

In another aspect, the invention features an isolated antibody that specifically binds VEGF, wherein the antibody comprises (a) a VH domain comprising the amino acid sequence of SEQ ID NO: 51 and (b) a VL domain comprising the amino acid sequence of SEQ ID NO: 38.

In another aspect, the invention features an isolated antibody that specifically binds VEGF, wherein the antibody comprises (a) a VH domain comprising the amino acid sequence of SEQ ID NO: 51 and (b) a VL domain comprising the amino acid sequence of SEQ ID NO: 35.

In another aspect, the invention features an isolated antibody that specifically binds VEGF, wherein the antibody comprises (a) a VH domain comprising the amino acid sequence of SEQ ID NO: 51 and (b) a VL domain comprising the amino acid sequence of SEQ ID NO: 37.

In another aspect, the invention features an isolated antibody that specifically binds VEGF, wherein the antibody comprises (a) a VH domain comprising the amino acid sequence of SEQ ID NO: 51 and (b) a VL domain comprising the amino acid sequence of SEQ ID NO: 12.

In another aspect, the invention features an isolated antibody that specifically binds VEGF, wherein the antibody comprises (a) a heavy chain comprising the amino acid sequence of SEQ ID NO: 48 and (b) a light chain comprising the amino acid sequence of SEQ ID NO: 50.

In another aspect, the invention features an isolated antibody that specifically binds VEGF, wherein the antibody comprises (a) a heavy chain comprising the amino acid sequence of SEQ ID NO: 49 and (b) a light chain comprising the amino acid sequence of SEQ ID NO: 50.

In some embodiments of any of the preceding aspects, the antibody is capable of inhibiting the binding of VEGF to a VEGF receptor. In some embodiments, the VEGF receptor is VEGF receptor 1 (Flt-1). In some embodiments, the VEGF receptor is VEGF receptor 2 (KDR).

In some embodiments of any of the preceding aspects, the antibody binds human VEGF (hVEGF) with a Kd of about 2 nM or lower. In some embodiments, the antibody binds hVEGF with a Kd between about 75 pM and about 2 nM. In some embodiments, the antibody binds hVEGF with a Kd between about 75 pM and about 600 pM. In some embodiments, the antibody binds hVEGF with a Kd between about 75 pM and about 500 pM. In some embodiments, the antibody binds hVEGF with a Kd of about 80 pM. In some embodiments, the antibody binds hVEGF with a Kd of about 60 pM.

In some embodiments of any of the preceding aspects, the antibody has a melting temperature (Tm) of greater than about 83.5° C. In some embodiments, the antibody has a Tm of about 85° C. to about 91° C. In some embodiments, the antibody has a Tm of about 89° C.

In some embodiments of any of the preceding aspects, the antibody has an isoelectric point (pI) of lower than 8. In some embodiments, the antibody has a pI from about 5 to about 7. In some embodiments, the antibody has a pI of from about 5 to about 6.

In some embodiments of any of the preceding aspects, the antibody is monoclonal, human, humanized, or chimeric.

In some embodiments of any of the preceding aspects, the antibody is an antibody fragment that binds VEGF. In some embodiments, the antibody fragment is selected from the group consisting of Fab, Fab-C, Fab'-SH, Fv, scFv, and (Fab')$_2$ fragments. In some embodiments, the antibody fragment is an Fab.

In some embodiments of any of the preceding aspects, the antibody is a monospecific antibody. In other embodiments of any of the preceding aspects, the antibody is a multispecific antibody. In some embodiments, the multispecific antibody is a bispecific antibody. In some embodiments, the bispecific antibody binds VEGF and a second biological molecule selected from the group consisting of interleukin 1β (IL-1); interleukin-6 (IL-6); interleukin-6 receptor (IL-6R); interleukin-13 (IL-13); IL-13 receptor (IL-13R); PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and a protein genetically linked to age-related macular degeneration (AMD) risk. In some embodiments, the VEGF receptor is VEGFR1, VEGFR2, VEGFR3, membrane-bound VEGF-receptor (mbVEGFR), or soluble VEGF receptor (sVEGFR). In some embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC, COL10A1; and TNFRSF10A.

In another aspect, the invention features a polynucleotide (e.g., an isolated polynucleotide) encoding any of the antibodies described herein. In another aspect, the invention features a vector (e.g., an expression vector) comprising the polynucleotide for expressing the antibody. In another aspect, the invention features host cells comprising the preceding polynucleotides and/or vectors. In some embodiments, the host cell is a mammalian cell. In some embodiments, the mammalian cell is a 293 cell, a Chinese hamster ovary (CHO) cell, a yeast cell, or a plant cell. In some embodiments, the host cell is a prokaryotic cell. In some embodiments, the prokaryotic cell is E. coli.

In another aspect, the invention features a method of producing any of the antibodies described herein, the method comprising culturing a host cell that comprises any of the preceding vectors (e.g., expression vectors) in a culture medium. In some embodiments, the method further comprises recovering the antibody from the host cell or the culture medium. In some embodiments, the mammalian cell is a 293 cell, a Chinese hamster ovary (CHO) cell, a yeast cell, or a plant cell. In some embodiments, the host cell is a prokaryotic cell. In some embodiments, the prokaryotic cell is E. coli.

In another aspect, the invention features a method of reducing or inhibiting angiogenesis in a subject having a disorder associated with pathological angiogenesis, comprising administering to the subject an effective amount of any one of the preceding antibodies, thereby reducing or inhibiting angiogenesis in the subject. In some embodiments, the disorder associated with pathological angiogenesis is an ocular disorder or a cell proliferative disorder. In some embodiments, the disorder associated with pathological angiogenesis is an ocular disorder. In some embodiments, the ocular disorder is selected from the group consisting of age-related macular degeneration (AMD), macular degeneration, macular edema, diabetic macular edema (DME) (including focal, non-center DME and diffuse, center-involved DME), retinopathy, diabetic retinopathy (DR) (including proliferative DR (PDR), non-proliferative DR (NPDR), and high-altitude DR), other ischemia-related retinopathies, retinopathy of prematurity (ROP), retinal vein occlusion (RVO) (including central (CRVO) and branched (BRVO) forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease. In some embodiments, the ocular disorder is AMD, DME, DR, or RVO. In some embodiments, the ocular disorder is AMD. In some embodiments, the AMD is wet AMD. In some embodiments, the disorder associated with pathological angiogenesis is a cell proliferative disorder. In some embodiments, the cell proliferative disorder is a cancer. In some embodiments, the cancer is selected from the group consisting of breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, and multiple myeloma.

In another aspect, the invention features a method for treating a disorder associated with pathological angiogenesis, the method comprising administering an effective amount of any one of the preceding antibodies to a subject in need of such treatment. In some embodiments, the disorder associated with pathological angiogenesis is an ocular disorder or a cell proliferative disorder. In some embodiments, the disorder associated with pathological angiogenesis is an ocular disorder. In some embodiments, the ocular disorder is selected from the group consisting of age-related macular degeneration (AMD), macular degeneration, macular edema, diabetic macular edema (DME) (including focal, non-center DME and diffuse, center-involved DME), retinopathy, diabetic retinopathy (DR) (including proliferative DR (PDR), non-proliferative DR (NPDR), and high-altitude DR), other ischemia-related retinopathies, retinopathy of prematurity (ROP), retinal vein occlusion (RVO) (including central (CRVO) and branched (BRVO) forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease. In some embodiments, the ocular disorder is AMD, DME, DR, or RVO. In some embodiments, the ocular disorder is AMD. In some embodiments, the AMD is wet AMD. In some embodiments, the disorder associated with pathological angiogenesis is a cell proliferative disorder. In some embodiments, the cell proliferative disorder is a cancer. In some embodiments, the cancer is selected from the group consisting of breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, and multiple myeloma.

In another aspect, the invention features a method of inhibiting vascular permeability in a subject suffering from a disorder associated with undesirable vascular permeability, the method comprising administering to the subject an effective amount of any one of the preceding antibodies, thereby inhibiting vascular permeability in the subject.

In another aspect, the invention features a method of treating a disorder associated with undesirable vascular permeability, the method comprising administering an effective amount of any one of the preceding antibodies to a subject in need of such treatment.

In some embodiments of any of the preceding aspects, the disorder associated with undesirable vascular permeability is selected from the group consisting of edema associated with brain tumors, ascites associated with malignancies, Meigs' syndrome, lung inflammation, nephrotic syndrome, pericardial effusion, pleural effusion, and permeability associated with cardiovascular diseases.

In some embodiments of any of the preceding aspects, the method further comprises administering to the subject an effective amount of a second agent, wherein the second agent is selected from the group consisting of another antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, a growth-inhibitory agent, and a compound that binds to a second biological molecule. In some embodiments, the anti-angiogenic agent is a VEGF antagonist. In some embodiments, the VEGF antagonist is an anti-VEGF antibody, an anti-VEGF receptor antibody, a soluble VEGF receptor fusion protein, an aptamer, an anti-VEGF DARPin®, or a VEGFR tyrosine kinase inhibitor. In some embodiments, the anti-VEGF antibody is ranibizumab (LUCENTIS®), RTH-258, or a bispecific anti-VEGF antibody. In some embodiments, the bispecific anti-VEGF antibody is an anti-VEGF/anti-Ang2 antibody. In some embodiments, the anti-VEGF/anti-Ang2 antibody is RG-7716. In some embodiments, the soluble VEGF receptor fusion protein is aflibercept (EYLEA®). In some embodiments, the aptamer is pegaptanib (MACUGEN®). In some embodiments, the anti-VEGF DARPin® is abicipar pegol. In some embodiments, the VEGFR tyrosine kinase inhibitor is selected from the group consisting of 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416), and SUTENT® (sunitinib). In some embodiments, the second biological molecule is selected from the group consisting of IL-1β; IL-6; IL-6R; IL-13; IL-13R; PDGF; angiopoietin; angiopoietin 2; Tie2; S1P; integrins αvβ3, αv5, and α5β1; betacellulin; apelin/APJ; erythropoietin; complement factor D; TNFα; HtrA1; a VEGF receptor; ST-2 receptor; and a protein genetically linked to AMD risk. In some embodiments, the VEGF receptor is VEGFR1, VEGFR2, VEGFR3, mbVEGFR, or sVEGFR. In some embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC, COL10A1; and TNFRSF10A. In some embodiments, the compound that binds a second biological molecule is an antibody or antigen-binding fragment thereof. In some embodiments, the antigen-binding antibody fragment is selected from the group consisting of Fab, Fab-C, Fab'-SH, Fv, scFv, and (Fab')$_2$ fragments.

In some embodiments of any of the preceding aspects, the antibody is administered intravitreally, ocularly, intraocularly, juxtasclerally, subtenonly, superchoroidally, topically, intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, intraperitoneally, peritoneally, intraventricularly, subcutaneously, subconjunctivally, intravesicularly, mucosally, intrapericardially, intraumbilically, intraorbitally, orally, transdermally, by inhalation, by injection, by eye drop, by implantation, by infusion, by continuous infusion, by localized perfusion bathing target cells directly, by catheter, by lavage, in cremes, or in lipid compositions. In some embodiments, the antibody is administered intravitreally, ocularly, intraocularly, juxtasclerally, subtenonly, superchoroidally, or topically. In some embodiments, the antibody is administered intravitreally by injection. In some embodiments, the antibody is administered topically by eye drop or ointment. In some embodiments, the antibody is administered by a port delivery device. In some embodiments, the subject is a human.

In another aspect, the invention features a pharmaceutical composition comprising any one of the preceding antibodies. In some embodiments, the pharmaceutical formulation further comprises a polymer. In some embodiments, the polymer is a biodegradable polymer. In some embodiments, the pharmaceutical composition is formulated as a polymer solvent depot, a polymer implant, or a polymer micelle. In some embodiments, the polymer is a polylactic acid polyglycolic acid (PLGA) copolymer. In some embodiments, the pharmaceutical composition is formulated as a PLGA rod. In some embodiments, the pharmaceutical composition is used for treating a disorder associated with pathological angiogenesis or a disorder associated with undesirable vascular permeability in a mammal. In some embodiments, the disorder associated with pathological angiogenesis is an ocular disorder or a cell proliferative disorder. In some embodiments, the disorder associated with pathological angiogenesis is an ocular disorder. In some embodiments, the ocular disorder is selected from the group consisting of age-related macular degeneration (AMD), macular degeneration, macular edema, diabetic macular edema (DME) (including focal, non-center DME and diffuse, center-involved DME), retinopathy, diabetic retinopathy (DR) (including proliferative DR (PDR), non-proliferative DR (NPDR), and high-altitude DR), other ischemia-related retinopathies, retinopathy of prematurity (ROP), retinal vein occlusion (RVO) (including central (CRVO) and branched (BRVO) forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease. In some embodiments, the ocular disorder is AMD, DME, DR, or RVO. In some embodiments, the ocular disorder is AMD. In some embodiments, the AMD is wet AMD. In some embodiments, the disorder associated with pathological angiogenesis is a cell proliferative disorder. In some embodiments, the cell proliferative disorder is a cancer. In some embodiments, the cancer is selected from the group consisting of breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, and multiple myeloma. In some embodiments, the disorder associated with undesirable vascular permeability is selected from the group consisting of edema associated with brain tumors, ascites associated with malignancies, Meigs' syndrome, lung inflammation, nephrotic syndrome, pericardial effusion, pleural effusion, and permeability associated with cardiovascular diseases. In some embodiments, the pharmaceutical composition further comprises a second agent, wherein the second agent is selected from the group consisting of another antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, a growth-inhibitory agent, and a compound that binds to a second biological molecule. In some embodiments, the anti-angiogenic agent is a VEGF antagonist. In some embodiments, the VEGF antagonist is an anti-VEGF antibody, an anti-VEGF receptor antibody, a soluble VEGF receptor fusion protein, an aptamer, an anti-VEGF DARPin®, or a VEGFR tyrosine kinase inhibitor. In some embodiments, the anti-VEGF antibody is ranibizumab (LUCENTIS®), RTH-258, or a bispecific anti-VEGF antibody. In some embodiments, the bispecific anti-VEGF antibody is an anti-VEGF/anti-Ang2 antibody. In some embodiments, the anti-VEGF/anti-Ang2 antibody is RG-7716. In some embodiments, the soluble VEGF receptor fusion protein is aflibercept (EYLEA®). In some embodiments, the aptamer is pegaptanib (MACUGEN®). In some embodiments, the anti-VEGF DARPin® is abicipar pegol. In some embodiments, the VEGFR tyrosine kinase inhibitor is selected from the group consisting of 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416), and SUTENT® (sunitinib). In some embodiments, the second biological molecule is selected from the group consisting of IL-1β; IL-6; IL-6R; IL-13; IL-13R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and a protein genetically linked to AMD risk. In some embodiments, the VEGF receptor is VEGFR1, VEGFR2, VEGFR3, mbVEGFR, or sVEGFR. In some embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC, COL10A1; and TNFRSF10A. In some embodiments, the compound that binds a second biological molecule is an antibody or antigen-binding fragment thereof. In some embodiments, the antigen-binding antibody fragment is selected from the group consisting of Fab, Fab-C, Fab'-SH, Fv, scFv, and (Fab')₂ fragments.

In another aspect, the invention features an antibody conjugate comprising (i) any one of the preceding antibodies and (ii) a hydrophilic polymer covalently attached to the antibody. In some embodiments, the hydrophilic polymer is a hyaluronic acid (HA) polymer or a polyethylene glycol (PEG) polymer. In some embodiments, the hydrophilic polymer is an HA polymer. In some embodiments, the HA polymer has a molecular weight of about 1 megadalton (MDa) or lower. In some embodiments of any of the preceding aspects, the HA polymer has a molecular weight between about 25 kDa and about 500 kDa. In some embodiments, the HA polymer has a molecular weight between about 100 kDa and about 250 kDa. In some embodiments, the HA polymer has a molecular weight of about 200 kDa. In some embodiments, the HA polymer is not cross-linked. In some embodiments, the antibody is an antibody fragment that binds VEGF. In some embodiments, the antibody fragment is selected from the group consisting of Fab, Fab-C, Fab', Fab'-SH, Fv, scFv, and (Fab')₂ fragments. In some embodiments, the antibody fragment is an Fab, Fab-C, or Fab'. In some embodiments, the antibody conjugate has a hydrodynamic radius between about 10 nm and about 60 nm. In some embodiments, the antibody conjugate has a hydrodynamic radius between about 25 nm and about 35 nm. In some embodiments, the hydrodynamic radius is about 28 nm. In some embodiments, the antibody conjugate has an ocular half-life that is increased relative to a reference antibody that is not covalently attached to the hydrophilic polymer. In some embodiments, the ocular half-life is increased at least about 2-fold relative to the reference antibody. In some embodiments, the ocular half-life is increased at least about 4-fold relative to the reference antibody. In some embodiments, the ocular half-life is a vitreal half-life. In some embodiments, the reference antibody is identical to the antibody of the antibody conjugate.

In another aspect, the invention features an antibody conjugate comprising (i) an antibody that specifically binds VEGF and (ii) an HA polymer covalently attached to the antibody, wherein the HA polymer has a molecular weight of 1 MDa or lower. In some embodiments of any of the preceding aspects, the HA polymer has a molecular weight between about 25 kDa and about 500 kDa. In some embodiments, the HA polymer has a molecular weight between about 100 kDa and about 250 kDa. In some embodiments, the HA polymer has a molecular weight of about 200 kDa. In some embodiments, the HA polymer is not cross-linked. In some embodiments, the antibody is an antibody fragment that binds VEGF. In some embodiments, the antibody fragment is selected from the group consisting of Fab, Fab-C, Fab', Fab'-SH, Fv, scFv, and (Fab')₂ fragments. In some embodiments, the antibody fragment is an Fab, Fab-C, or Fab'. In some embodiments, the antibody conjugate has a hydrodynamic radius between about 10 nm and about 60 nm. In some embodiments, the antibody conjugate has a hydrodynamic radius between about 25 nm and about 35 nm. In some embodiments, the hydrodynamic radius is about 28 nm. In some embodiments, the antibody conjugate has an ocular half-life that is increased relative to a reference antibody that is not covalently attached to the hydrophilic polymer. In some embodiments, the ocular half-life is increased at least about 2-fold relative to the reference antibody. In some embodiments, the ocular half-life is increased at least about 4-fold relative to the reference antibody. In some embodiments, the ocular half-life is a vitreal half-life. In some embodiments, the reference antibody is identical to the antibody of the antibody conjugate.

In some embodiments of any of the preceding aspects, the antibody is covalently attached to the polymer by a reversible prodrug linker. In some embodiments, the polymer is a hydrogel. In some embodiments, the hydrogel is a PEG-based hydrogel. In some embodiments, the hydrogel is in the shape of a microparticulate bead.

In another aspect, the invention features a fusion protein comprising any one of the preceding antibodies covalently attached to an HA binding domain. In some embodiments, the HA binding domain is covalently attached to the heavy chain or the light chain of the antibody. In some embodiments, the HA binding domain is covalently attached to the C-terminus of the heavy chain or to the C-terminus of the light chain. In some embodiments, the HA binding domain is covalently attached to the C-terminus of the heavy chain. In some embodiments, the HA binding domain is covalently attached to the C-terminus of the light chain. In some embodiments, the fusion protein further comprises a linker, the linker being positioned between the antibody and the HA binding domain. In some embodiments, the linker comprises the amino acid sequence of GGGGS (SEQ ID NO: 61). In some embodiments, the linker consists of the amino acid sequence of GGGGS (SEQ ID NO: 61). In some embodiments, the antibody is an antibody fragment that binds VEGF. In some embodiments, the antibody fragment is selected from the group consisting of Fab, Fab-C, Fab', Fab'-SH, Fv, scFv, and (Fab')$_2$ fragments. In some embodiments, the antibody fragment is an Fab. In some embodiments, the HA binding domain is covalently attached to the C-terminus of the CH1 domain of the Fab. In some embodiments, the HA binding protein is covalently attached to the C-terminus of the CL domain of the Fab. In some embodiments, the HA binding domain is selected from the group consisting of a link module, a G1 domain, and a lysine-rich oligopeptide. In some embodiments, the HA binding domain is a link module. In some embodiments, the link module is selected from the group consisting of tumor necrosis factor-stimulated gene 6 (TSG6), CD44, lymphatic vessel endothelial hyaluronan receptor 1 (LYVE-1), hyaluronan and proteoglycan link protein (HAPLN) 1, HAPLN2, HAPLN3, HAPLN4, aggrecan, brevican, neurocan, phosphacan, versican, CAB61358, KIA0527, stabilin-1, and stabilin-2 link modules. In some embodiments, the link module is a TSG6 link module. In some embodiments, the TSG6 link module is a human TSG6 link module or a rabbit TSG6 link module. In some embodiments, the TSG link module is a human TSG6 link module. In some embodiments, the human TSG6 link module comprises amino acid residues 36-128 of human TSG6.

In some embodiments of any of the preceding aspects, the fusion protein further comprises at least one additional HA binding domain. In some embodiments, the at least one additional HA binding domain is covalently attached to the heavy chain or the light chain of the antibody. In some embodiments, the at least one additional HA binding protein is linked to the antibody by a linker. In some embodiments, the linker comprises the amino acid sequence of GGGGS (SEQ ID NO: 61). In some embodiments, the linker consists of the amino acid sequence of GGGGS (SEQ ID NO: 61). In some embodiments, a first HA binding domain is covalently attached to the heavy chain and a second HA binding domain is covalently attached to the light chain. In some embodiments, the first HA binding domain is linked to the C-terminus of the heavy chain and the second HA binding domain is linked to the C-terminus of the light chain. In some embodiments, the at least one additional HA binding protein is selected from the group consisting of a link module, a G1 domain, and a lysine-rich oligopeptide. In some embodiments, the at least one additional HA binding protein is a link module. In some embodiments, the link module is a TSG6 link module. In some embodiments, the TSG6 link module is a human TSG6 link module or a rabbit TSG6 link module. In some embodiments, the TSG6 link module is a human TSG6 link module. In some embodiments, the human TSG6 link module comprises amino acid residues 36-128 of human TSG6.

In some embodiments of any of the preceding aspects, the fusion protein specifically binds to VEGF and HA. In some embodiments, the fusion protein binds HA with a Kd of about 2 µM or lower. In some embodiments, the fusion protein binds HA with a Kd between about 1 nM and about 500 nM. In some embodiments, the fusion protein binds HA with a Kd between about 1 nM and about 50 nM. In some embodiments, the fusion protein binds HA with a Kd of about 10 nM.

In some embodiments of any of the preceding aspects, the fusion protein has an ocular half-life that is increased relative to a reference antibody that is not covalently attached to a HA binding domain. In some embodiments, the ocular half-life is increased at least about 2-fold relative to the reference antibody. In some embodiments, the ocular half-life is increased at least about 4-fold relative to the reference antibody. In some embodiments, the ocular half-life is a vitreal half-life. In some embodiments, the reference antibody is identical to the antibody of the fusion protein.

In another aspect, the invention features a method of reducing or inhibiting angiogenesis in a subject having a disorder associated with pathological angiogenesis, comprising administering to the subject an effective amount of any one of the preceding antibody conjugates, thereby reducing or inhibiting angiogenesis in the subject.

In another aspect, the invention features a method for treating a disorder associated with pathological angiogenesis, the method comprising administering an effective amount of any one of the preceding antibody conjugates to a subject in need of such treatment.

In another aspect, the invention features a method of reducing or inhibiting angiogenesis in a subject having a disorder associated with pathological angiogenesis, comprising administering to the subject an effective amount of any one of the preceding fusion proteins, thereby reducing or inhibiting angiogenesis in the subject.

In another aspect, the invention features a method for treating a disorder associated with pathological angiogenesis, the method comprising administering an effective amount of any one of the preceding fusion proteins to a subject in need of such treatment.

In some embodiments of any of the preceding aspects, the disorder associated with pathological angiogenesis is an ocular disorder. In some embodiments, the ocular disorder is selected from the group consisting of AMD, macular degeneration, macular edema, DME (including focal, non-center DME and diffuse, center-involved DME), retinopathy, DR (including PDR, NPDR, and high-altitude DR), other ischemia-related retinopathies, ROP, RVO (including CRVO and BRVO forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, RP, hypertensive retinopathy, retinal angiomatous proliferation, macular telangiectasia, iris neovascularization, intraocular neovascularization, retinal degeneration, CME, vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease. In some embodiments, the ocular disorder is AMD, DME, DR, or RVO. In some embodiments, the ocular disorder is AMD. In some embodiments, the AMD is wet AMD.

In some embodiments of any of the preceding aspects, the method further comprises administering to the subject an effective amount of a second agent, wherein the second agent is selected from the group consisting of another antibody, an anti-angiogenic agent, a cytokine, a cytokine antagonist, a corticosteroid, an analgesic, and a compound that binds to a second biological molecule. In some embodiments, the anti-angiogenic agent is a VEGF antagonist. In some embodiments, the VEGF antagonist is an anti-VEGF antibody, an anti-VEGF receptor antibody, a soluble VEGF receptor fusion protein, an aptamer, an anti-VEGF DARPin®, or a VEGFR tyrosine kinase inhibitor. In some embodiments, the anti-VEGF antibody is ranibizumab (LUCENTIS®), RTH-258, or a bispecific anti-VEGF antibody. In some embodiments, the bispecific anti-VEGF antibody is an anti-VEGF/anti-Ang2 antibody. In some embodiments, the anti-VEGF/anti-Ang2 antibody is RG-7716. In some embodiments, the soluble VEGF receptor fusion protein is aflibercept (EYLEA®). In some embodiments, the aptamer is pegaptanib (MACUGEN®). In some embodiments, the anti-VEGF DARPin® is abicipar pegol. In some embodiments, the VEGFR tyrosine kinase inhibitor is selected from the group consisting of 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416), and SUTENT® (sunitinib). In some embodiments, the second biological molecule is selected from the group consisting of IL-1β; IL-6; IL-6R; IL-13; IL-13R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and a protein genetically linked to AMD risk. In some embodiments, the VEGF receptor is VEGFR1, VEGFR2, VEGFR3, mbVEGFR, or sVEGFR. In some embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC, COL10A1; and TNFRSF10A. In some embodiments, the compound that binds a second biological molecule is an antibody or antigen-binding fragment thereof. In some embodiments, the antigen-binding antibody fragment is selected from the group consisting of Fab, Fab-C, Fab'-SH, Fv, scFv, and (Fab')$_2$ fragments.

In some embodiments of any of the preceding aspects, the antibody conjugate is administered intravitreally, ocularly, intraocularly, juxtasclerally, subtenonly, superchoroidally, topically, intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, intraperitoneally, peritoneally, intraventricularly, subcutaneously, subconjunctivally, intravesicularly, mucosally, intrapericardially, intraumbilically, intraorbitally, orally, transdermally, by inhalation, by injection, by eye drop, by implantation, by infusion, by continuous infusion, by localized perfusion bathing target cells directly, by catheter, by lavage, in cremes, or in lipid compositions. In some embodiments, the antibody conjugate is administered intravitreally, ocularly, intraocularly, juxtasclerally, subtenonly, superchoroidally, or topically. In some embodiments, the antibody conjugate is administered intravitreally by injection. In some embodiments, the antibody conjugate is administered topically by eye drop or ointment. In some embodiments, the antibody conjugate is administered by a port delivery device.

In some embodiments of any of the preceding aspects, the fusion protein is administered intravitreally, ocularly, intraocularly, juxtasclerally, subtenonly, superchoroidally, topically, intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, intraperitoneally, peritoneally, intraventricularly, subcutaneously, subconjunctivally, intravesicularly, mucosally, intrapericardially, intraumbilically, intraorbitally, orally, transdermally, by inhalation, by injection, by eye drop, by implantation, by infusion, by continuous infusion, by localized perfusion bathing target cells directly, by catheter, by lavage, in cremes, or in lipid compositions. In some embodiments, the fusion protein is administered intravitreally, ocularly, intraocularly, juxtasclerally, subtenonly, superchoroidally, or topically. In some embodiments, the fusion protein is administered intravitreally by injection. In some embodiments, the fusion protein is administered topically by eye drop or ointment. In some embodiments, the fusion protein is administered by a port delivery device. In some embodiments, the subject is a human.

In another aspect, the invention features a pharmaceutical composition comprising any one of the preceding antibody conjugates.

In another aspect, the invention features a pharmaceutical composition comprising any one of the preceding fusion proteins.

In some embodiments of any of the preceding aspects, the pharmaceutical composition is used for treating a disorder associated with pathological angiogenesis in a mammal. In some embodiments, the disorder associated with pathological angiogenesis is an ocular disorder. In some embodiments, the ocular disorder is selected from the group consisting of AMD, macular degeneration, macular edema, DME (including focal, non-center DME and diffuse, center-involved DME), retinopathy, DR (including PDR, NPDR, and high-altitude DR), other ischemia-related retinopathies, ROP, RVO (including CRVO and BRVO forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, RP, hypertensive retinopathy, retinal angiomatous proliferation, macular telangiectasia, iris neovascularization, intraocular neovascularization, retinal degeneration, CME, vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease. In some embodiments, the ocular disorder is AMD, DME, DR, or RVO. In some embodiments, the ocular disorder is AMD. In some embodiments, the AMD is wet AMD.

In some embodiments of any of the preceding aspects, the pharmaceutical composition further comprises a second agent, wherein the second agent is selected from the group consisting of another antibody, an anti-angiogenic agent, a cytokine, a cytokine antagonist, a corticosteroid, an analgesic, and a compound that binds to a second biological molecule. In some embodiments, the anti-angiogenic agent is a VEGF antagonist. In some embodiments, the VEGF antagonist is an anti-VEGF antibody, an anti-VEGF receptor antibody, a soluble VEGF receptor fusion protein, an aptamer, an anti-VEGF DARPin®, or a VEGFR tyrosine kinase inhibitor. In some embodiments, the anti-VEGF antibody is ranibizumab (LUCENTIS®), RTH-258, or a bispecific anti-VEGF antibody. In some embodiments, the bispecific anti-VEGF antibody is an anti-VEGF/anti-Ang2 antibody. In some embodiments, the anti-VEGF/anti-Ang2 antibody is RG-7716. In some embodiments, the soluble VEGF receptor fusion protein is aflibercept (EYLEA®). In some embodiments, the aptamer is pegaptanib (MACU-GEN®). In some embodiments, the anti-VEGF DARPin® is abicipar pegol. In some embodiments, the VEGFR tyrosine kinase inhibitor is selected from the group consisting of 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-yl-propoxy)quinazoline (AZD2171), vatalanib (PTK787), semaxaminib (SU5416), and SUTENT® (sunitinib). In some embodiments, the second biological molecule is selected from the group consisting of IL-1β; IL-6; IL-6R; IL-13; IL-13R; PDGF; angiopoietin; angiopoietin 2; Tie2; S1P; integrins αvβ3, αv5, and α5β1; betacellulin; apelin/APJ; erythropoietin; complement factor D; TNFα; HtrA1; a VEGF receptor; ST-2 receptor; and a protein genetically linked to AMD risk. In some embodiments, the VEGF receptor is VEGFR1, VEGFR2, VEGFR3, mbVEGFR, or sVEGFR. In some embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC, COL10A1; and TNFRSF10A. In some embodiments, the compound that binds a second biological molecule is an antibody or antigen-binding fragment thereof. In some embodiments, the antigen-binding antibody fragment is selected from the group consisting of Fab, Fab-C, Fab'-SH, Fv, scFv, and (Fab')$_2$ fragments.

In another aspect, the invention features a method of identifying an amino acid residue alteration that confers enhanced binding of an antibody to a target molecule, the method comprising: (a) providing a display library comprising nucleic acids encoding candidate antibody variants, wherein each candidate antibody variant comprises an amino acid residue alteration in the VH or the VL compared to a reference antibody, and wherein amino acid residue alterations at every position of the VH or VL are present in the display library; (b) sorting the display library based on binding of the candidate antibody variants to the target molecule to form a sorted library, wherein the sorted library comprises candidate antibody variants with enhanced binding to the target molecule compared to the reference antibody; and (c) comparing the frequency at which each amino acid residue alteration is present in the display library and in the sorted library as determined by massively parallel sequencing, thereby determining whether each amino acid residue alteration is enriched in the sorted library compared to the display library, whereby the amino acid residue alteration is identified as conferring enhanced binding to the target molecule if it is enriched in the sorted library compared to the display library.

In another aspect, the invention features a method of identifying an amino acid residue alteration that confers enhanced stability to an antibody, the method comprising: (a) providing a display library comprising nucleic acids encoding candidate antibody variants, wherein each candidate antibody variant comprises an amino acid residue alteration in the VH or the VL compared to a reference antibody, and wherein amino acid residue alterations at every position of the VH or VL are present in the display library; (b) sorting the display library based on binding of the candidate antibody variants to the target molecule to form a sorted library, wherein the sorted library comprises candidate antibody variants with enhanced stability compared to the reference antibody; and (c) comparing the frequency at which each amino acid residue alteration is present in the display library and in the sorted library as determined by massively parallel sequencing, thereby determining whether each amino acid residue alteration is enriched in the sorted library compared to the display library, whereby the amino acid residue alteration is identified as conferring enhanced stability to the antibody if it is enriched in the sorted library compared to the display library.

In some embodiments of any of the preceding aspects, the method further comprises determining the frequency at which each amino acid alteration is present in the display library and the sorted library by massively parallel sequencing following step (b).

In some embodiments of any of the preceding aspects, the amino acid residue alteration is enriched at least 2-fold in the sorted library compared to the display library.

In some embodiments of any of the preceding aspects, the display library is selected from the group consisting of a phage display library, a bacterial display library, a yeast display library, a mammalian display library, a ribosome display library, and an mRNA display library. In some embodiments, the display library is a phage display library.

In some embodiments of any of the preceding aspects, the amino acid residue alteration is encoded by a degenerate codon set. In some embodiments, the degenerate codon set is an NNK or an NNS codon set, wherein N is A, C, G, or T; K is G or T; and S is C or G. In some embodiments, the degenerate codon set is an NNK codon set.

In some embodiments of any of the preceding aspects, the sorting of step (b) comprises contacting the display library with an immobilized target molecule or epitope.

In some embodiments of any of the preceding aspects, the sorting of step (b) comprises contacting the display library with a soluble target molecule or epitope.

In some embodiments of any of the preceding aspects, the display library comprises at least $1 \times 10^6$ candidate antibody variants. In some embodiments, the display library comprises at least $1 \times 10^8$ antibody variants. In some embodiments, the display library comprises at least $1 \times 10^9$ antibody variants.

In some embodiments of any of the preceding aspects, the massively parallel sequencing comprises deep sequencing, ultra-deep sequencing, and/or next-generation sequencing.

In some embodiments of any of the preceding aspects, the antibody is a monoclonal antibody.

In some embodiments of any of the preceding aspects, the antibody is an IgG antibody.

In some embodiments of any of the preceding aspects, the antibody is an antibody fragment. In some embodiments, antibody fragment is selected from the group consisting of Fab, scFv, Fv, Fab', Fab'-SH, F(ab')$_2$, and diabody. In some embodiments, the antibody fragment is an Fab.

In some embodiments of any of the preceding aspects, the method further comprises generating an antibody that comprises an amino acid residue alteration identified by the steps of the method.

In some aspects, any one of the preceding antibodies can be used in the manufacture of a medicament for reducing or inhibiting angiogenesis in a subject having a disorder associated with pathological angiogenesis.

In some aspects, any one of the preceding antibodies can be used in the manufacture of a medicament for treating a disorder associated with pathological angiogenesis in a subject in need of such treatment.

In some aspects, any one of the preceding antibodies can be used in the manufacture of a medicament for inhibiting vascular permeability in a subject suffering from a disorder associated with undesirable vascular permeability.

In some aspects, any one of the preceding antibodies can be used in a method of reducing or inhibiting angiogenesis in a subject having a disorder associated with pathological angiogenesis.

In some aspects, any one of the preceding antibodies can be used in a method of treating a disorder associated with pathological angiogenesis in a subject in need of such treatment.

In some aspects, any one of the preceding antibodies can be used in a method of inhibiting vascular permeability in a subject suffering from a disorder associated with undesirable vascular permeability.

In another aspect, the invention features a composition comprising any one of the preceding antibodies for use in a method of reducing or inhibiting angiogenesis in a subject having a disorder associated with pathological angiogenesis.

In another aspect, the invention features a composition comprising any one of the preceding antibodies for use in a method of treating a disorder associated with pathological angiogenesis in a subject in need of such treatment.

In another aspect, the invention features a composition comprising any one of the preceding antibodies for use in a method of inhibiting vascular permeability in a subject suffering from a disorder associated with undesirable vascular permeability.

In some aspects, any one of the preceding antibody conjugates can be used in the manufacture of a medicament for reducing or inhibiting angiogenesis in a subject having a disorder associated with pathological angiogenesis.

In some aspects, any one of the preceding antibody conjugates can be used in the manufacture of a medicament for treating a disorder associated with pathological angiogenesis in a subject in need of such treatment.

In some aspects, any one of the preceding antibody conjugates can be used in a method of reducing or inhibiting angiogenesis in a subject having a disorder associated with pathological angiogenesis.

In some aspects, any one of the preceding antibody conjugates can be used in a method of treating a disorder associated with pathological angiogenesis in a subject in need of such treatment.

In another aspect, the invention features a composition comprising any one of the preceding antibody conjugates for use in a method of reducing or inhibiting angiogenesis in a subject having a disorder associated with pathological angiogenesis.

In another aspect, the invention features a composition comprising any one of the preceding antibody conjugates for use in a method of treating a disorder associated with pathological angiogenesis in a subject in need of such treatment.

In some aspects, any one of the preceding fusion proteins can be used in the manufacture of a medicament for reducing or inhibiting angiogenesis in a subject having a disorder associated with pathological angiogenesis.

In some aspects, any one of the preceding fusion proteins can be used in the manufacture of a medicament for treating a disorder associated with pathological angiogenesis in a subject in need of such treatment.

In some aspects, any one of the preceding fusion proteins can be used in a method of reducing or inhibiting angiogenesis in a subject having a disorder associated with pathological angiogenesis.

In some aspects, any one of the preceding fusion proteins can be used in a method of treating a disorder associated with pathological angiogenesis in a subject in need of such treatment.

In another aspect, the invention features a composition comprising any one of the preceding fusion proteins for use in a method of reducing or inhibiting angiogenesis in a subject having a disorder associated with pathological angiogenesis.

In another aspect, the invention features a composition comprising any one of the preceding fusion proteins for use in a method of treating a disorder associated with pathological angiogenesis in a subject in need of such treatment.

It is to be understood that any of the embodiments described above with respect to methods of treatment (e.g., with respect to antibody properties, additional therapeutic agents, disorders associated with pathological angiogenesis (e.g., ocular disorders such as AMD, DME, DR, or RVO), administration routes (e.g., intravitreal injection), and the like) can be used in the context of the medicaments, uses, and compositions described above.

BRIEF DESCRIPTION OF THE DRAWINGS

The application file contains at least one drawing executed in color. Copies of this patent or patent application with color drawings will be provided by the Office upon request and payment of the necessary fee.

FIG. 1A shows the results obtained from panning the NNK walk VH library against anti-gD. FIG. 1B shows the results obtained from panning the NNK walk VH library against protein L. FIG. 1C shows the results obtained from panning the NNK walk VH library against protein A. FIG. 1D shows the results obtained from panning the NNK walk VL library against anti-gD. FIG. 1E shows the results obtained from panning the NNK walk VL library against protein L. FIG. 1F shows the results obtained from panning the NNK walk VL library against protein A.

FIG. 6A is a visualization of superimposed renderings of molecules present in the crystal structure of the antigen-free G6 Fab (PDB 2FJF) showing the different Fab elbow angles exhibited by the molecules. Molecules exhibiting a small elbow angle (see, e.g., Example 3) are colored in green, and molecules with a large elbow angle are colored in red.

FIGS. 6B-6C are renderings showing a detailed view of the VL-VH interface and the side chain conformation of LC-83F and LC-106I in molecules with a small Fab elbow angle (FIG. 6B, green) and with molecules with a large Fab elbow angle (FIG. 6C, red), respectively. The β-strand E, the helix α-1, and the loop connecting both elements are removed for clarity.

FIG. 8B is a graph showing the results of molecular dynamics simulations for the indicated molecules. The elbow angle is plotted as a function of time.

FIG. 10B is a graph showing the most common mutations at position LC-83 for IGKV1.39 sequences from the Public dataset described in FIG. 10A and Example 8 (Sanger) or the SMRT dataset (PacBio). IGKV1.39 carries a phenylalanine at position LC-83. Points are colored by the respective amino acid size. Large amino acids are colored in yellow and small amino acids are colored in dark red.

FIG. 10C is a graph showing the most common mutations at position LC-106 for all IGKJ sequences found in the Public dataset (Sanger) or in the SMRT dataset (PacBio). Points are colored by the respective amino acid size. Large amino acids are colored in yellow and small amino acids are colored in dark red.

FIG. 12 is a table showing fragmentation analysis by capillary electrophoresis-sodium dodecyl sulfate (CE-SDS) for the indicated antibody clones. Fragmentation is represented by the percentage of low molecular weight entities (% LMW) after 4 weeks, 12 weeks, and 24 weeks at 37° C. in PBS. The fragmentation is consistently reduced in all N94A variants compared to wild-type G6.31. High molecular weight entities (% HMW) indicate impurities or aggregates. The main peak size in this assay does not correlate directly with the extent of fragmentation, but depends on fragment size and extent of dye labeling. The anti-VEGF Fab ranibizumab served as a control.

DETAILED DESCRIPTION OF THE INVENTION

I. Definitions

Figure 1A:
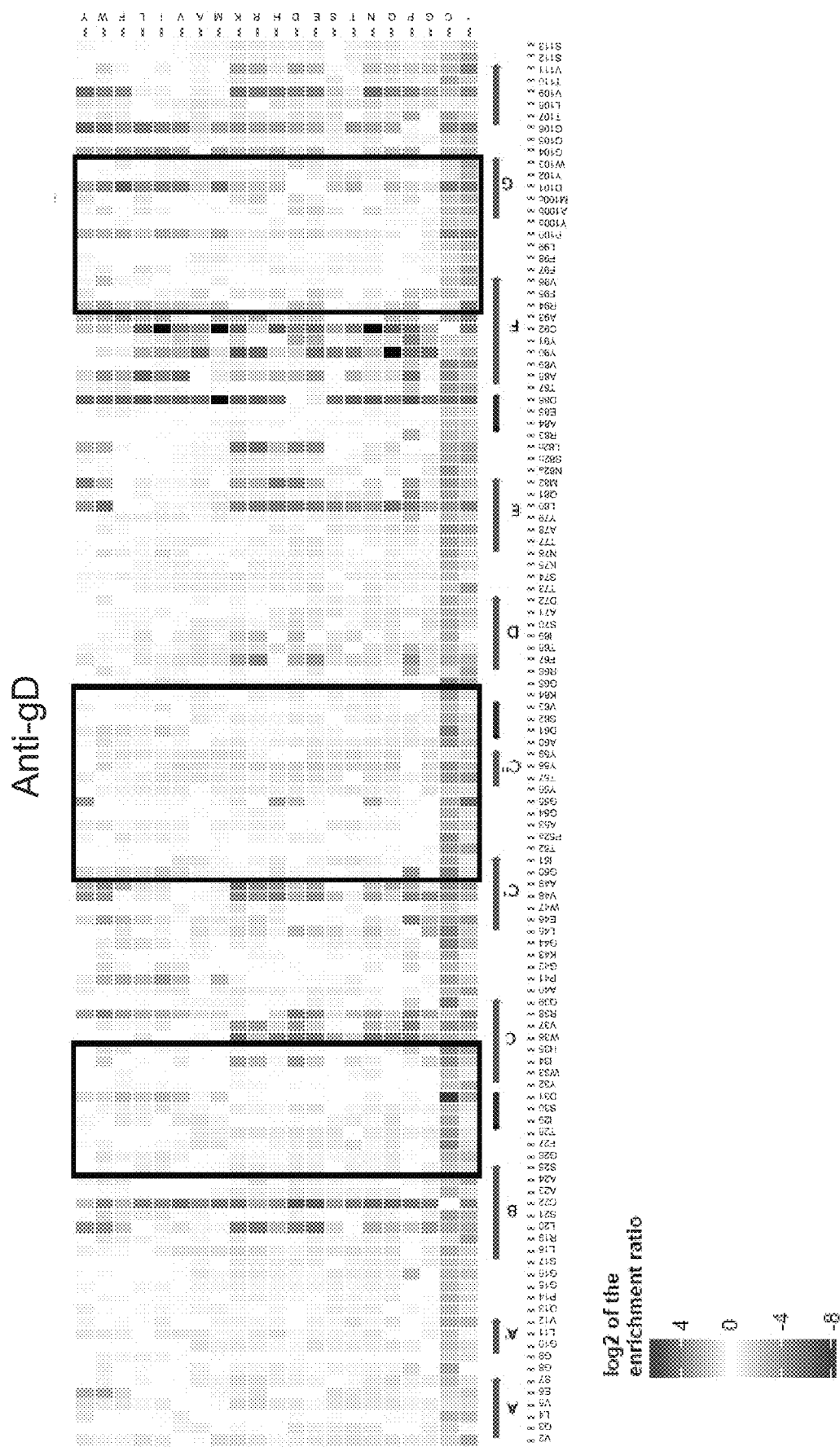
FIGS. 1A-1F are heatmaps showing the log 2 of the enrichment ratio (also referred to as log 2 enrichment ratio) for all mutations in the pannings obtained from the NNK walk VH (FIGS. 1A-1C) and VL (FIGS. 1D-1F) libraries against anti-gD tag antibody (anti-gD), protein L, or protein A. The amino acid sequence of wild-type G6.31 VH (FIGS. 1A-1C) or VL (FIGS. 1D-1F), beginning from position 2, is shown below each heat map.
Figure 1B:
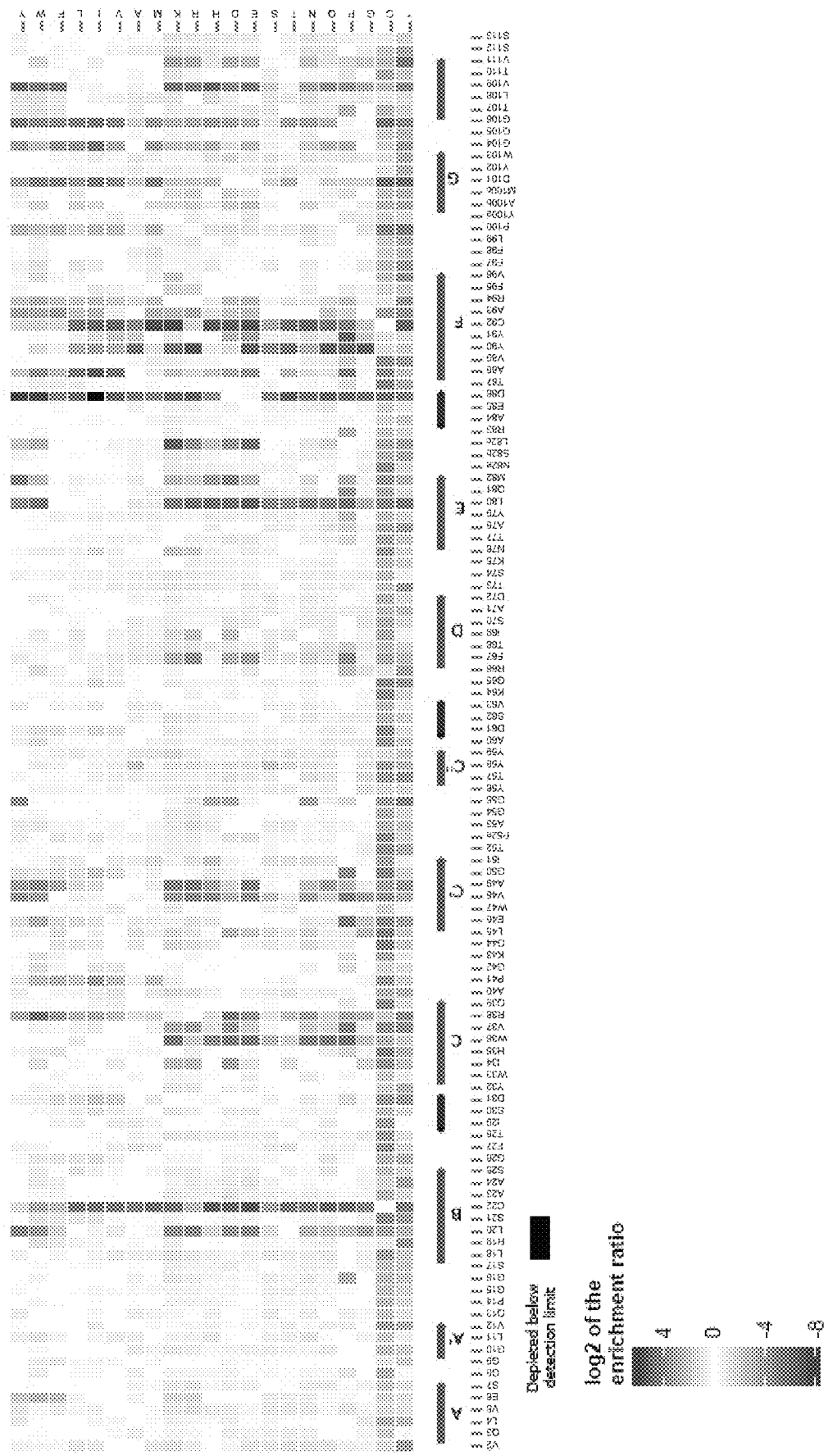
Figure 1C:
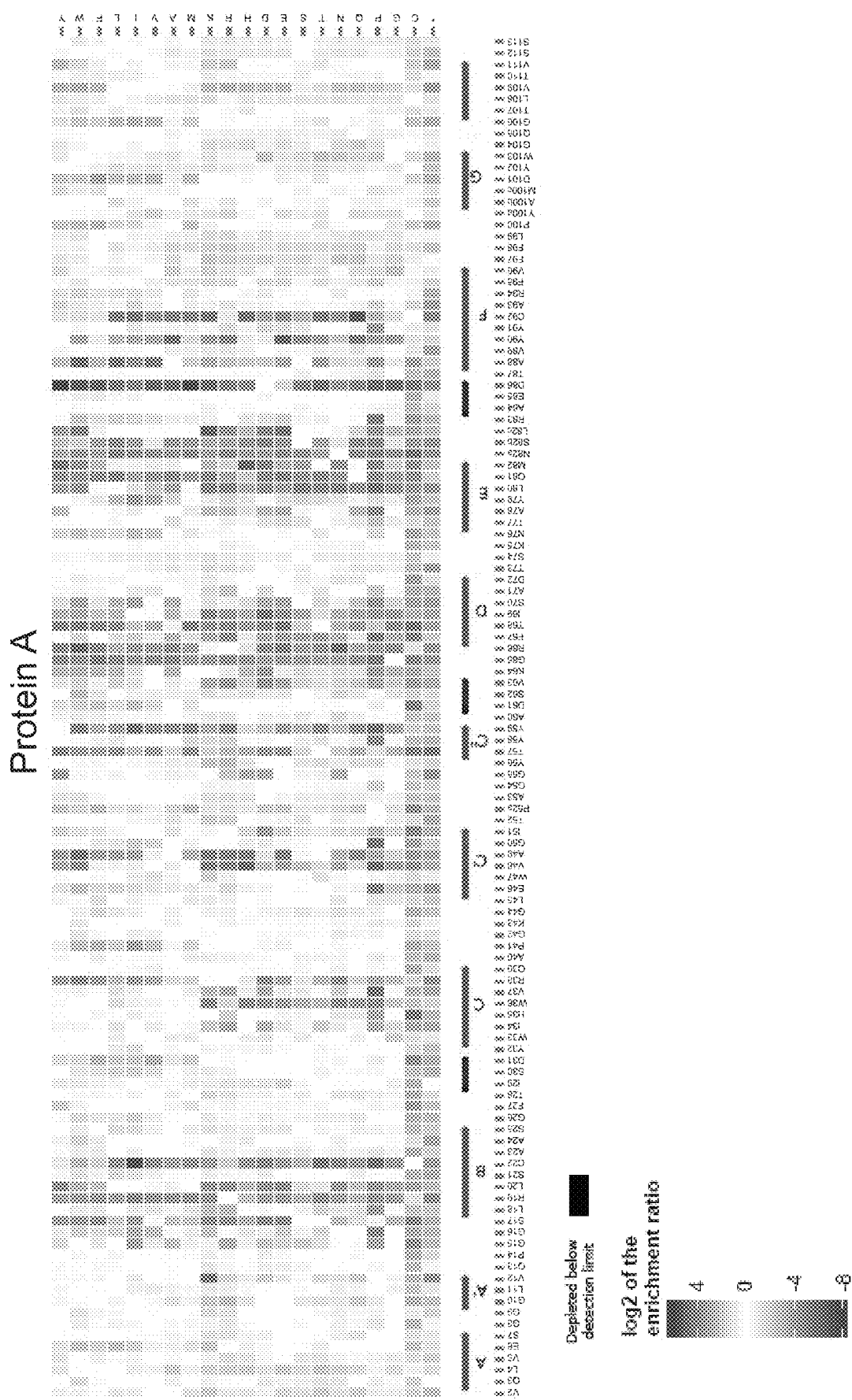
Figure 1D:
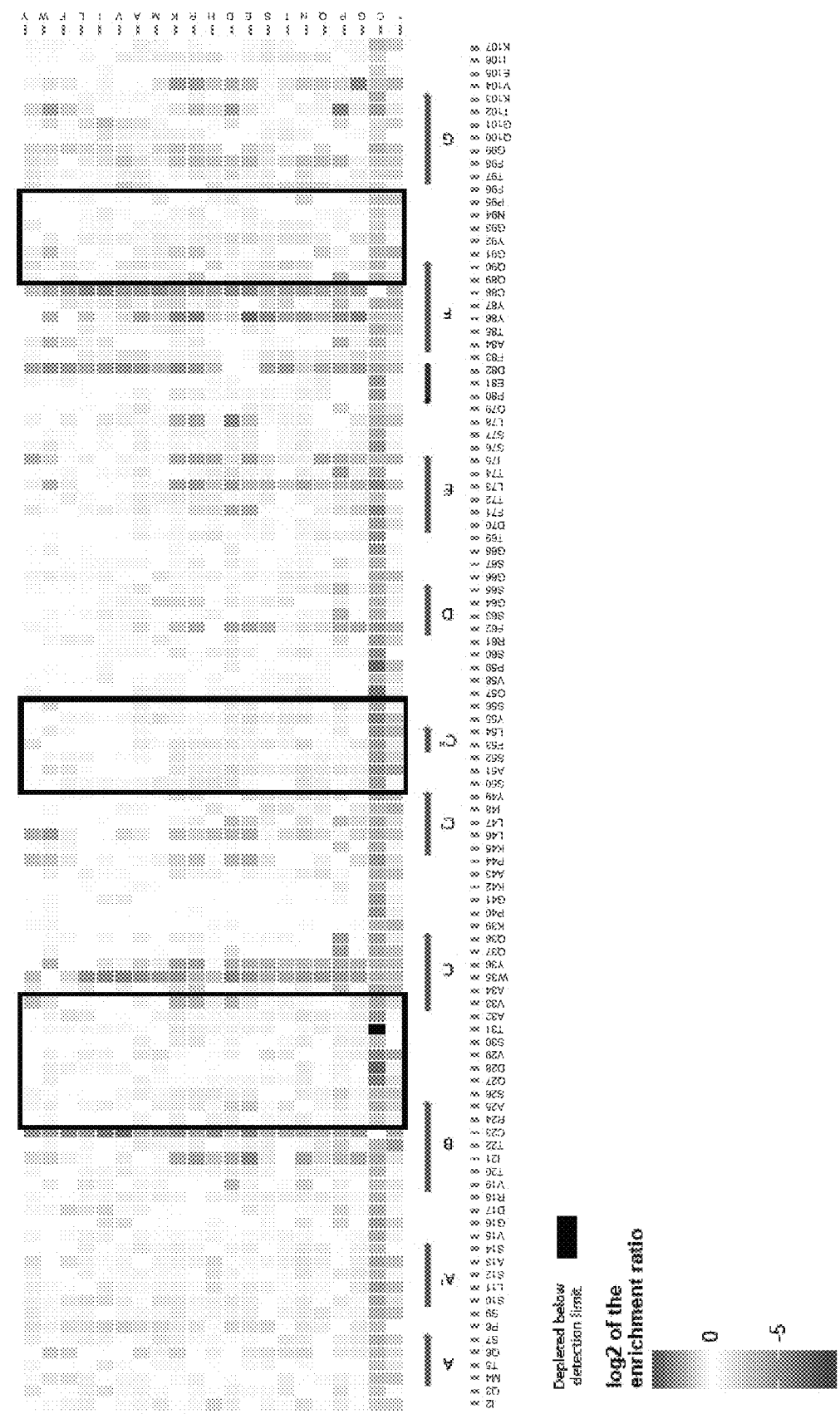
Figure 1E:
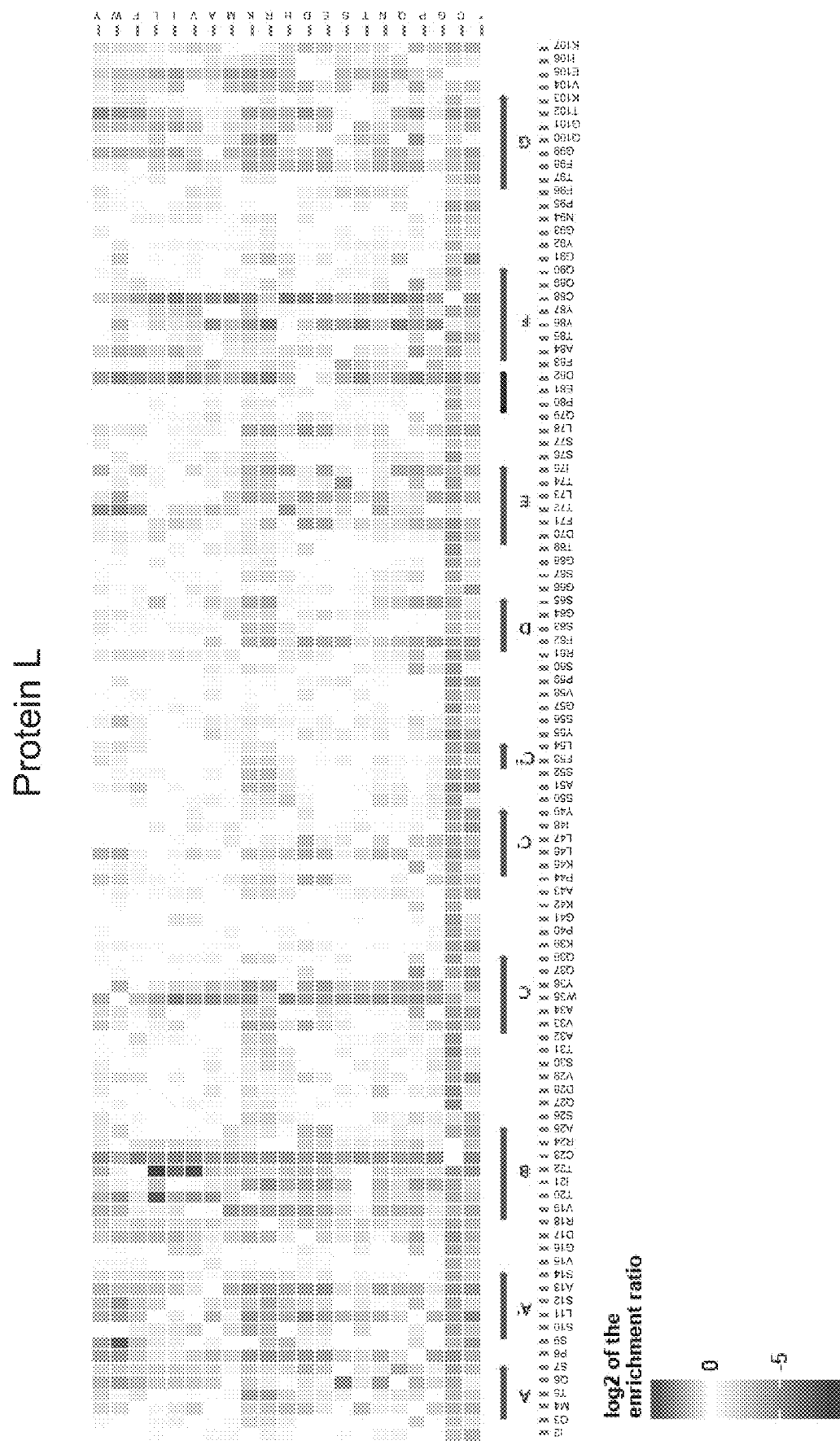
Figure 1F:

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs) and/or framework regions (FRs), compared to a parent antibody which does not possess such alterations, such alterations resulting in an improvement in the affinity of the antibody for antigen.

The term "vascular endothelial growth factor" or "VEGF" refers to vascular endothelial growth factor protein A, as exemplified by SEQ ID NO: 47 (see also Swiss Prot Accession Number P15692, Gene ID (NCBI): 7422). The term "VEGF" encompasses the protein having the amino acid sequence of SEQ ID NO: 47 as well as homologues and isoforms thereof. The term "VEGF" also encompasses the known isoforms, e.g., splice isoforms, of VEGF, e.g., $VEGF_{111}$, $VEGF_{121}$, $VEGF_{145}$, $VEGF_{165}$, $VEGF_{189}$, and $VEGF_{206}$, together with the naturally-occurring allelic and processed forms thereof, including the 110-amino acid human vascular endothelial cell growth factor generated by plasmin cleavage of $VEGF_{165}$ as described in Ferrara *Mol. Biol. Cell.* 21:687 (2010), Leung et al., *Science*, 246:1306 (1989), and Houck et al., *Mol. Endocrin.*, 5:1806 (1991). The term "VEGF" also refers to VEGFs from non-human species such as mouse, rat or primate. Sometimes the VEGF from a specific species are indicated by terms such as hVEGF for human VEGF, mVEGF for murine VEGF, and the like. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "$VEGF_{109}$," "VEGF (8-109)," "VEGF (1-109)" or "$VEGF_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. The term "VEGF variant" as used herein refers to a VEGF polypeptide which includes one or more amino acid mutations in the native VEGF sequence. Optionally, the one or more amino acid mutations include amino acid substitution(s). For purposes of shorthand designation of VEGF variants described herein, it is noted that numbers refer to the amino acid residue position along the amino acid sequence of the putative native VEGF (provided in Leung et al., supra and Houck et al., supra). Unless specified otherwise, the term "VEGF" as used herein indicates VEGF-A.

The terms "anti-VEGF antibody," an "antibody that binds to VEGF," and "antibody that specifically binds VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, for example, by a radioimmunoassay (RIA). In certain embodiments, an antibody that binds to VEGF has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$ M to $10^{-13}$ M). In certain embodiments, an anti-VEGF antibody binds to an epitope of VEGF that is conserved among VEGF from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab-C, Fab'-SH, F(ab')$_2$; diabodies; linear antibodies; single-chain antibody molecules (e.g., scFv); and multispecific antibodies formed from antibody fragments. In some instances, examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire light (L) chain along with the variable region domain of the heavy (H) chain (VH), and the first constant domain of one heavy chain (CH1). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab-C molecules are Fab molecules that are expressed such that the sequence is truncated at the first hinge cysteine, resulting in a Fab with a free cysteine directly upon expression (see, e.g., Shatz et al. *Mol. Pharmaceutics* 2016; PubMed identifier (PMID) 27244474). For example, a Fab-C molecule may have a free cysteine at position Cys227 of the heavy chain. In other instances, a Fab-C molecule may have a free cysteine at position Cys229 of the heavy chain. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD (1991).

"Fv" consists of a dimer of one heavy- and one light-chain variable region domain in tight, noncovalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although often at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

A "blocking" antibody or an "antagonist" antibody is one which inhibits or reduces biological activity of the antigen it binds. Certain blocking antibodies or antagonist antibodies substantially or completely inhibit the biological activity of the antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and β, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down-regulation of cell surface receptors (e.g. B cell receptor); and B cell activation.

"Framework" or "framework region" or "FR" refers to variable domain residues other than hypervariable region (HVR) residues. The FR of a variable domain generally consists of four FR domains: FR1, FR2, FR3, and FR4.

The terms "full-length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, FR residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "HVR" when used herein refers to the amino acid residues of an antibody which are responsible for antigen-binding. The hypervariable region generally comprises amino acid residues from, for example, around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al., *Sequences of Proteins of Immunological Interest*, 5th Ed. Public Health Service, National Institutes of Health, Bethesda, MD (1991)) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia and Lesk, *J. Mol. Biol.* 196:901-917 (1987). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, MD (1991)). Accordingly, the HVR and FR sequences generally appear in the following sequence in VH (or VL): FR1-H1(L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human $IgG_1$ EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For a review of methods for assessment of antibody purity, see, for example, Flatman et al., *J. Chromatogr. B* 848:79-87 (2007). In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "multispecific antibody" is used in the broadest sense and specifically covers an antibody comprising a heavy chain variable domain (VH) and a light chain variable domain (VL), where the VH-VL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fab'. Fab-C. Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an $IgG_1$ form binds to each epitope with an affinity of 5 µM to 0.001 pM, 3 µM to 0.001 pM, 1 µM to 0.001 pM, 0.5 µM to 0.001 pM or 0.1 µM to 0.001 pM. "Monospecific" refers to the ability to bind only one epitope.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

With regard to the binding of a antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a Kd in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and Kd values are inversely related. A high affinity for an antigen is measured by a low Kd value. In one embodiment, the term "specific binding" refers to binding where a molecule binds to a particular polypeptide or epitope on a particular polypeptide without substantially binding to any other polypeptide or polypeptide epitope.

A "nucleic acid encoding an anti-VEGF antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

As used herein, "administering" is meant a method of giving a dosage of a compound (e.g., an anti-VEGF antibody of the invention, an antibody conjugate of the invention, a fusion protein of the invention, a polymeric formulation of the invention, or a nucleic acid encoding an anti-VEGF antibody of the invention) or a composition (e.g., a pharmaceutical composition, e.g., a pharmaceutical composition including an anti-VEGF antibody of the invention, an antibody conjugate of the invention, a fusion protein of the invention, or a polymeric formulation of the invention) to a subject. The compositions utilized in the methods described herein can be administered, for example, intravitreally (e.g., by intravitreal injection), by eye drop, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

"Angiogenesis" refers to the process through which new blood vessels form from pre-existing blood vessels. Angiogenesis is distinct from vasculogenesis, which is the de novo formation of endothelial cells from mesoderm cell precursors. Disorders associated with pathological angiogenesis can be treated by compositions and methods of the invention. These disorders include both non-neoplastic disorders and cell proliferative disorders. Cell proliferative disorders include but are not limited those described below. Non-neoplastic disorders include but are not limited to ocular conditions (non-limiting ocular conditions include, for example, retinopathy including proliferative diabetic retinopathy, choroidal neovascularization (CNV), age-related macular degeneration (AMD), diabetic and other ischemia-related retinopathies, diabetic macular edema (DME), pathologic myopia, von Hippel-Lindau disease, histoplasmosis of the eye, retinal vein occlusion (including central (CRVO) and branched (BRVO) forms), corneal neovascularization, retinal neovascularization, retinopathy of prematurity (ROP), familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, and hypertensive retinopathy), autoimmune diseases (e.g., rheumatoid arthritis (RA), psoriasis, ankylosing spondylitis, and inflammatory bowel disease (e.g., Crohn's disease and ulcerative colitis)), undesired or aberrant hypertrophy, arthritis, psoriatic arthritis, psoriatic plaques, sarcoidosis, atherosclerosis, atherosclerotic plaques, arterial arteriosclerosis, vascular restenosis, arteriovenous malformations (AVM), meningioma, hemangioma, angiofibroma, thyroid hyperplasias (including Grave's disease), corneal and other tissue transplantation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), chronic asthma, uterine fibroids, premature labor, chronic inflammation such as IBD (Crohn's disease and ulcerative colitis), inflammatory renal diseases (including glomerulonephritis, especially mesangioproliferative glomerulonephritis, haemolytic uremic syndrome, diabetic nephropathy and hypertensive nephrosclerosis), diseases occurring after transplants, renal allograft rejection, inflammatory diseases, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion. Additional ocular disorders are described below.

Other disorders which may be associated with pathological angiogenesis include nonunion fractures (fractures that will not heal), pyogenic granuloma, trachoma, hemophilic joints, vascular adhesions and hypertrophic scars, graft rejection, fibrovascular tissue, acne rosacea, acquired immune deficiency syndrome, artery occlusion, atopic keratitis, bacterial ulcers, Bechet's disease, carotid obstructive disease, chronic inflammation, chronic retinal detachment, chronic uveitis, chronic vitritis, contact lens overwear, corneal graft rejection, corneal graft neovascularization, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, optic pits, osteoarthritis, Paget's disease, pars planitis, pemphigoid, phylectenulosis, polyarteritis, post-laser complications, protozoan infections, pseudoxanthoma elasticum, pterygium keratitis sicca, radial keratotomy, retrolental fibroplasias, sarcoid, scleritis, sickle cell anemia, Sjogren's syndrome, Stargarts disease, Steven's Johnson disease, superior limbic keratitis, syphilis, systemic lupus, Terrien's marginal degeneration, toxoplasmosis, trauma, vein occlusion, Vitamin A deficiency and Wegeners sarcoidosis, undesired angiogenesis associated with diabetes, parasitic diseases, abnormal wound healing, hypertrophy following surgery, injury or trauma, inhibition of hair growth, inhibition of ovulation and corpus luteum formation, inhibition of implantation and inhibition of embryo development in the uterus.

The term "ocular disorder," as used herein, includes any ocular disorder (also referred to interchangeably herein as "ocular condition") associated with pathogical angiogenesis. An ocular disorder may be characterized by altered or unregulated proliferation and/or invasion of new blood vessels into the structures of ocular tissues such as the retina or cornea. Non-limiting ocular disorders include, for example, AMD (e.g., wet AMD, dry AMD, intermediate AMD, advanced AMD, and geographic atrophy (GA)), macular degeneration, macular edema, DME (e.g., focal, non-center DME and diffuse, center-involved DME), retinopathy, diabetic retinopathy (DR) (e.g., proliferative DR (PDR), non-proliferative DR (NPDR), and high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis (also known as Leber's congenital amaurosis or LCA), uveitis (including infectious and non-infectious uveitis), choroiditis (e.g., multifocal choroiditis), ocular histoplasmosis, blepharitis, dry eye, traumatic eye injury, Sjögren's disease, and other ophthalmic diseases wherein the disease or disorder is associated with ocular neovascularization, vascular leakage, and/or retinal edema. Additional exemplary ocular disorders include diseases associated with rubeosis (neovascularization of the angle) and diseases caused by the abnormal proliferation of fibrovascular or fibrous tissue, including all forms of proliferative vitreoretinopathy.

Exemplary diseases associated with corneal neovascularization include, but are not limited to, epidemic keratoconjunctivitis, vitamin A deficiency, contact lens overwear, atopic keratitis, superior limbic keratitis, terygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegener's sarcoidosis, scleritis, Stevens-Johnson syndrome, periphigoid radial keratotomy, and corneal graph rejection.

Exemplary diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retinitis pigmentosa, retina edema (including macular edema), Eales disease, Behcet's disease, infections causing retinitis or choroiditis (e.g., multifocal choroidits), presumed ocular histoplasmosis, Best's disease (vitelliform macular degeneration), myopia, optic pits, Stargart's disease, pars planitis, retinal detachment (e.g., chronic retinal detachment), hyperviscosity syndromes, toxoplasmosis, trauma, and post-laser complications.

"Disorders associated with undesirable vascular permeability," as used herein, include, for example, edema associated with brain tumors, ascites associated with malignancies, Meigs' syndrome, lung inflammation, nephrotic syndrome, pericardial effusion, pleural effusion, permeability associated with cardiovascular diseases such as the condition following myocardial infarctions and strokes and the like.

It is to be understood that the classifications described above are not mutually exclusive, and a disorder may fall under multiple categories.

The terms "cell proliferative disorder" and "proliferative disorder" refer to disorders that are associated with some degree of abnormal cell proliferation. In one embodiment, the cell proliferative disorder is cancer.

The terms "cancer", "cancerous", "cell proliferative disorder", "proliferative disorder" and "tumor" are not mutually exclusive as referred to herein.

"Tumor", as used herein, refers to all neoplastic cell growth and proliferation, whether malignant or benign, and all pre-cancerous and cancerous cells and tissues.

An "angiogenic factor or agent" is a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, Del-1, fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor, especially PDGF-BB or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, for example, Klagsbrun and D'Amore, *Annu. Rev. Physiol.*, 53:217-39 (1991); Streit and Detmar, *Oncogene*, 22:3172-3179 (2003); Ferrara & Alitalo, *Nature Medicine* 5(12):1359-1364 (1999); Tonini et al., *Oncogene*, 22:6549-6556 (2003) (e.g., Table 1 listing known angiogenic factors); and Sato, *Int. J. Clin. Oncol.*, 8:200-206 (2003).

An "anti-angiogenesis agent" or "angiogenesis inhibitor" refers to a small molecular weight substance, an polynucleotide, an polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined above, e.g., VEGF antagonists (e.g., antibodies to VEGF-A or to the VEGF-A receptor (e.g., KDR receptor or Flt-1 receptor)), PDGF antagonists (e.g., anti-PDGFR inhibitors such as GLEEVEC™ (Imatinib Mesylate)). Anti-angiogenesis agents also include native angiogenesis inhibitors, e.g., angiostatin, endostatin, etc. See, for example, Klagsbrun and D'Amore, *Annu. Rev. Physiol.*, 53:217-39 (1991); Streit and Detmar, *Oncogene*, 22:3172-3179 (2003) (e.g., Table 3 listing anti-angiogenic therapy in malignant melanoma); Ferrara & Alitalo, *Nature Medicine* 5(12):1359-1364 (1999); Tonini et al., *Oncogene*, 22:6549-6556 (2003) (e.g., Table 2 listing known antiangiogenic factors); and, Sato *Int. J. Clin. Oncol.*, 8:200-206 (2003) (e.g., Table 1 lists anti-angiogenic agents used in clinical trials).

The term "VEGF antagonist," as used herein, refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF-mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and $VEGF_{121}$-gelonin (Peregrine). VEGF antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF-mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or $VEGF_{165}$.

As used herein VEGF antagonists can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGF antibodies (e.g., bevacizumab, sevacizumab, and ranibizumab), and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib). Additional VEGF antagonists are described below.

An "effective amount" of an agent, e.g., a pharmaceutical formulation, refers to an amount effective, at dosages and for periods of time necessary, to achieve the desired therapeutic or prophylactic result.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. A "subject" may be a "patient."

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. "Mammal" for purposes of treatment refers to any animal classified as a mammal, including humans, domestic and farm animals, nonhuman primates, and zoo, sports, or pet animals, such as dogs, horses, cats, cows, etc.

A "disorder" is any condition that would benefit from treatment with the antibody. For example, mammals who suffer from or need prophylaxis against abnormal angiogenesis (excessive, inappropriate or uncontrolled angiogenesis) or vascular permeability. This includes chronic and acute disorders or diseases including those pathological conditions which predispose the mammal to the disorder in question. Non-limiting examples of disorders to be treated herein include disorders associated with pathological angiogenesis (e.g., ocular disorders and cell proliferative disorders) and disorders associated with undesirable vascular permeability.

The term "anti-neoplastic composition" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA™), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, and the like. Combinations thereof are also included in the invention.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{88}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "chemotherapeutic agent" is a chemical compound useful in the treatment of cancer. Examples of chemotherapeutic agents include chemical compounds useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate;

an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Illinois), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (TARCEVA™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids, or derivatives of any of the above.

The term "prodrug" as used herein refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, 3-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "package insert" is used to refer to instructions customarily included in commercial packages of therapeutic products, that contain information about the indications, usage, dosage, administration, combination therapy, contraindications and/or warnings concerning the use of such therapeutic products.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "pharmaceutical formulation" refers to a preparation which is in such form as to permit the biological activity of an active ingredient (e.g., an anti-VEGF antibody, an antibody conjugate, a fusion protein, or a polymeric formulation) contained therein to be effective, and which contains no additional components which are unacceptably toxic to a subject to which the formulation would be administered.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention or other compositions that include an antibody of the invention (e.g., an antibody conjugate, a fusion protein, or a polymeric formulation) are used to delay development of a disease or to slow the progression of a disease.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "library" refers to a plurality of antibody or antibody fragment sequences (e.g., anti-VEGF antibodies of the invention), or the nucleic acids that encode these sequences, the sequences being different in the combination of variant amino acids that are introduced into these sequences according to the methods of the invention.

A "mutation" is a deletion, insertion, or substitution of a nucleotide(s) relative to a reference nucleotide sequence, such as a wild-type sequence.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, eg. NNK, NNS, XYZ, DVK and the like. Synthesis of oligonucleotides with selected nucleotide "degeneracy" at certain positions is well known in that art, for example the TRIM approach (Knappek et al., *J. Mol. Biol.* 296:57-86 (1999)); Garrard et al., *Gene* 128:103 (1993)). Such sets of oligonucleotides having certain codon sets can be synthesized using commercial nucleic acid synthesizers (available from, for example, Applied Biosystems, Foster City, CA), or can be obtained commercially (for example, from Life Technologies, Rockville, MD). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

"Phage display" is a technique by which variant polypeptides are displayed as fusion proteins to at least a portion of coat protein on the surface of phage, for example, filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.,* 3:355-362 (1992), and references cited therein. In a monovalent phage display, a protein or peptide library is fused to a gene III or a portion thereof, and expressed at low levels in the presence of wild-type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology,* 3:205-0216 (1991).

A "phagemid" is a plasmid vector having a bacterial origin of replication, for example, Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

A "variant" or "mutant" of a starting or reference polypeptide (e.g., a reference antibody or its variable domain(s)/HVR(s)), is a polypeptide that (1) has an amino acid sequence different from that of the starting or reference polypeptide and (2) was derived from the starting or reference polypeptide through either natural or artificial (man-made) mutagenesis. Such variants include, for example, deletions from, and/or insertions into and/or substitutions of, residues within the amino acid sequence of the polypeptide of interest, referred to herein as "amino acid residue alterations." Thus, a variant HVR refers to a HVR comprising a variant sequence with respect to a starting or reference polypeptide sequence (such as that of a source antibody or antigen binding fragment). An amino acid residue alteration, in this context, refers to an amino acid different from the amino acid at the corresponding position in a starting or reference polypeptide sequence (such as that of a reference antibody or fragment thereof). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type (WT)" or "reference" sequence or the sequence of a "wild-type" or "reference" protein/polypeptide, such as an HVR or a variable domain of a reference antibody, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man-induced means. The products of such processes are "variant" or "mutant" forms of the original "wild-type" protein or gene.

A "reference antibody," as used herein, refers to an antibody or fragment thereof whose antigen-binding sequence serves as the template sequence upon which diversification according to the criteria described herein is performed. An antigen-binding sequence generally includes an antibody variable region, preferably at least one HVR, preferably including framework regions.

By "massively parallel sequencing" or "massive parallel sequencing," also known in the art as "next-generation sequencing," or "second generation sequencing," is meant any high-throughput nucleic acid sequencing approach. These approaches typically involve parallel sequencing of a large number (e.g., thousands, millions, or billions) of spatially separated, clonally amplified DNA templates or single DNA molecules. See, for example, Metzker, *Nature Reviews Genetics* 11: 31-36, 2010.

"Enriched," as used herein, means that an entity (e.g., an amino acid residue alteration) is present at a higher frequency in a sorted library as compared to a corresponding reference library (e.g., an unsorted library, or a library that has been sorted for a different or non-relevant antigen). In contrast, "depleted" means that an entity (for example, an amino acid residue alteration) is present at a lower frequency in a sorted library as compared to a corresponding reference library (e.g., an unsorted library, or a library that has been sorted for a different or non-relevant antigen). The term "neutral," when used in reference to methods of identifying amino acid residue variants, means that an entity is neither enriched nor depleted, in other words, it is present at approximately the same frequency in a sorted library as compared to a corresponding reference library (e.g., an unsorted library, or a library that has been sorted for a different or non-relevant antigen).

By "isoelectric point (pI)" is meant the pH at which a molecule (e.g., a protein, such as an antibody) carries no net electrical charge, also referred to in the art as "pH(I)" or "IEP."

As used herein, an "antibody conjugate" is an antibody covalently attached to one or more polymers. Any suitable polymer may be conjugated to an antibody, for example, a hydrophilic polymer (e.g., hyaluronic acid (HA) or polyethylene glycol (PEG)) or a hydrophobic polymer (e.g., poly (lactic-co-glycolic acid) (PLGA)).

As used herein, the term "polymer" means a molecule that includes repeating structural units (i.e., monomers) connected by chemical bonds in a linear, circular, branched, crosslinked, or dendrimeric manner, or a combination thereof. A polymer may be synthetic or naturally occurring, or a combination thereof. It is to be understood that the term "polymer" encompasses copolymers, which are polymers that include two or more different monomers. A polymer may also be a homopolymer, which is a polymer that includes only a single type of monomer.

The terms "hyaluronic acid," "hyaluranon," and "HA," which are used interchangeably herein, refer to a polymeric glycosaminoglycan (GAG), which contains repeating disaccharide units of N-acetyl glucosamine and glucuronic acid. HA is an anionic, nonsulfated GAG, which can be found, for example, in extracellular matrix (e.g., in the vitreous of the eye), connective tissue, epithelial, and neural tissue.

The term "polyethylene glycol" or "PEG" as used herein, refers to a polyether compound that is also known as polyethylene oxide (PEO) or polyoxyethylene (POE), depending on its molecular weight. PEG may have a structure of $H-(O-CH_2-CH_2)_n-OH$, wherein n is any suitable integer. The PEG may be a branched PEG, a star PEG, or a comb PEG. The PEG may be, for example, a PEG tetramer, a PEG hexamer, or a PEG octamer.

As used herein, the term "fusion protein" refers to a protein in which a first peptide, protein, or polypeptide, e.g., an antibody (e.g., an anti-VEGF antibody (e.g., any anti-VEGF antibody described herein, e.g., G6.31 AARR)) is linked, directly or indirectly, to a second peptide, protein, or polypeptide, e.g., an ocular binding domain (e.g., an HA binding domain). In one example, the first peptide, protein, or polypeptide (e.g., an antibody) may be linked to the second peptide, protein, or polypeptide (e.g., an ocular binding domain (e.g., an HA binding domain)) by a linker. In the context of fusion proteins, the terms "links" and "linked," and grammatical variations thereof, are used interchangeably with the term "covalently attached," and refer to a direct or indirect covalent bonding (e.g., a peptide bond) between two moieties of the fusion protein. In general, the fusion proteins of the invention are antibody fusion proteins. The antibody may be an antibody fragment, for example, an Fab, an Fab', or an Fab-C. In some instances, the antibody fragment is an Fab.

The term "ocular binding domain" refers to a peptide, protein, polypeptide or fragment thereof that binds to a biological substance found in the eye (e.g., the cornea, vitreous, retina, retina pigment epithelium, or choroid). As one example, in some instances, the biological substance found in the eye is an extracellular matrix component, for example, a carbohydrate (e.g., a charged carbohydrate (e.g., a glycosaminoglycan)), a glycoprotein (e.g., fibrillin and opticin), or a protein (e.g., a collagen (e.g., collagen types I-XXVII, particularly collagen II, collagen IX, collagen V, collagen VI, collagen XI, and heterotypic collagen fibrils thereof), or other extracellular matrix components described, for example, in Le Goff et al., Eye 22:1214-1222, 2008. In some instances, the extracellular matrix component is a glycosaminoglycan, for example, HA or a proteoglycan (e.g., chondroitin sulfate or heparin sulfate). In one example, the ocular binding domain is a hyaluronic acid binding domain.

As used herein, the term "hyaluronic acid binding domain" or "HA binding domain" refers to a peptide, protein, polypeptide, or fragment thereof that binds HA. An HA binding domain may be derived from an HA binding protein (also referred to in the art as a "hyaladherin"), including, for example, tumor necrosis factor-stimulated gene 6 (TSG6), lymphatic vessel endothelial hyaluronan receptor 1 (LYVE-1), hyaluronan and proteoglycan link protein (HAPLN) 1, HAPLN2, HAPLN3, HAPLN4, aggrecan, brevican, neurocan, phosphacan, versican, CAB61358, KIA0527, stabilin-1, stabilin-2, RHAMM, bacterial HA synthase, and collagen VI. Other HA binding proteins are known in the art. Exemplary HA binding domains include link modules, G1 domains, and lysine-rich oligopeptides.

A "link module" (also referred to in the art as a "link domain") is a structural domain of approximately 100 amino acids (see, e.g., Yang et al. EMBO J., 13(2): 286-296; Mahoney et al., J. Biol. Chem. 276(25): 22764-22771, 2001; and Blundell et al. J. Biol. Chem. 278(49): 49261-49270, 2003) that binds HA. Exemplary, non-limiting link modules include those from TSG6, CD44, LYVE-1, HAPLN1, HAPLN2, HAPLN3, HAPLN4, aggrecan, brevican, neurocan, phosphacan, versican, CAB61358, KIA0527, stabilin-1, and stabilin-2 link modules, or variants thereof. As one example, the link module of the HA binding protein TSG6 may include amino acid residues 36-128 of human TSG6 (UniProt Accession No. P98066). A variant link module binds HA and may have, for example, at least 80% amino acid sequence identity (e.g., 80%, 85%, 90%, 91%, 92%, 93%, 94%, 95%, 96%, 97%, 98%, 99%, or higher sequence identity) to a wild-type or reference link module, and may include sequence variations such as insertions, deletions, and substitutions (e.g., conservative amino acid substitutions) relative to the wild-type or reference link module amino acid sequence.

In the context of fusion proteins, a "linker" may be a peptide or polypeptide that links (e.g., covalently links) a first moiety (e.g., an antibody (e.g., an anti-VEGF antibody (e.g., any anti-VEGF antibody described herein, e.g., G6.31 AARR))) to a second moiety (e.g., an ocular binding domain (e.g., an HA binding domain)). A linker may include an amino acid sequence of any suitable length, for example, 1, 2, 3, 4, 5, 6, 7, 8, 9, 10, 11, 12, 13, 14, 15, 16, 17, 18, 19, 20, or more amino acid residues. In some instances, a linker includes about 3, about 4, about 5, about 6, about 7, or about 8 residues. In some instances, a linker includes the amino acid sequence of GGGGS (SEQ ID NO: 61).

A "hydrogel," as used herein, refers to a hydrophilic or amphiphilic polymeric network composed of homopolymers or copolymers, which is insoluble due to the presence of covalent chemical crosslinks. The crosslinks may provide the network structure and physical integrity. Hydrogels may exhibit a thermodynamic compatibility with water, which allows them to swell in aqueous media.

As used herein, the term "reversible prodrug linker" means a moiety that is attached on one end to a biologically active moiety (e.g., a drug, such as an anti-VEGF antibody), through a reversible linkage, and is attached on another end through a permanent bond to a carrier (e.g., a hydrogel), thereby linking the biologically active moiety to the carrier. Such reversible prodrug linkers are non-enzymatically hydrolytically degradable, i.e., cleavable, under physiological conditions (e.g., aqueous buffer at pH 7.4, 37° C.) with half-lives ranging from, for example, one hour to twelve months. Reversible linkages include, for example, aconityls, acetals, amides, carboxylic anhydrides, esters, imines, hydrazones, maleamic acid amides, ortho esters, phosphamides, phosphoesters, phosphosilyl esters, silyl esters, sulfonic esters, aromatic carbamates, and combinations thereof. In contrast, permanent linkages are non-enzymatically hydrolytically degradable under physiological conditions (aqueous buffer at pH 7.4, 37° C.) with half-lives of more than twelve months. Exemplary reversible prodrug linkers are described, for example, in International Patent Application Publication No. WO 2014/056923, which is incorporated herein by reference in its entirety.

The term "clearance," as used herein, refers to the volume of a substance (e.g., an anti-VEGF antibody, an antibody conjugate, a fusion protein (e.g., a Fab fusion protein), or a polymeric formulation) cleared from a compartment (e.g., the eye (e.g., the vitreous)) per unit time.

The term "half-life" refers to the time required for the concentration of a substance (e.g., an anti-VEGF antibody, an antibody conjugate, a fusion protein (e.g., a Fab fusion protein), or a polymeric formulation) to decrease by one-half, in vivo (e.g., in the eye (e.g., the vitreous)) or in vitro.

II. Compositions and Methods

The invention provides novel antibodies that bind to VEGF, and methods of making and using the same, for example, for diagnostic and therapeutic uses. The invention also provides compositions that include anti-VEGF antibodies (including any anti-VEGF antibody described herein), including antibody conjugates, fusion proteins, and polymeric formulations, as well as methods of making and using the same, for example, for diagnostic and therapeutic uses. The invention also provides methods of identifying antibody variants with improved properties, for example, enhanced binding affinity, stability, and/or expression.

A. Exemplary Anti-VEGF Antibodies

In one aspect, the invention is based, in part, on antibodies that specifically bind to VEGF. Antibodies of the invention are useful, for example, for reducing angiogenesis and for treating or delaying the progression of a disorder associated with pathological angiogenesis (e.g., ocular disorders or cell proliferative disorders). Antibodies of the invention are also useful, for example, for inhibiting vascular permeability and treating disorders associated with undesirable vascular permeability.

In some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of $GX_1TPX_2GGX_3X_4X_5YX_6DSVX_7X_8$ (SEQ ID NO: 2), wherein $X_1$ is Ile or His, $X_2$ is Ala or Arg, $X_3$ is Tyr or Lys, $X_4$ is Thr or Glu, $X_5$ is Arg, Tyr, Gln, or Glu, $X_6$ is Ala or Glu, $X_7$ is Lys or Glu, and $X_8$ is Gly or Glu; (c) an HVR-H3 comprising the amino acid sequence of FVFFLPYAMDY (SEQ ID NO: 3); (d) an HVR-L1 comprising the amino acid sequence of $RASQX_1VSTAVA$ (SEQ ID NO: 4), wherein $X_1$ is Asp or Arg; (e) an HVR-L2 comprising the amino acid sequence of $X_1ASFLYS$ (SEQ ID NO: 5), wherein $X_1$ is Ser or Met; and (f) an HVR-L3 comprising the amino acid sequence of $X_1QGYGXPFT$ (SEQ ID NO: 6), wherein $X_1$ is Gln, Asn, or Thr and $X_2$ is Ala, Asn, Gln, or Arg, or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6.

For instance, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7), GITPAGGYEYYADSVKG (SEQ ID NO: 21), or GITPAG-GYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10) or QQGYGNPFT (SEQ ID NO: 23), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, 7-10, or 21-23.

For example, in some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, or 7-10. In a particular example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10).

In some instances, any of the preceding anti-VEGF antibodies may include one, two, three, or four of the following heavy chain variable domain framework regions (FRs): (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16).

In some instances, any of the preceding anti-VEGF antibodies may include one, two, three, or four of the following light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20).

For example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 11 and (b) a VL domain comprising an amino acid sequence of SEQ ID NO: 12.

For example, in some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, 8, 9, 22, or 23. In a particular example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23).

In some instances, any of the preceding anti-VEGF antibodies may include one, two, three, or four of the following heavy chain variable domain framework regions (FRs): (a) an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32).

In some instances, any of the preceding anti-VEGF antibodies may include one, two, three, or four of the following light chain variable domain FRs: (a) an FR-L1 comprising the amino acid sequence of DIQMTQSPSSL-SASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFA-TYYC (SEQ ID NO: 24); and (d) an FR-L4 comprising the amino acid sequence of FGQGTKVEIK (SEQ ID NO: 20).

For example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSEN-TAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFATYYC (SEQ ID NO: 24); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 38.

In some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYY-ADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23). In some instances, the anti-VEGF antibody includes the following four heavy chain variable domain FRs: (a) an FR-H1 comprising the amino acid sequence of EEQLVEEGGGLVQPGESLRLSCAASG-FEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSL-SASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFA-TYYC (SEQ ID NO: 24); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 38.

For example, in some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYEYY-ADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, 8-10, or 22. In a particular example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10).

In some instances, any of the preceding anti-VEGF antibodies may include one, two, three, or four of the following heavy chain variable domain framework regions (FRs): (a) an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTI-SADTSENTAYLQMNELRAEDTAVYYCAR (SEQ ID NO: 31); and (d) an FR-H4 comprising the amino acid sequence of WGQGELVTVSS (SEQ ID NO: 32).

In some instances, any of the preceding anti-VEGF antibodies may include one, two, three, or four of the following light chain variable domain FRs: (a) an FR-L1 comprising the amino acid sequence of DIQMTQSPSSL-SASVGDRVTITC (SEQ ID NO: 17), DIQMTQSPESL-SASVGDEVTITC (SEQ ID NO: 25), or DIQMTQSPSSL-SASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19) or GVPSRFSGSGSGTDFTLTIESLQPED- AATYYC (SEQ ID NO: 28); and (d) an FR-L4 comprising the amino acid sequence of FGQGTKVEIK (SEQ ID NO: 20).

For example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPESLSASVGDEVTITC (SEQ ID NO: 25); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 34.

For example, in other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGEAPKLLIY (SEQ ID NO: 27); (c) an FR-L3 comprising the amino acid sequence of GVPSRFSGSGSGTDFTLTIESLQPEDAATYYC (SEQ ID NO: 28); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 35.

For example, in other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGEAPKLLIY (SEQ ID NO: 27); (c) an FR-L3 comprising the amino acid sequence of GVPSRFSGSGSGTDFTLTIESLQPEDAATYYC (SEQ ID NO: 28); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 35.

For example, in yet other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPESLSASVGDEVTITC (SEQ ID NO: 25); (b) an FR-L2 comprising the amino acid sequence of WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 36.

For example, in still further instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 37.

In other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 37.

For example, in other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 12.

In other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLRLSCAASGFEIS (SEQ ID NO: 51); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 12.

In some instances, the anti-VEGF antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 11, 40, or 42; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 12, 41, or 46; or (c) a VH domain as in (a) and a VL domain as in (b). For example, in some instances, the antibody comprises a VH domain comprising the amino acid sequence of SEQ ID NO: 11 and a VL domain comprising the amino acid sequence of SEQ ID NO: 12. In some instances, the antibody comprises a VH domain comprising the amino acid sequence of SEQ ID NO: 40 and a VL domain comprising the amino acid sequence of SEQ ID NO: 12. In some instances, the antibody comprises a VH domain comprising the amino acid sequence of SEQ ID NO: 42 and a VL domain comprising the amino acid sequence of SEQ ID NO: 12. In some instances, the antibody comprises a VH domain comprising the amino acid sequence of SEQ ID NO: 42 and a VL domain comprising the amino acid sequence of SEQ ID NO: 41. In some instances, the antibody comprises a VH domain comprising the amino acid sequence of SEQ ID NO: 11 and a VL domain comprising the amino acid sequence of SEQ ID NO: 46.

In some instances, any of the preceding anti-VEGF antibodies may include one, two, three, or four of the following heavy chain variable domain framework regions (FRs): (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14) or WVRQEPGKGLEWVA (SEQ ID NO: 39); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16).

In some instances, any of the preceding anti-VEGF antibodies may include one, two, three, or four of the following light chain variable domain FRs: (a) an FR-L1 comprising the amino acid sequence of DIQMTQSPSSLSASVGDRVTITC (SEQ ID NO: 17) or DIQMTQSPSSLSASVGDRVTIDC (SEQ ID NO: 45); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19), GVPSRFSGSGSGTDFTLTISSLQPEDSATYYC (SEQ ID NO: 44), or GVPSRFSGSGSGTDFTLTISSLQPEDVATYYC (SEQ ID NO: 54); and (d) an FR-L4 comprising the amino acid sequence of FGQGTKVEIK (SEQ ID NO: 20) or FGQGTKVEVK (SEQ ID NO: 55).

In some instances, the antibody comprises a VH domain comprising the amino acid sequence of SEQ ID NO: 11 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGNPFTFGQGTKVEIK (SEQ ID NO: 59).

In some instances, the antibody comprises a VH domain comprising the amino acid sequence of SEQ ID NO: 33 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGNPFTFGQGTKVEIK (SEQ ID NO: 59).

In some instances, the antibody comprises a VH domain comprising the amino acid sequence of SEQ ID NO: 40 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGNPFTFGQGTKVEIK (SEQ ID NO: 59).

In some instances, the antibody comprises a VH domain comprising the amino acid sequence of SEQ ID NO: 42 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGNPFTFGQGTKVEIK (SEQ ID NO: 59).

In some instances, the antibody comprises a VH domain comprising the amino acid sequence of SEQ ID NO: 51 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGNPFTFGQGTKVEIK (SEQ ID NO: 59).

In some instances, the antibody comprises a VH domain comprising the amino acid sequence of SEQ ID NO: 11 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGAPFTFGQGTKVEIK (SEQ ID NO: 60).

In some instances, the antibody comprises a VH domain comprising the amino acid sequence of SEQ ID NO: 33 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGAPFTFGQGTKVEIK (SEQ ID NO: 60).

In some instances, the antibody comprises a VH domain comprising the amino acid sequence of SEQ ID NO: 40 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGAPFTFGQGTKVEIK (SEQ ID NO: 60).

In some instances, the antibody comprises a VH domain comprising the amino acid sequence of SEQ ID NO: 42 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGAPFTFGQGTKVEIK (SEQ ID NO: 60).

In some instances, the antibody comprises a VH domain comprising the amino acid sequence of SEQ ID NO: 51 and a VL domain comprising the amino acid sequence of DIQMTQSPSSLSASVGDRVTITCRASQDVSTAVAWYQQKPGKAPKLLIYSASFLYSGVPSRFSGSGSGTDFT LTISSLQPEDVATYYCQQGYGAPFTFGQGTKVEIK (SEQ ID NO: 60). For example, in some instances, the anti-VEGF antibody comprises (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 11; (b) a VL domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 11; or (c) a VH domain as in (a) and a VL domain as in (b). In some instances, the anti-VEGF antibody may include (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following heavy chain framework regions: (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16). In some instances, the anti-VEGF antibody includes the following light chain framework regions: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes a binding domain comprising (a) a VH domain comprising an amino acid sequence of SEQ ID NO: 11 and (b) a VL domain comprising an amino acid sequence of SEQ ID NO: 12. In some instances, the exemplary anti-VEGF is N94A.F83A.N82aR.Y58R.

In some instances, the anti-VEGF antibody comprises (a) VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 33 or 51; (b) a VL domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 12, 34, 35, 36, 37, or 38; or (c) a VH domain as in (a) and a VL domain as in (b). For example, in some instances, the antibody comprises a VH domain comprising the amino acid sequence of SEQ ID NO: 33 and a VL domain comprising the amino acid sequence of SEQ ID NO: 12. In some instances, the antibody comprises a VH domain comprising the amino acid sequence of SEQ ID NO: 33 and a VL domain comprising the amino acid sequence of SEQ ID NO: 34. In some instances, the antibody comprises a VH domain comprising the amino acid sequence of SEQ ID NO: 33 and a VL domain comprising the amino acid sequence of SEQ ID NO: 35. In some instances, the antibody comprises a VH domain comprising the amino acid sequence of SEQ ID NO: 33 and a VL domain comprising the amino acid sequence of SEQ ID NO: 36. In some instances, the antibody comprises a VH domain comprising the amino acid sequence of SEQ ID NO: 33 and a VL domain comprising the amino acid sequence of SEQ ID NO: 37. In some instances, the antibody comprises a VH domain comprising the amino acid sequence of SEQ ID NO: 33 and a VL domain comprising the amino acid sequence of SEQ ID NO: 38. In some instances, the antibody comprises a VH domain comprising the amino acid sequence of SEQ ID NO: 51 and a VL domain comprising the amino acid sequence of SEQ ID NO: 38. In some instances, the antibody comprises a VH domain comprising the amino acid sequence of SEQ ID NO: 51 and a VL domain comprising the amino acid sequence of SEQ ID NO: 35. In some instances, the antibody comprises a VH domain comprising the amino acid sequence of SEQ ID NO: 51 and a VL domain comprising the amino acid sequence of SEQ ID NO: 37. In some instances, the antibody comprises a VH domain comprising the amino acid sequence of SEQ ID NO: 51 and a VL domain comprising the amino acid sequence of SEQ ID NO: 12.

In some instances, any of the preceding anti-VEGF antibodies may include one, two, three, or four of the following heavy chain variable domain framework regions (FRs): an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 52); (b) an FR-H2 comprising the amino acid sequence of WVRQEPGEGLEWVA (SEQ ID NO: 30) or WVRQEPGKGLEWVA (SEQ ID NO: 39); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32).

In some instances, any of the preceding anti-VEGF antibodies may include one, two, three, or four of the following light chain variable domain FRs: (a) an FR-L1 comprising the amino acid sequence of DIQMTQSPSSLSASVGDRVTITC (SEQ ID NO: 17), DIQMTQSPESLSASVGDEVTITC (SEQ ID NO: 25), or DIQMTQSPSSLSASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19), GVPSRFSGSGSGTDFTLTISSLQPEDFATYYC (SEQ ID NO: 24), or GVPSRFSGSGSGTDFTLTIESLQPEDAATYYC (SEQ ID NO: 28); and (d) an FR-L4 comprising the amino acid sequence of FGQGTKVEIK (SEQ ID NO: 20).

In some instances, the invention provides an antibody comprising (a) a heavy chain comprising the amino acid sequence of SEQ ID NO: 48 and/or (b) a light chain comprising the amino acid sequence of SEQ ID NO: 50. In certain embodiments, the antibody is G6.31 AARR expressed in Fab format.

In some instances, the invention provides an antibody comprising (a) a heavy chain comprising the amino acid sequence of SEQ ID NO: 49 and/or (b) a light chain comprising the amino acid sequence of SEQ ID NO: 50. In certain embodiments, the antibody is a variant version of G6.31 AARR that lacks reactivity to anti-human IgG.

In a further aspect, an anti-VEGF antibody according to any of the above embodiments may incorporate any of the features, singly or in combination, as described in Sections 1-8 below:

1. Antibody Affinity

In certain embodiments, an antibody provided herein has a dissociation constant (Kd) of ≤1 µM, ≤100 nM, ≤10 nM, ≤1 nM, ≤0.1 nM, ≥0.01 nM, or ≤0.001 nM (e.g., $10^{-8}$ M or less, e.g., from $10^{-8}$ M to $10^{-13}$ M, e.g., from $10^{-9}$ M to $10^{-13}$ M). For example, in some instances, an antibody provided herein binds human VEGF (hVEGF) with a Kd of about 10 nM or lower. In some instances, an antibody provided herein binds hVEGF with a Kd of about 5 nM or lower. In some instances, an antibody provided herein binds hVEGF with a Kd of about 2 nM or lower. For example, in some instances, the antibody binds hVEGF with a Kd between about 25 pM and about 2 nM (e.g., about 25 pM, about 50 pM, about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM, about 625 pM, about 650 pM, about 675 pM, about 700 pM, about 725 pM, about 750 pM, about 775 pM, about 800 pM, about 825 pM, about 850 pM, about 875 pM, about 900 pM, about 925 pM, about 950 pM, about 975 pM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, or about 2 nM). In some instances, the antibody binds hVEGF with a Kd between about 75 pM and about 600 pM (e.g., about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM). In some instances, the antibody binds hVEGF with a Kd between about 75 pM and about 500 pM. In some instances, the antibody binds hVEGF with a Kd between about 75 pM and about 400 pM. In some instances, the antibody binds hVEGF with a Kd between about 75 pM and about 300 pM. In some instances, the antibody binds hVEGF with a Kd between about 75 pM and about 200 pM. In some instances, the antibody binds hVEGF with a Kd between about 75 pM and about 150 pM. In some instances, the antibody binds hVEGF with a Kd between about 75 pM and about 125 pM. In some instances, the antibody binds hVEGF with a Kd between about 75 pM and about 100 pM. In some instances, the antibody binds hVEGF with a Kd of about 80 pM. In some instances, the antibody binds hVEGF with a Kd of about 60 pM. In some instances, the antibody binds hVEGF with a Kd of about 40 pM.

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin (BSA) in phosphate buffered saline (PBS) for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillation (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, NJ) is performed at 25° C. with immobilized antigen CM5 chips at ~10 response units (RU). In one embodiment, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, for example, Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Stability

The invention provides antibodies with enhanced stability, for example, as compared to an anti-VEGF antibody, for instance, G6.31 (see, e.g., U.S. Pat. No. 7,758,859 and International Application Pub. No. WO 2005/012359, which are incorporated herein by reference in their entirety). The stability of an antibody may be determined using any method known in the art, for example, differential scanning fluorimetry (DSF), circular dichroism (CD), intrinsic protein fluorescence, differential scanning calorimetry, spectroscopy, light scattering (e.g., dynamic light scattering (DLS) and static light scattering (SLS), self-interaction chromatography (SIC). The anti-VEGF antibody may have, for example, an enhanced melting temperature ($T_m$), temperature of aggregation ($T_{agg}$), or other metrics of stability compared to an anti-VEGF antibody, for example, G6.31.

In certain embodiments, an antibody provided herein has a $T_m$ that is greater than or equal to about 80° C. (e.g., about 81° C., about 82° C., about 83° C., about 84° C., about 85° C., about 86° C., about 87° C., about 88° C., about 89° C., about 90° C., about 91° C., about 92° C., or about 93° C.). For example, in some instances, the anti-VEGF antibody has a $T_m$ that is greater than or equal to about 83.5° C. (e.g., about 83.5° C., about 84° C., about 85° C., about 86° C., about 87° C., about 88° C., about 89° C., about 90° C., about 91° C., about 92° C., or about 93° C.). In some instances, the anti-VEGF antibody has a $T_m$ of about 82° C. to about 92° C. (e.g., about 82° C., about 83° C., about 84° C., about 85° C., about 86° C., about 87° C., about 88° C., about 89° C., about 90° C., about 91° C., or about 92° C.). In some about instances, the anti-VEGF antibody has a $T_m$ of about 82° C. In some instances, any of the preceding $T_m$ values of an anti-VEGF antibody is determined using DSF. In some embodiments, the $T_m$ value of an anti-VEGF antibody is determined as described herein, for example, in Example 1.

3. Antibody Fragments

In certain embodiments, an antibody provided herein is an antibody fragment. Antibody fragments include, but are not limited to, Fab, Fab', Fab-C, Fab'-SH, F(ab')$_2$, Fv, and scFv fragments, and other fragments described below. For a review of certain antibody fragments, see Hudson et al., *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

4. Chimeric and Humanized Antibodies

In certain embodiments, an antibody provided herein is a chimeric antibody. Certain chimeric antibodies are described, for example, in U.S. Pat. No. 4,816,567; and Morrison et al., *Proc. Nat. Acad. Sci. USA*, 81:6851-6855 (1984). In one example, a chimeric antibody comprises a non-human variable region (e.g., a variable domain derived from a mouse, rat, hamster, rabbit, or non-human primate, such as a monkey) and a human constant domain. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, for example, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, for example, in Almagro and Fransson, *Front. Biosci.* 13:1619-1633 (2008), and are further described, for example, in Riechmann et al., *Nature* 332:323-329 (1988); Queen et al., *Proc. Natl Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al., *J. Immunol.* 151:2296 (1993)); framework regions derived from the consensus sequence of human antibodies of a particular subgroup of light or heavy chain variable regions (see, e.g., Carter et al., *Proc. Nat. Acad. Sci. USA,* 89:4285 (1992); and Presta et al., *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

5. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, for example, by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

6. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2):119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

7. Multispecific Antibodies

In certain embodiments, an antibody provided herein is a multispecific antibody, for example, a bispecific antibody. Multispecific antibodies are monoclonal antibodies that have binding specificities for at least two different sites. In certain embodiments, one of the binding specificities is for VEGF and the other is for any other antigen (e.g., a second biological molecule, e.g., interleukin-1 beta (IL-1β), interleukin-6 (IL-6); interleukin-6 receptor (IL-6R); interleukin-13 (IL-13); IL-13 receptor (IL-13R); PDGF (e.g., PDGF-BB); angiopoietin; angiopoietin 2 (Ang2); Tie2; S1P; integrins αvβ3, αvβ5, and α5β1; betacellulin; apelin/APJ; erythropoietin; complement factor D; TNFα; HtrA1; a VEGF receptor (e.g., VEGFR, VEGFR2, VEGFR3, membrane-bound VEGF-receptor (mbVEGFR), or soluble VEGF receptor (sVEGFR)); ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. Accordingly, the bispecific antibody may have binding specificity for VEGF and IL-13; VEGF and IL-6; VEGF and IL-6R; VEGF and IL-13; VEGF and IL-13R; VEGF and PDGF (e.g., PDGF-BB); VEGF and angiopoietin; VEGF and Ang2; VEGF and Tie2; VEGF and S1P; VEGF and integrin αvβ3; VEGF and integrin αvβ5; VEGF and integrin α5β1; VEGF and betacellulin; VEGF and apelin/APJ; VEGF and erythropoietin; VEGF and complement factor D; VEGF and TNFα; VEGF and HtrA1; VEGF and a VEGF receptor (e.g., VEGFR, VEGFR2, VEGFR3, mbVEGFR, or sVEGFR); VEGF and ST-2 receptor; VEGF and C2; VEGF and factor B; VEGF and factor H; VEGF and CFHR3; VEGF and C3b; VEGF and C5; VEGF and C5a; VEGF and C3a; VEGF and ARMS2; VEGF and TIMP3; VEGF and HLA; VEGF and IL-8; VEGF and CX3CR1; VEGF and TLR3; VEGF and TLR4; VEGF and CETP; VEGF and LIPC; VEGF and COL10A1; or VEGF and TNFRSF10A. In certain embodiments, bispecific antibodies may bind to two different epitopes of VEGF. Bispecific antibodies may also be used to localize cytotoxic agents to cells which express VEGF. Bispecific antibodies can be prepared as full length antibodies or antibody fragments (e.g., Fab, Fab', or Fab-C fragments).

In some instances, the bispecific antibody is a bispecific anti-VEGF/anti-angiopoietin 2 (Ang2) antibody disclosed in U.S. Patent Application No. US 2014/0017244, which is incorporated herein by reference in its entirety. For example, the anti-VEGF/anti-Ang2 bispecific antibody may include a first binding domain that binds VEGF (such as any of the anti-VEGF antibodies described herein) and a second binding domain that binds Ang2 that includes (a) an HVR-H1 comprising the amino acid sequence of GYYMH (SEQ ID NO: 62); (b) an HVR-H2 comprising the amino acid sequence of WINPNSGGTNYAQKFQG (SEQ ID NO: 63);

(c) an HVR-H3 comprising the amino acid sequence of SPNPYYYDSSGYYYPGAFDI (SEQ ID NO: 64); (d) an HVR-L1 comprising the amino acid sequence of GGNNIG-SKSVH (SEQ ID NO: 65); (e) an HVR-L2 comprising the amino acid sequence of DDSDRPS (SEQ ID NO: 66); and (f) an HVR-L3 comprising the amino acid sequence of QVWDSSSDHWV (SEQ ID NO: 67), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 62-67.

In some instances, the anti-VEGF/anti-Ang2 bispecific antibody may include a first binding domain that binds VEGF (such as any of the anti-VEGF antibodies described herein) and a second binding domain that binds to Ang2 and includes (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 68; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 69; or (c) a VH domain as in (a) and a VL domain as in (b). In some instances, the anti-VEGF/anti-Ang2 bispecific antibody may include a first binding domain that binds VEGF (such as any of the anti-VEGF antibodies described herein) and a second binding domain that specifically bind to Ang2, wherein the second binding domain is any antibody binding domain described in International Patent Application Publication No. WO 2010/069532, which is incorporated herein by reference in its entirety, or a variant thereof.

In other instances, the anti-VEGF/anti-Ang2 bispecific antibody is any anti-VEGF/anti-Ang2 bispecific antibody described in International Patent Application Publication No. WO 2016/073157.

In some instances, the bispecific antibody is a bispecific anti-VEGF/anti-IL-6 antibody. In some instances, an anti-VEGF/anti-IL-6 bispecific antibody may include a first binding domain that binds VEGF (such as any of the anti-VEGF antibodies described herein) and a second binding domain that binds IL-6. The second binding domain may be a binding domain of any anti-IL-6 antibody known in the art, for example, EBI-031 (Eleven Biotherapeutics; see, e.g., WO 2016/073890, which is incorporated herein by reference in its entirety), siltuximab (SYLVANT®), olokizumab, clazakizumab, sirukumab, elsilimomab, gerilimzumab, OPR-003, MEDI-5117, PF-04236921, or a variant thereof.

In some instances, the bispecific antibody is a bispecific anti-VEGF/anti-IL-6R antibody. In some instances, an anti-VEGF/anti-IL-6R bispecific antibody may include a first binding domain that binds VEGF (such as any of the anti-VEGF antibodies described herein) and a second binding domain that binds IL-6R. The second binding domain may be a binding domain any anti-IL-6R antibody known in the art, for example, tocilizumab (ACTEMRA®) (see, e.g., WO 1992/019579, which is incorporated herein by reference in its entirety), sarilumab, vobarilizumab (ALX-0061), SA-237, or a variant thereof.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, for example, in Tutt et al., *J. Immunol.* 147:60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to VEGF as well as another, different antigen (see, e.g., US 2008/0069820).

8. Antibody Variants

In certain embodiments, amino acid sequence variants (e.g., antibody variants including one or more amino acid residue alterations) of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |

TABLE 1-continued

| Original Residue | Exemplary Substitutions | Preferred Substitutions |
|---|---|---|
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues and/or FR residues of a parent antibody (e.g., a humanized or human antibody). Generally, the resulting variant(s) selected for further study will have modifications (e.g., improvements) in certain biological properties (e.g., increased affinity, increased stability, increased expression, altered pI, and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, for example, in Hoogenboom et al., in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

In certain embodiments, substitutions, insertions, or deletions may occur within one or more FRs so long as such alterations do not substantially reduce the ability of the antibody to bind antigen. Such alterations may, for example, improve antibody affinity and/or stability (e.g., as assessed by an increased melting temperature).

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, for example, US Patent Publication Nos. US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546 (Umana et al.). Antibody variants with at least one galactose residue in the oligosaccharide attached to the Fc region are also provided. Such antibody variants may have improved CDC function. Such antibody variants are described, for example, in WO 1997/30087; WO 1998/58964; and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG$_1$, IgG$_2$, IgG$_3$ or IgG$_4$ Fc region) comprising an amino acid residue alteration (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991).

Non-limiting examples of in vitro assays to assess ADCC activity of a molecule of interest are described in U.S. Pat. No. 5,500,362 (see, e.g. Hellstrom et al., *Proc. Nat'l Acad. Sci. USA* 83:7059-7063 (1986) and Hellstrom, I et al., *Proc. Nat'l Acad. Sci. USA* 82:1499-1502 (1985); U.S. Pat. No. 5,821,337; and Bruggemann et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, for example, in a animal model such as that disclosed in Clynes et al., *Proc. Nat'l Acad. Sci. USA* 95:652-656 (1998). C1q binding assays may also be carried out to confirm that the antibody is unable to bind C1q and hence lacks CDC activity. See, for example, C1q and C3c binding ELISA in WO 2006/029879 and WO 2005/100402. To assess complement activation, a CDC assay may be performed (see, e.g., Gazzano-Santoro et al., *J. Immunol. Methods* 202:163 (1996); Cragg et al., *Blood* 101:1045-1052 (2003); and Cragg et al., *Blood* 103:2738-2743 (2004)). FcRn binding and in vivo clearance/half life determinations can also be performed using methods known in the art (see, e.g., Petkova et al., *Int'l. Immunol.* 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001)).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), for example, as described in U.S. Pat. No. 6,194,551, WO 99/51642, and Idusogie et al., *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, and the like. Additional antibody conjugates are described herein, for example, in Section K below and in Example 13.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

f) Isoelectric Point Variants

The invention provides antibodies variants with altered isoelectric points. For example, the invention provides antibodies variants with a reduced isoelectric point (pI), for example, as compared to an anti-VEGF antibody, for instance, G6.31. In some instances, the surface charge is reduced at physiological pH. In some instances, the anti-VEGF antibody has a pI equal to or lower than about 8 (e.g., about 8, about 7, about 6, about 5, or about 4). In some instances, the antibody has a pI from about 4 to about 8 (e.g., about 4, about 5, about 6, about 7, or about 8). In some instances, the anti-VEGF antibody has a pI from about 5 to about 7 (e.g., about 5, about 6, or about 7). In some instances, the anti-VEGF antibody has a pI from about 5 to about 6 (e.g., about 5.1, about 5.2, about 5.3, about 5.4, about 5.5, about 5.6, about 5.7, about 5.8, about 5.9, or about 6).

Antibodies of the invention may be engineered to have a reduced pI, for example, by substituting wild-type amino acid residues at a given position with an amino acid having a lower pI. The pI of an amino acid can be determined based on the pKa values of the amine ($-NH_2$), carboxylic acid ($-COOH$), and side-chain of the amino acid, which are known in the art. In some embodiments, surface-exposed amino acid residues may be substituted to reduce the pI of an antibody. In one embodiment, surface-exposed amino acid residues may be substituted with glutamate (E). In one embodiment, surface-exposed amino acid residues may be substituted with aspartate (D).

B. Recombinant Methods and Compositions

Any of the antibodies (e.g., anti-VEGF antibodies) described herein may be produced using recombinant methods and compositions, for example, as described in U.S. Pat. No. 4,816,567. In one embodiment, an isolated nucleic acid encoding an anti-VEGF antibody described herein is provided. Such a nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such a nucleic acid are provided. In a further embodiment, a host cell comprising such a nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, for example, a Chinese Hamster Ovary (CHO) cell or lymphoid cell (e.g., Y0, NS0, Sp20 cell). In one embodiment, a method of making an anti-VEGF antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-VEGF antibody, nucleic acid encoding an antibody, for example, as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, for example, U.S. Pat. Nos. 5,648,237, 5,789,199, and 5,840,523. See also Charlton, *Methods in Molecular Biology, Vol.* 248 (B. K. C. Lo, ed., Humana Press, Totowa, NJ, 2003), pp. 245-254, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, for example, U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, for example, Yazaki and Wu, *Methods in Molecular Biology, Vol.* 248 (B. K. C. Lo, ed., Humana Press, Totowa, NJ), pp. 255-268 (2003).

C. Assays

Anti-VEGF antibodies provided herein, as well as compositions that include anti-VEGF antibodies (e.g., any anti-VEGF antibody provided herein), such as antibody conjugates, fusion proteins, and polymeric formulations, may be identified, screened for, or characterized for their physical/chemical properties and/or biological activities by various assays known in the art.

1. Binding Assays and Other Assays

In one aspect, an antibody of the invention, or an antibody conjugate, fusion protein, or polymeric formulation thereof, is tested for its antigen binding activity, e.g., by known methods such as ELISA, Western blot, etc.

In another aspect, competition assays may be used to identify an antibody that competes with an antibody as described herein, or an antibody conjugate, fusion protein, or polymeric formulation thereof, for binding to VEGF. In certain embodiments, such a competing antibody binds to the same epitope (e.g., a linear or a conformational epitope) that is bound by an antibody as described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized VEGF is incubated in a solution comprising a first labeled antibody that binds to VEGF and a second unlabeled antibody that is being tested for its ability to compete with the first antibody for binding to VEGF. The second antibody may be present in a hybridoma supernatant. As a control, immobilized VEGF is incubated in a solution comprising the first labeled antibody but not the second unlabeled antibody. After incubation under conditions permissive for binding of the first antibody to VEGF, excess unbound antibody is removed, and the amount of label associated with immobilized VEGF is measured. If the amount of label associated with immobilized VEGF is substantially reduced in the test sample relative to the control sample, then that indicates that the second antibody is competing with the first antibody for binding to VEGF. See Harlow and Lane (1988) *Antibodies: A Laboratory Manual* ch. 14 (Cold Spring Harbor Laboratory, Cold Spring Harbor, NY).

2. Activity Assays

In one aspect, assays are provided for identifying anti-VEGF antibodies, or antibody conjugates, fusion proteins, or polymeric formulations thereof, having biological activity. Biological activity may include, for example, binding to VEGF (e.g., VEGF in the blood stream), or a peptide fragment thereof, either in vivo, in vitro, or ex vivo. In certain embodiments, biological activity may include blocking or neutralizing VEGF, or preventing VEGF from binding to a ligand, for example, a receptor such as KDR or Flt-1. Antibodies, or antibody conjugates, fusion proteins, or polymeric formulations thereof, having such biological activity in vivo and/or in vitro are also provided. In certain embodiments, an antibody of the invention, or an antibody conjugate, fusion protein, or polymeric formulation thereof, is tested for such biological activity.

3. Stability Assays

In one aspect, assays are provided for determining the stability (e.g., thermostability) of an anti-VEGF antibody, or an antibody conjugate, fusion protein, or polymeric formulation thereof. For example, the stability of an antibody, or an antibody conjugate, fusion protein, or polymeric formulation thereof, may be determined using any method known in the art, for example, differential scanning fluorimetry (DSF), circular dichroism (CD), intrinsic protein fluorescence, differential scanning calorimetry, spectroscopy, light scattering (e.g., dynamic light scattering (DLS) and static light scattering (SLS), self-interaction chromatography (SIC). The stability of an assay may be determined as described herein, for example, using DSF as described, for example, in Examples 1 and 2.

D. Immunoconjugates

The invention also provides immunoconjugates comprising an anti-VEGF antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bloorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{88}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

E. Methods and Compositions for Affinity Purification, Diagnostics, and Detection The antibodies of the invention may be used as affinity purification agents. In this process, the antibodies are immobilized on a solid phase such a SEPHADEX® resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized antibody. Finally, the support is washed with another suitable solvent, such as glycine buffer, pH 5.0, that will release the antigen from the antibody.

In certain embodiments, any of the anti-VEGF antibodies provided herein is useful for detecting the presence of VEGF in a biological sample. The term "detecting" as used herein encompasses quantitative or qualitative detection. In certain embodiments, a biological sample comprises a cell or tissue, such as blood (e.g., whole blood, plasma, and/or serum), tissue samples (e.g., tumor samples), and the like.

In one embodiment, an anti-VEGF antibody for use in a method of diagnosis or detection is provided. In a further aspect, a method of detecting the presence of VEGF in a biological sample is provided. In certain embodiments, the method comprises contacting the biological sample with an anti-VEGF antibody as described herein under conditions permissive for binding of the anti-VEGF antibody to VEGF, and detecting whether a complex is formed between the anti-VEGF antibody and VEGF. Such method may be an in vitro or in vivo method. In one embodiment, an anti-VEGF antibody is used to select subjects eligible for therapy with an anti-VEGF antibody, for example, where VEGF is a biomarker for selection of patients.

Exemplary disorders that may be diagnosed using an antibody of the invention include disorders associated with pathological angiogenesis (e.g., ocular disorders and cell proliferative disorders) and/or disorders associated with undesirable vascular permeability (e.g., edema associated with brain tumors, ascites associated with malignancies, Meigs' syndrome, lung inflammation, nephrotic syndrome, pericardial effusion, pleural effusion, and permeability associated with cardiovascular diseases). In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis (also known as Leber's congenital amaurosis or LCA), uveitis (including infectious and non-infectious uveitis), choroiditis (e.g., multifocal choroiditis), ocular histoplasmosis, blepharitis, dry eye, traumatic eye injury, or Sjögren's disease. In some instances, the ocular disorder is retinopathy including proliferative diabetic retinopathy, choroidal neovascularization (CNV), age-related macular degeneration (AMD), diabetic and other ischemia-related retinopathies, diabetic macular edema (DME), pathologic myopia, von Hippel-Lindau disease, histoplasmosis of the eye, retinal vein occlusion (including central (CRVO) and branched (BRVO) forms), corneal neovascularization, retinal neovascularization, retinopathy of prematurity (ROP), familial exudative vitreoretinopathy (FEVR), Coats' disease, Norrie Disease, Osteoporosis-Pseudoglioma Syndrome (OPPG), subconjunctival hemorrhage, or hypertensive retinopathy. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma.

In certain embodiments, labeled anti-VEGF antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In another embodiment of the invention, the antibody need not be labeled, and the presence thereof can be detected using a labeled antibody which binds to the antibody.

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc. 1987).

Competitive binding assays rely on the ability of a labeled standard to compete with the test sample analyze for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyze that are bound to the antibodies may conveniently be separated from the standard and analyze which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, for example, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}$In, $^{99}$Tc, $^{14}$C, $^{131}$I, $^{125}$I, $^{3}$H, $^{32}$P or $^{35}$S) or a dye so that the tumor can be localized using immunoscintiography.

F. Diagnostic Kits

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

G. Pharmaceutical Formulations

Pharmaceutical formulations of an anti-VEGF antibody as described herein. or an antibody conjugate, fusion protein, or polymeric formulation thereof. are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration are generally sterile. Sterility may be readily accomplished, for example, by filtration through sterile filtration membranes.

In certain embodiments, the pharmaceutical formulation includes one or more additional compounds. In certain embodiments, the additional compound binds to a second biological molecule selected from the group consisting of IL-1β, IL-6; IL-6R; IL-13; IL-13R; PDGF; angiopoietin; angiopoietin 2; Tie2; S1P; integrins αvβ3, αv5, and α5β1; betacellulin; apelin/APJ; erythropoietin; complement factor D; TNFα; HtrA1; a VEGF receptor; ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. In certain embodiments, the additional compound is an antibody or antigen-binding fragment thereof.

For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157.

In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof.

In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

H. Therapeutic Methods and Compositions

Any of the anti-VEGF antibodies, antibody conjugates (e.g., HA conjugates, PEG conjugates, and prodrug antibody conjugates), fusion proteins, and polymeric formulations provided herein may be used in therapeutic methods.

In one aspect, an anti-VEGF antibody for use as a medicament is provided. In another aspect, an antibody conjugate for use as a medicament is provided. In yet another aspect, a fusion protein for use as a medicament is provided. In a still further aspect, a polymeric formulation for use as a medicament is provided. In further aspects, the invention provides an anti-VEGF antibody for use in treating a disorder associated with pathological angiogenesis. In another aspect, the invention provides an antibody conjugate for use in treating a disorder associated with pathological angiogenesis. In yet other aspects, the invention provides a fusion protein for use in treating a disorder associated with pathological angiogenesis. In other aspects, the invention provides a polymeric formulation for use in treating a disorder associated with pathogical angiogenesis. In some embodiments, the disorder associated with pathological angiogenesis is an ocular disorder or a cell proliferative disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma. In another aspect, an anti-VEGF antibody for use in treating a disorder associated with undesirable vascular permeability is provided. In some instances, the disorder associated with undesirable vascular permeability is edema associated with brain tumors, ascites associated with malignancies, Meigs' syndrome, lung inflammation, nephrotic syndrome, pericardial effusion, pleural effusion, or permeability associated with cardiovascular diseases.

In another aspect, an anti-VEGF antibody for use in a method of treatment is provided. In another aspect, an antibody conjugate for use in a method of treatment is provided. In yet another aspect, a fusion protein for use in a method of treatment is provided. In a still further aspect, a polymeric formulation for use in a method of treatment is provided. In certain instances, the invention provides an anti-VEGF antibody for use in a method of treating a subject having a disorder associated with pathological angiogenesis comprising administering to the individual an effective amount of the anti-VEGF antibody. The invention also provides an antibody conjugate for use in a method of treating a subject having a disorder associated with pathological angiogenesis comprising administering to the individual an effective amount of the antibody conjugate. The invention also provides a fusion protein for use in a method of treating a subject having a disorder associated with pathological angiogenesis comprising administering to the individual an effective amount of the fusion protein. The invention also provides a polymeric formulation for use in a method of treating a subject having a disorder associated with pathological angiogenesis comprising administering to the individual an effective amount of the polymeric formulation. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma.

In other instances, the invention provides an anti-VEGF antibody for use in a method of treating an individual having a disorder associated with undesirable vascular permeability. In some instances, the disorder associated with undesirable vascular permeability is edema associated with brain tumors, ascites associated with malignancies, Meigs' syndrome, lung inflammation, nephrotic syndrome, pericardial effusion, pleural effusion, or permeability associated with cardiovascular diseases. Any of the preceding uses may further include administering to the individual an effective amount of at least one additional therapeutic agent, for example, as described below.

In some instances, the invention provides an anti-VEGF antibody for use in reducing or inhibiting angiogenesis in a subject. In another aspect, an antibody conjugate for use in reducing or inhibiting angiogenesis in a subject is provided. In yet another aspect, a fusion protein for use in reducing or inhibiting angiogenesis in a subject is provided. In a still further aspect, a polymeric formulation for use in reducing or inhibiting angiogenesis in a subject is provided. In certain embodiments, the invention provides an anti-VEGF antibody for use in a method of reducing or inhibiting angiogenesis in a subject comprising administering to the individual an effective of the anti-VEGF antibody to reduce or inhibit angiogenesis. The invention also provides an antibody conjugate for use in a method of reducing or inhibiting angiogenesis in a subject comprising administering to the individual an effective amount of the antibody conjugate. The invention also provides a fusion protein for use in a method of reducing or inhibiting angiogenesis in a subject comprising administering to the individual an effective amount of the fusion protein. The invention also provides a polymeric formulation for use in a method of reducing or inhibiting angiogenesis in a subject comprising administering to the individual an effective amount of the polymeric formulation. In other instances, the invention provides an anti-VEGF antibody for use in reducing or inhibiting vascular permeability in a subject. In certain embodiments, the invention provides an anti-VEGF antibody for use in a reducing or inhibiting vascular permeability in a subject comprising administering to the individual an effective of the anti-VEGF antibody to reduce or inhibit vascular permeability. A "subject" according to any of the above uses may be a human.

In some instances, the invention provides an anti-VEGF antibody for use in treating an autoimmune disease in a subject. In some instances, the autoimmune disorder is rheumatoid arthritis, ankylosing spondylitis, psoriatic arthritis and Crohn's disease. Any of the preceding uses may further include administering to the individual an effective amount of at least one additional therapeutic agent, for example, as described below.

The invention provides for the use of an anti-VEGF antibody in the manufacture or preparation of a medicament. The invention also provides for the use of an antibody conjugate in the manufacture or preparation of a medicament. Further still, the invention provides for the use of a fusion protein in the manufacture or preparation of a medicament. The invention also provides for the use of a polymeric formulation in the manufacture or preparation of a medicament. For example, in one instance, the medicament is for treatment of a disorder associated with pathological angiogenesis. In a further instance, the medicament is for use in a method of treating a disorder associated with pathological angiogenesis comprising administering to a subject having a disorder associated with pathological angiogenesis an effective amount of the medicament. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma. In a further instance, the medicament is for reducing or inhibiting angiogenesis in a subject. In a further instance, the medicament is for use in a method of reducing or inhibiting angiogenesis in a subject comprising administering to the subject an amount effective of the medicament to reduce or inhibit angiogenesis. In any of the preceding uses of medicaments, the method may include administering to the individual an effective amount of at least one additional therapeutic agent, e.g., as described below.

In another instance, the medicament is for treatment of a disorder associated with undesirable vascular permeability. In some instances, the disorder associated with undesirable vascular permeability is edema associated with brain tumors, ascites associated with malignancies, Meigs' syndrome, lung inflammation, nephrotic syndrome, pericardial effusion, pleural effusion, or permeability associated with cardiovascular diseases. In a further instance, the medicament is for use in a method of treating a disorder associated with undesirable vascular permeability comprising administering to a subject having a associated with undesirable vascular permeability an effective amount of the medicament. In another instance, the medicament is for reducing or inhibiting vascular permeability in a subject. In a further instance, the medicament is for use in a method of reducing or inhibiting vascular permeability in a subject comprising administering to the subject an amount effective of the medicament to reduce or inhibit angiogenesis. In any of the preceding uses of medicaments, the method may include administering to the subject an effective amount of at least one additional therapeutic agent, e.g., as described below. A "subject" according to any of the above uses may be a human.

In another instance, the medicament is for treatment of an autoimmune disorder. In some instances, the autoimmune disorder is rheumatoid arthritis, ankylosing spondylitis, psoriatic arthritis and Crohn's disease. In a further instance, the medicament is for use in a method of treating an autoimmune disorder comprising administering to a subject having an autoimmune disorder an effective amount of the medicament. A "subject" according to any of the above uses may be a human.

The invention provides a method for treating a disorder associated with pathological angiogenesis. In one embodiment, the method comprises administering to an individual having a disorder associated with pathological angiogenesis an effective amount of an anti-VEGF antibody. In another example, the method comprises administering to an individual having a disorder associated with pathological angiogenesis an effective amount of an antibody conjugate. In yet another example, the method comprises administering to an individual having a disorder associated with pathological angiogenesis an effective amount of a fusion protein. In yet another example, the method comprises administering to an individual having a disorder associated with pathological angiogenesis an effective amount of a polymeric formulation. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In some instances, the cell proliferative disorder is cancer. In some instances, the cancer is breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, or multiple myeloma. In further instances, the method further comprises administering to the individual an effective amount of at least one additional therapeutic agent, as described below. A "subject" according to any of the above methods may be a human.

The invention provides a method for treating a disorder associated with undesirable vascular permeability. In one embodiment, the method comprises administering to an individual having a disorder associated with undesirable vascular permeability an effective amount of an anti-VEGF antibody. In some instances, the disorder associated with undesirable vascular permeability is edema associated with brain tumors, ascites associated with malignancies, Meigs' syndrome, lung inflammation, nephrotic syndrome, pericardial effusion, pleural effusion, or permeability associated with cardiovascular diseases. In further instances, the method further comprises administering to the individual an effective amount of at least one additional therapeutic agent, as described below. A "subject" according to any of the above methods may be a human.

It is contemplated that the antibody of the present invention, or antibody conjugate, fusion protein, or polymeric formulation thereof, may be used to treat a mammal. In one embodiment, the antibody, or antibody conjugate, fusion protein, or polymeric formulation thereof, is administered to a nonhuman mammal for the purposes of obtaining preclinical data, for example. Exemplary nonhuman mammals to be treated include nonhuman primates, dogs, cats, rodents (e.g., mice and rats) and other mammals in which preclinical studies are performed. Such mammals may be established animal models for a disease to be treated with the antibody or may be used to study toxicity or pharmacokinetics of the antibody of interest. In each of these embodiments, dose escalation studies may be performed in the mammal. The antibody may be administered to a host rodent in a solid tumor model, for example. The antibody, or antibody conjugate, fusion protein, or polymeric formulation thereof, may be administered to a host (e.g., a rodent, e.g., a rabbit) for ocular pharmacokinetic studies, for example, by intravitreal administration (e.g., intravitreal injection) or using a port delivery device.

In a further aspect, the invention provides pharmaceutical formulations comprising any of the anti-VEGF antibodies, antibody conjugates, fusion proteins, and/or polymeric formulations provided herein, for example, for use in any of the above therapeutic methods. In one embodiment, a pharmaceutical formulation comprises any of the anti-VEGF antibodies, antibody conjugates, fusion proteins, and/or polymeric formulations provided herein and a pharmaceutically acceptable carrier. In another embodiment, a pharmaceutical formulation comprises any of the anti-VEGF antibodies, antibody conjugates, fusion proteins, and/or polymeric formulations provided herein and at least one additional therapeutic agent, for example, as described below. In certain embodiments, the pharmaceutical formulation comprises one or more additional compounds. In certain embodiments, the additional compound binds to a second biological molecule selected from the group consisting of IL-1β; IL-6; IL-6R; IL-13; IL-13R; PDGF; angiopoietin; Ang2; Tie2; S1P; integrins αvβ3, αv5, and α5β1; betacellulin; apelin/APJ; erythropoietin; complement factor D; TNFα; HtrA1; a VEGF receptor; ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC, COL10A1; and TNFRSF10A. In certain embodiments, the additional compound is an antibody or antigen-binding fragment thereof. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

Antibodies of the invention, or antibody conjugates, fusion proteins, or polymeric formulations thereof, can be used either alone or in combination with other agents in a therapy. For instance, an antibody of the invention, or an antibody conjugate, fusion protein, and/or polymeric formulation thereof, may be co-administered with at least one additional therapeutic agent. In certain embodiments, an additional therapeutic agent is another antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, a growth-inhibitory agent, or combinations thereof.

For example, in certain embodiments, any of the preceding methods further comprises administering one or more additional compounds. In certain embodiments, the anti-VEGF antibody, antibody conjugate, fusion protein, or polymeric formulation is administered simultaneously with the additional compound(s). In certain embodiments, the anti-VEGF antibody, antibody conjugate, fusion protein, or polymeric formulation is administered before or after the additional compound(s). In certain embodiments, the additional compound binds to a second biological molecule selected from the group consisting of IL-1β; IL-6; IL-6R; IL-13; IL-13R; PDGF; angiopoietin; Ang2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. In certain embodiments, the additional compound is an antibody or antigen-binding fragment thereof. In certain embodiments according to (or as applied to) any of the embodiments above, the ocular disorder is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including CRVO and BRVO, corneal neovascularization, retinal neovascularization, and retinopathy of prematurity (ROP). For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

In some instances, an antibody of the invention, or an antibody conjugate, fusion protein, and/or polymeric formulation thereof, may be administered in combination with at least one additional therapeutic agent for treatment of an ocular disorder, for example, an ocular disorder described herein (e.g., AMD (e.g., wet AMD), DME, DR, or RVO). Exemplary additional therapeutic agents for combination therapy for treatment of ocular disorders include, without limitation, anti-angiogenic agents, such as VEGF antagonists, including, for example, anti-VEGF antibodies (e.g., the anti-VEGF Fab LUCENTIS® (ranibizumab)), soluble receptor fusion proteins (e.g., the recombinant soluble receptor fusion protein EYLEA® (aflibercept, also known as VEGF Trap Eye; Regeneron/Aventis)), aptamers (e.g., the anti-VEGF pegylated aptamer MACUGEN® (pegaptanib sodium; NeXstar Pharmaceuticals/OSI Pharmaceuticals)), and VEGFR tyrosine kinase inhibitors (e.g., 4-(4-bromo-2-fluoroanilino)-6-methoxy-7-(1-methylpiperidin-4-yl-methoxy)quinazoline (ZD6474), 4-(4-fluoro-2-methylindol-5-yloxy)-6-methoxy-7-(3-pyrrolidin-1-ylpropoxy) quinazoline (AZD2171), vatalanib (PTK787), semaxaminib (SU5416; SUGEN), and SUTENT® (sunitinib)); Tryptophanyl-tRNA synthetase (TrpRS); squalamine; RETAANE® (anecortave acetate for depot suspension; Alcon, Inc.); Combretastatin A4 Prodrug (CA4P); MIFEPREX® (mifepristone-ru486); subtenon triamcinolone acetonide; intravitreal crystalline triamcinolone acetonide; matrix metalloproteinase inhibitors (e.g., Prinomastat (AG3340; Pfizer)); fluocinolone acetonide (including fluocinolone intraocular implant; Bausch & Lomb/Control Delivery Systems); linomide; inhibitors of integrin β3 function; angiostatin, and combinations thereof. These and other therapeutic agents that can be administered in combination with an antibody of the invention are described, for example, in U.S. Patent Application No. US 2014/0017244, which is incorporated herein by reference in its entirety.

Further examples of additional therapeutic agents that can be used in combination with an antibody of the invention, or an antibody conjugate, fusion protein, and/or polymeric formulation thereof, for treatment of an ocular disorder (e.g., AMD, DME, DR, or RVO), include, but are not limited to, VISUDYNE® (verteporfin; a light-activated drug that is typically used in conjunction with photodynamic therapy with a non-thermal laser), PKC412, Endovion (NS 3728; NeuroSearch A/S), neurotrophic factors (e.g., glial derived neurotrophic factor (GDNF) and ciliary neurotrophic factor (CNTF)), diltiazem, dorzolamide, PHOTOTROP®, 9-cis-retinal, eye medication (e.g., phospholine iodide, echothiophate, or carbonic anhydrase inhibitors), veovastat (AE-941; AEterna Laboratories, Inc.), Sirna-027 (AGF-745; Sima Therapeutics, Inc.), neurotrophins (including, by way of example only, NT-4/5, Genentech), Cand5 (Acuity Pharmaceuticals), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc), ATX-S10 (Hamamatsu Photonics), TGF-beta 2 (Genzyme/Celtrix), tyrosine kinase inhibitors (e.g., those from Allergan, SUGEN, or Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, therapeutic agents used in photodynamic therapy (e.g., VISUDYNE®; receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; and motexafin lutetium, Pharmacyclics, Inc.), antisense oligonucleotides (including, by way of example, products tested by Novagali Pharma SA and ISIS-13650, Isis Pharmaceuticals), and combinations thereof.

An antibody of the invention, or an antibody conjugate, fusion protein, and/or polymeric formulation thereof, may be administered in combination with a therapy or surgical procedure for treatment of an ocular disorder (e.g., AMD, DME, DR, or RVO), including, for example, laser photocoagulation (e.g., panretinal photocoagulation (PRP)), drusen lasering, macular hole surgery, macular translocation surgery, implantable miniature telescopes, PHI-motion angiography (also known as micro-laser therapy and feeder vessel treatment), proton beam therapy, microstimulation therapy, retinal detachment and vitreous surgery, scleral buckle, submacular surgery, transpupillary thermotherapy, photosystem I therapy, use of RNA interference (RNAi), extracorporeal rheopheresis (also known as membrane differential filtration and rheotherapy), microchip implantation, stem cell therapy, gene replacement therapy, ribozyme gene therapy (including gene therapy for hypoxia response element, Oxford Biomedica; Lentipak, Genetix; and PDEF gene therapy, GenVec), photoreceptor/retinal cells transplantation (including transplantable retinal epithelial cells, Diacrin, Inc.; retinal cell transplant, Cell Genesys, Inc.), acupuncture, and combinations thereof.

In some instances, an antibody of the invention, or an antibody conjugate, fusion protein, and/or polymeric formulation thereof, can be administered in combination with an anti-angiogenic agent for treatment of an ocular disorder (e.g., AMD, DME, DR, or RVO). Any suitable anti-angiogenic agent can be used in combination with an antibody of the invention, including, but not limited to, those listed by Carmeliet et al. *Nature* 407:249-257, 2000. In some embodiments, the anti-angiogenic agent is a VEGF antagonist, including, but not limited to, an anti-VEGF antibody (e.g., the anti-VEGF Fab LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoietin 2 bispecific antibody such as RG-7716; Roche)), a soluble recombinant receptor fusion protein (e.g., EYLEA® (aflibercept)), a VEGF variant, a soluble VEGFR fragment, an aptamer capable of blocking VEGF (e.g., pegaptanib) or VEGFR, a neutralizing anti-VEGFR antibody, a small molecule inhibitor of VEGFR tyrosine kinases, an anti-VEGF DARPin® (e.g., abicipar pegol), a small interfering RNAs which inhibits expression of VEGF or VEGFR, a VEGFR tyrosine kinase inhibitor (e.g., 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416; SUGEN), and SUTENT® (sunitinib)), and combinations thereof. In some instances, the bispecific anti-VEGF antibody binds to a second biological molecule, including but not limited to IL-13; IL-6; IL-6R; PDGF (e.g., PDGF-BB); angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, mbVEGFR, or sVEGFR); ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof.

Other suitable anti-angiogenic agents that may be administered in combination with an antibody of the invention, or an antibody conjugate, fusion protein, and/or polymeric formulation thereof, for treatment of an ocular disorder (e.g., AMD, DME, DR, or RVO) include corticosteroids, angiostatic steroids, anecortave acetate, angiostatin, endostatin, tyrosine kinase inhibitors, matrix metalloproteinase (MMP) inhibitors, insulin-like growth factor-binding protein 3 (IGFBP3), stromal derived factor (SDF-1) antagonists (e.g., anti-SDF-1 antibodies), pigment epithelium-derived factor (PEDF), gamma-secretase, Delta-like ligand 4, integrin antagonists, hypoxia-inducible factor (HIF)-1α antagonists, protein kinase CK2 antagonists, agents that inhibit stem cell (e.g., endothelial progenitor cell) homing to the site of neovascularization (e.g., an anti-vascular endothelial cadherin (CD-144) antibody and/or an anti-SDF-1 antibody), and combinations thereof.

In a further example, in some instances, an antibody of the invention, or an antibody conjugate, fusion protein, and/or polymeric formulation thereof, can be administered in combination with an agent that has activity against neovascularization for treatment of an ocular disorder (e.g., AMD, DME, DR, or RVO), such as an anti-inflammatory drug, a mammalian target of rapamycin (mTOR) inhibitor (e.g., rapamycin, AFINITOR® (everolimus), and TORISEL® (temsirolimus)), cyclosporine, a tumor necrosis factor (TNF) antagonist (e.g., an anti-TNFα antibody or antigen-binding fragment thereof (e.g., infliximab, adalimumab, certolizumab pegol, and golimumab) or a soluble receptor fusion protein (e.g., etanercept)), an anti-complement agent, a nonsteroidal antiinflammatory agent (NSAID), or combinations thereof.

In a still further example, in some instances, an antibody of the invention, or an antibody conjugate, fusion protein, and/or polymeric formulation thereof, can be administered in combination with an agent that is neuroprotective and can potentially reduce the progression of dry AMD to wet AMD, such as the class of drugs called the "neurosteroids," which include drugs such as dehydroepiandrosterone (DHEA) (brand names: PRASTERA™ and FIDELIN®), dehydroepiandrosterone sulfate, and pregnenolone sulfate.

Any suitable AMD therapeutic agent can be administered as an additional therapeutic agent in combination with an antibody of the invention, or an antibody conjugate, fusion protein, and/or polymeric formulation thereof, for treatment of an ocular disorder (e.g., AMD, DME, DR, or RVO), including, but not limited to, a VEGF antagonist, for example, an anti-VEGF antibody (e.g., LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoietin 2 bispecific antibody such as RG-7716; Roche)), a soluble VEGF receptor fusion protein (e.g., EYLEA® (aflibercept)), an anti-VEGF DARPin® (e.g., abicipar pegol; Molecular Partners AG/Allergan), or an anti-VEGF aptamer (e.g., MACUGEN® (pegaptanib sodium)); a platelet-derived growth factor (PDGF) antagonist, for example, an anti-PDGF antibody, an anti-PDGFR antibody (e.g., REGN2176-3), an anti-PDGF-BB pegylated aptamer (e.g., FOVISTA®; Ophthotech/Novartis), a soluble PDGFR receptor fusion protein, or a dual PDGF/VEGF antagonist (e.g., a small molecule inhibitor (e.g., DE-120 (Santen) or X-82 (TyrogeneX)) or a bispecific anti-PDGF/anti-VEGF antibody)); VISUDYNE® (verteporfin) in combination with photodynamic therapy; an antioxidant; a complement system antagonist, for example, a complement factor C5 antagonist (e.g., a small molecule inhitor (e.g., ARC-1905; Opthotech) or an anti-C5 antibody (e.g., LFG-316; Novartis), a properdin antagonist (e.g., an anti-properdin antibody, e.g., CLG-561; Alcon), or a complement factor D antagonist (e.g., an anti-complement factor D antibody, e.g., lampalizumab; Roche)); a visual cycle modifier (e.g., emixustat hydrochloride); squalamine (e.g., OHR-102; Ohr Pharmaceutical); vitamin and mineral supplements (e.g., those described in the Age-Related Eye Disease Study 1 (AREDS1; zinc and/or antioxidants) and Study 2 (AREDS2; zinc, antioxidants, lutein, zeaxanthin, and/or omega-3 fatty acids)); a cell-based therapy, for example, NT-501 (Renexus); PH-05206388 (Pfizer), huCNS-SC cell transplantation (StemCells), CNTO-2476 (Janssen), OpRegen (Cell Cure Neurosciences), or MA09-hRPE cell transplantation (Ocata Therapeutics); a tissue factor antagonist (e.g., hI-con1; Iconic Therapeutics); an alpha-adrenergic receptor agonist (e.g., brimonidine tartrate); a peptide vaccine (e.g., S-646240; Shionogi); an amyloid beta antagonist (e.g., an anti-beta amyloid monoclonal antibody, e.g., GSK-933776); an S1P antagonist (e.g., an anti-S1P antibody, e.g., iSONEP™; Lpath Inc); a ROBO4 antagonist (e.g., an anti-ROBO4 antibody, e.g., DS-7080a; Daiichi Sankyo); a lentiviral vector expressing endostatin and angiostatin (e.g., RetinoStat); and any combination thereof. In some instances, AMD therapeutic agents (including any of the preceding AMD therapeutic agents) can be co-formulated. For example, the anti-PDGFR antibody REGN2176-3 can be co-formulated with aflibercept (EYLEA®). In some instances, such a co-formulation can be administered in combination with an antibody of the invention. In some instances, the ocular disorder is AMD (e.g., wet AMD).

An antibody of the invention, or an antibody conjugate, fusion protein, and/or polymeric formulation thereof, can be administered in combination with LUCENTIS® (ranibizumab) for treatment of an ocular disorder (e.g., AMD, DME, DR, or RVO). LUCENTIS® (ranibizumab) may be administered, for example, at 0.3 mg/eye or 0.5 mg/eye by intravitreal injection, for example, every month. In some instances, the ocular disorder is AMD (e.g., wet AMD).

An antibody of the invention, or an antibody conjugate, fusion protein, and/or polymeric formulation thereof, can be administered in combination with EYLEA® (aflibercept) for treatment of an ocular disorder (e.g., AMD, DME, DR, or RVO). EYLEA® (aflibercept) may be administered, for example, at 2 mg/eye by intravitreal injection, for example, every four weeks (Q4W), or Q4W for the first three months, followed by injections once every two months for maintenance. In some instances, the ocular disorder is AMD (e.g., wet AMD).

An antibody of the invention, or an antibody conjugate, fusion protein, and/or polymeric formulation thereof, can be administered in combination with MACUGEN® (pegaptanib sodium) for treatment of an ocular disorder (e.g., AMD, DME, DR, or RVO). MACUGEN® (pegaptanib sodium) may be administered, for example, at 0.3 mg/eye by intravitreal injection every six weeks. In some instances, the ocular disorder is AMD (e.g., wet AMD).

An antibody of the invention, or an antibody conjugate, fusion protein, and/or polymeric formulation thereof, can be administered in combination with VISUDYNE® (verteporfin) in combination with photodynamic therapy for treatment of an ocular disorder (e.g., AMD, DME, DR, or RVO). VISUDYNE® can be administered, for example, by intravenous infusion at any suitable dose (e.g., 6 mg/m² of body surface area) and delivered once every three months (e.g., over 10 minutes of infusion). In some instances, the ocular disorder is AMD (e.g., wet AMD).

An antibody of the invention, or an antibody conjugate, fusion protein, and/or polymeric formulation thereof, can be administered in combination with a PDGF antagonist for treatment of an ocular disorder (e.g., AMD, DME, DR, or RVO). Exemplary PDGF antagonists which may be used in combination with an antibody of the invention include an anti-PDGF antibody, an anti-PDGFR antibody, a small molecule inhibitor (e.g., squalamine), an anti-PDGF-B pegylated aptamer such as FOVISTA® (E10030; Ophthotech/Novartis), or a dual PDGF/VEGF antagonist (e.g., a small molecule inhibitor (e.g., DE-120 (Santen) or X-82 (TyrogeneX)) or a bispecific anti-PDGF/anti-VEGF antibody). For example, FOVISTA® can be administered as an adjunct therapy to an antibody of the invention. FOVISTA® can be administered at any suitable dose, for example, from 0.1 mg/eye to 2.5 mg/eye, e.g., at 0.3 mg/eye or 1.5 mg/eye, for example, by intravitreal injection, for example every four weeks (Q4W). OHR-102 (squalamine lactate ophalmic solution, 0.2%) can be administered by eye drop, for example, twice daily. OHR-102 can be administered in combination with VEGF antagonists such as LUCENTIS® or EYLEA®. In some embodiments, an antibody of the invention can be administered in combination with OHR-102, LUCENTIS®, and/or EYLEA®. In some instances, the ocular disorder is AMD (e.g., wet AMD).

An antibody of the invention, or an antibody conjugate, fusion protein, and/or polymeric formulation thereof, can be administered in combination with RTH-258 for treatment of an ocular disorder (e.g., AMD, DME, DR, or RVO). RTH-258 can be administered, for example, by intravitreal injection or eye infusion. For intravitreal injection, RTH-258 can be administered at any suitable dose (e.g., 3 mg/eye or 6 mg/eye), for example, once every four weeks (Q4W) for the first three months as loading, followed by injection every 12 weeks (Q12W) or every eight weeks (Q8W) for maintenance. In some instances, the ocular disorder is AMD (e.g., wet AMD).

An antibody of the invention, or an antibody conjugate, fusion protein, and/or polymeric formulation thereof, can be administered in combination with abicipar pegol for treatment of an ocular disorder (e.g., AMD, DME, DR, or RVO). Abicipar pegol can be administered, for example, by intravitreal injection. Abicipar pegol can be administered at any suitable dose (e.g., 1 mg/eye, 2 mg/eye, 3 mg/eye, 4 mg/eye, or 4.2 mg/eye), for example, once every four weeks (Q4W) for the first three months as loading, followed by injection every 12 weeks (Q12W) or every eight weeks (Q8W) for maintenance. In some instances, the ocular disorder is AMD (e.g., wet AMD).

Any suitable DME and/or DR therapeutic agent can be administered in combination with an antibody of the invention, or an antibody conjugate, fusion protein, and/or polymeric formulation thereof, for treatment of an ocular disorder (e.g., AMD, DME, DR, or RVO), including, but not limited, to a VEGF antagonist (e.g., LUCENTIS® or EYLEA®), a corticosteroid (e.g., a corticosteroid implant (e.g., OZURDEX® (dexamethasone intravitreal implant) or ILUVIEN® (fluocinolone acetonide intravitreal implant)) or a corticosteroid formulated for administration by intravitreal injection (e.g., triamcinolone acetonide)), or combinations thereof. In some instances, the ocular disorder is DME and/or DR.

An antibody of the invention, or an antibody conjugate, fusion protein, and/or polymeric formulation thereof, can be administered in combination with LUCENTIS® (ranibizumab) for treatment of DME and/or DR (e.g., NPDR or PDR). LUCENTIS® (ranibizumab) may be administered, for example, at 0.3 mg/eye or 0.5 mg/eye by intravitreal injection, for example, every four weeks (Q4W).

An antibody of the invention, or an antibody conjugate, fusion protein, and/or polymeric formulation thereof, can be administered in combination with EYLEA® (aflibercept) for treatment of DME and/or DR (e.g., NPDR or PDR). EYLEA® (aflibercept) may be administered, for example, at 2 mg/eye by intravitreal injection, for example, every four weeks (Q4W), or Q4W for the first five months, followed by injections once every eight weeks (Q8W) for maintenance.

An antibody of the invention, or an antibody conjugate, fusion protein, and/or polymeric formulation thereof, can be administered in combination with OZURDEX® (dexamethasone intravitreal implant) for treatment of DME and/or DR. OZURDEX® can be administered as a 0.7 mg dexamethasone intravitreal implant, which can be administered up to every six months.

An antibody of the invention, or an antibody conjugate, fusion protein, and/or polymeric formulation thereof, can be administered in combination with ILUVIEN® (dexamethasone intravitreal implant) for treatment of DME and/or DR. OZURDEX® can be administered as a 0.19 mg fluocinolone acetonide intravitreal implant, which can be eluted at a rate of 0.25 µg/day, and can last up to about 36 months.

In some cases, the TAO/PRN treatment regimen or TAE treatment regimen may be used to administer an AMD therapeutic agent (e.g., ranibizumab or aflibercept) in combination with an antibody of the invention, or an antibody conjugate, fusion protein, and/or polymeric formulation thereof. For the TAO/PRN regimen, following initial intravitreal injections every four weeks (Q4W) (typically for about 3 months), the subject is monitored monthly or every other month (or at even longer intervals), with injections administered in the event of evidence of disease activity (e.g., a decline in visual acuity or fluid on optical coherence tomography (OCT)). For the TAE regimen, a subject may be treated every four weeks (Q4W), followed by extending the interval of treatment by a fixed number of weeks (e.g., +2 weeks) for each subsequent visit up to a maximal interval (e.g., every 6 weeks, ever 8 weeks, every 10 weeks, or every 12 weeks). The eye(s) may be observed and treated at each visit, even if there is no evidence of disease activity. If the macula appears wet (e.g., by OCT), the interval for injections can be shortened (e.g., −2 weeks) until the macula appears dry again. In some instances, the ocular disorder is AMD (e.g., wet AMD).

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-VEGF antibody, antibody conjugate, fusion protein, or polymeric formulation and administration of an additional therapeutic agent occur within about one, two, three, four, or five months, or within about one, two or three weeks, or within about one, two, three, four, five, or six days, of each other. Antibodies, antibody conjugates, fusion proteins, and polymeric formulations of the invention can also be used in combination with radiation therapy.

An antibody, antibody conjugate, fusion protein, or polymeric formulation of the invention (and any additional therapeutic agent) for prevention or treatment of an ocular disease or condition can be administered by any suitable means, including but not limited to, for example, ocular, intraocular, and/or intravitreal injection, and/or juxtascleral injection, and/or subtenon injection, and/or superchoroidal injection, and/or topical administration in the form of eye drops and/or ointment. Such antibodies, antibody conjugates, fusion proteins, or polymeric formulations of the invention may be delivered by a variety of methods, for example, intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a mini pump and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). Additional approaches which may be used are described in Section K below.

Formulations for ocular, intraocular, or intravitreal administration can be prepared by methods and using excipients known in the art. An important feature for efficient treatment is proper penetration through the eye. Unlike diseases of the front of the eye, where drugs can be delivered topically, retinal diseases typically benefit from a more site-specific approach. Eye drops and ointments rarely penetrate the back of the eye, and the blood-ocular barrier hinders penetration of systemically administered drugs into ocular tissue. Accordingly, a method of choice for drug delivery to treat retinal disease, such as AMD and CNV, is typically direct intravitreal injection. Intravitreal injections are usually repeated at intervals which depend on the patient's condition, and the properties and half-life of the drug delivered. Additional approaches which may be used are described in Section K below.

The amount of antibody, antibody variant thereof, antibody conjugate, fusion protein, or polymeric formulation thereof which will be effective in the treatment of a particular ocular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans.

Additional suitable administration means include parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein. In some instances, an anti-VEGF antibody, antibody conjugate, fusion protein, or polymeric formulation of the invention may be administered intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, intraperitoneally, peritoneally, intraventricularly, subcutaneously, subconjunctivally, intravesicularly, mucosally, intrapericardially, intraumbilically, intraorbitally, orally, topically, transdermally, by inhalation, by injection, by implantation, by infusion, by continuous infusion, by localized perfusion bathing target cells directly, by catheter, by lavage, in cremes, or in lipid compositions For the prevention or treatment of disease, the appropriate dosage of an antibody, antibody conjugate, fusion protein, or polymeric formulation of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody, antibody conjugate, fusion protein, or polymeric formulation is suitably administered to the patient at one time or over a series of treatments. Depending on the type and severity of the disease, about 1 μg/kg to 15 mg/kg (e.g., 0.1 mg/kg, 0.2 mg/kg, 0.4 mg/kg, 0.6 mg/kg, 0.8 mg/kg, 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg) of antibody can be an initial candidate dosage for administration to the patient, whether, for example, by one or more separate administrations, or by continuous infusion. In some embodiments, the antibody used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be a separate administration of one or more of the therapeutic agents described above.

It is understood that any of the above formulations or therapeutic methods may be carried out using an immunoconjugate of the invention in place of or in addition to an anti-VEGF antibody.

It is understood that any of the above formulations or therapeutic methods may be carried out using an antibody conjugate, fusion protein, or polymeric formulation of the invention (e.g., any described herein, e.g., in Section K below) in place of or in addition to an anti-VEGF antibody.

I. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of, or in addition to, an anti-VEGF antibody.

It is understood that any of the above articles of manufacture may include an antibody conjugate, fusion protein, or polymeric formulation of the invention in place of, or in addition to, an anti-VEGF antibody.

J. Methods of Identifying Antibody Variants and Improving Antibodies

The invention provides methods of improving antibodies and identifying antibody variants. In some instances, the methods involve identifying one or more amino acid residue alterations that confers enhanced binding of an antibody to a target molecule. In some instances, the methods involve identifying one or more amino acid residue alterations that confers enhanced stability (e.g., thermal stability), functional expression, and/or protein folding of an antibody. In some instances, the invention provides methods of improving the binding affinity of an antibody to a target molecule. In some instances, the invention provides methods of improving the stability (e.g., thermal stability), functional expression, and/or protein folding of an antibody. In some instances, the invention provides methods of improving the binding affinity of an antibody to a target molecule and improving the stability (e.g., thermal stability) of the antibody.

For example, the invention provides methods of identifying an amino acid residue alteration that confers enhanced binding of an antibody to a target molecule that involve one or more (e.g., 1, 2, or 3) of the following steps: (a) providing a display library comprising nucleic acids encoding candidate antibody variants, wherein each candidate antibody variant comprises an amino acid residue alteration in the VH or the VL compared to a reference antibody, and wherein amino acid residue alterations at every position of the VH or VL are present in the display library; (b) sorting the display library based on binding of the candidate antibody variants to the target molecule to form a sorted library, wherein the sorted library comprises candidate antibody variants with enhanced binding to the target molecule compared to the reference antibody; and (c) comparing the frequency at which each amino acid residue alteration is present in the display library and in the sorted library as determined by massively parallel sequencing, thereby determining whether each amino acid residue alteration is enriched in the sorted library compared to the display library, whereby the amino acid residue alteration is identified as conferring enhanced binding to the target molecule if it is enriched in the sorted library compared to the display library. In some instances, the method further includes identifying an amino acid residue that confers enhanced stability to the antibody, for example, as described below.

In another example, the invention provides methods of identifying an amino acid residue alteration that confers enhanced stability to an antibody that involve one or more (e.g., 1, 2, or 3) of the following steps: (a) providing a display library comprising nucleic acids encoding candidate antibody variants, wherein each candidate antibody variant comprises an amino acid residue alteration in the VH or the VL compared to a reference antibody, and wherein amino acid residue alterations at every position of the VH or VL are present in the display library; (b) sorting the display library based on binding of the candidate antibody variants to the target molecule to form a sorted library, wherein the sorted library comprises candidate antibody variants with enhanced stability compared to the reference antibody; and (c) comparing the frequency at which each amino acid residue alteration is present in the display library and in the sorted library as determined by massively parallel sequencing, thereby determining whether each amino acid residue alteration is enriched in the sorted library compared to the display library, whereby the amino acid residue alteration is identified as conferring enhanced stability to the antibody if it is enriched in the sorted library compared to the display library. In some instances, the method further includes identifying an amino acid residue that confers enhanced binding of an antibody to a target molecule, for example, as described above.

Any of the preceding methods may further include determining the frequency at which each amino acid alteration is present in the display library and the sorted library by massively parallel sequencing following step (b).

In some instances, an amino acid residue alteration may be enriched at least 2-fold in the sorted library compared to the display library. For example, an amino acid residue alteration may be enriched 1.25-fold, 1.5-fold, 2-fold, 3-fold, 4-fold, 5-fold, 6-fold, 7-fold, 8-fold, 9-fold, 10-fold, 11-fold, 12-fold, 14-fold, 16-fold, or more in the sorted library compared to the display library.

A display library may include any suitable number of antibody variants, for example, from about $1\times10^3$ to about $1\times10^{12}$ or more (e.g., about $1\times10^3$, about $1\times10^4$, about $1\times10^5$, about $1\times10^6$, about $1\times10^7$, about $1.5\times10^7$, about $2.5\times10^7$, about $1\times10^8$, about $5\times10^8$, about $1\times10^9$, about $5\times10^9$, about $1\times10^{10}$, about $1\times10^{11}$, about $1\times10^{12}$ or more) antibody variants. In some embodiments, the display library may include about $3\times10^9$ antibody variants. In other embodiments, the display library may include about $8\times10^8$ antibody variants.

In any of the preceding methods, an amino acid residue alteration may be encoded by any suitable codon set. For example, in some instances, the amino acid residue alteration is encoded by a degenerate codon set. Methods of substituting an amino acid of choice into a template nucleic acid are well established in the art, some of which are described herein. See also U.S. Pat. No. 7,985,840, which is incorporated herein by reference in its entirety. For example, libraries as described above or in the Examples section below can be created by amino acid substitution with variant amino acids using the Kunkel method. See, for example, Kunkel et al., *Methods Enzymol.* 154:367-382, 1987.

An amino acid residue alteration may be encoded by any suitable codon set. A codon set is a set of different nucleotide triplet sequences used to encode desired variant amino acids. Codon sets can be represented using symbols to designate particular nucleotides or equimolar mixtures of nucleotides as shown in below according to the IUB code.

IUB CODES
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

As an illustrative example, in the codon set DVK, D can be nucleotides A or G or T; V can be A or G or C; and K can be G or T. This codon set can present 18 different codons and can encode amino acids Ala, Trp, Tyr, Lys, Thr, Asn, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In any of the preceding methods, a degenerate codon set may be used to encode amino acid residue alterations. In some instances, the degenerate codon set is an NNK or an NNS codon set, wherein N is A, C, G, or T; K is G or T; and S is C or G. In particular instances, the degenerate codon set is an NNK codon set.

It is to be understood that any suitable display approach known in the art or described herein may be used in conjunction with any of the preceding methods. For example, the methods may involve phage display, bacterial display, yeast display, mammalian display, ribosome display, and/or mRNA display. In any of the preceding methods, any suitable display library may be used. For example, the display library may be selected from the group consisting of a phage display library, a bacterial display library, a yeast display library, a mammalian display library, a ribosome display library, and an mRNA display library. In particular embodiments, the display library is a phage display library.

Fusion polypeptides of an antibody variable domain can be displayed on the surface of a cell, virus, phagemid, or other particle in a variety of formats. These formats include, for example, scFv, Fab, and multivalent forms of these fragments. The multivalent forms may be a dimer of ScFv, Fab, or Fab', herein referred to as $(ScFv)_2$, $Fab_2$ and $F(ab')_2$, respectively. Methods for displaying fusion polypeptides comprising antibody fragments, on the surface of bacteriophage, are well known in the art, for example as described in patent publication number WO 92/01047 and herein. Other patent publications, for example, WO 92/20791; WO 93/06213; WO 93/11236, and WO 93/19172, describe related methods. Other publications have shown the identification of antibodies with artificially rearranged V gene repertoires against a variety of antigens displayed on the surface of phage (see, e.g., Hoogenboom et al., *J. Mol. Biol.* 227: 381-388, 1992; and as disclosed in WO 93/06213 and WO 93/11236).

In any of the preceding methods, the display library may be sorted (selected) and/or screened to identify, for example, high-affinity binders to an antigen. Sorting may be performed as described herein or by other approaches known in the art. See, for example, U.S. Pat. No. 7,985,840. In some embodiments, sorting may involve contacting the display library with an immobilized antigen (e.g., target molecule or epitope thereof). In other embodiments, sorting may involve contacting the display library with a soluble antigen. Antibody variants that have been selected can be further screened to characterize the antibody variant in terms of binding affinity (e.g., by SPR), stability, folding, structure (e.g., by X-ray crystallography), or other attributes.

Any of the preceding methods may involve massively parallel sequencing, for example, to determine the frequency that an amino acid residue alteration appears in a library following sorting (referred to as a sorted library) as compared to the frequency that the amino acid residue alteration appears in an unsorted library. A wide variety of approaches for massively parallel sequencing are known in the art, and any suitable approach may be used in the methods of the invention. See, for example, Metzker, *Nature Reviews Genetics* 11: 31-36, 2010, which is incorporated by reference herein in its entirety. Exemplary approaches include massively parallel signature sequencing (MPSS), polony sequencing, pyrosequencing (454/Roche Diagnostics), ion semiconductor sequencing, single-molecule real-time sequencing, sequencing by synthesis, sequencing by ligation. Commercially-available massively parallel sequencing platforms are available from Roche Diagnostics and other companies. The sequencing may be deep sequencing, ultra-deep sequencing, and/or next-generation sequencing.

In any of the preceding methods, the method may involve determining the sequence of at least about 100,000 reads or more (e.g., 100,000 reads; 200,000 reads; 300,000 reads; 400,000 reads; 500,000 reads; 600,000 reads; 700,000 reads; 800,000 reads; 900,000 reads; 1,000,000 reads; $2\times10^6$ reads; $3\times10^6$ reads; $4\times10^6$ reads; $5\times10^6$ reads; $6\times10^6$ reads; $7\times10^6$ reads; $8\times10^6$ reads; $9\times10^6$ reads; $10^7$ reads; $10^8$ reads; 109 reads; or $10^{10}$ reads or more). The method may involve sequencing at any suitable depth.

In any of the preceding methods, the antibody may be a monoclonal antibody. In any of the preceding methods, the antibody may be an IgG antibody. In any of the preceding methods, the antibody may be an antibody fragment. The antibody fragment may be selected from the group consisting of Fab, scFv, Fv, Fab', Fab-C, Fab'-SH, F(ab')$_2$, and diabody. In particular instances, the antibody fragment is a Fab.

In any of the preceding methods, the dual-specific antibody may be a monoclonal antibody. In any of the preceding methods, the dual-specific antibody may be an IgG antibody. In any of the preceding methods, the dual-specific antibody may be an antibody fragment. The antibody fragment may be selected from the group consisting of Fab, scFv, Fv, Fab-C, Fab', Fab'-SH, F(ab')$_2$, and diabody. In particular instances, the antibody fragment is a Fab.

Any of the preceding methods may further involve generating an antibody that has been identified by the steps of the method. The methods described above may be used with any of the antibodies described herein.

K. Ocular Long-Acting Delivery Approaches for Anti-VEGF Antibodies

The invention provides compositions for treatment of ocular disorders, which may be used for long-acting delivery of anti-VEGF antibodies (including any anti-VEGF antibody described herein, such as G6.31 AARR) to the eye. For example, the invention provides antibody conjugates that include an anti-VEGF antibody described herein (e.g., Fab or Fab-C antibody conjugates). The invention also provides fusion proteins (e.g., Fab fusion proteins). In other aspects, the invention provides formulations (e.g., polymeric formulations) that include an anti-VEGF antibody described herein. The invention also provides devices that can be used for ocular administration of an anti-VEGF antibody described herein. The invention further provides pharmaceutical compositions that include antibody conjugates, fusion proteins, and/or formulations (e.g., polymeric formulations) described herein. These compositions can be used in any of the therapeutic methods described herein, for example, methods of treating an ocular disorder (e.g., AMD (e.g., wet AMD), DME, DR (e.g., NPDR or PDR), or RVO (e.g., CRVO or BRVO)).

1. Antibody Conjugates

The invention provides antibody conjugates that include an anti-VEGF antibody and a polymer covalently attached to the antibody. The anti-VEGF antibody may be covalently attached to the polymer in an irreversible fashion or a reversible fashion. Any suitable polymer may be used, including those described herein or others known in the art. The polymer may be a hydrophilic polymer or a hydrophobic polymer. It is to be understood that a hydrophilic polymer may be a water-soluble polymer. Any suitable hydrophilic polymer may be used, for example, a hydrophilic polymer described in International Patent Application Publication No. WO 2011/066417 and/or Pelegri-O'Day et al. *J. Am. Chem. Soc.* 136:14323-14332, 2014, which are incorporated herein by reference in their entirety. Exemplary, non-limiting hydrophilic polymers that can be used include hyaluronic acid (HA), polyethylene glycol (PEG; also known as poly(ethylene glycol)) (e.g., straight-chain PEG, branched PEG, comb-like PEG, and dendritic PEG), poly[ethylene oxide)-co-(methylene ethylene oxide)], poly (poly(ethylene glycol) methyl ether methacrylate) (pPEGMA), agarose, alginate, carageenans, carboxymethylcellulose, cellulose, cellulose derivatives, chitosan, chondroitin sulfate, collagen, dermatan sulfate, dextran, dextran sulfate, fibrin, fibrinogen, fibronectin, fucoidan, gelatin, glycosaminoglycans (GAGs), a glycopolymer, heparin, heparin sulfate, a highly-branched polysaccharide (e.g., a galactose dendrimer), keratan sulfate, methyl cellulose, hydroxypropylmethylcellulose (HPMC), poly(N-(2-hydroxypropyl) methacrylamide) (pHPMA), pectins, pectin derivatives, pentosane polysulfate, starch, hydroxylethyl starch (HES), styrene, vitronectin, poly(acrylic acid), poly(methacrylic acid), poly(acrylamide), poly(acrylic acid), poly(amines), poly(amino acids), poly(carboxybetaine) (PCB), polyelectrolytes, poly(glutamic acid) (PGA), poly(glycerol) (PG) (e.g., linear, midfunctional, hyperbranched, or linear hyperbranched PG), poly(maleic acid), poly(2-oxazoline) (POZ), poly(2-ethyl-2-oxazoline, polysialic acid (PSA), polystyrene, polystyrene derivatives (e.g., charged polystyrene derivatives), poly(styrenesulfonate-co-PEGMA), polyvinylpyrrolidone (PVP), poly(N-acryloylmorpholine) (pNAcM), and copolymers thereof. In some instances, the polymer is a hydrophobic polymer, for example, poly(lactic-co-glycolic acid) (PLGA), polylactide (PLA), and polyglycolide (PGA). The polymer may be biodegradable and/or biocompatible.

By way of example, the polymer may include any suitable number of monomers, for example, between 2 and about $1\times10^4$ monomers (e.g., about 10, about 50, 100, about 200, about 300, about 400, about 500, about 600, about 700, about 800, about 900, about 1000, about 2000, about 3000, about 4000, about 5000, about 6000, about 7000, about 8000, about 9000, or about $1\times10^4$ monomers), or more. For example, the polymer may include between about 50 and about 250 monomers, about 50 and about 500 monomers, between about 50 and about 1000 monomers, between about 50 and about 2000 monomers, between about 50 and about 3000 monomers, between about 50 and about 4000 monomers, between about 50 and about 5000 monomers, between about 50 and about 6000 monomers, between about 50 and about 7000 monomers, between about 50 and about 8000 monomers, between about 50 and about 9000 monomers, between about 50 and about 10000 monomers, between about 100 and about 250 monomers, about 100 and about 500 monomers, between about 100 and about 1000 monomers, between about 100 and about 2000 monomers, between about 100 and about 3000 monomers, between about 100 and about 4000 monomers, between about 100 and about 5000 monomers, between about 100 and about 6000 monomers, between about 100 and about 7000 monomers, between about 100 and about 8000 monomers, between about 100 and about 9000 monomers, between about 100 and about 10000 monomers, between about 250 and about 500 monomers, between about 250 and about 1000 monomers, between about 250 and about 2000 monomers, between about 250 and about 3000 monomers, between about 250 and about 4000 monomers, between about 250 and about 5000 monomers, between about 250 and about 6000 monomers, between about 250 and about 7000 monomers, between about 250 and about 8000 monomers, between about 250 and about 9000 monomers, between about 250 and about 10000 monomers. between about 500 and about 1000 monomers, between about 500 and about 2000 monomers, between about 500 and about 3000 monomers, between about 500 and about 4000 monomers, between about 500 and about 5000 monomers, between about 500 and about 6000 monomers, between about 500 and about 7000 monomers, between about 500 and about 8000 monomers, between about 500 and about 9000 monomers, or between about 500 and about 10000 monomers. In some instances, the polymer may include about 500 monomers.

The invention provides an antibody conjugate that includes an anti-VEGF antibody (e.g., an anti-VEGF antibody described herein, such as G6.31 AARR) covalently attached to a HA polymer. Such antibody conjugates are sometimes referred to herein as "HA conjugates." In some instances, the HA polymer has a molecular weight of about 2.5 megadalton (MDa) or lower (e.g., about 2.5 MDa or lower, about 2.4 MDa or lower, about 2.3 MDa or lower, about 2.2. MDa or lower, about 2.1 MDa or lower, about 2.0 MDa or lower, about 1.9 MDa or lower, about 1.8 MDa or lower, about 1.7 MDa or lower, about 1.6 MDa or lower, about 1.5 MDa or lower, about 1.4 MDa or lower, about 1.3 MDa or lower, about 1.2 MDa or lower, about 1.1 MDa or lower, about 1.0 MDa or lower, about 900 kDa or lower, about 800 kDa or lower, about 700 kDa or lower, about 600 kDa or lower, about 500 kDa or lower, about 400 kDa or lower, about 300 kDa or lower, about 200 kDa or lower, or about 100 kDa or lower). In some instances, the HA polymer has a molecular weight of about 1 MDa or lower (e.g., about 1.0 MDa or lower, about 900 kDa or lower, about 800 kDa or lower, about 700 kDa or lower, about 600 kDa or lower, about 500 kDa or lower, about 400 kDa or lower, about 300 kDa or lower, about 200 kDa or lower, or about 100 kDa or lower). In some instances, the HA polymer has a molecular weight between about 25 kDa and about 2.5 MDa (e.g., between about 25 kDa and about 2.5 mDa, between about 25 kDa and about 2 MDa, between about 25 kDa and about 1.5 MDa, between about kDa and about 1 MDa, between about 25 kDa and about 900 kDa, between about 25 kDa and about 800 kDa, between about 25 kDa and about 700 kDa, between about 25 kDa and about 600 kDa, between about kDa and about 500 kDa, between about 100 kDa and about 2.5 mDa, between about 100 kDa and about 2 MDa, between about 100 kDa and about 1.5 MDa, between about 100 kDa and about 1 MDa, between about 100 kDa and about 900 kDa, between about 100 kDa and about 800 kDa, between about 100 kDa and about 700 kDa, between about 100 kDa and about 600 kDa, between about 100 kDa and about 500 kDa, between about 250 kDa and about 2.5 MDa, between about 250 kDa and about 2 MDa, between about 250 kDa and about 1.5 MDa, between about 250 kDa and about 1 MDa, between about 250 kDa and about 900 kDa, between about 250 kDa and about 800 kDa, between about 250 kDa and about 700 kDa, between about 250 kDa and about 600 kDa, between about 250 kDa and about 500 kDa, between about 500 kDa and about 2.5 MDa, between about 500 kDa and about 2 MDa, between about 500 kDa and about 1.5 MDa, between about 500 kDa and about 1 MDa, between about 500 kDa and about 900 kDa, between about 500 kDa and about 800 kDa, between about 500 kDa and about 700 kDa, between about 500 kDa and about 600 kDa, between about 1 MDa and about 2.5 MDa, between about 1 MDa and about 2 MDa, between about 1 MDa and about 1.5 MDa, between about 1 MDa and about 1.25 MDa, between about 1.25 MDa and about 2.5 MDa, between about 1.25 MDa and about 2 MDa, between about 1.25 MDa and about 1.5 MDa, between about 1.5 MDa and about 2.5 MDa, between about 1.5 MDa and about 2 MDa, between about 1.5 MDa and about 1.75 MDa, or between 1.75 MDa and about 2.5 MDa).

In some instances, the HA polymer has a molecular weight between about 25 kDa and about 500 kDa (e.g., between about 25 kDa and about 500 kDa, between about 25 kDa and about 450 kDa, between about 25 kDa and about 400 kDa, between about 25 kDa and about 350 kDa, between about 25 kDa and about 300 kDa, between about 25 kDa and about 300 kDa, between about 25 kDa and about 250 kDa, between about 25 kDa and about 200 kDa, between about 25 kDa and about 150 kDa, between about 25 kDa and about 100 kDa, between about 25 kDa and about 50 kDa, between about 40 kDa and about 500 kDa, between about 40 kDa and about 450 kDa, between about 40 kDa and about 400 kDa, between about 40 kDa and about 350 kDa, between about 40 kDa and about 300 kDa, between about 40 kDa and about 300 kDa, between about 40 kDa and about 250 kDa, between about 40 kDa and about 200 kDa, between about kDa and about 150 kDa, between about 40 kDa and about 100 kDa, between about 40 kDa and about 50 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 300 kDa, between about 50 kDa and about 250 kDa, between about 50 kDa and about 200 kDa, between about 50 kDa and about 150 kDa, between about 50 kDa and about 100 kDa, between about 50 kDa and about 75 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 100 kDa and about 300 kDa, between about 100 kDa and about 250 kDa, between about 100 kDa and about 200 kDa, between about 100 kDa and about 150 kDa, between about 150 kDa and about 500 kDa, between about 150 kDa and about 450 kDa, between about 150 kDa and about 400 kDa, between about 150 kDa and about 350 kDa, between about 150 kDa and about 300 kDa, between about 150 kDa and about 300 kDa, between about 150 kDa and about 250 kDa, between about 150 kDa and about 200 kDa, between about 175 kDa and about 500 kDa, between about 175 kDa and about 450 kDa, between about 175 kDa and about 400 kDa, between about 175 kDa and about 350 kDa, between about 175 kDa and about 300 kDa, between about 175 kDa and about 300 kDa, between 175 200 kDa and about 250 kDa, between about 175 kDa and about 225 kDa, between about 200 kDa and about 500 kDa, between about 200 kDa and about 450 kDa, between about 200 kDa and about 400 kDa, between about 200 kDa and about 350 kDa, between about 200 kDa and about 300 kDa, between about 200 kDa and about 300 kDa, between about 200 kDa and about 250 kDa, or between about 200 kDa and about 225 kDa).

In some instances, the HA polymer has a molecular weight between about 100 kDa and about 250 kDa (e.g., about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, or about 250 kDa). In particular instances, the HA polymer has a molecular weight of about 200 kDa.

Any of the preceding molecular weights may be a weight-average molecular weight (also known as weight-average molar mass).

In some instances, any of the preceding HA polymers is linear, i.e., not cross-linked.

In other instances, the invention provides an antibody conjugate that includes an anti-VEGF antibody (e.g., an anti-VEGF antibody described herein) covalently attached to a PEG polymer. Such antibody conjugates are sometimes referred to as "PEG conjugates" herein. Any suitable PEG polymer may be used. The PEG may be a branched PEG, a star PEG, or a comb PEG. The PEG polymer may be, for example, a PEG tetramer, a PEG hexamer, or a PEG octamer. In some instances, the antibody conjugate includes an anti-VEGF antibody (e.g., an anti-VEGF antibody described herein, such as G6.31 AARR) covalently attached to a PEG dendrimer. PEG polymers are commercially available, for example, from JenKem Technology, Quanta BioDesign, NOF America Corporation, and other vendors.

In some instances, the PEG polymer has a molecular weight between about 1 kDa and about 500 kDa (e.g., between about 1 kDa and about 500 kDa, between about 1 kDa and about 450 kDa, between about 1 kDa and about 400 kDa, between about 1 kDa and about 350 kDa, between about 1 kDa and about 300 kDa, between about 1 kDa and about 300 kDa, between about 1 kDa and about 250 kDa, between about 1 kDa and about 200 kDa, between about 1 kDa and about 150 kDa, between about 1 kDa and about 100 kDa, between about 1 kDa and about 50 kDa, between about 10 kDa and about 500 kDa, between about 10 kDa and about 450 kDa, between about 10 kDa and about 400 kDa, between about 10 kDa and about 350 kDa, between about 10 kDa and about 300 kDa, between about 10 kDa and about 300 kDa, between about kDa and about 250 kDa, between about 10 kDa and about 200 kDa, between about 10 kDa and about 150 kDa, between about 10 kDa and about 100 kDa, between about 10 kDa and about 50 kDa, between about 20 kDa and about 500 kDa, between about 20 kDa and about 450 kDa, between about 20 kDa and about 400 kDa, between about 20 kDa and about 350 kDa, between about 20 kDa and about 300 kDa, between about kDa and about 300 kDa, between about 20 kDa and about 250 kDa, between about 20 kDa and about 200 kDa, between about 20 kDa and about 150 kDa, between about 20 kDa and about 100 kDa, between about kDa and about 75 kDa, between about 30 kDa and about 500 kDa, between about 30 kDa and about 450 kDa, between about 30 kDa and about 400 kDa, between about 30 kDa and about 350 kDa, between about kDa and about 300 kDa, between about 30 kDa and about 300 kDa, between about 30 kDa and about 250 kDa, between about 30 kDa and about 200 kDa, between about 30 kDa and about 150 kDa, between about kDa and about 500 kDa, between about 40 kDa and about 450 kDa, between about 40 kDa and about 400 kDa, between about 40 kDa and about 350 kDa, between about 40 kDa and about 300 kDa, between about kDa and about 300 kDa, between about 40 kDa and about 250 kDa, between about 40 kDa and about 200 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 300 kDa, between 50 200 kDa and about 250 kDa, or between about 50 kDa and about 225 kDa).

In some instances, the PEG polymer has a molecular weight between about 5 kDa and about 250 kDa (e.g., about 1 kDa, about 5 kDa, about 10 kDa, about 15 kDa, about 20 kDa, about 25 kDa, about 30 kDa, about 35 kDa, about 40 kDa, about 50 kDa, about 60 kDa, about 70 kDa, about 80 kDa, about 90 kDa, 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, or about 250 kDa). In particular instances, the PEG polymer has a molecular weight of about 20 kDa. In other instances, the PEG polymer has a molecular weight of about 40 kDa.

Any of the preceding molecular weights may be a weight-average molecular weight (also known as weight-average molar mass).

In some instances, the PEG polymer is a PEG tetramer. PEG tetramers are commercially available, for example, NOF America SUNBRIGHT® PTE-400MA, PTE-200MA, PTE-100MA, and JenKem Technology USA 4 arm PEG maleimide (Cat. No. 4ARM-MAL). In some instances, the PEG tetramer has a pentaerythritol core. For example, in some instances, the PEG tetramer includes a structure of formula (I), wherein n is independently any suitable integer:

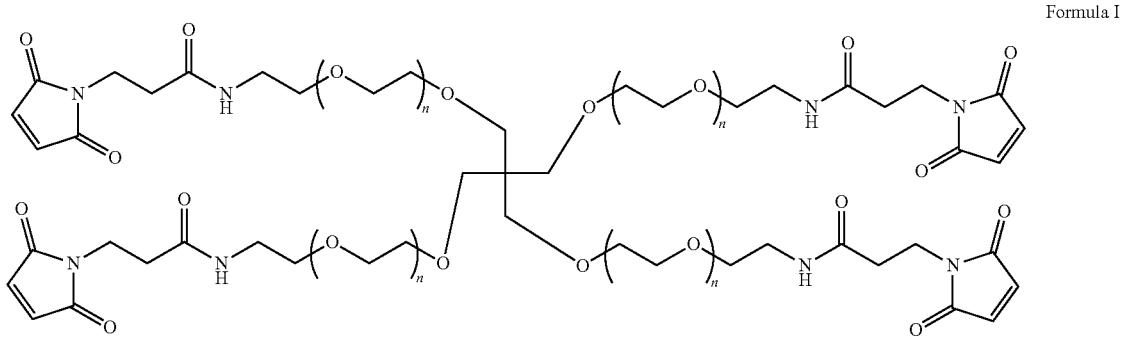

Formula I

In another example, in some instances, the PEG polymer is a PEG hexamer. PEG hexamers are commercially available, for example, JenKem Technology USA 6 arm PEG amine (Cat. No. 6ARM(DP)-NH2HCl), or PEG hexamers from Quanta BioDesign. In some instances, the PEG hexamer includes a dipentylerythritol core.

In some instances, the PEG polymer is a PEG octamer. PEG octamers are commercially available, for example, NOF America SUNBRIGHT® HGEO series or JenKem Technology USA 8 arm PEG maleimide (Cat. No. 8ARM (TP)-MAL). In some instances, the PEG octamer may include a tripentaerithritol core. For example, in some instances, the PEG octamer includes a structure of formula (II), wherein n is independently any suitable integer:

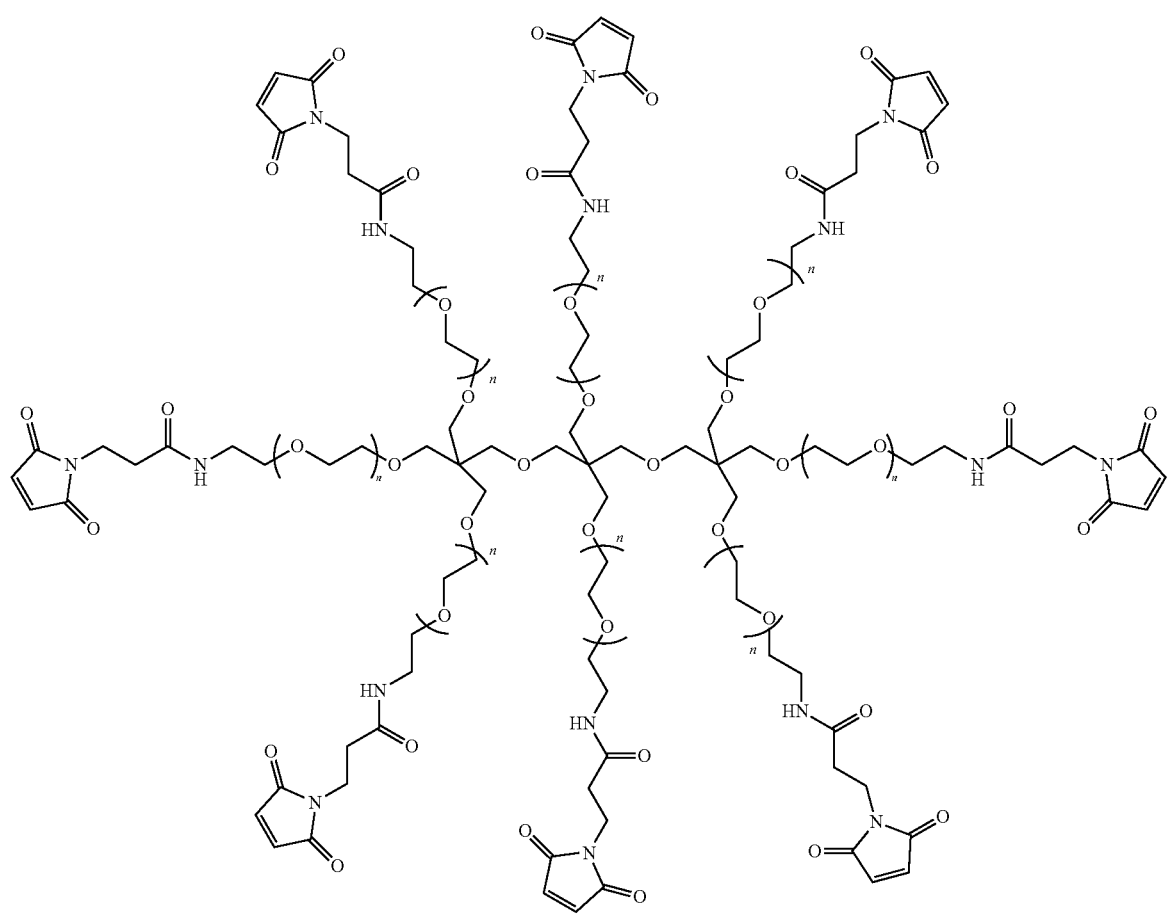

Formula II

In yet another example, in some instances, the PEG octamer includes a tripentaerythritol core.

It is to be understood that any suitable conjugation approach, including those described herein and others known in the art, may be used to conjugate an anti-VEGF antibody of the invention to a polymer. For example, the polymer may be conjugated to any suitable protein functional group, including a primary amine group, a carboxyl group, a sulfhydryl group, or a carbonyl group. Any suitable chemical reactive group may be used to target the protein functional group, for example, carbodiimide (e.g., EDC), NHS ester, imidoester, pentafluorophenyl ester, hydroxymethyl phosphine, maleimide, haloacetyl (e.g., bromoacetyl or iodoacetyl), pyridyldisulfide, thiosulfonate, vinylsulfone, hydrazine, alkoxyamine, diazirine, aryl azide, isocyanate, or others known in the art. See, for example, Hermanson, Bioconjugate Techniques, 3rd Edition, 2013.

Any of the preceding antibody conjugates may have a hydrodynamic radius between about 5 nm and about 200 nm (e.g., about 5 nm, about 10 nm, about 20 nm, about 30 nm, about 40 nm, about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, or about 200 nm). In some instances, the antibody conjugate has a hydrodynamic radius between about 5 nm and about 150 nm (e.g., about 5 nm, about 10 nm, about 20 nm, about 30 nm, about 40 nm, about 50 nm, about 60 nm, about 70 nm, about 80 nm, about 90 nm, about 100 nm, about 110 nm, about 120 nm, about 130 nm, about 140 nm, or about 150 nm). In some instances, the antibody conjugate has a hydrodynamic radius between about 5 nm and about 100 nm (e.g., about 5 nm, about 10 nm, about 20 nm, about 30 nm, about 40 nm, about 50 nm, about 60 nm, about 70 nm, about 80 nm, about 90 nm, or about 100 nm). In some instances, the antibody conjugate has a hydrodynamic radius between about 5 nm and about 60 nm (e.g., about 5 nm, about 10 nm, about 20 nm, about 30 nm, about 40 nm, about 50 nm, or about 60 nm). In some instances, the antibody conjugate has a hydrodynamic radius between about 25 nm and about 35 nm (e.g., about 25 nm, about 26 nm, about 27 nm, about 28 nm, about 29 nm, about 30 nm, about 31 nm, about 32 nm, about 33 nm, about 34 nm, or about 35 nm). In some instances, the hydrodynamic radius is about 28 nm.

In some instances, the antibody conjugate has a hydrodynamic radius between about 10 nm and about 200 nm, between about 10 nm and about 180 nm, between about 10 nm and about 160 nm, between about 10 nm and about 140 nm, between about 10 nm and about 120 nm, between about 10 nm and about 100 nm, between about 10 nm and about 80 nm, between about 10 nm and about 60 nm, between about 10 nm and about 50 nm, between about 10 nm and about 40 nm, between about 10 nm and about 30 nm, between about 20 nm and about 200 nm, between about 20 nm and about 180 nm, between about 20 nm and about 160 nm, between about 20 nm and about 140 nm, between about 20 nm and about 120 nm, between about 20 nm and about 100 nm, between about 20 nm and about 80 nm, between about 20 nm and about 60 nm, between about 20 nm and about 50 nm, between about 20 nm and about 40 nm, between about 20 nm and about 30 nm, between about 30 nm and about 200 nm, between about 30 nm and about 180 nm, between about 30 nm and about 160 nm, between about 30 nm and about 140 nm, between about nm and about 120 nm, between about 30 nm and about 100 nm, between about 30 nm and about 80 nm, between about 30 nm and about 60 nm, between about 30 nm and about 50 nm, between about 30 nm and about 40 nm, between about 40 nm and about 200 nm, between about 40 nm and about 180 nm, between about 40 nm and about 160 nm, between about 40 nm and about 140 nm, between about 40 nm and about 120 nm, between about 40 nm and about 100 nm, between about 40 nm and about 80 nm, between about 40 nm and about 60 nm, between about 40 nm and about 50 nm, between about 50 nm and about 200 nm, between about 50 nm and about 180 nm, between about 50 nm and about 160 nm, between about 50 nm and about 140 nm, between about 50 nm and about 120 nm, between about 50 nm and about 100 nm, between about 50 nm and about 80 nm, between about 50 nm and about 60 nm, between about 60 nm and about 200 nm, between about 60 nm and about 180 nm, between about 60 nm and about 160 nm, between about 60 nm and about 140 nm, between about 60 nm and about 120 nm, between about 60 nm and about 100 nm, or between about 60 nm and about 80 nm.

In some instances, the antibody conjugate is a prodrug antibody conjugate (also referred to as a carrier-linked prodrug) in which an anti-VEGF antibody (e.g., an anti-VEGF antibody described herein, e.g., G6.31 AARR) is reversibly conjugated to a carrier (e.g., a hydrogel), for example, via a linker (e.g., a reversible prodrug linker). This approach is described further, for example, in International Patent Application Publication Nos. WO 2006/003014, WO 2009/095479, WO 2011/012715, WO 2013/053856, and WO 2014/056923, which are incorporated herein by reference in their entirety. Such prodrug antibody conjugates are commercially available from Ascendis Pharma (e.g., the TransCon technology platform). The linker may have inherent self-cleaving properties (e.g., the linker may be non-enzymatically hydrolyzed upon administration to the eye), leading to time-controlled release of the anti-VEGF antibody in the eye (e.g., vitreous).

For example, in some instances, the invention provides a prodrug antibody conjugate which includes an anti-VEGF antibody (e.g., an anti-VEGF antibody described herein, e.g., G6.31 AARR) that is covalently attached to a carrier by a linker. In particular instances, the linker is a reversible prodrug linker. In some instances, the carrier includes a polymer, for example, PEG. The PEG may be linear, branched, multi-arm, or dendritic PEG, for example. In some instances, the carrier is a hydrogel, including a biodegradable hydrogel. Any suitable hydrogel can be used, for example, a PEG-based hydrogel. A PEG-based hydrogel may include, for example, at least 10% PEG, at least 20% PEG, at least 30% PEG, or more. The hydrogel may be in the shape of microparticulate beads. Such microparticulate beads can have a diameter of about 1 μm to about 1000 μm, e.g., about 5 μm to about 500 μm, about 10 μm to about 100 μm, about 20 μm to about 100 μm, or about 20 μm to about 80 μm. Bead diameters can be measured when the microparticulate beads are suspended in an isotonic aqueous buffer. In some instances, the hydrogel may be any hydrogel disclosed in WO 2006/003014 or WO 2011/012715.

In any of the preceding antibody conjugates, the antibody may be an antibody fragment that binds VEGF, for example, an antibody fragment of an anti-VEGF antibody described herein that binds VEGF. In some instances, the antibody fragment is selected from the group consisting of Fab, Fab', Fab-C, Fab'-SH, Fv, scFv, and (Fab')$_2$ fragments. In particular instances, the antibody fragment is an Fab, an Fab', or an Fab-C. In some instances, the antibody fragment is an Fab-C.

Any of the preceding antibody conjugates may have an ocular half-life that is increased relative to a reference antibody that is not covalently attached to the polymer (e.g., the hydrophilic polymer). In some instances, the ocular half-life is increased at least about 2-fold (e.g., about 2-fold, about 3-fold, about 4-fold, about 5-fold, about 6-fold, about 7-fold, about 8-fold, about 9-fold, about 10-fold, about 12-fold, about 14-fold, about 16-fold, about 18-fold, about 20-fold, or more) relative to the reference antibody. In some instances, the ocular half-life is increased at least about 4-fold relative to the reference antibody. In some instances, the ocular half-life is a vitreal half-life. In some instances, the reference antibody is identical to the antibody of the antibody conjugate. In other cases, the reference antibody is non-identical to the antibody of the antibody conjugate.

Any of the preceding antibody conjugates may have an ocular clearance that is that is decreased relative to a reference antibody that is not covalently attached to the polymer (e.g., the hydrophilic polymer). In some instances, the clearance is decreased at least about 2-fold (e.g., about 2-fold, about 3-fold, about 4-fold, about 5-fold, about 6-fold, about 7-fold, about 8-fold, about 9-fold, about 10-fold, about 12-fold, about 14-fold, about 16-fold, about 18-fold, about 20-fold, or more) relative to the reference antibody. In some instances, the clearance is decreased at least about 4-fold relative to the reference antibody. In some instances, the clearance is clearance from the vitreous. In some instances, the reference antibody is identical to the antibody of the antibody conjugate. In other cases, the reference antibody is non-identical to the antibody of the antibody conjugate.

In some instances, the time period between two intraocular administrations (e.g., by intravitreal injection) of any of the preceding antibody conjugates (e.g., HA conjugates, PEG conjugates, and prodrug antibody conjugates) is at least 1 month, e.g., at least 1 month, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 20 weeks, at least 24 weeks, at least 28 weeks, at least 32 weeks, at least 36 weeks, at least 40 weeks, at least 44 weeks, at least 48 weeks, at least 52 weeks or more. In some cases, the maximum period between two intraocular administrations is no longer then four years, e.g., no longer than three years, no longer than two years, or no longer than one year. The antibody conjugate can be administered, for example, every two to twelve months, e.g., every four to ten months. In some instances, the antibody conjugate is administered every six months.

The invention also provides compositions (e.g., pharmaceutical compositions) that include any of the antibody conjugates described above (e.g., HA conjugates, PEG conjugates, and prodrug antibody conjugates). In certain embodiments, the composition comprises one or more additional compounds. In certain embodiments, the additional compound binds to a second biological molecule selected from the group consisting of: IL-13; IL-6; IL-6R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. In certain embodiments, the additional compound is an antibody or antigen-binding fragment thereof. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

The invention further provides compositions (e.g., pharmaceutical compositions) that include any of the antibody conjugates described above (e.g., HA conjugates, PEG conjugates, and prodrug antibody conjugates) and an additional VEGF antagonist.

2. Fusion Proteins

The invention provides fusion proteins that include an anti-VEGF antibody (e.g., any anti-VEGF antibody described herein, e.g., G6.31 AARR) and an ocular binding domain. The ocular binding domain may bind, for example, to a biological substance found in the eye (e.g., the cornea, vitreous, retina, retina pigment epithelium, or choroid), which may increase ocular (e.g., vitreal) residence time (for example, by increasing the half-life and/or decreasing clearance) of the antibody. The ocular binding domain may bind to any suitable biological substance, including, for example, an extracellular matrix component. For example, suitable biological substances in the eye (e.g., the vitreous) may include an extracellular matrix component such as a carbohydrate (e.g., a charged carbohydrate (e.g., a glycosaminoglycan)), a glycoprotein (e.g., fibrillin and opticin), and a protein (e.g., a collagen (e.g., collagen types I-XXVII, particularly collagen II, collagen IX, collagen V, collagen VI, collagen XI, and heterotypic collagen fibrils thereof), or other extracellular matrix components described, for example, in Le Goff et al., Eye 22:1214-1222, 2008. In some instances, the extracellular matrix component is a glycosaminoglycan, for example, hyaluronic acid (HA) or a proteoglycan (e.g., chondroitin sulfate or heparin sulfate). In particular instances, the glycosaminoglycan is HA. HA binding domains, as well as fusion proteins that include HA binding domains, are described, for example, in Park et al., Molecular Pharmaceutics 6(3):801-812, 2009; U.S. Pat. Nos. 5,986,052, 7,183,377, 7,723,472, and 8,846,034; U.S. Patent Application Publication No. 2004/005277; and International Patent Application Nos. WO 1998/052590, WO 2010/045506, WO 2014/099997, WO 2015/198243, WO 2015/110809, which are incorporated herein by reference in their entirety. The ocular binding domain may be covalently attached to the antibody, for example, by being recombinantly fused to the anti-VEGF antibody. In other instances, the ocular binding domain may be covalently conjugated or non-covalently conjugated (e.g., by a biotin-strepavidin linkage) to the anti-VEGF antibody.

For example, the invention provides a fusion protein that includes an anti-VEGF antibody (e.g., any anti-VEGF antibody described herein, such as G6.31 AARR) covalently attached to an HA binding domain. In some instances, the HA binding domain is covalently attached to the heavy chain or the light chain of the antibody. For example, the HA binding domain is covalently attached to the heavy chain. In another example, the HA binding domain is covalently attached to the light chain. The HA binding domain can be covalently attached to the anti-VEGF antibody at any suitable site, for example, the N-terminus, the C-terminus, or an internal site (e.g., an insertion). The HA binding domain can be covalently attached to the C-terminus of the heavy chain or to the C-terminus of the light chain. For example, in some instances, the HA binding domain is covalently attached to the C-terminus of the heavy chain. In other instances, the HA binding domain is covalently attached to the C-terminus of the light chain.

In any of the preceding fusion proteins, the fusion protein may further include a linker, the linker being positioned between the antibody and the HA binding domain. Any suitable linker may be used, for example, a $(Gly_n\text{-}Ser_n)_n$ or $(Ser_n\text{-}Gly_n)_n$ linker, where n is independently an integer equal to or greater than 1 (e.g., 1, 2, 3, 4, 5, 6, 7, 8, 9, 10, 11, 12, 13, or more). WO 2014/099997 describes a number of linkers, any of which may be used in the fusion proteins of the invention. In some instances, a linker may include the amino acid sequence of GGGGS (SEQ ID NO: 61). In some instances, a linker may consist of the amino acid sequence of GGGGS (SEQ ID NO: 61). Other suitable linkers include $(Gly_4Ser)_4$, $(Gly_4Ser)_3$, and the like. In some instances, serine can be replaced with alanine (e.g., $(Gly_4Ala)$ or $(Gly_3Ala)$).

In any of the preceding fusion proteins, the antibody may be an antibody fragment that binds VEGF. In some instances, the antibody fragment is selected from the group consisting of Fab, Fab', Fab-C, Fab'-SH, Fv, scFv, and (Fab')$_2$ fragments. For example, in some instances, the antibody fragment is an Fab, an Fab', or an Fab-C. In some instances, the HA binding domain is covalently attached to the C-terminus of the CH1 domain of the Fab. In other instances, the HA binding protein is covalently attached to the C-terminus of the CL domain of the Fab.

In any of the preceding fusion proteins, the HA binding domain may be selected from the group consisting of a link module, a G1 domain, a lysine-rich oligopeptide, and other HA binding domains known in the art. For example, the HA binding domain may be any HA binding domain described in Park et al., Molecular Pharmaceutics 6(3):801-812, 2009; U.S. Pat. Nos. 5,986,052, 7,183,377, 7,723,472, and 8,846,034; U.S. Patent Application Publication No. 2004/005277; and/or International Patent Application Nos. WO 1998/052590, WO 2010/045506, WO 2014/099997, WO 2015/198243, WO 2015/110809. For example, the HA binding domain may be HA10, HA10.1, HA10.2, HA11, or HA11.1, as described in WO 2014/099997.

In some instances, the HA binding domain is a link module. Any suitable link module may be used. For example, in some instances, the link module is selected from the group consisting of TSG6, CD44, lymphatic vessel endothelial hyaluronan receptor 1 (LYVE-1), hyaluronan and proteoglycan link protein (HAPLN) 1, HAPLN2, HAPLN3, HAPLN4, aggrecan, brevican, neurocan, phosphacan, versican, CAB61358, KIA0527, stabilin-1, and stabilin-2 link modules, or variants thereof. In some instances, the link module is a TSG6 link module, for example, a human TSG6 link module. In some instances, the link module of the HA binding protein TSG6 may include amino acid residues 36-128 of human TSG6 (UniProt Accession No. P98066).

Any of the preceding fusion proteins may further include at least one additional HA binding domain. For example, the fusion protein may further include at least 1, 2, 3, 4, 5, 6, 7, or 8 additional HA binding domain(s). In some instances, the at least one additional HA binding domain is covalently attached to the heavy chain or the light chain of the antibody. For example, in some instances, the at least one additional HA binding domain is covalently attached to the heavy chain of the antibody. In other instances, the at least one additional HA binding domain is covalently attached to the light chain of the antibody. In some instances, the at least one additional HA binding protein is linked to the antibody by a linker. Any suitable linker may be used, such as a linker described above. In some instances, the linker includes the amino acid sequence of GGGGS (SEQ ID NO: 61). In some instances, the linker consists of the amino acid sequence of GGGGS (SEQ ID NO: 61). In some instances, a first HA binding domain is covalently attached to the heavy chain, and a second HA binding domain is covalently attached to the light chain. The at least one additional HA binding domain can be covalently attached to the anti-VEGF antibody at any suitable site, for example, the N-terminus, the C-terminus, or an internal site (e.g., an insertion). In instances where the antibody includes more than one additional HA binding domains in an antibody, the insertions may be at a single site in the antibody or at multiple distinct sites in the antibody. For example, in some instances, the first HA binding domain is linked to the C-terminus of the heavy chain and the second HA binding domain is linked to the C-terminus of the light chain. In some instances, the at least one additional HA binding protein is selected from the group consisting of a link module, a G1 domain, and a lysine-rich oligopeptide. For example, in some instances, the at least one additional HA binding protein is a link module. The link module may be any link module described herein or known in the art. In some instances, the link module is a TSG6 link module, for example, a human TSG6 link module. In some instances, the link module of the HA binding protein TSG6 may include amino acid residues 36-128 of human TSG6 (UniProt Accession No. P98066).

Any of the preceding fusion proteins may specifically bind to VEGF and HA. In some instances, the fusion protein binds HA with a Kd of about 10 µM or lower. For example, in some instances, the fusion protein binds HA with a Kd of about 10 µM or lower, 8 µM or lower, 6 µM or lower, 4 µM or lower, 2 µM or lower, 1 µM or lower, 750 nM or lower, 500 nM or lower, 250 nM or lower, 100 nM or lower, 50 nM or lower, nm or lower, or 1 nm or lower. In some instances, the fusion protein binds HA with a Kd of about 2 nM or lower. In some instances, the fusion protein binds HA with a Kd between about 1 nM and about 2 µM, for example, between about 1 nM and about 1.8 µM, between about 1 nM and about 1.6 µM, between about 1 nM and about 1.4 µM, between about 1 nM and about 1.2 µM, between about 1 nM and about 1.0 µM, between about 1 nM and about 900 nM, between about 1 nM and about 800 nM, between about 1 nM and about 700 nM, between about 1 nM and about 600 nM, between about 1 nM and about 500 nM, between about 1 nM and about 400 nM, between about 1 nM and about 300 nM, between about 1 nM and about 200 nM, between about 1 nM and about 100 nM, between about 1 nM and about 50 nM, between about 1 nM and about 40 nM, between about 1 nM and about 30 nM, between about 1 nM and about 20 nM, between about 1 nM and about 10 nM, between about 5 nM and about 100 nM, between about 5 nM and about 50 nM, between about 5 nM and about 25 nM, between about 5 nM and about 15 nM, or between about 5 nM and about 10 nM. In some instances, the fusion protein binds HA with a Kd of about 10 nM.

Any of the preceding fusion proteins may have an ocular half-life that is increased relative to a reference antibody that is not covalently attached to a HA binding domain. In some instances, the ocular half-life is increased at least about 2-fold (e.g., about 2-fold, about 3-fold, about 4-fold, about 5-fold, about 6-fold, about 7-fold, about 8-fold, about 9-fold, about 10-fold, about 12-fold, about 14-fold, about 16-fold, about 18-fold, about 20-fold, or more) relative to the reference antibody. In some instances, the ocular half-life is increased at least about 4-fold relative to the reference antibody. In some instances, the ocular half-life is a vitreal half-life. In some instances, the reference antibody is identical to the antibody of the fusion protein. In other cases, the reference antibody is non-identical to the antibody of the fusion protein.

Any of the preceding fusion proteins may have an ocular clearance that is decreased relative to a reference antibody that is not covalently attached to a HA binding domain. In some instances, the clearance is decreased at least about 2-fold (e.g., about 2-fold, about 3-fold, about 4-fold, about 5-fold, about 6-fold, about 7-fold, about 8-fold, about 9-fold, about 10-fold, about 12-fold, about 14-fold, about 16-fold, about 18-fold, about 20-fold, or more) relative to the reference antibody. In some instances, the clearance is decreased at least about 4-fold relative to the reference antibody. In some instances, the clearance is clearance from the vitreous. In some instances, the reference antibody is identical to the antibody of the fusion protein. In other cases, the reference antibody is non-identical to the antibody of the fusion protein.

In some instances, the time period between two intraocular administrations (e.g., by intravitreal injection) of any of the preceding fusion proteins is at least 1 month, e.g., at least 1 month, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 20 weeks, at least 24 weeks, at least 28 weeks, at least 32 weeks, at least 36 weeks, at least 40 weeks, at least 44 weeks, at least 48 weeks, at least 52 weeks or more. In some cases, the maximum period between two intraocular administrations is no longer then four years, e.g., no longer than three years, no longer than two years, or no longer than one year. The fusion protein can be administered, for example, every two to twelve months, e.g., every four to ten months. In some instances, the fusion protein is administered every six months.

The invention also provides compositions (e.g., pharmaceutical compositions) that include any of the fusion proteins described above. In certain embodiments, the composition comprises one or more additional compounds. In certain embodiments, the additional compound binds to a second biological molecule selected from the group consisting of IL-1β; IL-6; IL-6R; PDGF; angiopoietin; angiopoietin 2; Tie2; S1P; integrins αvβ3, αv5, and α5β1; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. In certain embodiments, the additional compound is an antibody or antigen-binding fragment thereof. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

The invention also provides compositions (e.g., pharmaceutical compositions) that include any of the fusion proteins described above and an additional VEGF antagonist.

3. Polymeric Formulations

The invention provides formulations that include an anti-VEGF antibody of the invention and a polymer. The polymeric formulation may be, for example, a microsphere, an implant, a hydrogel, an organogel, a nano-assembly, a micelle, an in situ forming depot, or another type of polymeric formulation known in the art. Any suitable polymer may be used in the polymeric formulations of the invention. For example, the polymer may be a hydrophilic polymer or a hydrophobic polymer. It is to be understood that a hydrophilic polymer may be a water-soluble polymer. Any suitable hydrophilic polymer may be used, for example, a hydrophilic polymer described in International Patent Application Publication No. WO 2011/066417 or Pelegri-O'Day et al. J. Am. Chem. Soc. 136:14323-14332, 2014. In other instances, hydrophobic polymers may be used, for example. The polymer may be biodegradable and/or biocompatible.

Exemplary, non-limiting hydrophilic polymers that can be used include hyaluronic acid (HA), polyethylene glycol (PEG; also known as poly(ethylene glycol)) (e.g., straight-chain PEG, branched PEG, comb-like PEG, and dendritic PEG), poly[ethylene oxide)-co-(methylene ethylene oxide)], poly(poly(ethylene glycol) methyl ether methacrylate) (pPEGMA), agarose, alginate, carageenans, carboxymethylcellulose, cellulose, cellulose derivatives, chitosan, chondroitin sulfate, collagen, dermatan sulfate, dextran, dextran sulfate, fibrin, fibrinogen, fibronectin, fucoidan, gelatin, glycosaminoglycans (GAGs), a glycopolymer, heparin, heparin sulfate, a highly-branched polysaccharide (e.g., a galactose dendrimer), keratan sulfate, methyl cellulose, hydroxypropylmethylcellulose (HPMC), poly(N-(2-hydroxypropyl) methacrylamide) (pHPMA), pectins, pectin derivatives, pentosane polysulfate, starch, hydroxylethyl starch (HES), styrene, vitronectin, poly(acrylic acid), poly(methacrylic acid), poly(acrylamide), poly(acrylic acid), poly(amines), poly(amino acids), poly(carboxybetaine) (PCB), polyelectrolytes, poly(glutamic acid) (PGA), poly(glycerol) (PG) (e.g., linear, midfunctional, hyperbranched, or linear hyperbranched PG), poly(maleic acid), poly(2-oxazoline) (POZ), poly(2-ethyl-2-oxazoline, polysialic acid (PSA), polystyrene, polystyrene derivatives (e.g., charged polystyrene derivatives), poly(styrenesulfonate-co-PEGMA), polyvinylpyrrolidone (PVP), poly(N-acryloylmorpholine) (pNAcM), and copolymers thereof. In other instances, any suitable hydrophobic polymer can be used, including, for example, poly(lactic-co-glycolic acid) (PLGA), polylactide (PLA), and polyglycolide (PGA).

The invention provides anti-VEGF antibodies formulated as polymer solvent depots (also known as in situ forming implants). For example, a polymer solvent depot may include a polymer (e.g., any of the polymers described herein, e.g., a hydrophobic polymer such as PLGA), a solvent (e.g., an organic solvent), and an anti-VEGF antibody (e.g., any anti-VEGF antibody described herein). The solvent may have a low water miscibility. Exemplary organic solvents that may be used include triacetin (glycerol acetate), N-methyl-2-pyrrolidone, poly(ethylene glycol) dimethyl ether, and ethylbenzoate. In one working example, a polymer solvent depot can be prepared by dispersing a spray-dried powder of an anti-VEGF antibody (e.g., any anti-VEGF antibody described herein, e.g., G6.31 AARR) within a PLGA-triacetin solution (see, e.g., Chang et al. J. Pharm. Sci. 104(10):3404-17, 2015, which is incorporated herein by reference in its entirety). The PLGA can have a molecular weight of about 10 kDa, about 41 kDa, or about 56 kDa, for example. PLGA polymers are commercially available, e.g., RG 752S, RG755S, and RG 756S (Evonik Industries, Darmstadt, Germany). The PLGA concentration can be about 7.5%, about 10%, about 12.5%, about 15%, about 20%, or more (% wt). The antibody concentration can be about 1%, about 1.5%, about 2%, about 2.5%, about 3%, about 4%, about 5%, or more (% wt). In some instances, the antibody concentration is about 1.5% (% wt). Any of the polymer solvent depot formulations can be injectable, for example, through a 27 gauge (27 G) needle. Upon administration (e.g., by injection (e.g., intravitreal injection)), such polymer solvent depot formulations can transform into a gel or solid depot in the eye. The gel or solid depot may form as a result of demixing of the aqueous and nonaqueous phases. Depending in part on the solvent transfer rate to aqueous phase, the injected depot can transition to a solid or gel material because of polymer precipitation and physically entrap the anti-VEGF antibody (and any additional therapeutic agents or compounds). In other instances, in situ cross-linking or in situ-solidifying organogels, for example, can be used to form a gel or solid depot. The polymer solvent depot may allow long-term delivery, for example, over about 30 days or more, e.g., about 30 days, about 40 days, about 50 days, about 60 days, about 70 days, about 80 days, about 90 days, about 100 days, about 110 days, about 120 days, about 130 days, or more. In some cases, the polymer solvent depot may allow long-term delivery for about 80 days in the eye.

The invention also provides an anti-VEGF antibody (e.g., any anti-VEGF antibody described herein) formulated as a polymer micelle. A polymer micelle can be formed, for example, by self-assembly of a polymer (e.g., an amphiphilic block (e.g., diblock or multiblock) copolymer) into a nanoparticle having a hydrophobic core and a hydrophilic shell. A polymer micelle may have any suitable diameter (e.g., average diameter), for example, a diameter of about 1 nm to about 1000 nm (e.g., about 1 nm, about 10 nm, about 100 nm, about 200 nm, about 300 nm, about 400 nm, about 500 nm, about 600 nm, about 700 nm, about 800 nm, about 900 nm, about 1000 nm), or larger. In some instances, a polymer micelle may have a diameter (e.g., average diameter) of about 5 nm to about 100 nm (e.g., about 5, about 10, about 20, about 30, about 40, about 50, about 60, about 70, about 80, about 90, or about 100 nm). Any suitable polymer can be used, including, for example, amphiphilic block copolymers such as poly(propylene oxide) (PPO), poly(D,L-lactic acid) (PDLLA), poly(ε-caprolactone) (PCL), poly(L-aspartate), and poloxamers (e.g., a poly(ethylene oxide)-block-poly(propylene oxide)-block-poly(ethylene oxide) copolymers (e.g., PLURONICS®)). Other amphiphilic block copolymers are known in the art. In some instances, the anti-VEGF antibody may be attached to the hydrophilic shell of the polymer micelle, for example, by a covalent attachment to the polymer. Accordingly, in some instances, an antibody conjugate described above may be used to prepare a polymer micelle that includes an anti-VEGF antibody.

The invention also provides an anti-VEGF antibody (e.g., any anti-VEGF antibody described herein, e.g., G6.31 AARR) formulated as a polymer implant. A polymer implant is a rigid object in which a solid drug formulation (e.g., an antibody) is evenly distributed within a hydrophobic polymer (e.g., PLGA). A polymer implant is typically millimeter-sized (e.g., 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.5 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 m, or larger). A polymer implant may be administered to an eye, for example, by a surgical procedure (e.g., microsurgery) or by injection (e.g., by intravitreal injection) using a suitable device. The polymeric implant can be formulated for administration to any suitable site in the eye, for example, the vitreous, anterior or posterior chambers of the eye, or intraretinal, subretinal, intrachoroidal, suprachoroidal, episcleral, subconjunctival, intracorneal, or epicorneal sites of the eye. In particular instances, the polymeric implant is formulated for administration to the vitreous.

A polymer implant that includes an anti-VEGF antibody (e.g., any anti-VEGF antibody described herein, e.g., G6.31 AARR) can be prepared using a hot-melt extrusion (HME) process. Heat is applied to melt (fluidize) the polymer, and then mechanical shear can be imparted to blend and microcompound a solid drug formulation within the fluid polymer phase. The drug-polymer admixture can then be extruded through a millimeter-sized die (e.g., a circular die). When the extrudate is allowed to cool (e.g., to room temperature), it forms rods (e.g., cylindrical rods) that can be cut to any desired length. In some instances, the polymer implant may be a PLGA rod that includes an anti-VEGF antibody and PLGA. Polymer implants that can be used in the context of the present invention are described, for example, in Rajagopal et al. *J. Pharmaceutical Sciences* 102(8):2655-2666, 2013 and International Patent Application Publication No. WO 2006/093758, which are incorporated herein by reference in their entirety.

In one working example, an anti-VEGF antibody (e.g., any anti-VEGF antibody described herein) can be prepared as a spray-dried formulation, which can include trehalose and histidine-HCl buffer for stability at elevated temperatures, which can then be added to a hydrophobic polymer such as PLGA and undergo HME to form a polymeric implant (see, e.g., Rajagopal et al. supra). For example, the spray-dried formulation may include an antibody at any suitable concentration (e.g., 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 20 mg/mL, 25 mg/mL, 30 mg/mL), trehalose at any suitable concentration (e.g., 1 mg/mL, 2 mg/mL, 3 mg/mL, 3.3 mg/mL, 4 mg/mL, 5 mg/mL, 6 mg/mL, 7 mg/mL, 10 mg/mL, and/or a buffer (e.g., 10 mM histidine HCl). The spray-dried formulation can have any suitable pH, for example, a pH of about between about 5 and about 8 (e.g., about 5, about 6, about 7, or about 8). In some instances, the spray-dried formulation can have a pH of about 6 or about 6.2. In particular instances, the spray dried formulation includes an anti-VEGF antibody, 3.3 mg/mL trehalose, and 10 mM histidine-HCl, pH 6.2. The polymeric implant may be prepared by HME of the spray-dried formulation with a hydrophobic polymer such as PLGA. For example, solid PLGA pellets and the spray-dried formulation can be premixed at room temperature and fed into a conical, counter-rotating twin-screw extruder. The combination can be microcompounded, followed by extrusion at 100° C. through a 0.5 mm circular die. In some instances, the spray-dried formulation is exposed to 100° C. for less than 30 min.

The polymer implant may contain, for example, from about 1% to about 90% anti-VEGF antibody by weight (e.g., about 1%, about 5%, about 10%, about 20%, about 30%, about 40%, about 50%, about 60%, about 70%, about 80%, or about 90%) by weight. In some instances, the polymer implant includes about 10% anti-VEGF antibody by weight. The polymeric implant may have any suitable dimensions, for example, in some instances, the implant has a diameter of about 0.1 to about 1 mm (e.g., about 0.5 mm) and a length of about 1 to about 30 mm (e.g., about 14 mm). For PLGA implants (e.g., PLGA rods), the percentage of polylactic acid in the PLGA copolymer can be 0-100%, for example, about 15-85%, about 35-65%, or 50%. In some instances, a PLGA implant (e.g., a PLGA rod) may further include one or more additional polymers, for example, hydroxypropylmethylcellulose (HPMC).

In any of the preceding polymeric formulations (e.g., polymer solvent depots, polymer micelles, and polymer implants), the antibody may be an antibody fragment that binds VEGF. In some instances, the antibody fragment is selected from the group consisting of Fab, Fab', Fab-C, Fab'-SH, Fv, scFv, and (Fab')$_2$ fragments. For example, in some instances, the antibody fragment is an Fab, an Fab', or a Fab-C.

Any of the preceding polymeric formulations (e.g., polymer solvent depots, polymer micelles, and polymer implants) may have an ocular half-life that is increased relative to a reference antibody that is not formulated as a polymeric formulation. In some instances, the ocular half-life is increased at least about 2-fold (e.g., about 2-fold, about 3-fold, about 4-fold, about 5-fold, about 6-fold, about 7-fold, about 8-fold, about 9-fold, about 10-fold, about 12-fold, about 14-fold, about 16-fold, about 18-fold, about 20-fold, or more) relative to the reference antibody. In some instances, the ocular half-life is increased at least about 4-fold relative to the reference antibody. In some instances, the ocular half-life is a vitreal half-life. In some instances, the reference antibody is identical to the antibody of the polymeric formulation. In other cases, the reference antibody is non-identical to the antibody of the polymeric formulation.

Any of the preceding polymeric formulations (e.g., polymer solvent depots, polymer micelles, and polymer implants) may have an ocular clearance that is decreased relative to a reference antibody that is not formulated as a polymeric formulation. In some instances, the clearance is decreased at least about 2-fold (e.g., about 2-fold, about 3-fold, about 4-fold, about 5-fold, about 6-fold, about 7-fold, about 8-fold, about 9-fold, about 10-fold, about 12-fold, about 14-fold, about 16-fold, about 18-fold, about 20-fold, or more) relative to the reference antibody. In some instances, the clearance is decreased at least about 4-fold relative to the reference antibody. In some instances, the clearance is clearance from the vitreous. In some instances, the reference antibody is identical to the antibody of the polymeric formulation. In other cases, the reference antibody is non-identical to the antibody of the polymeric formulation.

In some instances, the time period between two intraocular administrations (e.g., by intravitreal injection) of any of the preceding polymeric formulations is at least 1 month, e.g., at least 1 month, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least weeks, at least 24 weeks, at least 28 weeks, at least 32 weeks, at least 36 weeks, at least 40 weeks, at least 44 weeks, at least 48 weeks, at least 52 weeks or more. In some cases, the maximum period between two intraocular administrations is no longer then four years, e.g., no longer than three years, no longer than two years, or no longer than one year. The polymeric formulation can be administered, for example, every two to twelve months, e.g., every four to ten months. In some instances, the polymeric formulation is administered every six months.

The invention also provides compositions (e.g., pharmaceutical compositions) that include any of the polymeric formulations (e.g., polymer solvent depots, polymer micelles, and polymer implants) described above. In certain embodiments, the composition comprises one or more additional compounds. In certain embodiments, the additional compound binds to a second biological molecule selected from the group consisting of IL-13, IL-6; IL-6R; PDGF; angiopoietin; angiopoietin 2; Tie2; S1P; integrins $\alpha v\beta 3$, $\alpha v\beta 5$, and $\alpha 5\beta 1$; betacellulin; apelin/APJ; erythropoietin; complement factor D; TNF$\alpha$; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. In certain embodiments, the additional compound is an antibody or antigen-binding fragment thereof. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

The invention also provides compositions (e.g., pharmaceutical compositions) that include any of the polymeric formulations (e.g., polymer solvent depots, polymer micelles, and polymer implants) described above and an additional VEGF antagonist.

4. Devices

Any of the compositions described herein (e.g., anti-VEGF antibodies, antibody conjugates, fusion proteins, and polymeric formulations) can be administered to the eye using a port delivery device. A port delivery device is an implantable, refillable device that can release a therapeutic agent (e.g., an anti-VEGF antibody) over a period of months (e.g., 1, 2, 3, 4, 5, 6, 7, 8, 9, 10, 11, 12, or more months). Exemplary port delivery devices that may be used include those from ForSight Labs, LLC and/or ForSight VISION4, for example, as described in International Patent Application Publication Nos. WO 2010/088548, WO2015/085234, WO 2013/116061, WO 2012/019176, WO 2013/040247, and WO 2012/019047, which are incorporated herein by reference in their entirety.

For example, the invention provides port delivery devices that include reservoirs containing any of the compositions described herein (e.g., anti-VEGF antibodies, antibody conjugates, fusion proteins, and polymeric formulations). The port delivery device may further include a proximal region, a tubular body coupled to the proximal region in fluid communication with the reservoir, and one or more outlets in fluid communication with the reservoir and configured to release the composition into the eye. The tubular body may have an outer diameter configured to be inserted through an incision or opening in the eye of about 0.5 mm or smaller. The device may be about 1 mm to about 15 mm in length (e.g., about 1 mm, about 2 mm, about 4 mm, about 5 mm, about 6 mm, about 7 mm, about 9 mm, about 11 mm, about 13 mm, or about 15 mm in length). The reservoir may have any suitable volume. In some instances, the reservoir has a volume of about 1 µl to about 100 µl (e.g., about 1 µl, about 5 µl, about 10 µl, about 20 µl, about 50 µl, about 75 µl, or about 100 µl). The device or its constituent parts may be made of any suitable material, for example, polyimide.

In some instances, the port delivery device includes a reservoir containing any of the compositions described herein (e.g., anti-VEGF antibodies, antibody conjugates, fusion proteins, and polymeric formulations) and one or more additional compounds. In certain embodiments, the additional compound binds to a second biological molecule selected from the group consisting of IL-1β; IL-6; IL-6R; PDGF; angiopoietin; angiopoietin 2; Tie2; S1P; integrins $\alpha v\beta 3$, $\alpha v\beta 5$, and $\alpha 5\beta 1$; betacellulin; apelin/APJ; erythropoietin; complement factor D; TNF$\alpha$; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. In certain embodiments, the additional compound is an antibody or antigen-binding fragment thereof. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

In some instances, the port delivery device includes any of the compositions described herein (e.g., anti-VEGF antibodies, antibody conjugates, fusion proteins, and polymeric formulations) and an additional VEGF antagonist.

III. EXAMPLES

The following are examples of methods and compositions of the invention. It is understood that various other embodiments may be practiced, given the general description provided above.

Example 1: Deep Scanning Mutagenesis of G6.31 Identifies Positions Important for Assembly of a Stable Assembled Fab G6.31 is a high affinity anti-VEGF antibody (Fuh et al., *J. Biol. Chem.* 281(10):6625-6631 (2006); Liang et al., *J. Biol. Chem.* 281(2):951-961 (2006). G6.31 is considered representative of human antibodies as its heavy and light chain variable domains are frequently used human germlines IGHV3-23 and IGKV1-39 origin, respectively.

To systematically assess the effect of single mutations in the VH and VL domains of G6.31, a saturated single site mutagenesis library for each variable domain (VL positions 2-107 and VH positions 2-113 according to the Kabat numbering scheme) were generated. These libraries are referred to as the VH and VL NNK walk libraries, respectively. Using these libraries in a deep mutational scanning experiment allowed the calculation of an enrichment ratio (ER) for each mutation in the two libraries during selection, which serve as an assessment of the impact of the mutation on the fitness of the molecule. The ER of a particular mutation aggregates a variety of effects, including the impact of the mutation on functional expression, the impact of the mutation on the stability of the fold, and the impact of the mutation on binding to the selection protein (e.g., anti-gD (a peptide tag fused to the C-terminus of the light chain), protein A, protein L, or VEGF).

Figure 2A:
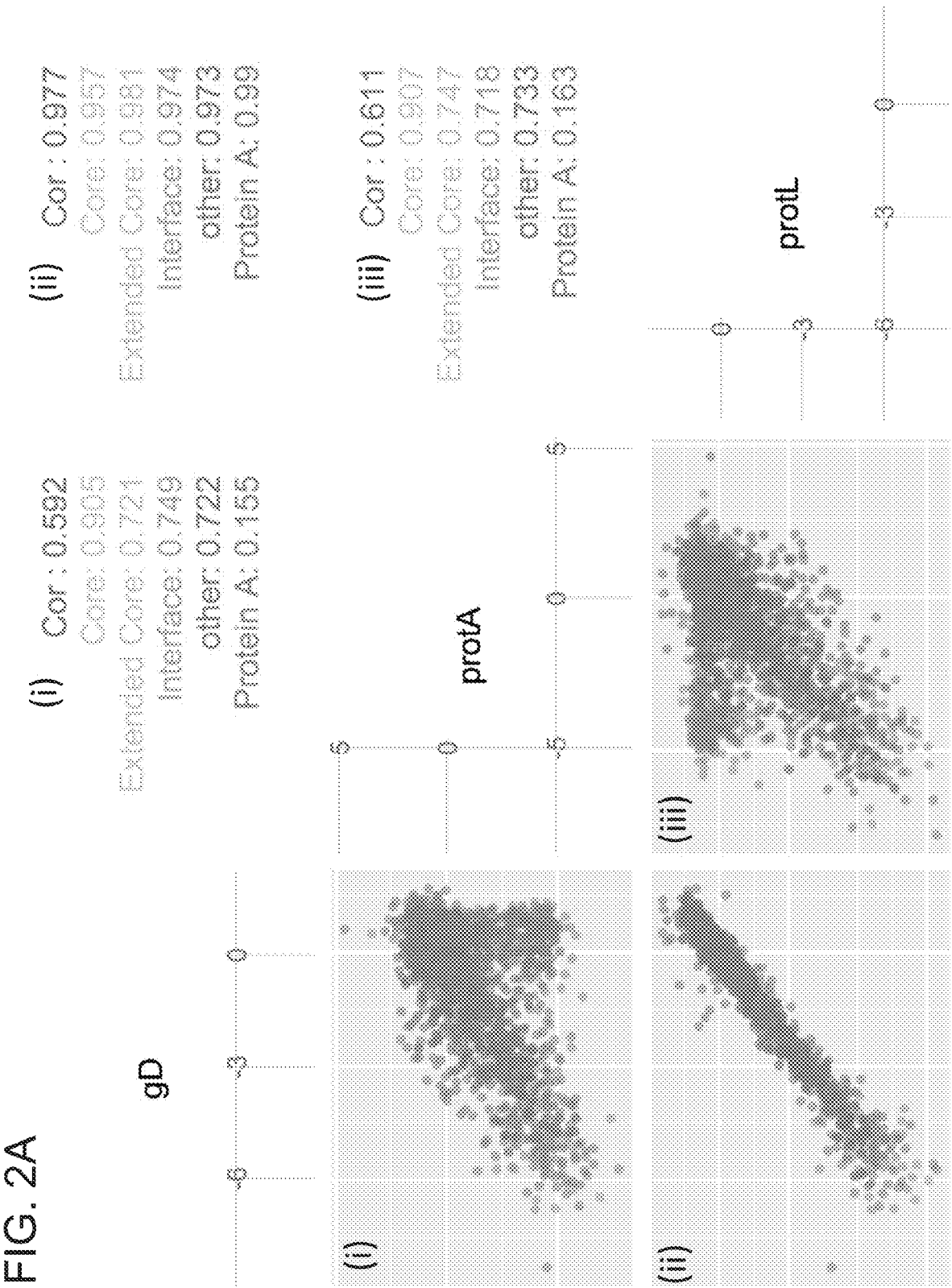
FIGS. 2A-2B are a series of graphs and tables showing the correlation between log 2 enrichment ratios from panning of the VH (FIG. 2A) and the VL (FIG. 2B) against anti-gD-tag antibody ("gD"), protein A ("protA"), and protein L ("protL"). The tables show the Pearson correlation coefficient ($r^2$; "Cor") for the comparison between (i) gD and protA; (ii) gD and protL; and (iii) protA and protL. The correlation for enrichment ratios of mutations in positions classified as belonging to the hydrophobic core ("core"), extended hydrophobic core ("extended core"), VH/VL interface ("interface"), or positions which form important hydrogen bonds, salt bridges, or are otherwise of interest ("other") was also determined. These figures show that using an anti-gD antibody, protein A, or protein L to detect the folding of the Fab molecule on phage gives similar results. The only mutations which differed significantly in their enrichment ratios in the different pannings are those located directly in the Protein A or Protein L binding sites. Those residues are labeled as "Protein A," "Protein L 1," and "Protein L 2" (two binding sites for Protein L exist), respectively. The binding sites for protein L are described in Graille et al. *Structure* 9(8): 679-687, 2001, which is incorporated herein by reference in its entirety. The binding sites for protein G are described in Graille et al. *Proc. Nat. Acad. Sci. USA* 97(10): 5399-5404, 2000, which is incorporated herein by reference in its entirety.
Figure 2B:
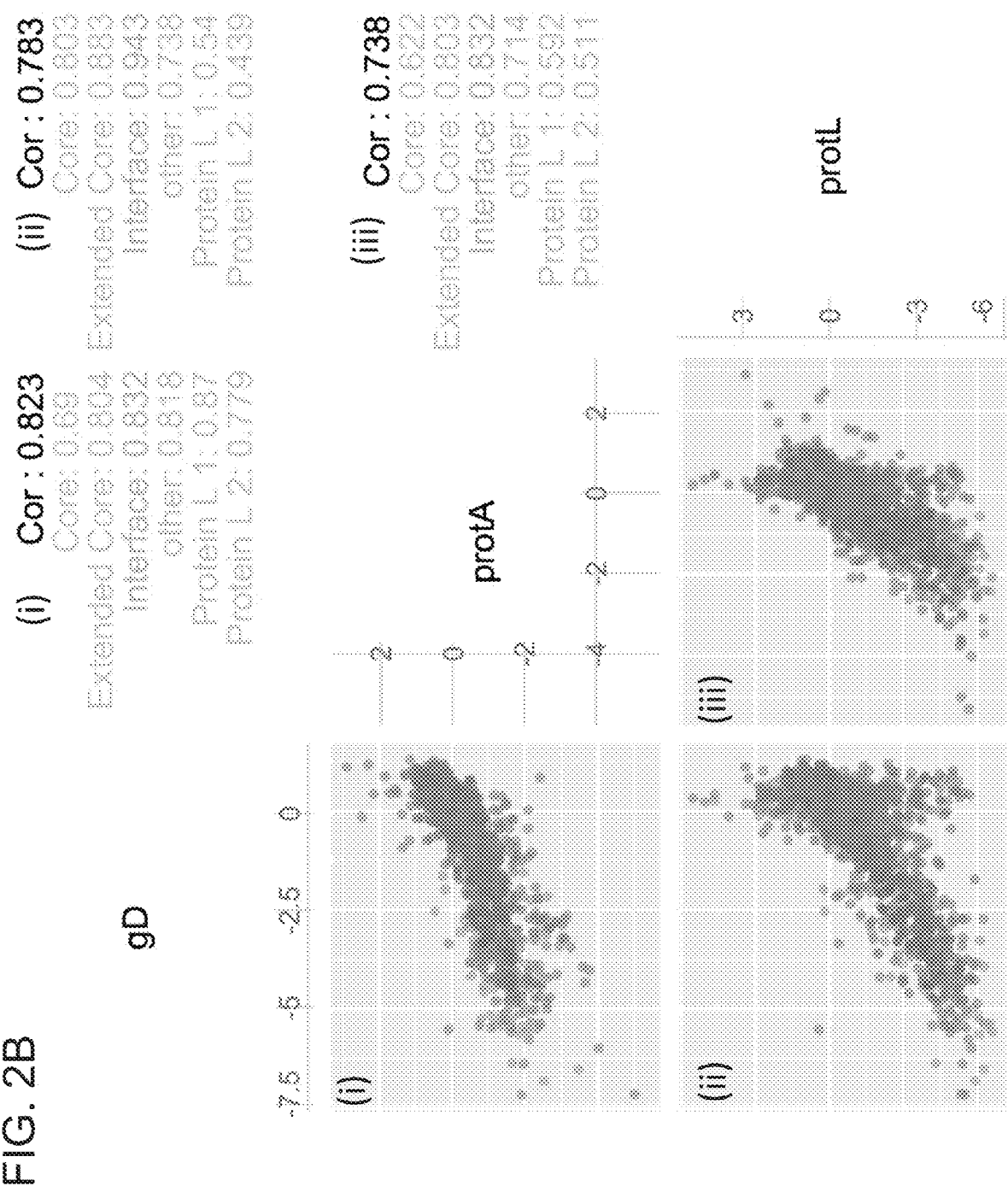

To assess the impact of each mutation on functional expression and fold stability of the Fab, the VH and VL libraries were panned separately against anti-gD, protein A, or protein L. These panning strategies detect whether a Fab molecule is displayed on phage and, to some extent, whether it is properly folded and assembled. The ERs of 2331 and 2226 amino acid substitutions (including stops) and the respective wild-type amino acid at a given position of the heavy chain library and light chain library, respectively, were determined for each of the three pannings (FIGS. 1A-1F). A comparison of the three heavy chain panning strategies or the three light chain pannings demonstrates that very similar results were obtained (FIGS. 2A-2B). For example, the ERs show a good linear relationship ($r^2$=0.98) between anti-gD and protein L panning (FIG. 2A). A comparison between the protein A panning dataset and the protein L panning dataset showed a lower linear correlation ($r^2$=0.611), which can be attributed to the subset of mutations that have a direct impact on protein A binding and therefore a differential enrichment in the two selections. A similar pattern was observed for the light chain (FIG. 2B).

Figure 3A:
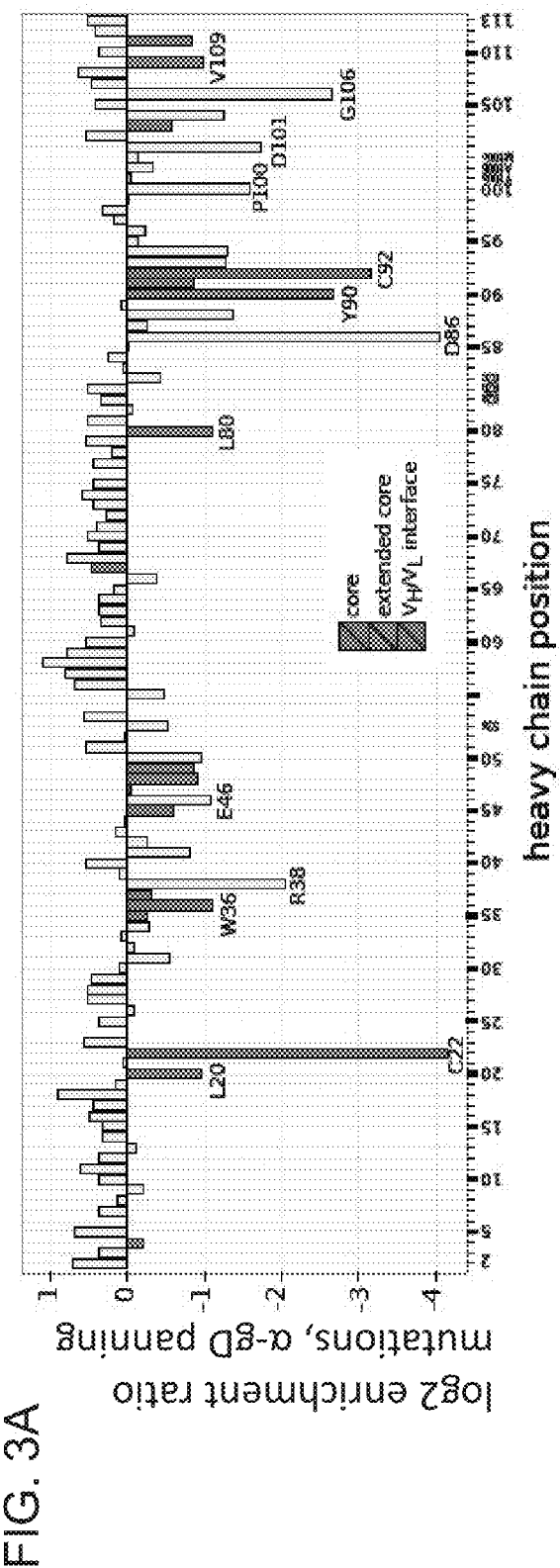
FIGS. 3A-3B are graphs showing the log 2 enrichment ratio for all mutations at a given position in the VH (FIG. 3A) and VL (FIG. 3B). Positions are colored according to whether they are located in the hydrophobic core (green), in the extended hydrophobic core (red), or in the VH/VL interface (violet). Positions that are conserved and do not tolerate mutations (log 2 enrichment ratio Z-score<−0.5) are labeled.
Figure 3B:
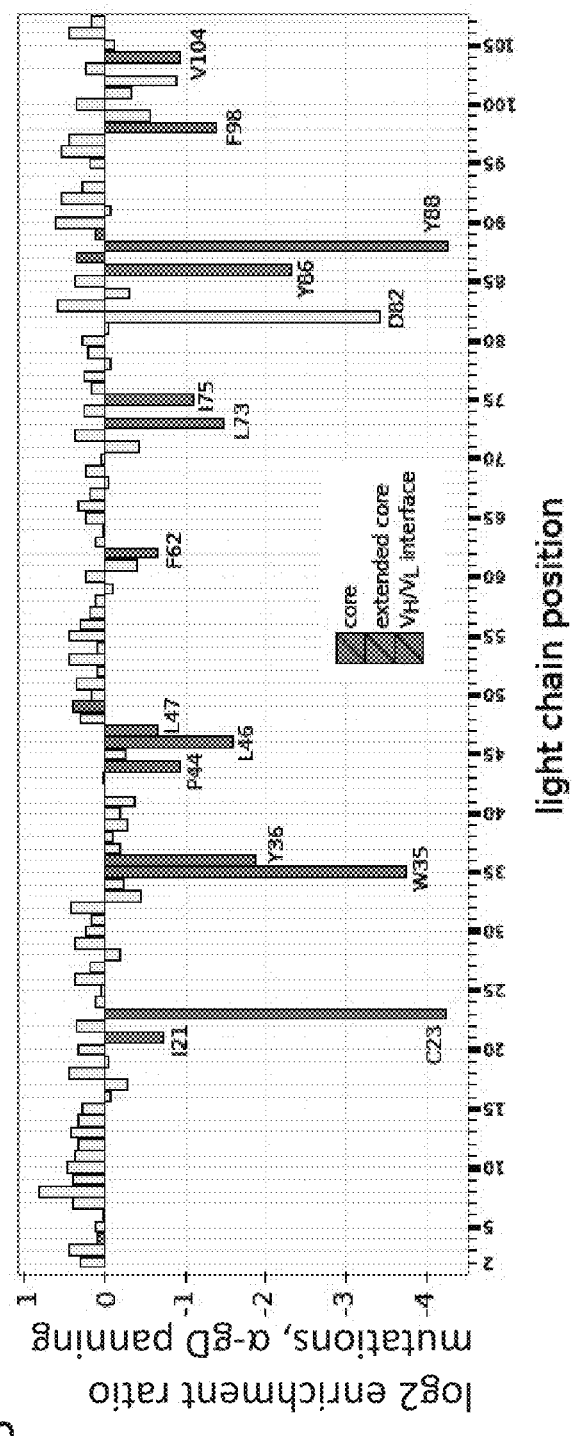
Figure 3C:
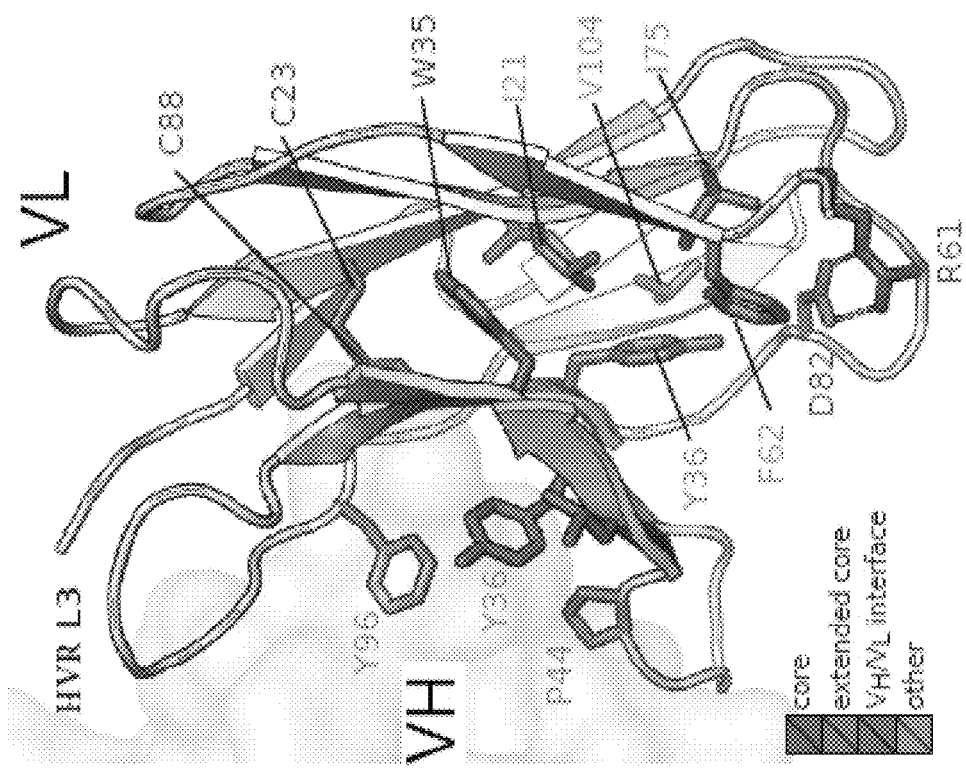
FIGS. 3C-3D are renderings of the crystal structure of the antigen-free G6 Fab (Protein Data Bank (PDB) code: 2FJF) showing the location of conserved positions in the structure of the VH (FIG. 3C) and VL (FIG. 3D), respectively. The color scheme is the same as in FIGS. 3A-3B. In addition, conserved positions which form important hydrogen bonds, salt bridges, or are otherwise important are colored pink.
Figure 3D:
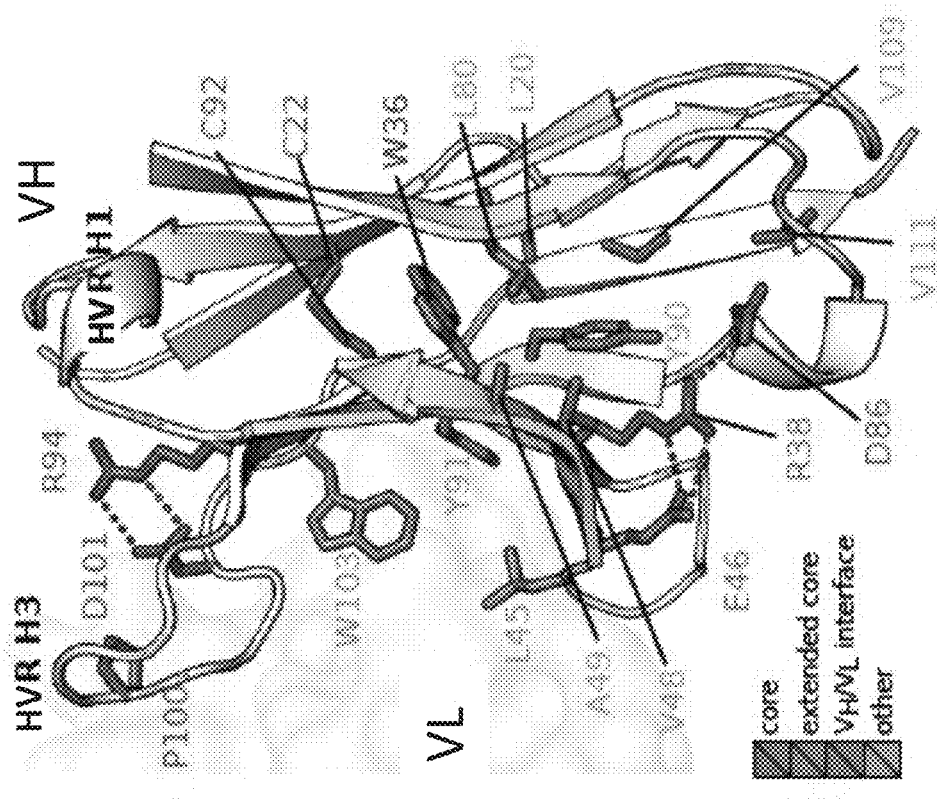

In one approach to identify positions which impact the functional expression and stability of the Fab, the positions that were conserved and that do not tolerate mutations during the selection were determined. Using the data set obtained from anti-gD panning as a representative scan, the average enrichment ratio of all mutations at a given position ($ER_{pos}$) was calculated for each position as a measure of conservation (FIGS. 3A-3B). In both the VH and the VL domain, the central core residues, which consist of a cysteine pair (HC-C22, HC-C93; LC-C23, LC-88) between the β-strands B and F as well as an adjacent tryptophan residue (HC-W36, LC-W35), were highly conserved (FIGS. 3A-3D). The hydrophobic core of the immunoglobulin fold is described, for example, in Halaby et al. *Protein Engineering* 12(7): 563-571, 1999. Adjacent to the central core are a few hydrophobic residues located in the lower half of the molecule (when the Fab is orientated such that the HVRs face upward) which are part of the extended hydrophobic core. They were conserved but showed smaller $ER_{pos}$ values than the central core residues. Among these residues is a tyrosine (HC-Y90, HC-86), which has been shown previously to be important for the stability of the Ig-fold (see, e.g., Hamill et al., *J. Mol. Biol.* 295(3):641-649 (2000). The third group of conserved residues was located in the VH/VL interface (HC-L45, HC-Y91, HC-W103, LC-P44, LC-Y36, LC-Y96). VH/VL interface residues were not only conserved in pannings with indirect selection (e.g., VH data from protein L panning), but also direct selection (e.g., VH data from Protein A panning), indicating that mutations at the mentioned interface positions resulted in an assembled Fab with reduced stability. The fourth group of conserved residues (HC-E46, HC-R38, HC-D86, LC-R61, LC-D82) includes residues in a hydrogen bond network at the lower half of the Fab that are important for stability. Especially the aspartate residue in α1-helix belongs to the positions, which showed one of the highest conservation in the dataset. Mutation at position LC-R61 and LC-D82 have been shown previously to induce fibril formation and induce aggregation in light chains (see Helms et al., *J. Mol. Biol.* 257(1):77-86 (1996)). Last, four positions in the HVR-H3 were identified as being highly conserved: HC-A93, HC-R94, HC-P100, HC-D101. Since these panning strategies were not selecting for antigen binding, these results indicated that the HVR3 loop conformation is involved in the stability of the Fab.

In summary, with the exception of a few positions of the variable domains being highly conserved, many positions can tolerate mutations without affecting the overall stability and expression of the Fab molecule in these selections. Further, even some positions that have a small $ER_{pos}$ can tolerate conserved amino acid substitutions. For example, the mutagenesis data suggested that hydrophobic residues of the lower core can be substituted with similar hydrophobic residue without affecting the stability of the Fab (FIGS. 1A-1F). The tolerance of the VH/VL stability for single substitutions contrasts the results obtained from a deep mutagenesis scan of the CH3 domain of a human IgG₁, in which the majority of residues did not tolerate any mutations (see Traxlmayr et al., *J. Mol. Biol.* 423(3):397-412 (2012)).

Materials and Methods

A. Full Variable Domain NNK Walk Library Design and Generation

The full VH (residues 2-113) and VL (residues 2-107) of G6.31 were subject to randomization. 10-12 subsequent residues were randomized per sub-library. Within the sub-library, a TAA codon was introduced at each randomized position by Kunkel mutagenesis (Kunkel, *Proc. Natl. Acad. Sci. USA* 83(2):488-492 (1985)). 10 VL sub-library and 12 VH sub-library stop templates were generated. For library design, each position was randomized by oligonucleotide-directed mutagenesis with an NNK codon, where N is any of the four natural nucleotides, and K is 50% T (thymine) and 50% G (guanine). The NNK codon can encode any of the 20 natural amino acids. The sub-libraries for the light chain and heavy chain were made separately and then the respectively libraries for each chain were combined to form a VL library and a VH library. The combined libraries are also referred to as VH or VL NNK walk libraries. Libraries were made in a phage Fab fragment display vector. The VH NNK walk library had a size of $3 \times 10^9$ members, while the VL NNK walk library had a size of $8 \times 10^8$ members.

B. Phage Panning Selection on Anti-gD, Protein L, or Protein A

Binding clones were selected by incubating the VH or VL NNK walk phage display library with 5, 0.5, 0.1 nM biotinylated VEGF in successive rounds of selection, and then competed with 100 nM non-biotinylated VEGF at room temperature or 37° C. to reduce binding of the lower affinity clones to VEGF. Bound clones were captured on ELISA plates coated with neutravidin, washed, and eluted in 100 mM HCl for 20 minutes at room temperature. The eluted phage was neutralized with $\frac{1}{10}$ volume of 1 M Tris pH 8.0 and used to infect E. coli for amplification for the next round of selection.

For selection with anti-gD, protein L, or protein A, binding clones were selected by incubating the VH or VL NNK walk phage display library on ELISA plates coated with anti-gD, protein L, or protein A, washed, and eluted in 100 mM HCl for 20 minutes at room temperature. The eluted phage was neutralized with $\frac{1}{10}$ volume of 1 M Tris pH 8.0 and used to infect E. coli for amplification for the next round of selection.

C. Illumina Sequencing of G6.31 Deep Mutational Scanning Libraries

For deep sequencing, phagemid DNA was isolated from E. coli XL1 cells carrying phagemid vectors from either the unselected or the selected VH or VL NNK walk library. Purified DNA was used as template for a limited cycle PCR-based amplification of VL and VH regions. PCR products were purified by agarose gel extraction and clean-up (Qiagen Gel Extraction Kit). Eluted amplicon DNA was used as the basis for deep sequencing library preparation with standard Illumina library preparation methods, using TRUSEQ™ DNA Sample Prep (Illumina). Adapter-ligated libraries were subjected to a single cycle of PCR and sequenced on the Illumina MISEQ®, paired-end 300 bp to cover the entire length of the amplicon.

D. Deep Scanning Mutagenesis Data Analysis

Sequenced paired end reads were merged using FLASh (Magoc et al., *Bioinformatics* 27(21):2957-2963 (2011)). Further sequencing data analysis was performed using the statistical programming language R (Team RC "R: A language and environment for statistical computing" R Foundation for Statistical Computing (2014)) and the ShortRead (Morgan et al., *Bioinformatics* 25(19):2607-2608 (2009)) package. The first step in quality control was filtering for sequences which carried the respective HC and LC barcode. In a second step, the flanking regions of the VH and VL domain were identified for each merged read and checked for the correct length in order to remove the vast majority of reads with insertion or deletion mutations (indels). To further correct for sequencing errors, non-NNK mutations were converted back to the wild-type base and reads which contained more than two NNK mutations were filtered out. Position weight matrices were generated by calculating the frequency of all mutations of every randomized position. Enrichment ratios for all mutations were calculated by dividing the frequency of a given mutation at a given position in the sorted sample with the frequency of the very same mutation in the unsorted sample, as described previously (Fowler et al., *Nature Methods* 7(9):7412-746 (2010)).

Figure 4A:
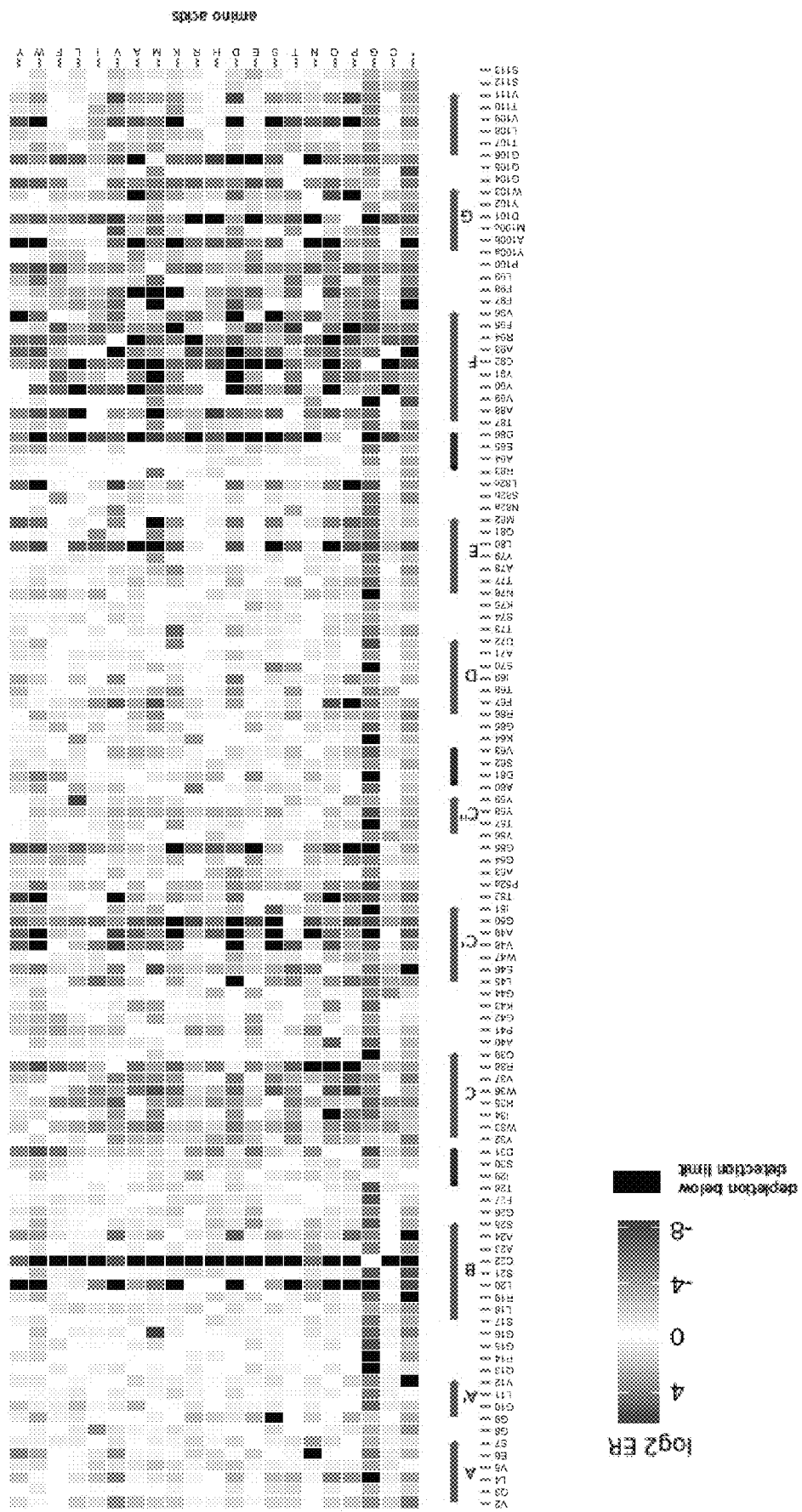
FIGS. 4A-4B are heatmaps showing the log 2 enrichment ratio of all single amino acid substitutions obtained by panning the NNK walk VH (FIG. 4A) and VL (FIG. 4B) libraries against VEGF.
Figure 4B:
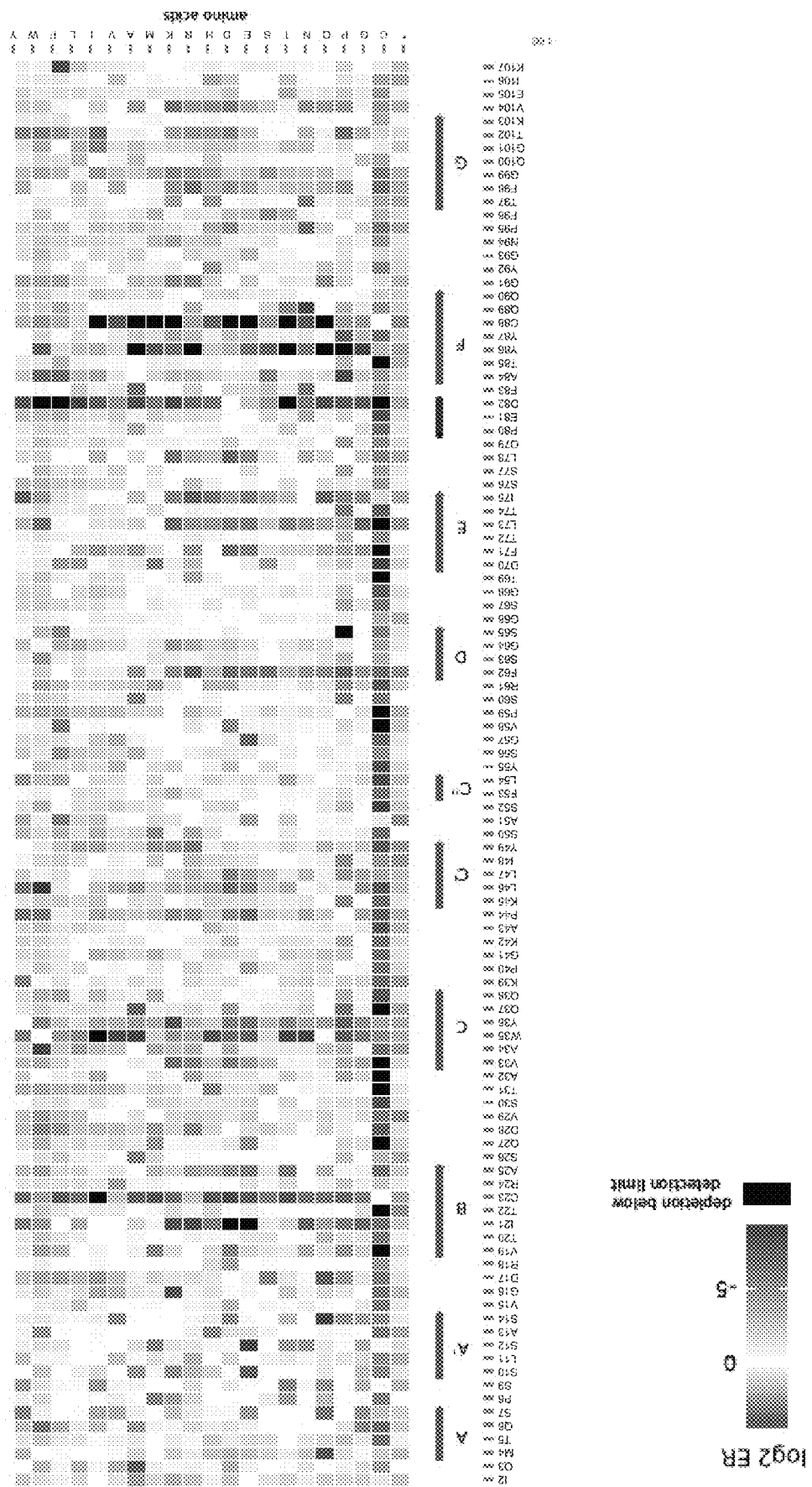
Figure 5A:
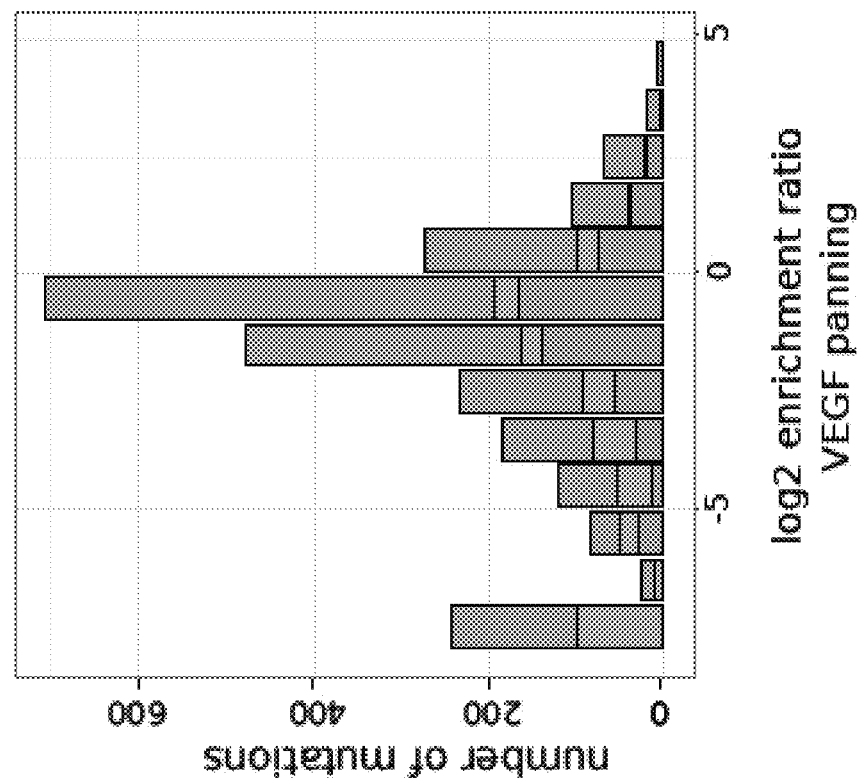
FIGS. 5A-5B are graphs showing that the log 2 enrichment ratios obtained from VEGF panning of the VH (FIG. 5A) and VL (FIG. 5B) libraries have a bi-modal distribution. Mutations which were depleted beyond the detection limit were set to the maximum observed depletion for the particular experiment. Mutations are colored accordingly to their location in the HVRs (grey), in the conserved framework as identified using the gD panning (orange), or the remainder of the framework (blue).
Figure 5B:
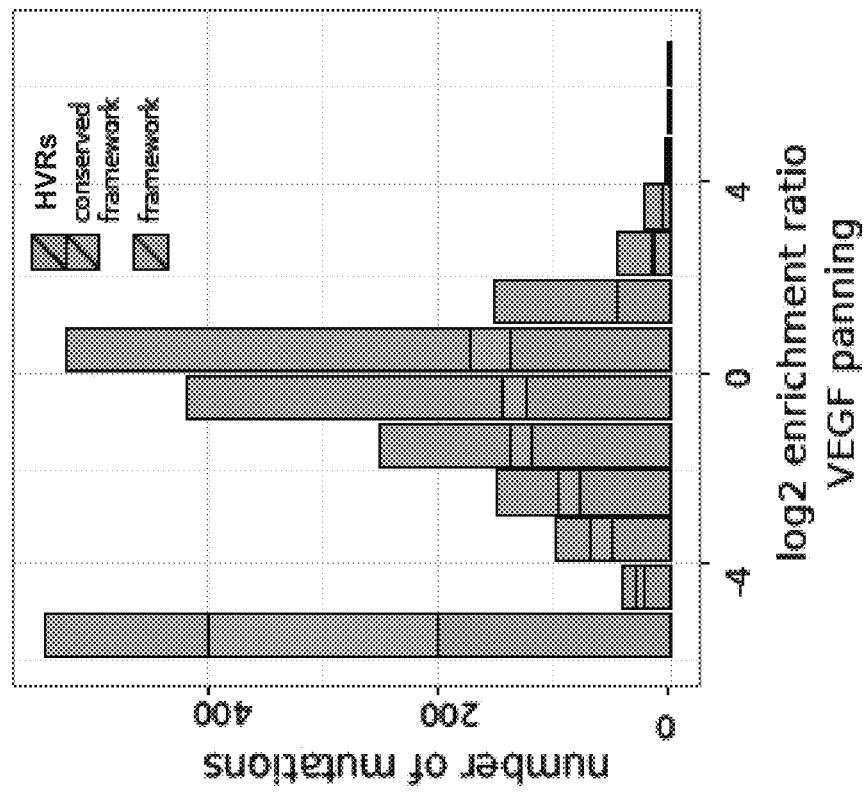

Example 2: Deep Scanning Mutagenesis Screen of G6.31 Identifies Amino Acid Residue Variants with Enhanced Stability and/or Improved Binding Affinity to VEGF To obtain a comprehensive overview of the impact of single substitutions of G6.31 on antigen binding, the VH and VL NNK walk libraries described in Example 1 were panned against VEGF (FIGS. 4A-4B). The obtained enrichment ratio (ER) values showed a bimodal distribution (FIGS. 5A-5B). A subset of mutations had a strong negative effect on the binding function, while the majority of mutations were neutral, and a few mutations had a strong positive effect on fitness. Mutations which had a negative impact on binding were for the most part located in either the HC-HVRs, as those loops are considered to provide most of the binding function of G6.31, or in the conserved residues of the framework as identified in the anti-gD panning (see Example 1). Strongly enriched mutations were located mostly in the less-conserved section of the framework regions and the HC-HVRs. These results confirm the observation from the gD panning described above (see Example 1) that the variable domains are robust and can tolerate many single mutations without substantially affecting the antigen-binding function of the Fab.

To confirm the results obtained from the deep mutagenesis scanning, selected mutations were expressed and purified, and their affinity towards VEGF was measured using BIACORE® surface plasmon resonance (SPR) and their thermostability (as assessed by melting temperature, $T_m$) was measured using differential scanning fluorimetry (DSF). The effect of selected strongly enriched mutations on antigen binding and folding was evaluated. Further, mutations with high enrichment were selected based on their occurrence at a given position in human antibodies according to the Abysis database. In addition, some mutations which were strongly depleted were also tested as negative controls. The Kd and $T_m$ of the indicated G6.31 variants is shown in Table 2. The Kd values listed in Table 2 were measured using single cycle kinetic analysis using a BIACORE® T200 device.

TABLE 2

Characterization of G6.31 Variants Identified By Deep Scanning Mutagenesis

| Clone | $k_{on}$ (1/Ms) | $k_{off}$ (1/s) | Kd (nM) | Fold difference (relative to G6.31) | Melting Temperature (° C.) |
|---|---|---|---|---|---|
| G6.31 WT | 4.45E+05 | 6.86E−04 | 1.54 | — | 83.4 |
| LC-Q3A | 3.89E+05 | 3.59E−04 | 0.92 | 1.7 | 82.8 |
| LC-M4Q | 5.93E+05 | 6.57E−04 | 1.11 | 1.4 | 72.8 |
| LC-S7Q | 7.31E+05 | 6.71E−04 | 0.92 | 1.7 | 83.2 |

TABLE 2-continued

Characterization of G6.31 Variants Identified By Deep Scanning Mutagenesis

| Clone | $k_{on}$ (1/Ms) | $k_{off}$ (1/s) | Kd (nM) | Fold difference (relative to G6.31) | Melting Temperature (° C.) |
|---|---|---|---|---|---|
| LC-S9Q | 1.47E+06 | 6.55E-04 | 0.44 | 3.5 | 83.2 |
| LC-S12M | 8.94E+05 | 6.79E-04 | 0.76 | 2.0 | 82.9 |
| LC-G16K | 3.67E+05 | 3.56E-04 | 0.97 | 1.6 | 79.1 |
| LC-T22D | 4.87E+05 | 3.48E-04 | 0.72 | 2.1 | 81.8 |
| LC-D28R | 1.17E+06 | 6.55E-04 | 0.56 | 2.8 | 80.6 |
| LC-Y36G | 2.25E+05 | 5.58E-04 | 2.47 | 0.6 | 66.8 |
| LC-Q37A | 6.03E+05 | 5.15E-04 | 0.85 | 1.8 | 81.6 |
| LC-S50M | 4.67E+05 | 6.11E-04 | 1.31 | 1.2 | 84.5 |
| LC-L73G | 5.89E+05 | 6.44E-04 | 1.09 | 1.4 | 68.8 |
| LC-F83A | 8.55E+05 | 4.33E-04 | 0.50 | 3.1 | 88.8 |
| LC-Q89N | 9.91E+05 | 4.35E-04 | 0.44 | 3.5 | 79.6 |
| LC-Q89T | 1.17E+06 | 4.93E-04 | 0.42 | 3.7 | 79.1 |
| LC-T97N | 4.32E+05 | 8.02E-04 | 1.86 | 0.8 | 81 |
| LC-N94A | 3.34E+05 | 1.31E-03 | 3.93 | 0.4 | 85.8 |
| LC-N94Q | 2.78E+05 | 1.33E-03 | 4.78 | 0.3 | 84.6 |
| HC-V2R | 4.64E+05 | 3.41E-04 | 0.73 | 2.1 | 81.6 |
| HC-S7L | 7.36E+05 | 5.68E-04 | 0.77 | 2.0 | 83 |
| HC-Q13M | 1.26E+06 | 5.19E-04 | 0.41 | 3.8 | 83.1 |
| HC-A40E | 1.13E+06 | 4.66E-04 | 0.41 | 3.8 | 83 |
| HC-I51H | 2.48E+06 | 1.52E-03 | 0.62 | 2.5 | 83.1 |
| HC-A53R | 8.29E+05 | 3.50E-04 | 0.42 | 3.7 | 84.3 |
| HC-T57E | 1.93E+06 | 4.02E-04 | 0.2 | 7.7 | 84.4 |
| HC-Y58R | 1.48E+06 | 2.55E-04 | 0.17 | 9.1 | 83.2 |
| HC-Y58Q | 3.52E+05 | 3.58E-04 | 1.02 | 1.5 | 84.2 |
| HC-Y59T | 3.60E+05 | 9.74E-04 | 2.71 | 0.6 | 82.9 |
| HC-A60M | 3.86E+05 | 7.29E-04 | 1.89 | 0.8 | 82.8 |
| HC-S70H | 6.58E+05 | 6.60E-04 | 1 | 1.5 | 83 |
| HC-T73N | 6.78E+05 | 5.75E-04 | 0.85 | 1.8 | 83.1 |
| HC-Q81S | 1.07E+06 | 4.87E-04 | 0.45 | 3.4 | 83 |
| HC-Q81W | 1.20E+06 | 5.42E-04 | 0.45 | 3.4 | 83.2 |
| HC-N82aR | 1.39E+06 | 3.22E-04 | 0.23 | 6.7 | 83.1 |

Figure 5C:
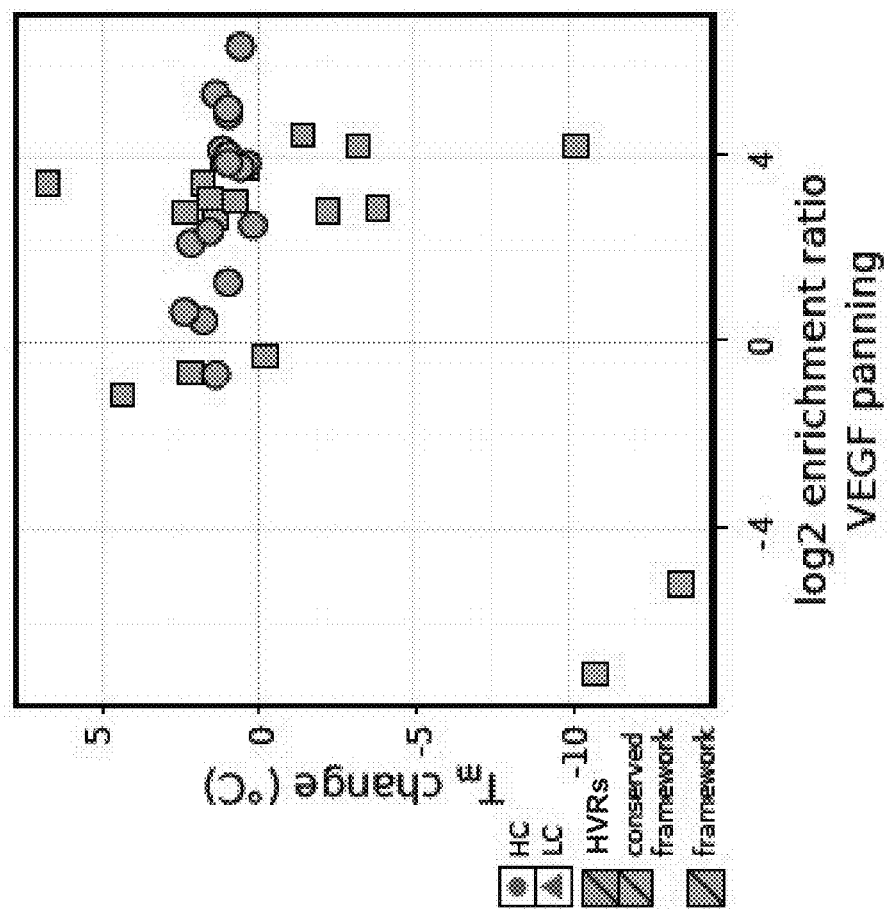
FIGS. 5C-5D are graphs showing a comparison between the log 2 enrichment ratio from VEGF panning of selected mutations with the change in Kd relative to the parental antibody G6.31 (FIG. 5C) or the change in melting temperature ($T_m$) relative to G6.31 (FIG. 5D). The same color scheme as in FIGS. 5A-5B is used.
Figure 5D:
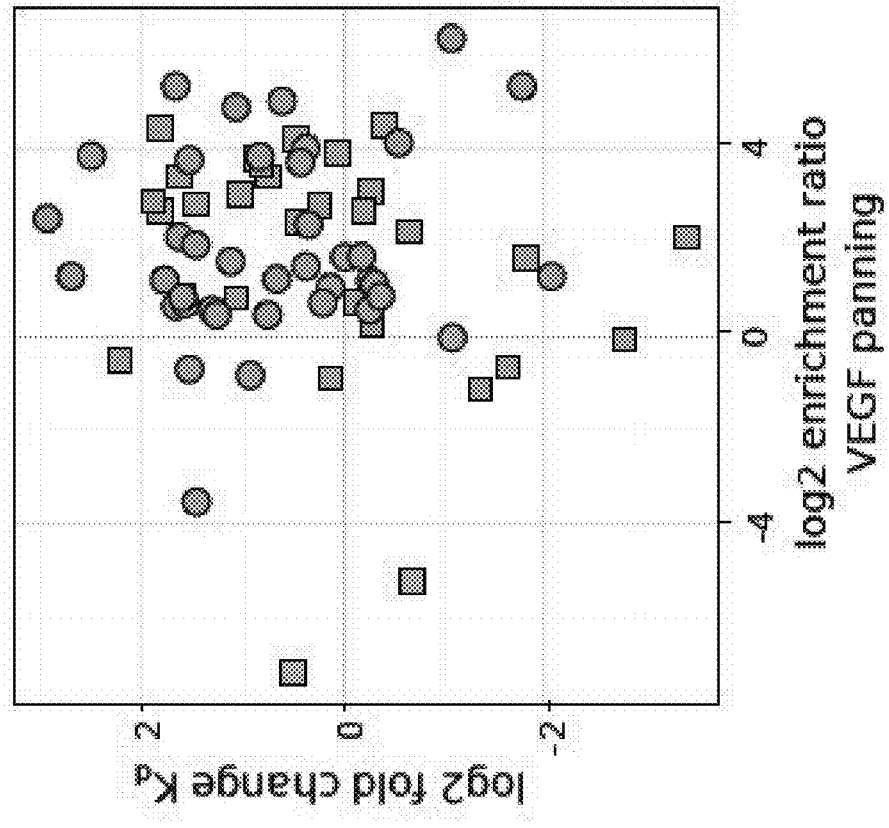

Using the data from 34 mutations (16 on the VH and 18 on the VL), no linear relationship between the enrichment ratio and the obtained gain in affinity or stability was observed (FIGS. 5C-5D). Without wishing to be bound by theory, this could reflect the fact that ER is influenced by a variety of factors including functional expression in *E. coli*, stability of the Fab on the phage particle, as well as binding to the selection protein. One example that illustrates this is the mutation LC-L73G, which is part of the hydrophobic core of the light chain. Replacing the hydrophobic leucine at this position with a glycine likely decreases the packing in the core and leads to a less-stable light chain. The $T_m$ of the LC-L73G mutant was 14.4° C. lower that the wild-type G6.31 Fab. The LC-L73G mutation was depleted in the VEGF panning experiment although it did not have a marked impact on antigen binding affinity as measured by BIACORE® SPR (approximately 1.6-fold increase (i.e., lower $K_d$) in affinity compared to wild-type G6.31). The depletion of G6.31LC$_{L73G}$ was likely an effect of the reduced display of the mutant on phage, and this effect dominated the selection of this mutant over the actual antigen selection. Furthermore, the opposite is also true: a mutation which increases the display (for example, by enhancing expression and/or stability) could be enriched although the actual antigen binding function is impaired or not changed compare to the wild-type (generating a false positive). Therefore variants identified by enrichment may be improved for either binding affinity, stability, expression, and/or other properties.

Figures 5E, 5F:
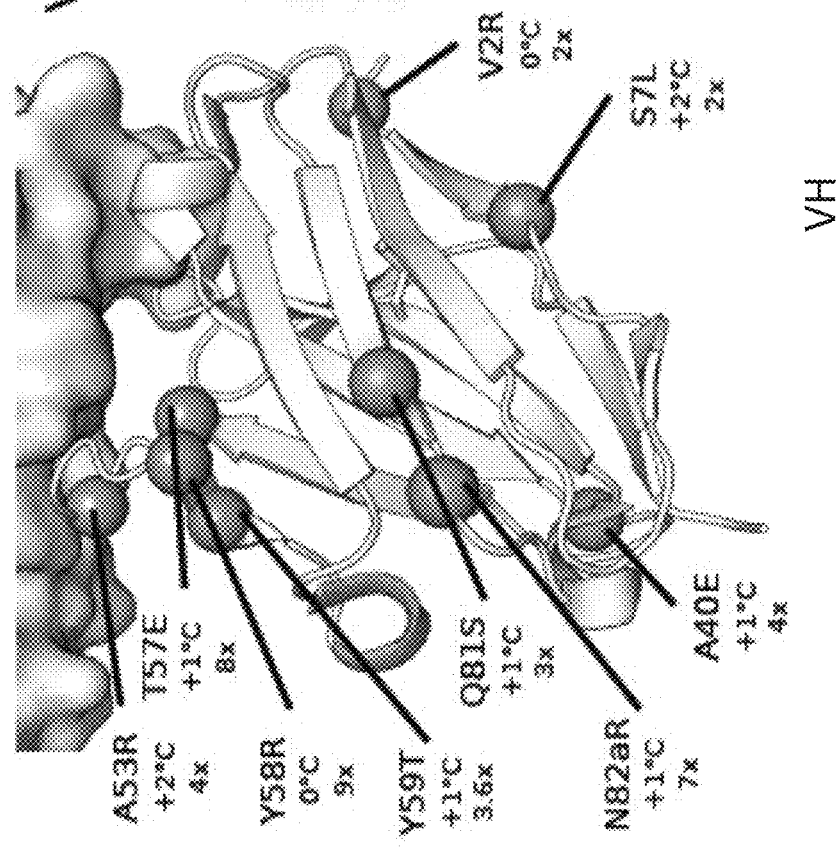
FIGS. 5E-5F are renderings of the crystal structure of the VEGF-bound form of the VH (FIG. 5E) and VL (FIG. 5F) of the G6 Fab (PDB code 2FJG) showing the location of selected mutations as spheres. The surface of VEGF is shown as a surface representation. The same color scheme as in FIGS. 5A-5B is used. The label shows the change in $T_m$ (° C.) and fold change in binding affinity (Kd) compared to G6.31.

Two mutations in HVR-H2 identified by the deep scanning mutagenesis approach, HC-T57E and HC-Y58R, had the highest increase in affinity (8- to 9-fold) compared to wild-type G6.31 (FIG. 5E). A framework region mutation, HC-N82aR, led to an approximate 6.6-fold affinity increase compared to wild-type G6.31 (FIG. 5E). Several other framework region mutations showed a 2- to 4-fold increase in affinity compared to wild-type G6.31 (FIGS. 5E-5F). The highest increase in thermostability was obtained in the light chain mutation LC-F83A (+5.4° C.) (FIG. 5F). In addition to the increase in melting temperature, LC-F83A increased the affinity of G6.31 to VEGF by 3-fold. Surprisingly, many of the mutations which resulted in an increase in affinity were located distal to the antigen-binding site (FIGS. 5E-5F). Among these were HC-N82aR, which is located in the loop between helix α1 and strand p E, more than 22 Å away from the antigen-binding site, and LC-F83A, which is located in the interface between the VL and the light chain constant domain (CL), more than 25 Å away from the HVRs.

In summary, the deep scanning mutagenesis of G6.31 using VH and VL NNK walk libraries and next-generation sequencing identified amino acid residue alterations that increased the binding affinity to VEGF and/or the stability of the Fab.

Materials and Methods

A. Phage Panning Selection on VEGF

Binding clones were selected by incubating the VH or VL NNK walk phage display library (described in Example 1) with 5, 0.5, 0.1 nM biotinylated VEGF in successive rounds of selection, and then competed with 100 nM non-biotinylated VEGF at room temperature or 37° C. to reduce binding of the lower affinity clones to VEGF. Bound clones were captured on ELISA plates coated with neutravidin, washed, and eluted in 100 mM HCl for 20 minutes at room temperature. The eluted phage was neutralized with ¹/₁₀ volume of 1 M Tris pH 8.0 and used to infect *E. coli* for amplification for the next round of selection.

B. Illumina Sequencing of G6.31 Deep Mutational Scanning Libraries and Data Analysis For deep sequencing, phagemid DNA was isolated from *E. coli* XL1 cells carrying phagemid vectors from either the unselected or the selected VH and VL NNK walk libraries panned against VEGF. Purified DNA was used as template for a limited cycle PCR-based amplification of VL and VH regions. PCR products were purified by agarose gel extraction and clean-up (Qiagen Gel Extraction Kit). Eluted amplicon DNA was used as basis for deep sequencing library preparation with standard Illumina library prep methods, using TRUSEQ™ DNA Sample Prep (Illumina). Adapter-ligated libraries were subjected to a single cycle of PCR and sequenced on the Illumina MISEQ®, paired-end 300 bp to cover the entire length of the amplicon. Data analysis was performed as in Example 1 to calculate position weight matrices and enrichment ratios.

C. Antibody Expression

VH and VL sequences of selected variants were cloned into a mammalian Fab vector for expression. Plasmids for both the heavy and light chains were transfected (15 μg) into 30 ml 293T cells for 7 days. The supernatant was harvested to purify by protein G column.

D. Antibody Affinity Determinations by BIACORE® SPR

To determine the binding affinity of selected Fab variants, SPR measurement with a BIACORE® T200 instrument was used. Briefly, series S sensor chip CM5 was activated with 1-ethyl-3-(3-dimethylaminopropyl) carbodiimide (EDC) and N-hydroxysuccinimide (NHS) reagents according to the supplier's instructions, and human VEGF (hVEGF) was coupled to achieve 50-80 response units (RU), then following by blocking un-reacted groups with 1M ethanolamine.

Three-fold serial dilutions of Fab in HBS-P buffer (0.01 M HEPES pH 7.4, 0.15 M NaCl, 0.005% surfactant P20) from low (0.02 nM) to high (50 nM) were injected (flow rate: 30 µl/min). The binding responses on hVEGF were corrected by subtracting of RU from a blank flow cell. The sensorgram was recorded and subject to reference and buffer subtraction before evaluating by BIACORE® T200 Evaluation Software (version 2.0). Association rates ($k_{on}$) and dissociation rates ($k_{off}$) were calculated using a simple one-to-one Langmuir binding model. The equilibrium dissociation constant (Kd) was calculated as the ratio $k_{off}/k_{on}$.

E. Melting Temperature ($T_m$) Determination by Differential Scanning Fluorimetry Differential scanning fluorimetry (DSF) monitors thermal unfolding of proteins in the presence of a fluorescent dye and is typically performed by using a real-time PCR instrument (e.g., Bio-Rad CFX). SYPRO® Orange dye (Invitrogen, Cat. No. S6650) was diluted 1:20 in phosphate buffered saline (PBS). 1 µl of diluted dye was added into 24 µl Fab protein (approximately 100 µg/ml) per well. The temperature was increased from 20° C. to 100° C. using a real-time PCR instrument (Bio-Rad CFX), and the fluorescence intensity was plotted and the inflection point of the transition curve ($T_m$) was calculated using equations such as the Boltzmann equation (see, e.g., Niesen et al., *Nature Protocols* 2(9):2212-2221 (2007)).

Example 3: Conformational Changes of LC-F83 Correlate with the Fab Elbow Conformation in G6 Structures To understand how mutations spatially remote from the antigen binding site could have such a strong impact on antigen binding and stability, the structural effect of the LC-F83A mutation was examined in more detail. The parental antibody of G6.31, G6, has been crystallized previously in the VEGF-bound and VEGF-free forms (Fuh et al., supra). G6.31 carries only four substitutions in the HVR-L3 compared to G6. The crystal structure of G6 was therefore used as a model for G6.31. The crystal structure of the VEGF-free form of G6 contains 12 Fab molecules in the asymmetric unit. The Fab structures can be clustered into two different groups based on the orientation of the constant domains to the variable domains (V-C interface) (FIG. 6A), which is a result of different conformations in the Fab elbow region and can be quantified by measuring the Fab elbow angle (see, e.g., Stanfield et al., *J. Mol. Bio.* 357(5):1566-1574 (2006)).

Figure 7A:
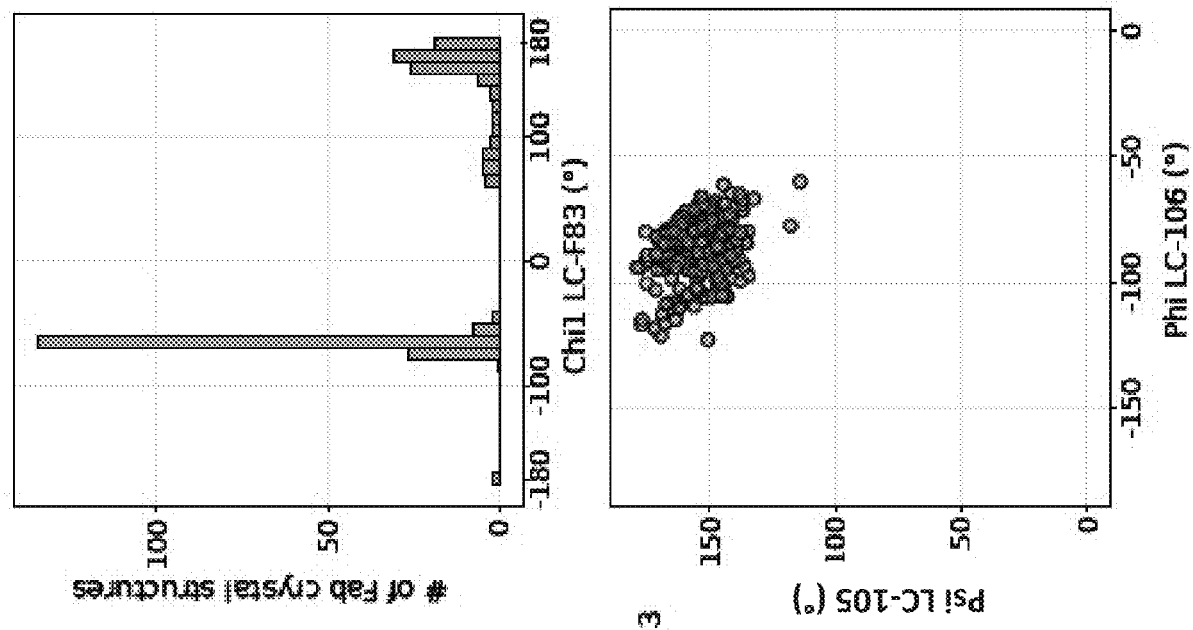
FIG. 7A is a graph (right panel) showing the chi1 ($\lambda_1$) angle of position LC-F83 from 319 human antibody structures from the PDB. The rendering (left panel) shows the position of LC-F83 in the "in" (light red) and "out" (green) conformations.
Figure 7B:
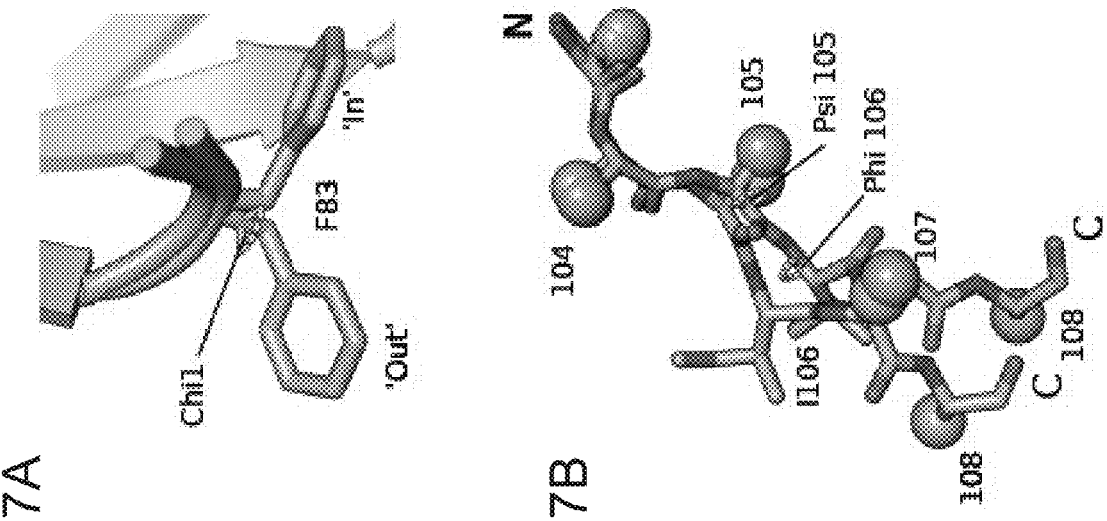
FIG. 7B is a graph (right panel) showing the elbow angle backbone conformation for psi ($\Psi$) angle at position 105 and phi ($\Phi$) angle at position 106. Structures are colored according to their chi1 angle as shown in FIG. 7A. The rendering (left panel) shows light chain (LC) positions 103-108 in the "in" (red) and "out" (green) conformations.
Figure 7C:
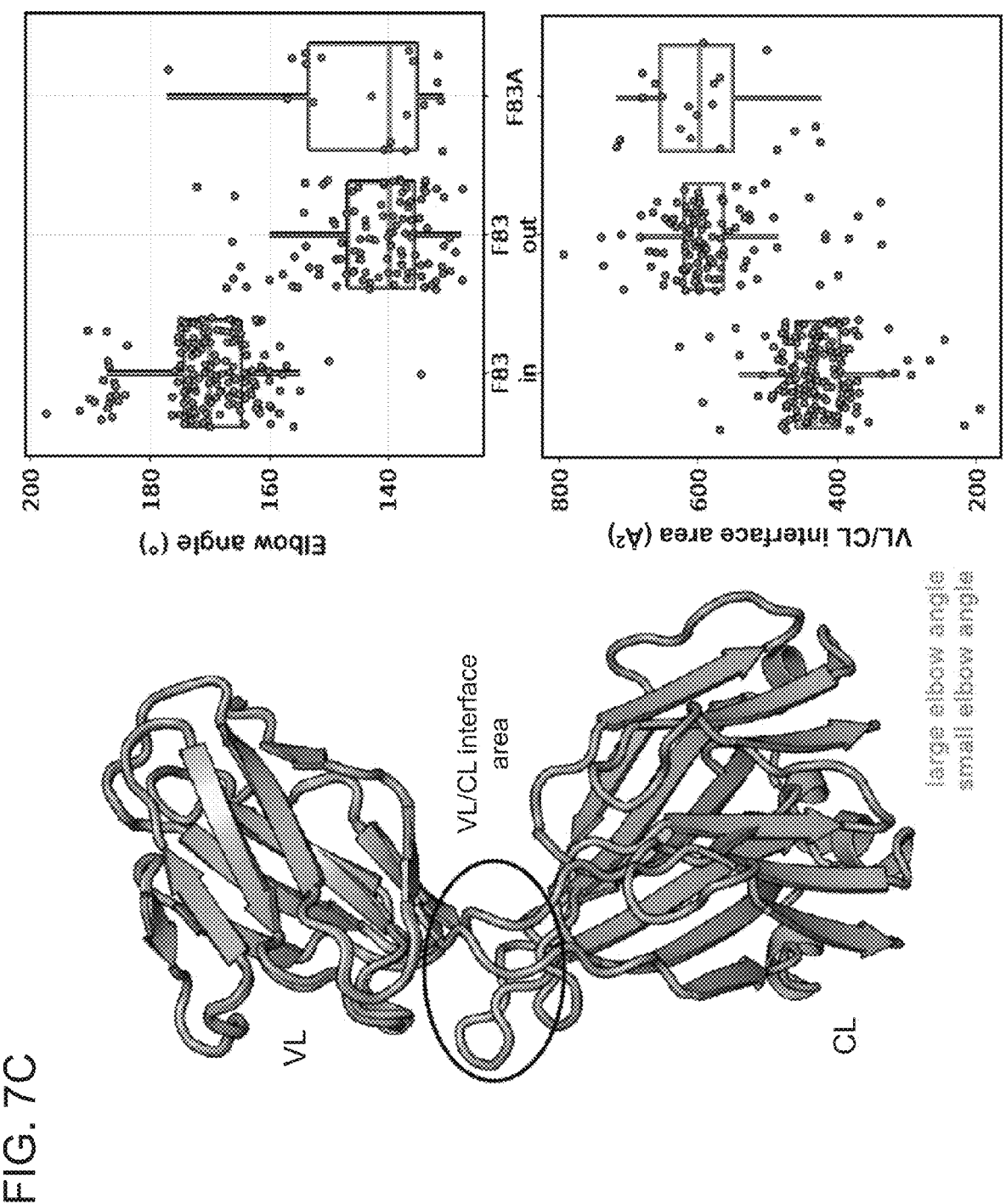
FIG. 7C is a series of graphs showing the elbow angle (top right) and VL/CL interface area (bottom right) for antibody structures with LC-F83 in an "in"-conformation (red) and in an "out"-conformation (green). The results are compared with the Fab elbow angle and the VL/CL interface size of 319 human Fab structures from the PDB carrying LC-F83 and 22 human structures carrying LC-83A. The left panel shows superimposed renderings of G6 molecules having a large elbow angle (light red) and a small elbow angle (green). The VL/CL interface area is indicated by the circle.

The flexibility of the Fab elbow angle is influenced by a ball-socket joint in the heavy chain (see, e.g., Lesk et al., *Nature* 335(6186):188-190 (1988)), but also, and perhaps more importantly, dominated by the light chain class. While kappa light chain antibodies are typically restricted in the elbow angle they can adopt and show a bimodal distribution peaking at approximately 140° and approximately 175°, rarely exceeding 180°, lambda light chain antibodies can adopt a wider range of angles (see, e.g., Stanfield et al., supra). Six G6 molecules in crystal structure have small elbow angles (143-155°) and a tight packing of the DE-loop of CL domain against α1 of the VL, while the other six molecules have a large elbow angle (170-187°) with a loosely packed VL-CL interface (FIGS. 6B-6C). The interface area distribution of different Fab molecules having a loosely packed or a tight packed VL-CL interface is shown in FIG. 7C. The tight packed interface area is, on average, approximately 600 Å, while the loosely packed interface area is approximately 450 A. Further and more detailed analysis revealed that six $G6_{free}$ molecules have small elbow angles (143-155°) which is associated with a tightly packed VL-CL interface (comprising the DE-loop of CL domain packed against α1 of VL, 304±48 Å²), whereas the other six have a large elbow angle (170-187°) with a less tightly packed VL-CL interface (234±29 Å² interface area). Thus, the G6 crystal structure reveals that G6 behaves like a typical human kappa light chain antibody with elbow angles below 180° (FIGS. 6A-6C).

The side chain conformation of LC-F83 correlated with the changes in the Fab elbow angle. In the large elbow angle structures, LC-F83 is tightly bound in a hydrophobic pocket (referred to as the "in" conformation) in the distal capping region of the VL domain (FIG. 6C). In the small elbow structures, LC-F83 is flipped out (referred to as the "out" conformation) from the hydrophobic pocket and is partially solvent-exposed (FIG. 6B). Although located spatially close to the Fab elbow region, LC-F83 is not part of the elbow. However, LC-F83's conformational changes are mirrored by changes in the side chain position of the elbow residue LC-I106. In structures in which LC-F83 is the 'out' conformation, the side chain of LC-F106I moves "up" and occupies the hydrophobic pocket. In contrast, in structures in which LC-F83 is in an "in" conformation, the side chain of LC-I106 is moved "down" (note that "up" and "down" orientations are described with reference to the HVRs as being "up" and the constant domain being "down"). In contrast to LC-F83, the movement of LC-I106 is not limited to the side chain and results also in conformational changes in the protein backbone (LC-105 ψ-angle, LC-106 ψ-angle), likely resulting in the different elbow angles observed. In summary, the crystal structures of G6 suggested that changes in the elbow angle in G6 require conformational changes at position LC-I106 and LC-F83.

Example 4: The Coupling of Conformations of LC-83F with LC-106I is a Common Feature in Human Antibody Structures G6/G6.31 originated from a phage library, which is built on common framework regions for the heavy and the light chain (Lee et al., *J. Mol. Biol.* 340(5):1073-1093 (2004)). The closest germline genes for the light chain are IGKV1-39 and IGKJ1. The most common used human IGKV subgroups, according to the IMGT database (Lefranc et al., *In Silico Biology* 5(1):45-60 (2005)), IGKV1 and IGKV3 carry a phenylalanine at position LC-83, while the other less frequently used germlines typically carry a valine (IGKV2 and IGKV4) or an alanine (IGKV5 and IGKV6) at position 83. The isoleucine at position LC-106 is conserved in all five human IGKJ germline genes.

To determine whether the coupling of the side chain conformation of position F83 with the Fab elbow conformation is a common feature in human antibodies, the conformation of LC-F83 was determined in 319 human Fab crystal structures from the Protein Data Bank (PDB). The structures were grouped as structures with LC-F83 in an "in" conformation (dihedral angle chi1 between −50° and −100°) and structures in an "out" conformation (chi1 angle mostly between 50° and 180°) (FIG. 7A). The LC-F83 conformation correlated in the vast majority of structures with changes in the Fab elbow region at position LC-106 (FIG. 7B). Further, the two groups exhibited significant differences in the elbow angle (FIG. 7C) as well as in the area of the V-C interface, demonstrating that structures with a large elbow angle have smaller, less tight packed V-C interface, while structures with a large elbow angle have a large V-C interface (FIG. 7C).

Since the LC-F83A mutation resulted in higher thermostability and higher affinity towards the antigen, the elbow angle of 20 human Fab structures available in the PDB carrying LC-83A and LC-106I was determined. These structures mirrored the properties of the LC-83F "out" confirmation structures: they exhibited a small elbow angle and large V-C interface (FIG. 7C).

In summary, these results demonstrated that the bimodal distribution in the Fab elbow angle of human kappa light chain antibodies as observed previously (Stanfield et al., supra) is mainly a result of different conformations of the phenylalanine side chain at position LC-83. The data further showed that the type of amino acid which is present at position LC-83 has a large influence on the Fab elbow angle.

Materials and Methods

Human antibody structures were obtained from the structural antibody database (SAbDab, Dunbar et al., *Nucleic Acids Research* 42:D1140-1146 (2014)). Additional structure filtering and structure handling (amino acid renumbering, dihedral angle determination, structural alignments) was performed using Bio3D (Grant et al., *Bioinformatics* 22(21):2695-2696 (2006)). The interface area between constant and variable domains was calculated using a local instance of CCP4-Pisa (Krissinel et al., *J. Mol. Biol.* 372 (3):774-797 (2007)). ABangle (Dunbar et al., *Protein Eng. Des. Se.* 26(10):611-620 (2013)) was used to characterize the VH-VL interaction. Pymol and a publically-available script was used to calculate the elbow angle.

Figure 8A:
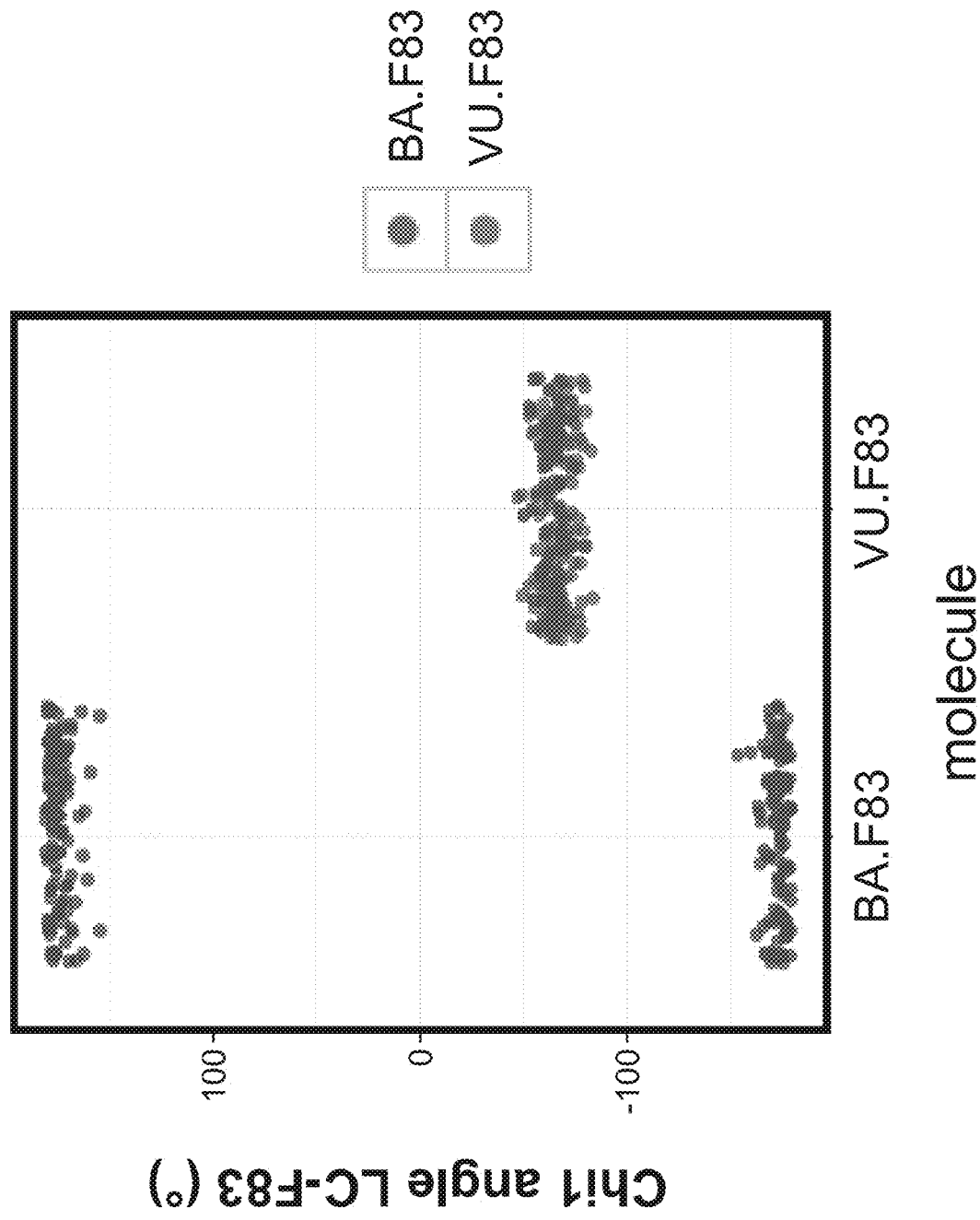
FIG. 8A is a graph showing the chi1 angle for LC-F83 for a G6 Fab crystal structure with a large elbow angle (G6 chains VU, G6-VU) and a crystal structure with a small elbow angle (G6 chains BA, G6-BA).
Figure 8C:
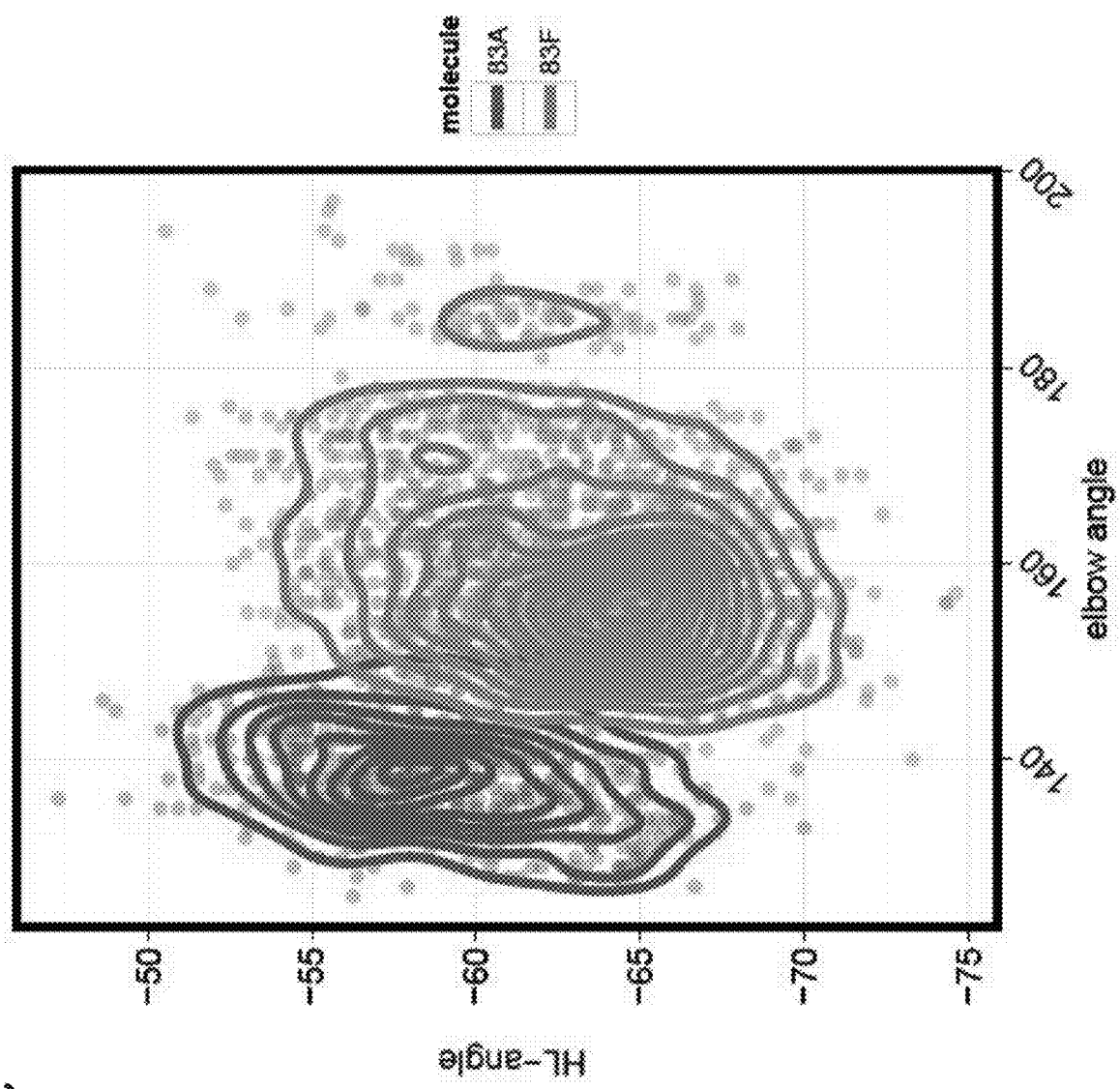
FIG. 8C is a graph showing the results of molecular dynamics simulations plotting Fab elbow angle as a function of VH/VL torsion angle ("HL-angle"). The scatter/contour plot shows the VH/VL torsion angle and elbow angle that VU.F83 (red) and VU.F83A (green) adopt during the molecular dynamics simulation. Two distinct populations are visible for the two molecules.

Example 5: Molecular Dynamics Simulation Confirms that Position LC-83 Acts Like Switch to Transition Between a Large and Small Fab Elbow Conformation Molecular dynamics was used to gain further insight into the effects of the LC-F83A mutation identified in the structural meta-analysis described in Example 4. The effect of the LC-F83A mutation was simulated in two different structural backgrounds. A G6 Fab crystal structure with a large elbow angle (G6 chains VU, "VU.F83") and a crystal structure with a small elbow angle (G6 chains BA, "BA.F83") were used. Both structures in addition to the mutated structures (VU.F83A and BA.F83A) were simulated for 100 ns in water. During the time of the simulation, no changes in the conformation of F83 were observed: in the case of VU.F83, LC-F83 stayed in an "in" conformation, while in case of BA.F83, the residue stayed in an "out" conformation (FIG. 8A). A comparison of the changes in the elbow angle over time during the simulation revealed that the elbow angles of all four molecules stayed fairly stable during the simulation after an initial equilibration phase of about 25 ns (FIG. 8B).

Figure 9B:
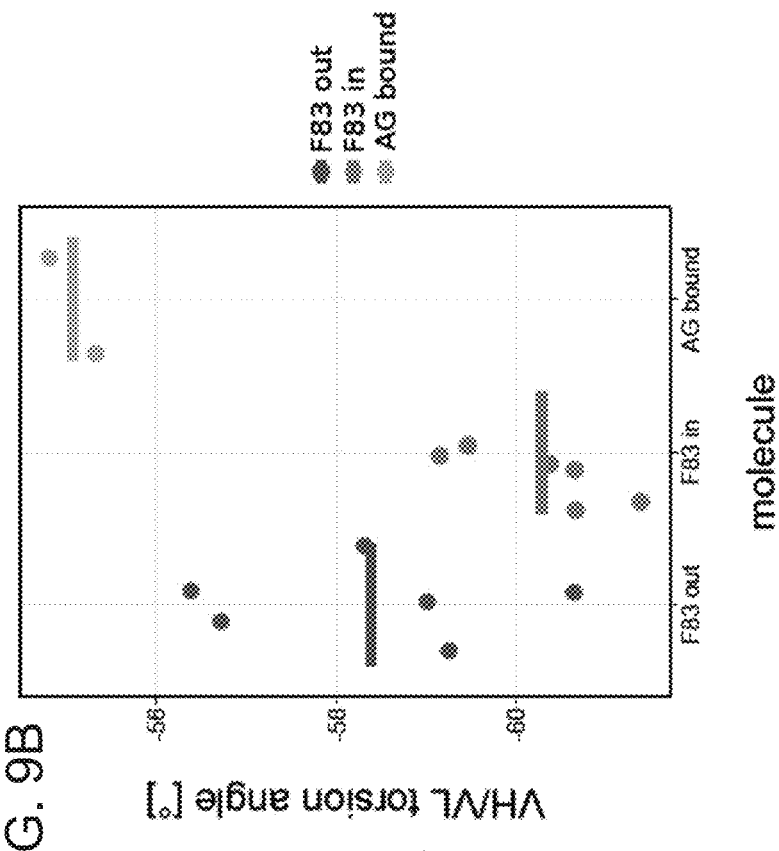
FIG. 9B is a graph showing the VH/VL torsion for five molecules of $G6_{unbound}$ with LC-F83 in an "out" conformation (red) and the five molecules with $G6_{unbound}$ with LC-F83 in an "in" conformation (green) as well as the VH/VL torsion angle of the VEGF-bound G6 structures ("AG bound," orange).
Figure 9A:
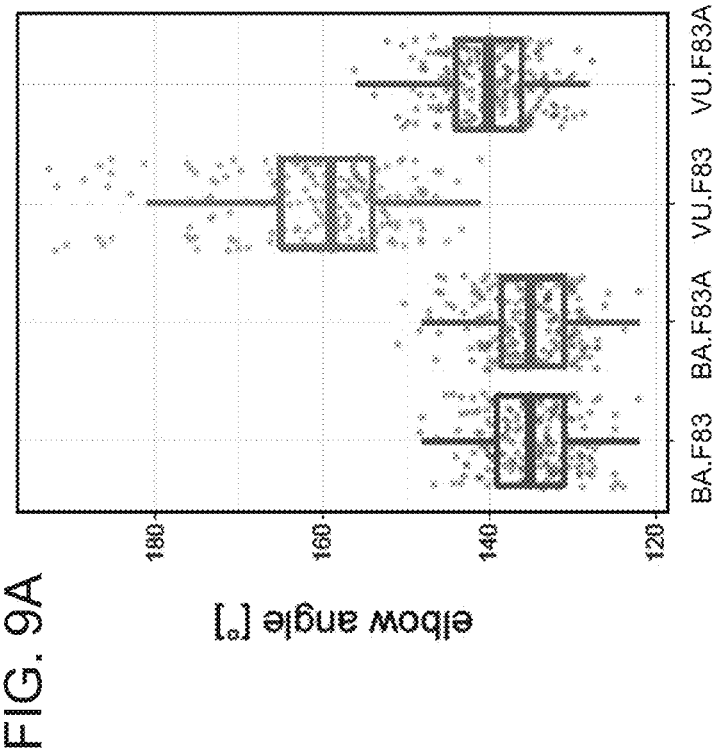
FIG. 9A is a graph showing the Fab elbow angle distribution for the molecules BA-F83 (LC-F83 in an "out"-conformation), BA-F83A, VU-F93 (LC-F83 in an "in"-conformation) and VU-F83A obtained during the last 75 ns of a 100 ns molecular dynamics simulation. All samples were significantly different (p<0.001), except BA-F83 and BA-F83A, as determined by an analysis of variance (ANOVA)/Tukey's Honest significant difference (HSD) test.

No statistically significant difference in the elbow angle distribution of BA.F83 and BA.F83A was observed. For both molecules, the elbow angle fluctuated around 135°. However, there was a significant difference between the elbow angle of VU.F83 and VU.F83A during the simulation. During the first 25 ns of the simulation, the elbow angle of VU.F83A collapsed and fluctuated around 140°, while the elbow angle of VU.F83 stayed stable at a large angle of 161° (FIG. 9A).

The results presented above demonstrate the importance of the LC-F83 "in" conformation to stabilize a large Fab elbow angle. The LC-F83A mutation resulted in an immediate transition to a small elbow angle and a larger VL-CL interface in the molecular dynamics simulation. Because no transition of the LC-F83 side chain from an "in" to an "out" conformation and visa versa could be observed, these results suggest that LC-F83 imposes a significant energy barrier on changes in the elbow angle of the molecule.

Taken together, the increase in thermostability of G6.31$_{LC-F83A}$ compared to G6.31 can be explained by an increase in the V-C interface interaction area, which in turn further stabilizes the fold of the four domains of the Fab. Further, the tighter packing in the V-C interface reduces the solvent exposure of hydrophobic residues like LC-I106.

Materials and Methods

Molecular dynamics simulations were performed using amber12 (Case et al., *J. Comput. Chem.* 26(16):1668-1688 (2005)). If not otherwise noted, 100 ns were simulated at constant pressure and 300K. Before simulation, sections in the constant domains of the G6 structures which were not resolved because of missing electron density were complemented using the PDB entry 4hh9. The obtained simulated structures were analyzed using VMD (Humphrey et al., *Journal of Molecular Graphics* 14(1):33-38, 27-38 (1996)), Bio3d, CCP4-Pisa, Pymol and ABangle.

Example 6: Elbow Angle Dynamics of the G6 Fab Influence the Antigen-Binding Interface by Modulating the VH-VL Torsion Angle While the change in Fab elbow angle explained the increase in melting temperature in the LC-F83A variant, the effect of this mutation on antigen binding was not directly explained by the change in Fab elbow dynamics. Without wishing to be bound by theory, the LC-F83A mutation could influence antigen binding indirectly via the change in Fab elbow angle, or could influence antigen binding directly, as LC-F83A sits close to the VH-VL interface and could affect the orientation of the VH and VL domains towards each other. The VH-VL interface, although not in direct contact with the antigen, can have a strong influence in antigen binding affinity (see, e.g., Masuda et al., *FEBS J.* 273(10): 2184-2194 (2006); Khalifa et al., *Journal of Molecular Recognition* 13(3):127-139 (2000)). Further, in the antigen-free state, the VH-VL interface of a Fab is typically flexible, with antigen binding resulting in an increase in rigidity (Dunbar et al., *Prot. Eng. Des. Sel.* 26(10):611-620 (2013)). In addition, the VH-VL orientation can vary substantially between the ligand-free and the antigen-bound form (see, e.g., Stanfield et al., *Structure* 1(2):83-93 (1993)).

Indeed the crystal structures of G6 showed flexibility and significant differences in VH/VL torsion angle (HL torsion angle) between different G6 antigen-free structures (G6$_{unbound}$) and the VEGF-bound structures (G6$_{bound}$). The mean VH/VL torsion angle (HL torsion angle) of the six G6$_{free}$ molecules, which have a large elbow angle is approximately 60°, while it is approximately 58° for the six molecules which have a small elbow. This is in turn substantially closer to the mean HL torsion angle of G6$_{VEGF}$, which is −55° (FIG. 9B).

Figure 9D:
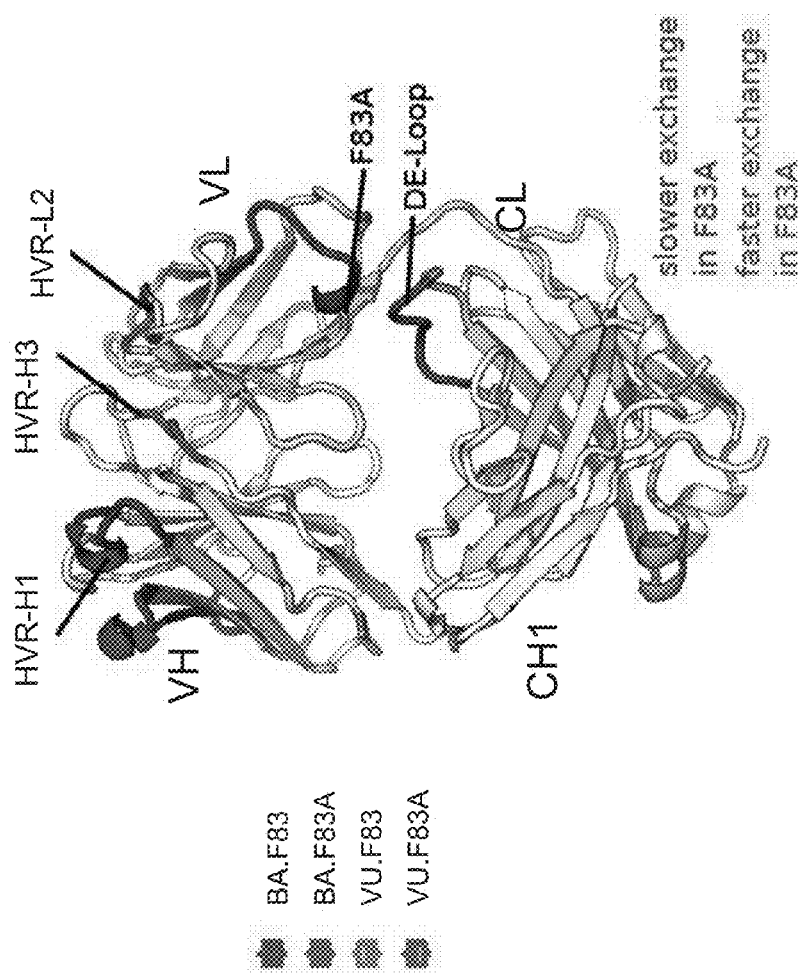
FIG. 9D is a rendering of the crystal structure of unbound G6 showing regions having different hydrogen-deuterium exchange patterns between G6.31 and $G6.31_{LC-F83A}$. Regions colored in blue had slower exchange in $G6.31_{LC-F83A}$ compared to G6.31, while regions colored in red had faster exchange in $G6.31_{LC-F83A}$ compared to G6.31. The positions of the F83A mutation and the DE loop are indicated by lines.
Figure 9C:
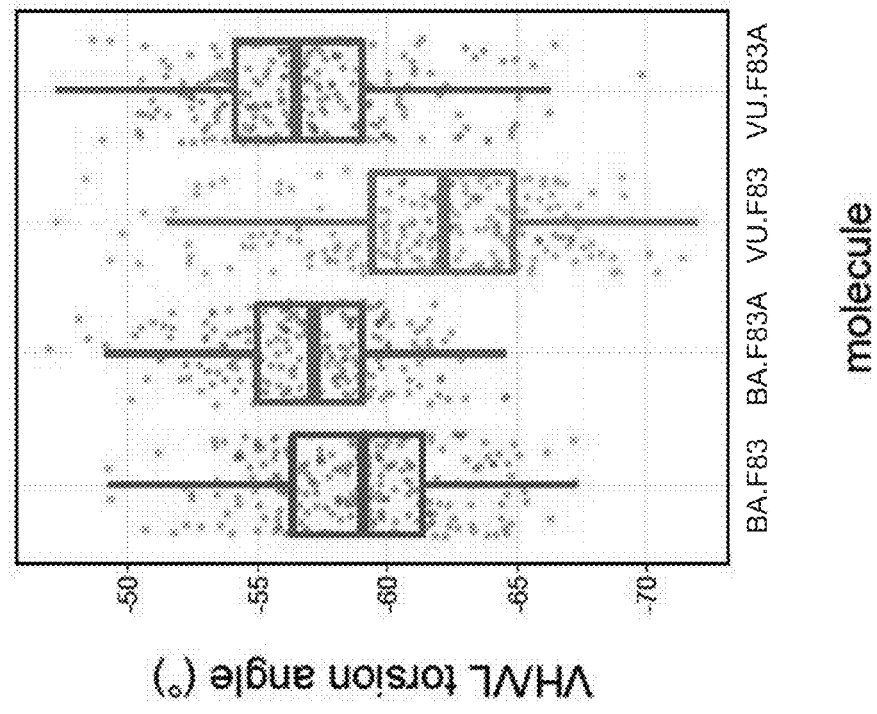
FIG. 9C is a graph showing the VH/VL torsion angle distribution of the same molecules as in FIG. 9A during the same 100 ns molecular dynamics simulation. All samples were significantly different (p<0.001), except BA-F83A and VU-F83A, as determined by an ANOVA/Tukey HSD test.

Molecular dynamics simulation was used to exclude the possibility that these changes in torsion angle were an artifact of crystallization. The median HL torsion angle for VU.F83 is approximately 62° while it was approximately 59° for BA.F83, conforming the results found in G6$_{unbound}$ crystal structures. Moreover, the two mutant Fabs (BA.F83A and VU.F83A) exhibited an even smaller torsion angle (approximately 57° and approximately 57°, respectively), which is even closer to the torsion angle observed in G6$_{bound}$ structures (FIG. 9C). Moreover, the mutation at LC-F83A suggested an additional effect of the mutation on the VH-VL interface, as the HL-angle of BA.F83A was significantly smaller than that of BA.F83 (p<0.0001)

These results indicated that the LC-F83A mutation influenced the HL torsion angle and in turn antigen binding by two different mechanisms. First, the LC-F83A mutation mediates this indirectly by changing the Fab elbow angle. Structural data and molecular dynamics simulations showed that there is a correlation between the elbow angle and the HL-angle (FIGS. 8A-8C and 9A-9D). Second, LC-83 directly influences the VH-VL interface. There was an additional significant increase in the HL torsion angle when LC-F83A was introduced (FIGS. 9A-9D, compare molecule BA.F83 and BA.F83A). The result is an antigen binding site configuration in the antigen-free form of G6.31$_{LC-F83A}$ which is closer to the one observed in the structure of G6$_{VEGF}$. Without wishing to be bound by theory, the rearranged antigen binding interface of G6.31$_{LC-F83A}$ could result in lower energy cost for VEGF binding, and thus the observed increase in affinity (decreased Kd) of G6.31$_{LC-F83A}$. Additionally, the presumably better packing of the VH-VL interface in G6.31$_{LC-F83A}$ could provide an alternative or additional fold stabilization mechanism (see, e.g., Rothlisberger et al., *J. Mol. Biol.* 347(4):773-789 (2005)) to explain the observed increase in T$_m$.

Materials and Methods

Structural analysis and molecular dynamics simulations were performed as described in Examples 3-5.

Example 7: Hydrogen-Deuterium Exchange Mass Spectrometry (HDX-MS) Confirms Conformational Changes in the Constant Variable Interface as Well in the Antigen Binding Region in G6.31$_{F83A}$ Compared to G6.31

HDX-MS was used to demonstrate that the changes in inter-domain dynamics of the Fab molecule due to the LC-F83A mutation described in Examples 3-6 can be observed in solution. HDX-MS measures the exchange rate of backbone amide hydrogen atoms with deuterium. Backbone amide hydrogen atoms typically exchange faster if they are solvent-exposed and not involved in the formation of hydrogen bonds compared to when they are buried and/or involved in the formation of hydrogen bonds. Several regions show differences when the hydrogen-deuterium exchange pattern of G6.31 is compared to G6.31$_{LC-F83A}$ (FIG. 9D). The DE-loop of the CL domain, which forms the VL-CL interface and is in proximity to the LC-F83A mutation, exchanged slower in G6.31$_{LC-F83A}$ compared to G6.31. Changes in the exchange rate of HVR loops and neighboring regions were also observed. The HVR loops H1 and L2 exchanged slower in G6.31$_{LC-F83A}$ compared to G6.31, while the adjacent regions of the HVR-H3 loop which sit in the VH-VL interface exchanged faster. The HVR-L2 and HVR-H3 loop are part of the VH-VL interface (see, e.g., Vargas-Madrazo et al., *Journal of Molecular Recognition* 16(3):113-120 (2003); Aburatani et al., *J. Biochem.* 132(5):775-782 (2002); Padlan, *Molecular Immunology* 31(3):169-217 (1994)). Therefore, the changes in the exchange pattern observed in the HVRs and the VL-CL interface in HDX-MS between G6.31 and G6.31$_{LC-F83A}$ independently confirmed the results obtained from the structural analysis and molecular dynamics simulation.

Materials and Methods

G6.31 WT and F83A mutant samples (45 µM) were diluted 15-fold into a 20 mM histidine-acetate buffer at pD 7.0 and 50 mM NaCl with >90% D20 content to begin the labeling reaction at 20° C. At six logarithmically-spaced time intervals spanning 30 seconds to 1000 minutes, the labeling reaction was quenched by pH reduction (pH 2.5) and the addition of 2M guanidinium chloride (GdmCl) and 0.25 M tris(2-carboxyethyl)phosphine (TCEP) before injection onto a cold online system (see, e.g., Mayne et al. *J. Am. Soc. Mass Spectrom.* 22(11):1898-1905, 2011).

Briefly, quenched samples were first passed through an immobilized pepsin column (2.1×30 mm, Applied Biosystems) at 0° C. for proteolysis and then bound to a trap column for desalting (ACQUITY VANGUARD™ C8) before being separated by a reverse-phase chromatography (ACQUITY UPLC® BEH C18, 1.7 µm particle size, 1.0×50 mm) and introduced into the mass spectrometer (Thermo ORBITRAP ELITE™, 120 k Hz resolution at m/z 400) for measurement of deuterium content. Chromatographic mobile phases were prepared as described previously (Walters et al. *J. Am. Soc. Mass Spectrom.* 23(12):2132-2139, 2012) with pH of 2.25 to maximize deuterium recovery which averaged 82% by measurement of fully deuterated controls. Mutant and wild-type experiments were interleaved and randomized timepoints were collected in triplicate; the entire process was automated by the LEAPv1 robotics platform (Leap Technologies, Carrboro, NC) which performed all sample handling steps. This process resulted in 152 unique peptides, consistently identified by the ExMS program (Kan et al. *J. Am. Soc. Mass Spectrom.* 22(11):1906-1915, 2011) for both wild-type and mutant samples, providing sequence coverage of roughly 95%. Analysis of deuterium content involved the use of previously described custom python scripts (Kan et al. supra; Walters et al. *Proc. Nat. Acad. Sci. USA* 110(47):18898-18903, 2013; and Hu et al. *Proc. Natl. Acad. Sci. USA* 110(19):7684-7689, 2013), and significant differences in deuterium uptake levels between wild-type and mutant were identified by Student's t-test as having a p-value<0.05, described previously for HDX-MS experiments (Leurs et al. *Anal. Chem.* 86(23):11734-11741, 2014).

Example 8: Somatic Hypermutation Target LC-83 and LC-106 in Human Antibodies

Position LC-83 is located close to an AID hotspot motif (RGYW, where R is a purine, Y is a pyrimidine, and W is A or T) in the IGKV1-39 germline light chain gene. The increase in thermostability caused by the LC-F83A mutation was transferable to other antibodies which originate from the same germlines as G6.31. Therefore, the frequency of somatic mutations at position LC-83 in human antibodies was evaluated. In addition, LC-106 was also included in this analysis.

Figure 10A:
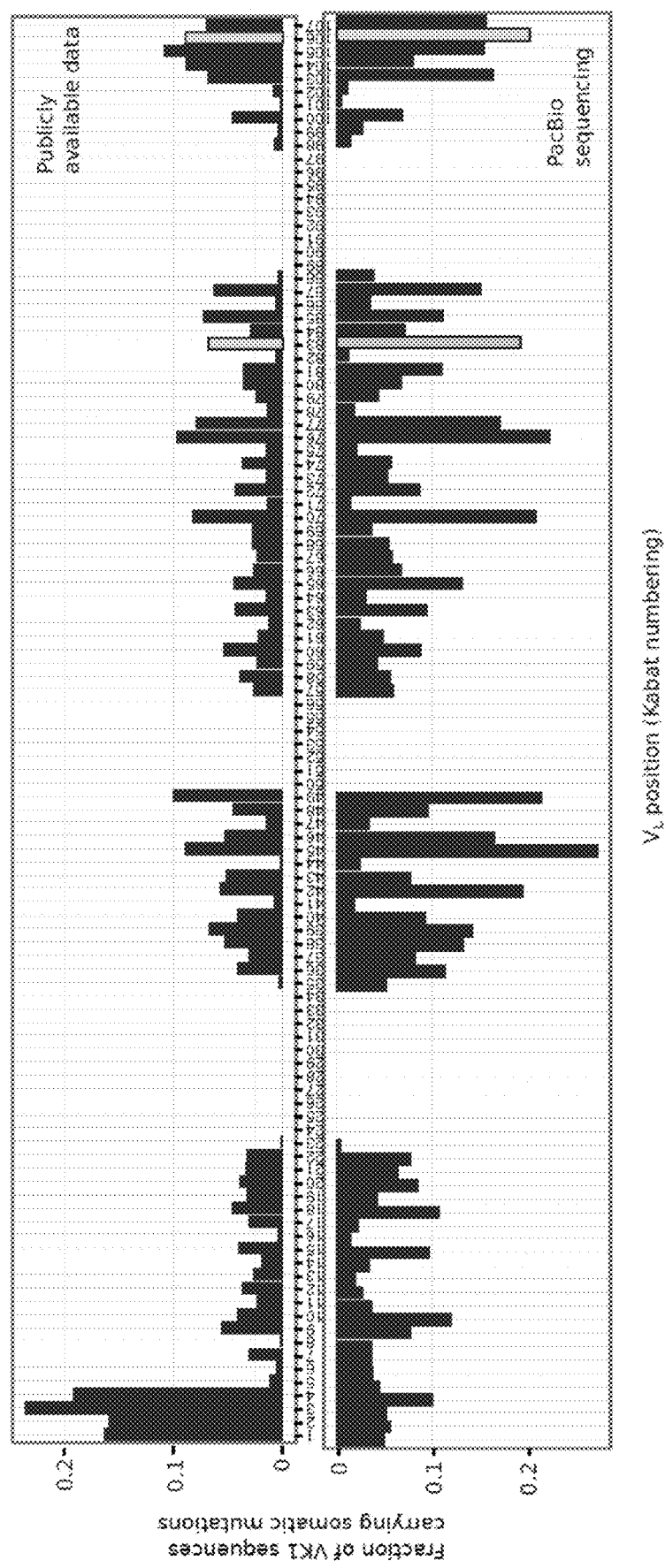
FIG. 10A is a graph showing the distribution of somatic mutations for the indicated VL positions of antibody sequences originating from IGKV1 germlines. The mutational distribution in the upper panel was obtained using publicly available human antibody sequences from Genbank, the Protein Database (PDB), the Kabat database, the Abysis database, and the IMGT database ("Public dataset"). The mutational distribution in the lower panel was obtained using single molecule real-time sequencing (SMRT) of cDNA obtained from over 1000 individual human lymphoid tissues. The high mutation rates at the N-terminus of publically available sequences likely come from cloning artifacts.

Two approaches were used to examine the distribution of somatic hypermutation (SHM) in light chain sequences originating from IGKV1 germlines. The first was to collate the somatic mutations of 4623 unique human IGKV1 light chain sequences available in several publicly available databases (FIG. 10A, upper panel). The second was by amplifying IGKV1 sequences from RNA originating from over 1000 individual human lymphoid tissues followed by high-fidelity single molecule real-time sequencing (SMRT) and SHM collating. Despite the different origin of the two datasets, a very similar distribution of somatic mutations was observed (FIGS. 10A-10C). LC-83 is one of the most frequently mutated positions in the VL segment; 7% and 19% of all IGKV1 sequences carry a mutation at LC-83 in the two datasets, respectively. Interestingly, position LC-106 also frequently mutated in IGKV1 sequences (9% and 20%, respectively), and the most common mutation is valine. The closest germline gene segments for the G6 VL are IGKV1-39 and IGJ1. Therefore, the antibodies of IGKV1.39 germline source were examined, which revealed that somatic mutations at LC-F83 primarily result in smaller side chains (including serine, valine, and leucine) (FIGS. 10A-10C). Alanine substitutions in antibodies of IGKV1.39 were not observed, likely because an alanine mutation would require a two-base substitution in the codon at LC-F83 that rarely occurs.

Figure 10D:
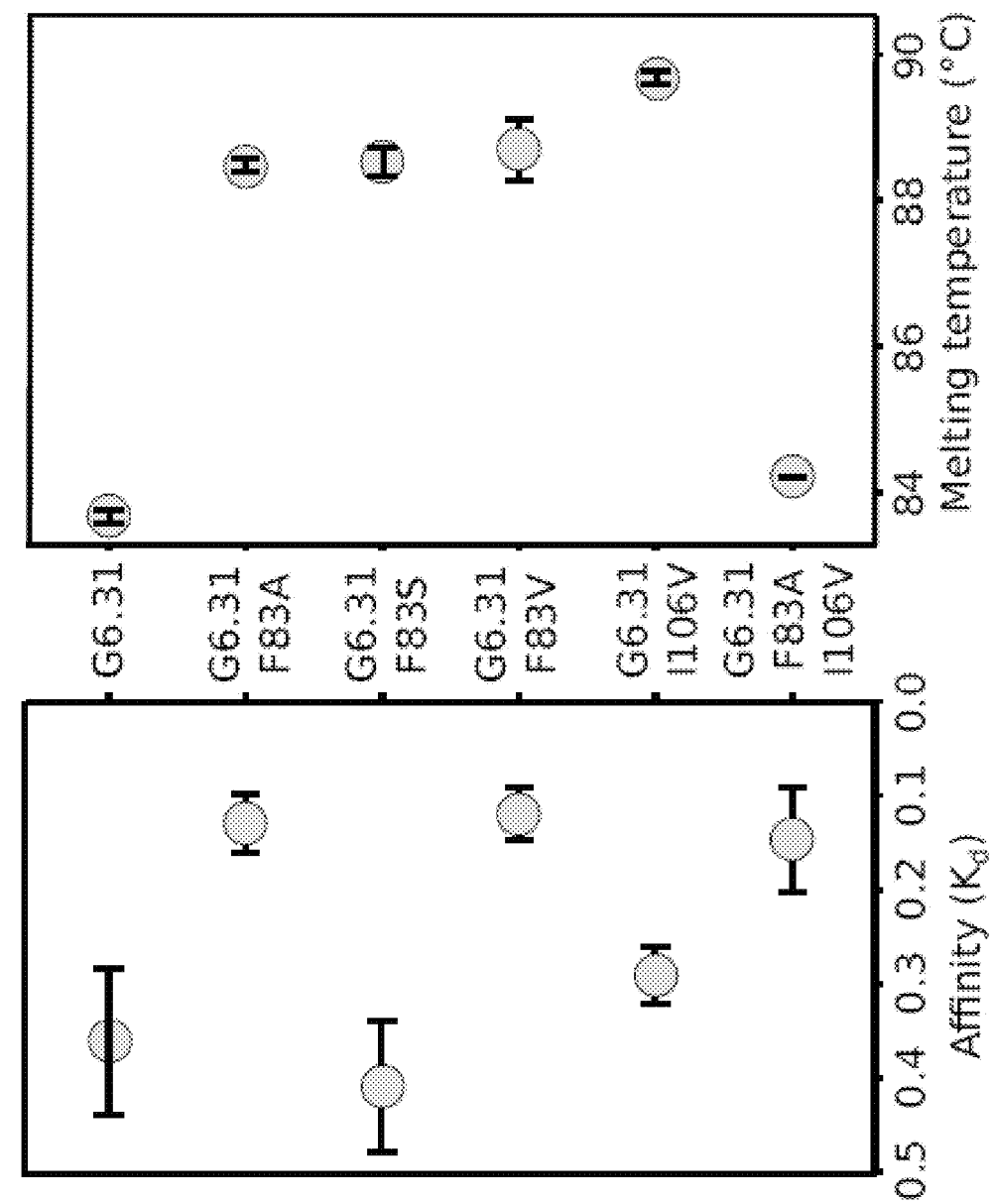
FIG. 10D is a series of graphs showing affinity (Kd) of selected mutant variants of G6.31 as measured by BIA-CORE® surface plasmon resonance (left panel) and the melting temperature $T_m$ for selected G6.31 mutant variants as determined by differential scanning fluorimetry (DSF) (right panel). The circles in the left panel represent the mean from three replicates with the respective standard deviation shown by error bars. The circles in the right panel represent the mean from three replicates and the respective standard deviation shown by error bars.

Next, G6.31 Fab variants carrying the most frequent somatic mutations for position LC-83 and LC-106 were generated, and their effect on antigen binding and thermostability was determined (FIG. 10D). All single mutation variants increased the $T_m$ by 4.8° C. to 6° C., presumably by decreasing the Fab elbow angle and increasing the VL-CL interface area. Consistently, the double mutation LC-F83A/LC-I106V did not result in a significant increase in $T_m$. Without wishing to be bound by theory, simultaneously reducing the size of both side chains would leave a void in the hydrophobic cavity typically occupied by LC-F83 or LC-I106, and reduce the ability of the VL to stably pack against the CL. The effect of the LC-83 mutation on VEGF affinity is mixed. LC-F83V leads to a 3-fold increase in affinity, similar to LC-F83A, whereas the mutations LC-F83S and LC-I106V showed nearly no increase in affinity. The effect of the LC-83 mutation on antigen affinity may be context dependent. LC-F83A mutations were introduced into another antibody originated from the same germline as G6.31 and a similar increase in thermostability and affinity was observed. Additionally, an LC-F83S mutation has been reported to increase the affinity of an anti-estradial antibody.

In summary, LC-83 and LC-106 are frequently mutated in human antibodies. Given the influence of these two positions on the affinity and stability, optimization of the overall Fab domain dynamics is a molecular mechanism that may be highly utilized during antibody affinity maturation in vivo.

Materials and Methods

Human light chain sequences were obtained from various publicly available sources: Abysis (Available at the bioinf.org.uk/abysis website), Kabat database (Martin, Proteins 25(1):130-133 (1996)), IMGT database (Lefranc, Molecular Biotechnology 40(1):101-111 (2008)), GenBank (Benson et al., *Nucleic Acids Research* 43:D30-35 (2015)), and Protein Data Bank (Berman et al., *Nucleic Acids Research* 28(1): 235-242 (2000)). Duplicated sequences were removed and the closest germline genes were assigned for the respective V-segments using IGBlast (Ye et al., *Nucleic Acids Research* 41:W34-40 (2013)). Sequences for which a mouse or rat germline was assigned were removed from the dataset. Sequences were Kabat numbered (see, e.g., Wu et al., *J. Exp. Med.* 132(2):211-250 (1970)), and somatic mutations in the framework of the V-segment were identified. Mutations in the HVR regions (as defined by the Kabat numbering schema) were not considered in this analysis.

The second source of human antibody sequences was from the commercially available RNA from human spleen, tonsil, bone marrow, and peripheral blood lymphocytes originated from 1088 individuals (Clonetech and Amsbio). The RNA was first transcribed into cDNA using the SMARTER® RACE cDNA Amplification Kit (Clonetech). IGKV-specific DNA was amplified using 5' RACE (Advantage 2 PCR Kit, Clonetech) with a custom primer annealing the 5' region of the IGKC region (5'-CATCAGATGGCGG-GAAGATGAAGACAGATGGTGC-3' (SEQ ID NO: 56)), while IGKV1 segments were enriched in a second PCR step using primers: forward: 5'-GCCATCCA-GATGACCCAGTCTCC-3' (SEQ ID NO: 57) and reverse: 5'-GGCTGCACCATCTGTCTTC-3' (SEQ ID NO: 58). The PCR product was gel purified and sequenced using Pacific Bioscience RSII (EA Genomic Services). A total of 994.8 Mbp were obtained. The consensus sequence of each read was created using Pacific Bioscience's SMRT Analysis 2.3 software package. The germline annotation of the consensus sequences was performed using VDJFasta (Glanville et al. *Proc. Natl. Acad. Sci. USA* 106(48):20216-20221). Sequences were Kabat numbered and somatic mutations in the framework of the V-segment were identified. In total, 19034 sequences were annotated as IGKV1, of which 3796 contained at least three framework regions and two HVRs and were included to generate the SHM distributions.

Example 9: Identification of Surface Charge Variants of G6.31

To isolate mutations which could be used to lower the pI of G6.31, surface-exposed positions were identified within the variable domains using structural information from the G6 crystal structure. Positions for which a substitution to glutamate showed an enrichment ratio of 1 or greater based on the VEGF panning of the NNK walk VH and VL libraries (Example 2) were selected to test their impact on VEGF binding affinity by single cycle kinetic analysis using a BIACORE® T200 system and thermostability (DSF) (Table 3A). Mutant variants containing substitutions to glutamate, as well as other charged residues (e.g., arginine, lysine), were generated, expressed, and purified as described above (see Example 2, Materials and Methods). Note that, in some instances, the overall Kd listed in Table 3A for some variants is weaker as compared to the results in Table 4 due to fitting differences between single cycle kinetic analysis (Table 3A) and multiple cycle kinetic analysis (Table 4). Table 3B shows the yield, percent monomer (% monomer), and elution time for the indicated variants.

TABLE 3A

Characterization of Surface-Exposed Charge Variants

| Variant | $k_{on}$ (1/Ms) | $k_{off}$ (1/s) | Kd (M) | Fold change (relative to G6.31) | $T_m$ |
|---|---|---|---|---|---|
| G6.31 (WT) | 3.01E+05 | 5.13E−04 | 1.7E−09 | — | 83.8 |
| LC-S7E | 3.56E+05 | 4.43E−04 | 1.24E−09 | 1.4 | 85.8 |
| LC-S9E | 1.24E+06 | 4.57E−04 | 3.68E−10 | 4.6 | 85.4 |
| LC-S10E | 2.63E+05 | 4.29E−04 | 1.63E−09 | 1.0 | 86 |
| LC-S12E | 2.01E+05 | 4.58E−04 | 2.27E−09 | 0.7 | 84 |
| LC-A13E | 4.83E+05 | 3.94E−04 | 8.17E−10 | 2.1 | 79.2 |
| LC-T20E | 2.46E+05 | 4.57E−04 | 1.86E−09 | 0.9 | 84.6 |
| LC-Q27E | 2.30E+05 | 4.50E−04 | 1.96E−09 | 0.9 | 84.6 |
| LC-P40E | 3.03E+04 | 5.41E−04 | 1.79E−08 | 0.1 | 83 |
| LC-A51E | 1.72E+05 | 4.62E−04 | 2.68E−09 | 0.6 | 76.8 |
| LC-Y55E | 4.53E+04 | 5.31E−04 | 1.17E−08 | 0.1 | 80.8 |
| LC-G57E | 4.29E+05 | 4.18E−04 | 9.74E−10 | 1.7 | 83 |
| LC-P59E | 2.84E+05 | 4.44E−04 | 1.56E−09 | 1.1 | 82.8 |
| LC-S77E | 7.11E+05 | 3.99E−04 | 5.62E−10 | 3.0 | 84.6 |
| LC-Y92E | 4.97E+05 | 1.03E−03 | 2.07E−09 | 0.8 | 80 |
| LC-G93E | 2.48E+05 | 1.49E−03 | 5.98E−09 | 0.3 | 76.2 |
| LC-A13R | 3.25E+05 | 4.58E−04 | 1.41E−09 | 1.2 | 81.6 |
| LC-G16K | 3.11E+05 | 4.46E−04 | 1.43E−09 | 1.2 | 79.6 |
| LC-S50R | 2.45E+05 | 4.64E−04 | 1.89E−09 | 0.9 | 84 |
| LC-T31R | 2.71E+05 | 4.89E−04 | 1.80E−09 | 0.9 | 84 |
| LC-T72R | 2.92E+05 | 4.46E−04 | 1.53E−09 | 1.1 | 84.4 |
| HC-V2E | 3.00E+05 | 3.95E−04 | 1.32E−09 | 1.3 | 83.4 |
| HC-S5E | 7.88E+05 | 4.54E−04 | 5.76E−10 | 3.0 | 84 |
| HC-S7E | 7.61E+05 | 3.81E−04 | 5.01E−10 | 3.4 | 85.2 |
| HC-G8E | 6.57E+05 | 4.55E−04 | 6.93E−10 | 2.5 | 83.4 |
| HC-L11E | 5.63E+05 | 5.07E−04 | 9.01E−10 | 1.9 | 82 |
| HC-G16E | 7.30E+05 | 4.54E−04 | 6.22E−10 | 2.7 | 83.2 |
| HC-T28E | 6.21E+05 | 3.52E−04 | 5.66E−10 | 3.0 | 85.2 |
| HC-S30E | 7.85E+04 | 5.58E−04 | 7.1E−09 | 0.2 | 84 |
| HC-A40E | 1.97E+05 | 5.17E−04 | 2.63E−09 | 0.6 | 83.8 |
| HC-P41E | 1.52E+05 | 5.48E−04 | 3.6E−09 | 0.5 | 84.4 |
| HC-K43E | 3.80E+05 | 4.82E−04 | 1.27E−09 | 1.3 | 84.2 |
| HC-Y58E | 8.20E+05 | 5.08E−04 | 6.2E−10 | 2.7 | 84 |
| HC-A60E | 5.24E+05 | 5.65E−04 | 1.08E−09 | 1.6 | 83.2 |
| HC-K64E | 5.52E+05 | 3.95E−04 | 7.15E−10 | 2.4 | 84 |
| HC-G65E | 3.02E+05 | 4.72E−04 | 1.56E−09 | 1.1 | 84.2 |
| HC-T68E | 2.15E+05 | 4.40E−04 | 2.05E−09 | 0.8 | 84.8 |
| HC-A71E | 2.57E+05 | 3.79E−04 | 1.48E−09 | 1.1 | 84.8 |
| HC-T73E | 5.50E+05 | 4.34E−04 | 7.88E−10 | 2.2 | 84.6 |
| HC-S74E | 2.36E+05 | 4.99E−04 | 2.11E−09 | 0.8 | 84.4 |
| HC-K75E | 2.17E+05 | 4.44E−04 | 2.04E−09 | 0.8 | 84.2 |
| HC-N76E | 2.71E+05 | 4.67E−04 | 1.72E−09 | 1.0 | 81.4 |
| HC-T77E | 2.48E+05 | 4.77E−04 | 1.93E−09 | 0.9 | 84.8 |
| HC-Q81E | 2.25E+05 | 4.95E−04 | 2.2E−09 | 0.8 | 85 |
| HC-S82bE | 4.37E+05 | 4.33E−04 | 9.91E−10 | 1.7 | 84.2 |
| HC-Q105E | 1.09E+05 | 4.63E−04 | 4.24E−09 | 0.4 | 84.6 |
| HC-T107E | 4.16E+05 | 5.94E−04 | 1.43E−09 | 1.2 | 85.8 |
| HC-L11R | 8.90E+05 | 4.35E−04 | 4.88E−10 | 3.5 | 81.4 |
| HC-T28K | 9.75E+05 | 4.10E−04 | 4.20E−10 | 4.0 | 85.4 |
| HC-P41R | 5.71E+05 | 5.54E−04 | 9.70E−10 | 1.8 | 84.6 |
| HC-Y56K | 7.24E+05 | 6.99E−04 | 9.65E−10 | 1.8 | 84.8 |
| HC-T68K | 3.97E+05 | 5.13E−04 | 1.29E−09 | 1.3 | 84.6 |
| HC-T77K | 2.03E+06 | 4.50E−04 | 2.22E−10 | 7.7 | 84 |

TABLE 3B

Purification Parameters for Surface-Exposed Charge Variants

| Variant | Yield (mg) | % Monomer | Elution Time (min) |
|---|---|---|---|
| G6.31 (WT) | 0.57 | 97.86 | 12.74 |
| LC-S7E | 0.24 | 77.02 | 12.39 |
| LC-S9E | 0.32 | 77.19 | 12.43 |
| LC-S10E | 0.05 | 54.64 | 12.44 |
| LC-S12E | 0.28 | 74.57 | 12.41 |
| LC-A13E | 0.31 | 67.58 | 12.4 |
| LC-T20E | 0.32 | 73.31 | 12.36 |
| LC-Q27E | 0.26 | 78.98 | 12.19 |
| LC-P40E | 0.34 | 67.56 | 12.43 |
| LC-A51E | 0.31 | 67.73 | 12.28 |
| LC-Y55E | 0.3 | 68.83 | 12.42 |
| LC-G57E | 0.3 | 67.9 | 12.28 |
| LC-P59E | 0.35 | 71.85 | 12.41 |
| LC-S77E | 0.36 | 73.49 | 12.37 |
| LC-Y92E | 0.31 | 100 | 12.2 |
| LC-G93E | 0.3 | 100 | 12.55 |
| LC-A13R | 0.35 | 70.15 | 12.41 |
| LC-G16K | 0.32 | 72.84 | 12.36 |
| LC-S50R | 0.33 | 100 | 12.13 |
| LC-T31R | 0.34 | 74.87 | 12.49 |
| LC-T72R | 0.28 | 72.31 | 12.41 |
| HC-V2E | 0.3 | 97.45 | 12.32 |
| HC-S5E | 0.36 | 97.14 | 12.44 |
| HC-S7E | 0.32 | 100 | 12.5 |
| HC-G8E | 0.33 | 100 | 12.36 |
| HC-L11E | 0.33 | 100 | 12.48 |
| HC-G16E | 0.36 | 100 | 12.46 |
| HC-T28E | 0.29 | 97.52 | 12.08 |
| HC-S30E | 0.36 | 94.81 | 11.9 |
| HC-A40E | 0.34 | 95.91 | 12.41 |
| HC-P41E | 0.38 | 100 | 12.62 |
| HC-K43E | 0.36 | 100 | 12.54 |
| HC-Y58E | 0.37 | 100 | 11.97 |
| HC-A60E | 0.27 | 97.58 | 12.39 |
| HC-K64E | 0.31 | 97.83 | 12.36 |
| HC-G65E | 0.32 | 98.01 | 12.41 |
| HC-T68E | 0.35 | 100 | 12.41 |
| HC-A71E | 0.42 | 100 | 12.53 |
| HC-T73E | 0.37 | 100 | 12.14 |
| HC-S74E | 0.36 | 100 | 12.36 |
| HC-K75E | 0.27 | 94.47 | 12.38 |
| HC-N76E | 0.37 | 95.68 | 12.02 |
| HC-T77E | 0.41 | 97.5 | 12.51 |
| HC-Q81E | 0.33 | 97.72 | 12.49 |
| HC-S82bE | 0.4 | 93.54 | 12.47 |
| HC-Q105E | 0.37 | 98.41 | 12.55 |
| HC-T107E | 0.32 | 98.04 | 12.23 |
| HC-L11R | 0.37 | 99.81 | 12.53 |
| HC-T28K | 0.39 | 97.98 | 12.43 |
| HC-P41R | 0.34 | 100 | 12.6 |
| HC-Y56K | 0.39 | 100 | 12.13 |
| HC-T68K | 0.42 | 100 | 12.39 |
| HC-T77K | 0.33 | 94.64 | 12.51 |

As shown in Table 3A, several surface-exposed charge variants were identified that had comparable or improved binding affinity to VEGF as compared to G6.31.

Example 10: Generation and Characterization of Combination Variants with Improved Binding Affinity to VEGF and Improved Stability A. Generation of Variants with Improved Binding Affinity to VEGF and Improved Stability G6.31 contains an autocleavage site in HVR-L3 (N94-P95) which could affect its stability. Combinations of the single variants described in Example 2 (see, e.g., Table 2) were combined in order to identify clones with increased binding affinity and increased stability. Four mutations in particular were focused on: LC-F83A (provides improved thermostability and affinity), LC-N94A (removes the autocleavage site), HC-Y58R (improves affinity) and HC-N82aR (improves affinity). Several other substitutions at position LC-N94 intended to remove the autocleavage site were also tested for their effect on binding affinity to VEGF by multiple cycle kinetic measurement as well as stability by DSF (Table 4). Removal of the autocleavage site consistently reduced fragmentation, as assessed by the percentage of low molecular weight entities determined using non-reduced capillary electrophoresis sodium dodecyl sulfate (CE-SDS) (FIG. 12).

TABLE 4

Affinity and Thermostability of Auto-Cleavage Site Variants

| Variant | $k_{on}$ (1/Ms) | $k_{off}$ (1/s) | Kd (nM) | $T_m$ (° C.) | $T_m$ increase (relative to WT) |
|---|---|---|---|---|---|
| G6.31 WT | 7.54E+05 | 3.95E−04 | 0.525 | 84 | — |
| LC-N94A | 1.59E+06 | 1.69E−03 | 1.06 | 85.6 | 1.6° C. |
| LC-N94Q | 3.18E+05 | 3.62E−04 | 1.14 | 84.6 | 0.6° C. |
| LC-N94R | 1.94E+05 | 4.07E−04 | 2.09 | 85.2 | 1.2° C. |

Combination of the LC-F83A, LC-N94A, HC-Y58R, and HC-N82aR variants into a single clone ("Y58R.N94A.N82aR.F83A," also referred to as "G6.31 AARR") resulted in a markedly increased binding affinity for VEGF (Kd=80 pM), a 6.6-fold improvement compared to G6.31. Y58R.N94A.N82aR.F83A also had a markedly improved thermostability compared to G6.31, with a 4.8° C. increase in $T_m$. (Table 5). The amino acid sequence of the VH domain of Y58R.N94A.N82aR.F83A is shown in SEQ ID NO: 11, and the amino acid sequence of the VL domain is shown in SEQ ID NO: 12.

TABLE 5

Combination variant Y58R.N94A.N82aR.F83A has improved binding affinity to VEGF and improved stability compared to G6.31

| Variant | $k_{on}$ (1/Ms) | koff (1/s) | Kd (nM) | Fold improved (relative to WT) | $T_m$ (° C.) | $T_m$ increase (relative to WT) |
|---|---|---|---|---|---|---|
| G6.31 WT | 7.54E+05 | 3.95E−04 | 0.525 | — | 84.0 | — |
| LC-F83A | 1.65E+06 | 2.18E−04 | 0.132 | 4.0 | 89.0 | 5.0° C. |
| LC-N94A | 1.59E+06 | 1.69E−03 | 1.06 | 0.5 | 85.6 | 1.6° C. |
| HC-Y58R | 2.42E+06 | 1.84E−04 | 0.076 | 6.9 | 83.2 | 0.8° C. |
| HC-N82aR | 1.62E+06 | 1.24E−04 | 0.077 | 6.8 | 84.0 | 0.0° C. |
| Y58R.N94A.N82aR.F83A | 4.00E+06 | 3.20E−04 | 0.080 | 6.6 | 88.8 | 4.8° C. |
| Y58R.N94A.F83A | 2.22E+06 | 3.01E−04 | 0.135 | 3.9 | 89.2 | 5.2° C. |

B. Generation of Surface-Exposed Charged Variants with Altered pI

To generate variants with lower pI, several glutamate substitutions were introduced into the sequence of G6.31. Based on the single surface-exposed charged variant mutation data (Tables 3A-3B) variants which did not have a large negative impact on VEGF binding were selected for further engineering. The expression level (as assessed by yield) and reduced aggregation (as assessed by high % monomer) were also considered in selecting mutations. The iso-electrostatic surface of G6.31 was calculated using APBS (Baker et al. Proc Natl. Acad. Sci. USA 98(18):10037-10041 (2001)). Selected glutamate mutations were mapped onto the electrostatic surface and combinations of glutamate mutations were chosen which (i) avoided mutations which were located spatially close together and (ii) which favored mutations which were located within a strong positively-charged patch. Two heavy chain combination variants (with and without R19E) and five light chain combination variants were generated for further characterization (Table 6). All light chain combination variants contained the LC-N94A mutation to remove the auto-cleavage site and the LC-F83A mutation to improve the thermostability of the antibody. Several of the variants showed improved affinity to VEGF (see Table 6, Table 7, and Table 9). For example, HCLC2 and HCLC5 showed improved affinity and a markedly reduced pI compared to G6.31 (pI 5.3 and 5.6, respectively, compared to pI 8.9 for G6.31) (see Table 7 and Table 9).

TABLE 6

Combination Surface-Exposed Charge Variants

| Variant | Type | SEQ ID NO: | Mutations |
|---|---|---|---|
| HCcombo | VH | 33 | V2E, S7E, R19E, T28E, A40E, G16E, K43E, T57E, K64E, K75E, S82BE, T107E |

TABLE 6-continued

Combination Surface-Exposed Charge Variants

| Variant | Type | SEQ ID NO: | Mutations |
|---|---|---|---|
| R19HCcombo | VH | 51 | V2E, S7E, T28E, A40E, G16E, K43E, T57E, K64E, K75E, S82BE, T107E |
| LCcombo1 | VL | 34 | S9E, R18E, F83A, N94A |
| LCcombo2 | VL | 35 | R18E, K42E, S76E, F83A, N94A |
| LCcombo3 | VL | 36 | S9E, R18E, K42E, F83A, N94A |
| LCcombo4 | VL | 37 | R18E, F83A, N94A |
| LCcombo5 | VL | 12 | F83A, N94A |

TABLE 7

Combination Surface-Exposed Charge Variants Binding Kinetics to VEGF

| Antibody Name | $k_{on}$ (1/Ms) | $k_{off}$ (1/s) | Kd (M) | VH | VL |
|---|---|---|---|---|---|
| HCcombo | 2.05E+06 | 2.74E−04 | 1.34E−10 | HCcombo | G6.31 WT |
| HCLC2 | 2.12E+06 | 6.23E−04 | 2.93E−10 | HCcombo | LCcombo2 |
| HCLC4 | 2.03E+06 | 6.08E−04 | 2.99E−10 | HCcombo | LCcombo4 |
| HCLC5 | 1.81E+06 | 5.73E−04 | 3.16E−10 | HCcombo | LCcombo5 |
| HCLC3 | 1.84E+06 | 6.08E−04 | 3.30E−10 | HCcombo | LCcombo3 |
| HCLC1 | 1.37E+06 | 6.07E−04 | 4.42E−10 | HCcombo | LCcombo1 |
| G6.31 WT | 9.99E+05 | 5.99E−04 | 5.99E−10 | G6.31 WT | G6.31 WT |
| LCcombo2 | 5.99E+05 | 6.67E−04 | 1.11E−09 | G6.31 WT | LCcombo2 |
| LCcombo3 | 5.74E+05 | 7.68E−04 | 1.34E−09 | G6.31 WT | LCcombo3 |
| LCcombo5 | 5.37E+05 | 7.66E−04 | 1.43E−09 | G6.31 WT | LCcombo5 |
| LCcombo4 | 4.63E+05 | 8.08E−04 | 1.75E−09 | G6.31 WT | LCcombo4 |
| LCcombo1 | 4.47E+05 | 1.01E−03 | 2.27E−09 | G6.31 WT | LCcombo1 |
| R19HCLC2 | 8.89E+05 | 4.67E−05 | 9.49E−11 | R19HCcombo | LCcombo2 |
| R19HCLC4 | 2.84E+05 | 4.79E−05 | 1.69E−10 | R19HCcombo | LCcombo4 |
| R19HCLC5 | 7.07E+05 | 4.41E−05 | 6.24E−11 | R19HCcombo | LCcombo5 |

In addition, several other combination variants were generated that included selected surface-exposed glutamate substitutions and single variants that improved affinity and/or stability (Table 8).

TABLE 8

Binding Kinetics of Additional Combination Variants

| Variants | $k_{on}$ (1/Ms) | $k_{off}$ (1/s) | Kd (M) |
|---|---|---|---|
| HC-A40E, HC-T57E | 2.96E+06 | 8.04E−04 | 2.72E−10 |
| LC-F83A, LC-N94A | 6.48E+05 | 1.11E−03 | 1.71E−9 |
| LC-F83A, LC-N94A, LC-T22D | 1.33E+06 | 7.44E−04 | 5.58E−10 |
| HC-A40E, HC-T57E, LC-F83A, LC-N94A | 1.27E+06 | 7.41E−04 | 5.84E−10 |
| HC-A40E, HC-T57E, LC-F83A, LC-N94A, LC-T22D | 1.20E+06 | 7.18E−04 | 5.97E−10 |

Table 9 shows a summary of binding affinity, stability, and pI data for selected combination variants. Antibody pI was calculated using an in-house program and by running an isoelectric focusing (IE) gel with standard pI control. Table 10 shows the corresponding VH and VL amino acid sequences for these antibodies. Table 11 shows the VL HVR amino acid sequences for these antibodies. Table 12 shows the VH HVR amino acid sequences for these antibodies.

TABLE 9

Summary of Selected Combination Variants

| Antibody Name | $k_{on}$ (1/Ms) | $k_{off}$ (1/s) | Kd (nM) | Fab Tm (° C.) | pI |
|---|---|---|---|---|---|
| G6.31 | 7.54E+05 | 3.95E−04 | 0.525 | 83.8 | 8.9 |
| LC-N94A | 1.56E+06 | 1.69E−03 | 1.060 | 85.8 | 8.9 |
| LC-N94A.LC-F83A | 6.48E+05 | 1.11E−03 | 1.710 | 88 | 8.9 |
| LC-N94A.LC-F83A. HC-A40E.HC-T57E (G6.31 AAEE) | 1.27E+06 | 7.41E−04 | 0.580 | 88 | 8.5 |
| N94A.F83A.N82aR.Y58R (G6.31 AARR) | 2.22E+06 | 3.01E−04 | 0.135 | 88.2 | 9.3 |
| HCcombo | 2.05E+06 | 2.74E−04 | 0.134 | 71.2 | 5.6 |
| HCLC2 | 2.12E+06 | 6.23E−04 | 0.293 | 72.6 | 5.3 |
| HCLC4 | 2.03E+06 | 6.08E−04 | 0.299 | 73.4 | 5.4 |
| HCLC5 | 1.81E+06 | 5.73E−04 | 0.316 | 73.8 | 5.6 |
| HCLC3 | 1.84E+06 | 6.08E−04 | 0.330 | 73.8 | 5.3 |
| HCLC1 | 1.37E+06 | 6.07E−04 | 0.442 | 73.6 | 5.4 |
| R19HCLC2 | 8.89E+05 | 4.67E−05 | 0.095 | 74.8 | 5.7 |
| R19HCLC4 | 2.84E+05 | 4.79E−05 | 0.169 | 76.2 | 5.8 |
| R19HCLC5 | 7.07E+05 | 4.41E−05 | 0.062 | 76.2 | 6 |

TABLE 10

VH and VL Amino Acid Sequences for Antibodies from Table 9

| Antibody Name | Variant VH (SEQ ID NO) | Variant VL (SEQ ID NO) |
|---|---|---|
| G6.31 WT | G6.31 WT (SEQ ID NO: 42) | G6.31 WT (SEQ ID NO: 38) |
| LC-N94A | G6.31 WT (SEQ ID NO: 42) | N94A (SEQ ID NO: 41) |
| LC-N94A.LC-F83A | G6.31 WT (SEQ ID NO: 42) | N94A.F83A (SEQ ID NO: 12) |
| LC-N94A.LC-F83A. HC-A40E.HC-T57E (G6.31 AAEE) | A40E.T57E (SEQ ID NO: 40) | N94A.F83A (SEQ ID NO: 12) |
| N94A.F83A.N82aR.Y58R (G6.31 AARR) | N82aR.Y58R (SEQ ID NO: 11) | N94A.F83A (SEQ ID NO: 12) |
| HCcombo | HCcombo (SEQ ID NO: 33) | G6.31 WT (SEQ ID NO: 38) |
| HCLC2 | HCcombo (SEQ ID NO: 33) | LCcombo2 (SEQ ID NO: 35) |
| HCLC4 | HCcombo (SEQ ID NO: 33) | LCcombo4 (SEQ ID NO: 37) |
| HCLC5 | HCcombo (SEQ ID NO: 33) | N94A.F83A (SEQ ID NO: 12) |
| HCLC3 | HCcombo (SEQ ID NO: 33) | LCcombo3 (SEQ ID NO: 36) |
| HCLC1 | HCcombo (SEQ ID NO: 33) | LCcombo1 (SEQ ID NO: 34) |
| R19HCcombo | R19HCcombo (SEQ ID NO: 51) | G6.31 WT (SEQ ID NO: 38) |
| R19HCLC2 | R19HCcombo (SEQ ID NO: 51) | LCcombo2 (SEQ ID NO: 35) |
| R19HCLC4 | R19HCcombo (SEQ ID NO: 51) | LCcombo4 (SEQ ID NO: 37) |
| R19HCLC5 | R19HCcombo (SEQ ID NO: 51) | N94A.F83A (SEQ ID NO: 12) |

TABLE 11

VL HVR Sequences for Antibodies from Table 9

| Antibody Name | HVR-L1 | HVR-L2 | HVR-L3 |
|---|---|---|---|
| G6.31 WT | RASQDVSTAVA (SEQ ID NO: 8) | SASFLYS (SEQ ID NO: 9) | QQGYGNPFT (SEQ ID NO: 23) |
| LC-N94A | RASQDVSTAVA (SEQ ID NO: 8) | SASFLYS (SEQ ID NO: 9) | QQGYGAPFT (SEQ ID NO: 10) |
| LC-N94A.LC-F83A | RASQDVSTAVA (SEQ ID NO: 8) | SASFLYS (SEQ ID NO: 9) | QQGYGAPFT (SEQ ID NO: 10) |
| LC-N94A.LC-F83A. HC-A40E.HC-T57E (G6.31 AAEE) | RASQDVSTAVA (SEQ ID NO: 8) | SASFLYS (SEQ ID NO: 9) | QQGYGAPFT (SEQ ID NO: 10) |
| N94A.F83A.N82aR.Y58R (G6.31 AARR) | RASQDVSTAVA (SEQ ID NO: 8) | SASFLYS (SEQ ID NO: 9) | QQGYGAPFT (SEQ ID NO: 10) |
| HCcombo | RASQDVSTAVA (SEQ ID NO: 8) | SASFLYS (SEQ ID NO: 9) | QQGYGNPFT (SEQ ID NO: 23) |
| HCLC2 | RASQDVSTAVA (SEQ ID NO: 8) | SASFLYS (SEQ ID NO: 9) | QQGYGAPFT (SEQ ID NO: 10) |
| HCLC4 | RASQDVSTAVA (SEQ ID NO: 8) | SASFLYS (SEQ ID NO: 9) | QQGYGAPFT (SEQ ID NO: 10) |
| HCLC5 | RASQDVSTAVA (SEQ ID NO: 8) | SASFLYS (SEQ ID NO: 9) | QQGYGAPFT (SEQ ID NO: 10) |
| HCLC3 | RASQDVSTAVA (SEQ ID NO: 8) | SASFLYS (SEQ ID NO: 9) | QQGYGAPFT (SEQ ID NO: 10) |
| HCLC1 | RASQDVSTAVA (SEQ ID NO: 8) | SASFLYS (SEQ ID NO: 9) | QQGYGAPFT (SEQ ID NO: 10) |
| R19HCcombo | RASQDVSTAVA (SEQ ID NO: 8) | SASFLYS (SEQ ID NO: 9) | QQGYGNPFT (SEQ ID NO: 23) |
| R19HCLC2 | RASQDVSTAVA (SEQ ID NO: 8) | SASFLYS (SEQ ID NO: 9) | QQGYGAPFT (SEQ ID NO: 10) |
| R19HCLC4 | RASQDVSTAVA (SEQ ID NO: 8) | SASFLYS (SEQ ID NO: 9) | QQGYGAPFT (SEQ ID NO: 10) |
| R19HCLC5 | RASQDVSTAVA (SEQ ID NO: 8) | SASFLYS (SEQ ID NO: 9) | QQGYGAPFT (SEQ ID NO: 10) |

TABLE 12

VH HVR Sequences for Antibodies from Table 9

| Antibody Name | HVR-H1 | HVR-H2 | HVR-H3 |
|---|---|---|---|
| G6.31 WT | DYWIH (SEQ ID NO: 1) | GITPAGGYTYYADSVKG (SEQ ID NO: 53) | FVFFLPYAMDY (SEQ ID NO: 3) |
| LC-N94A | DYWIH (SEQ ID NO: 1) | GITPAGGYTYYADSVKG (SEQ ID NO: 53) | FVFFLPYAMDY (SEQ ID NO: 3) |
| LC-N94A.LC-F83A | DYWIH (SEQ ID NO: 1) | GITPAGGYTYYADSVKG (SEQ ID NO: 53) | FVFFLPYAMDY (SEQ ID NO: 3) |
| LC-N94A.LC-F83A. HC-A40E.HC-T57E (G6.31 AAEE) | DYWIH (SEQ ID NO: 1) | GITPAGGYEYYADSVKG (SEQ ID NO: 21) | FVFFLPYAMDY (SEQ ID NO: 3) |
| N94A.F83A.N82aR.Y58R (G6.31 AARR) | DYWIH (SEQ ID NO: 1) | GITPAGGYTRYADSVKG (SEQ ID NO: 7) | FVFFLPYAMDY (SEQ ID NO: 3) |
| HCcombo | DYWIH (SEQ ID NO: 1) | GITPAGGYEYYADSVEG (SEQ ID NO: 22) | FVFFLPYAMDY (SEQ ID NO: 3) |

TABLE 12-continued

VH HVR Sequences for Antibodies from Table 9

| Antibody Name | HVR-H1 | HVR-H2 | HVR-H3 |
|---|---|---|---|
| HCLC2 | DYWIH (SEQ ID NO: 1) | GITPAGGYEYYADSVEG (SEQ ID NO: 22) | FVFFLPYAMDY (SEQ ID NO: 3) |
| HCLC4 | DYWIH (SEQ ID NO: 1) | GITPAGGYEYYADSVEG (SEQ ID NO: 22) | FVFFLPYAMDY (SEQ ID NO: 3) |
| HCLC5 | DYWIH (SEQ ID NO: 1) | GITPAGGYEYYADSVEG (SEQ ID NO: 22) | FVFFLPYAMDY (SEQ ID NO: 3) |
| HCLC3 | DYWIH (SEQ ID NO: 1) | GITPAGGYEYYADSVEG (SEQ ID NO: 22) | FVFFLPYAMDY (SEQ ID NO: 3) |
| HCLC1 | DYWIH (SEQ ID NO: 1) | GITPAGGYEYYADSVEG (SEQ ID NO: 22) | FVFFLPYAMDY (SEQ ID NO: 3) |
| R19HCcombo | DYWIH (SEQ ID NO: 1) | GITPAGGYEYYADSVEG (SEQ ID NO: 22) | FVFFLPYAMDY (SEQ ID NO: 3) |
| R19HCLC2 | DYWIH (SEQ ID NO: 1) | GITPAGGYEYYADSVEG (SEQ ID NO: 22) | FVFFLPYAMDY (SEQ ID NO: 3) |
| R19HCLC4 | DYWIH (SEQ ID NO: 1) | GITPAGGYEYYADSVEG (SEQ ID NO: 22) | FVFFLPYAMDY (SEQ ID NO: 3) |
| R19HCLC5 | DYWIH (SEQ ID NO: 1) | GITPAGGYEYYADSVEG (SEQ ID NO: 22) | FVFFLPYAMDY (SEQ ID NO: 3) |

The upper hinge region of the Fab heavy chain of any of the antibodies listed above, for example, G6.31 AARR, can be mutated to remove reactivity to anti-IgG1 hinge autoantibodies that has been reported in the literature. See, e.g., Brezski et al., *J. Immunol.* 181:3183-3192, 2008 and Brezski et al., *mAbs* 2:3, 212-220, 2010. Thus, the C-terminal amino acid of G6.31 AARR heavy chain can be either a T (wild-type (WT) version) or L (variant version that lacks reactivity to anti-human IgG Fab). The full-length heavy chain amino acid sequence of wild-type G6.31 AARR is SEQ ID NO: 48. The full-length heavy chain amino acid sequence of the variant version that lacks reactivity anti-human IgG Fab is SEQ ID NO: 49. The full-length light chain amino acid sequence for both G6.31 AARR and the variant version that lacks reactivity to anti-human IgG Fab is SEQ ID NO: 50.

In summary, combinations of variants identified by deep scanning mutagenesis resulted in antibodies with improved properties. In some instances, the antibodies had improved binding affinity to VEGF as well as improved stability (as judged by markedly increased $T_m$) as compared to G6.31. Some of the variants (e.g., the antibodies HCcombo, HCLC1, HCLC2, HCLC3, HCLC4, and HCLC5) had both improved binding affinity to VEGF and markedly reduced pI. For the variants with reduced pI, reverting the R19E mutation in the heavy chain back to the original arginine at position 19 (e.g., as in R19HCcombo, R19HCLC2, R19HCLC4, and R19HCLC5), resulted in variants with further affinity improvement and increased $T_m$ (by about 2.2-2.8° C.).

Example 11: Ocular and Systemic Pharmacokinetics of G6.31 Variants Following Intravitreal Administration in Rabbits To assess the pharmacokinetic (PK) properties of G6.31 variants in vivo, the following experiment was performed using New Zealand White (NZW) rabbits. Ocular half-life was determined for two different G6.31 variants, G6.31 AAEE (LC-N94A.LC-F83A.HC-A40E.HC-T57E) and G6.31 AARR (Y58R.N94A.N82aR.F83A), as well as the parent G6.31 WT. In each case, Fabs of each of the antibodies were formulated in PBS at a concentration of 10 mg/mL. 50 µL (0.5 mg) was injected intravitreally into anesthetized rabbits. The rabbits (in groups of 10) were dosed once/eye. Group 1 was dosed with G6.31 AAEE, Group 2 was dosed with G6.31 WT, and Group 3 was dosed with G6.31 AARR. Tissues (the vitreous humor, the aqueous humor, and serum) were collected pre-dose, at 2 hours, 6 hours, 1 day, 2 day, 4 days, 8 days, 15 days and 21 days post-dose. Samples were assayed for the level of anti-VEGF using the Total Fab ELISA described below.

Figure 11A:
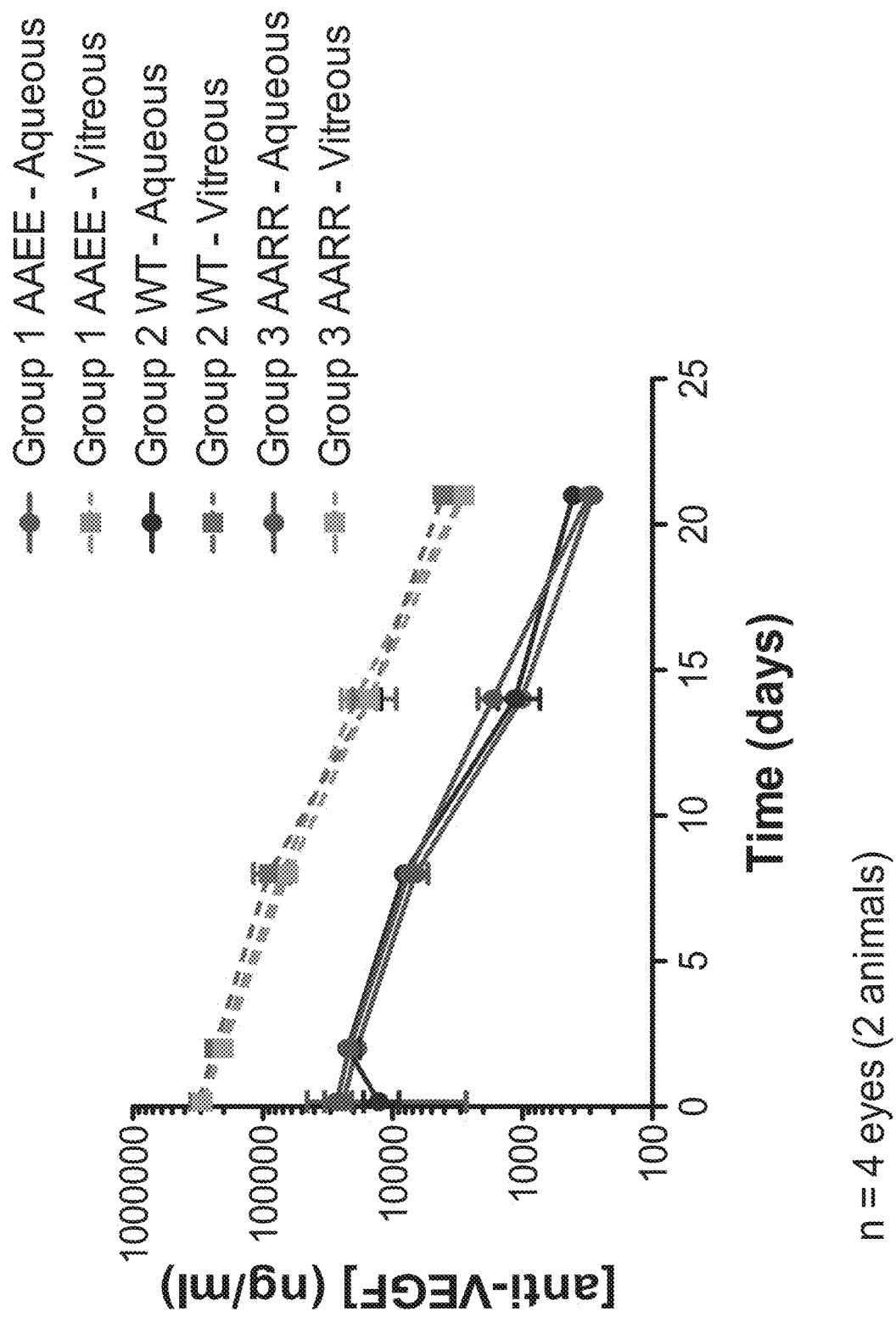
FIG. 11A is a graph showing the aqueous and vitreous pharmacokinetics for each of G6.31 AAEE, G6.31 WT, and G6.31 AARR following intravitreal administration of the respective Fab in rabbit eyes, as described in Example 11.

The results of the pharmacokinetic analysis of each variant and WT in each of the vitreous humor and aqueous humor are presented in FIG. 11A. The results show that the PK of G6.31 AAEE and of G6.31 AARR are essentially the same as the PK for WT G6.31 in both the vitreous humor and the aqueous humor. The vitreous and aqueous half-lives were calculated and those results are presented in Table 13 below. The half-lives of the variant G6.31 Fabs were similar to WT and also were consistent with ocular half-lives of Fabs reported in the literature.

TABLE 13

Half-life of G6.31 variants and G6.31 WT

| Antibody | Vitreous Half-life (days) | Aqueous half-life (days) |
|---|---|---|
| G6.31 AAEE | 3.13 | 3.02 |
| G6.31 WT | 3.23 | 3.03 |
| G6.31 AARR | 3.1 | 2.81 |

Figure 11B:
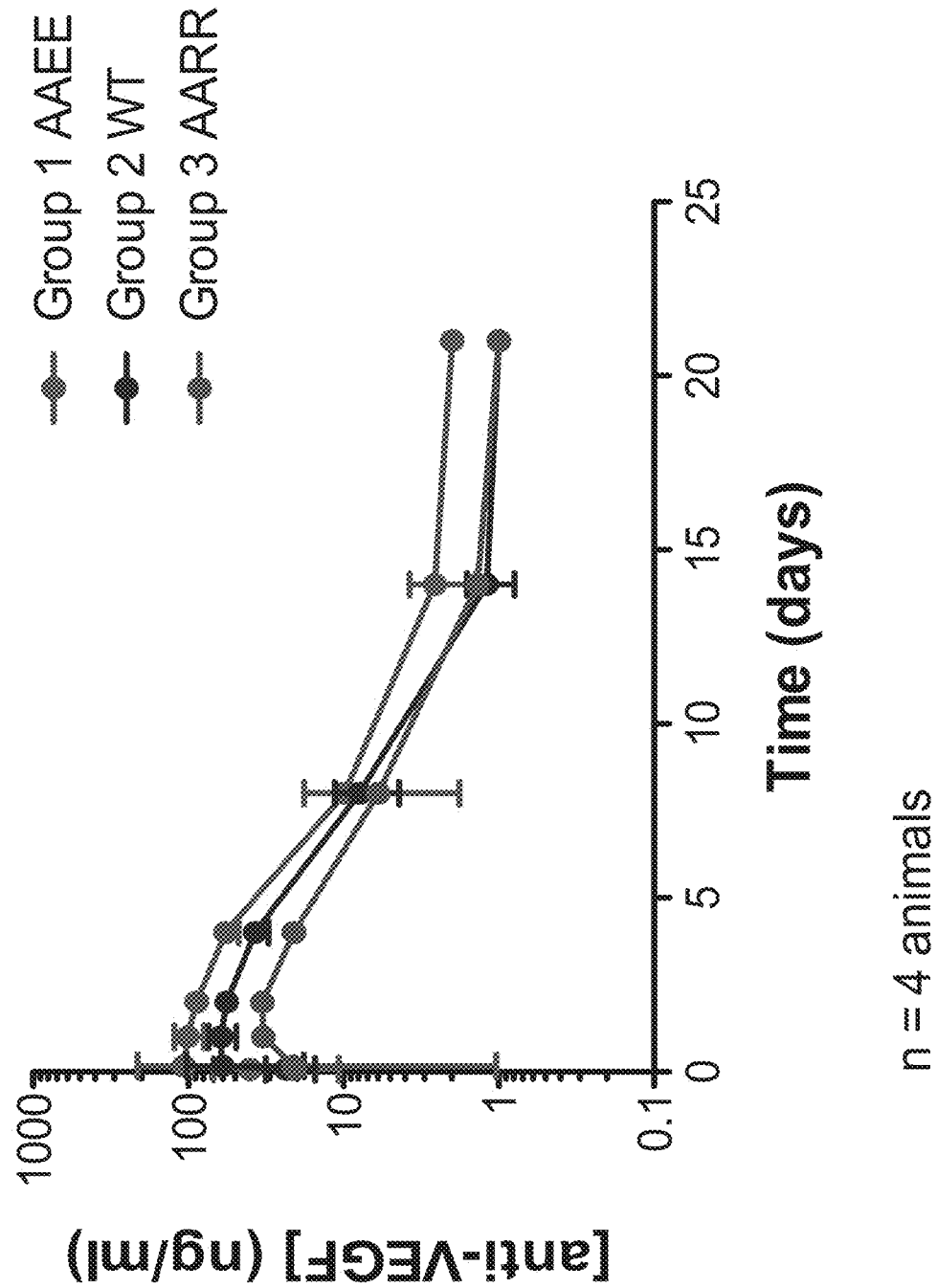
FIG. 11B is a graph showing the clearance from serum of each of G6.31 AAEE, G6.31 WT, and G6.31 AARR following intravitreal administration of the respective Fab in rabbit eyes, as described in Example 11.

Systemic exposure to Fabs following intravitreal injection was assessed by measuring the levels of anti-VEGF in the serum. Serum samples were assayed for anti-VEGF. The results are shown in FIG. 11B. The clearance (ml/kg/day)

was calculated and those results are shown in Table 14 below. Serum was also assayed for anti-therapeutic antibodies (ATA). ATA was present in all animals from day 14 on.

TABLE 14

Clearance of G6.31 variants and G6.31 WT

| Antibody | Clearance (ml/kg/day) |
|---|---|
| G6.31 AAEE | 733 |
| G6.31 WT | 1238 |
| G6.31 AARR | 2133 |

As shown by the results shown in Table 14, if all three Fabs have the same bioavailability, then G6.31 AARR had the fastest clearance, which indicates a lower systemic exposure compared to G6.31 WT and to G6.31 AAEE. Such a lower systemic exposure may result in a better safety profile for G6.31 AARR compared to G6.31 WT and GG6.31 AAEE.

Materials and Methods

A. Total Fab ELISA

ELISA plates were coated with AffiniPure F(ab')$_2$ fragment goat anti-human IgG overnight at 4° C. Plates were then washed 3 times prior to incubation with blocking buffer (PBS pH 7.4, 0.5% BSA, and 15 ppm PROCLIN™). After 3 washes, aqueous and vitreous samples collected from NZW rabbits dosed with WT G6.31, G6.31 AARR, or G6.31 AAEE were incubated in the plates for 2 h at room temperature under gentle agitation. The G6.31 molecules that bound to the coating antibodies were then detected with an F(ab')$_2$ peroxidase conjugated goat anti-human IgG for 1 h at room temperature. After 3 washes, the TMBE-1000 substrate solution was added to the plates for 30 min and the reaction was stopped using 1M H$_3$PO$_4$. The signal was recorded at 450/620 nm.

Concentrations of G6.31 molecules were determined using a standard curve.

Example 12: VEGF-Induced HUVEC Migration Assays

G6.31 variants were tested for the ability to inhibit VEGF-induced HUVEC migration. HUVEC migration assays of the variants indicated in Table 15 were performed using Falcon 24-multiwell insert systems (BD Biosciences cat. 351184). The inserts were pre-coated with 8 mg/ml mouse laminin (LifeTechnologies 23017-015) overnight. HUVECs were starved overnight, harvested, and resuspended in assay medium (EBM-2, 0.1% BSA). Cells (5×10$^4$) were added to the upper chamber, and 20 ng/mL of VEGF was added to the lower chamber to stimulate migration in the presence or absence of various dose levels of blocking antibodies for 16 h. After fixing and scraping from the upper face membrane, cells on the lower face were fixed with methanol and stained with SYTOX® green (LifeTechnologies S7020). Images were acquired using an inverted fluorescent microscope, and cell number was analyzed using ImageJ software.

Figure 13:
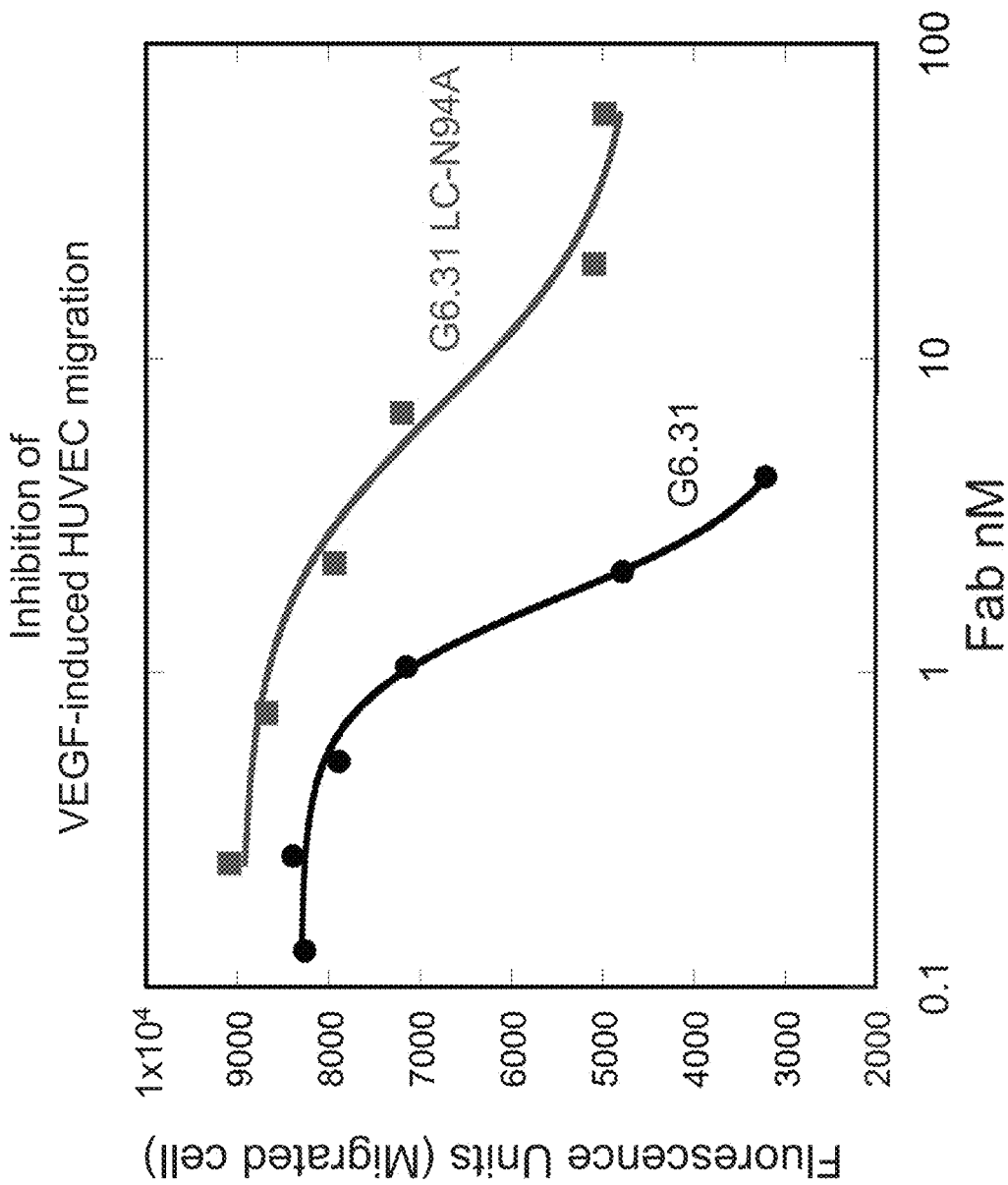
FIG. 13 is a graph showing a plot of inhibition of VEGF-induced HUVEC migration by the G6.31 variant LC-N94A compared to the parent G6.31 at varying Fab concentrations, as described in Example 12.

FIG. 13 shows a plot of inhibition of VEGF-induced HUVEC migration by G6.31 LC-N94A compared to the parent G6.31 at varying Fab concentrations. As can be seen from FIG. 13, the single LC-N94A mutation was significantly less potent, by about five-fold, in the VEGF-induced HUVEC migration assay compared to the WT G6.31 parent. As shown in Table 15, the double mutant, LC-N94A.LC-F83A was also about five-fold less potent in this assay compared to the WT G6.31 parent. The quadruple mutant, LC-N94A.LC-F83A.HC-A40E.HC-T57E (G6.31 AAEE) restored and slightly improved potency (Table 15). Surprisingly, the quadruple mutant, N94A.F83A.N82aR.Y58R (G6.31 AARR) had significantly improved potency, by about two-fold, compared to the WT G6.31 parent (Table 15).

TABLE 15

Cell potency of G6.31 variants determined by IC50 in HUVEC Migration Assay

| Fab | IC50 relative to G6.31 |
|---|---|
| G6.31 | 1 |
| LC-N94A | 5.2 |
| LC-N94A.LC-F83A (AA) | 5.1 |
| LC-N94A.LC-F83A.<br>HC-A40E.HC-T57E<br>(G6.31 AAEE) | 0.9 |
| N94A.F83A.N82aR.Y58R<br>(G6.31 AARR) | 0.5 |
| ranibizumab | 0.9 |

Example 13: Conjugation of Hyaluronic Acid (HA) to G6.31 AARR and Other Antibodies Current approaches for treatment of ocular disorders associated with pathological angiogenesis (e.g., AMD (e.g., wet AMD), DME, DR, or RVO) typically involve intravitreal injection of VEGF antagonists (e.g., the anti-VEGF Fab ranibizumab). Because the site of action of anti-VEGF Fabs is in the back of the eye at the retina, and also because Fabs can have relatively short residence time in the eye, maximum patient benefit from anti-VEGF Fabs is typically obtained by relatively frequent dosings (e.g., Q4W) by intravitreal injection. Long-acting delivery of anti-VEGF antibodies or antibody fragments (e.g., Fabs) for ocular disorders may be desired, at least in part, to decrease dosing frequency, which results in improved patient convenience and compliance. In this Example, the effects of conjugating linear, uncrosslinked hyaluronic acid (HA) to the G6.31 variant G6.31 AARR were evaluated. The molecular properties of the conjugates, pharmacokinetic parameters (e.g., vitreal half-life and clearance), thermodynamic stability, and VEGF inhibitory potency were analyzed.

A model rabbit Fab (rabFab; Shatz et al. *Mol. Pharmaceutics* 2016; PubMed identifier (PMID) 27244474) was used as part of this analysis. Development of delivery technologies for protein therapeutics typically involves testing in relevant animal models to demonstrate in vivo utility. Rabbit models are commonly employed during early studies of ocular pharmacokinetics. Unfortunately, most human and humanized antibodies are immunogenic in rabbits, precluding estimation of key pharmacokinetic parameters using long-acting delivery technologies. To address this problem a surrogate compound was developed, which is a species-matched rabbit Fab ("rabFab") that is useful for evaluating delivery technologies in rabbit models. The rabFab described herein was derived from a rabbit monoclonal antibody that binds to human phospho c-Met. Methods of making rabbit antibodies, including rabbit monoclonal antibodies, are well known in the art. See, for example, U.S. Pat.

Nos. 5,675,063 and/or 7,429,487. An exemplary rabbit monoclonal antibody that binds to human phospho c-Met is commercially available from Abcam (Cambridge, MA, USA), product number ab68141.

In the present experiments, G6.31 AARR or rabFab Fab-C molecules were conjugated to linear, uncrosslinked HA of various weight-average molar masses (Mw), including 40 kDa (HA40K-), 100 kDa (HA100K-), 200 kDa (HA200K-), and 600 kDa (HA600K-). Fab-C molecules are Fab molecules that are expressed such that the sequence is truncated at the first hinge cysteine, resulting in a Fab with a free cysteine directly from expression. Fab' molecules, which are Fab molecules with a free cysteine generated by digestion of a full-length monoclonal antibody, can also be used. For the HA conjugates described in this Example, the Fab-C molecules were covalently attached to carboxylic acid groups on the glucuronic acid saccharide units of HA. In the first step of synthesis, a certain percentage of these acid groups on HA were converted to maleimides (typically 2-10% of acid groups were converted). The Fab-C molecules were then conjugated to the maleimide groups through the free cysteine on the Fab-C molecule. However, slight modifications to the conjugation chemistry can be used to conjugate Fab molecules or other antibody formats to HA.

Figure 14:
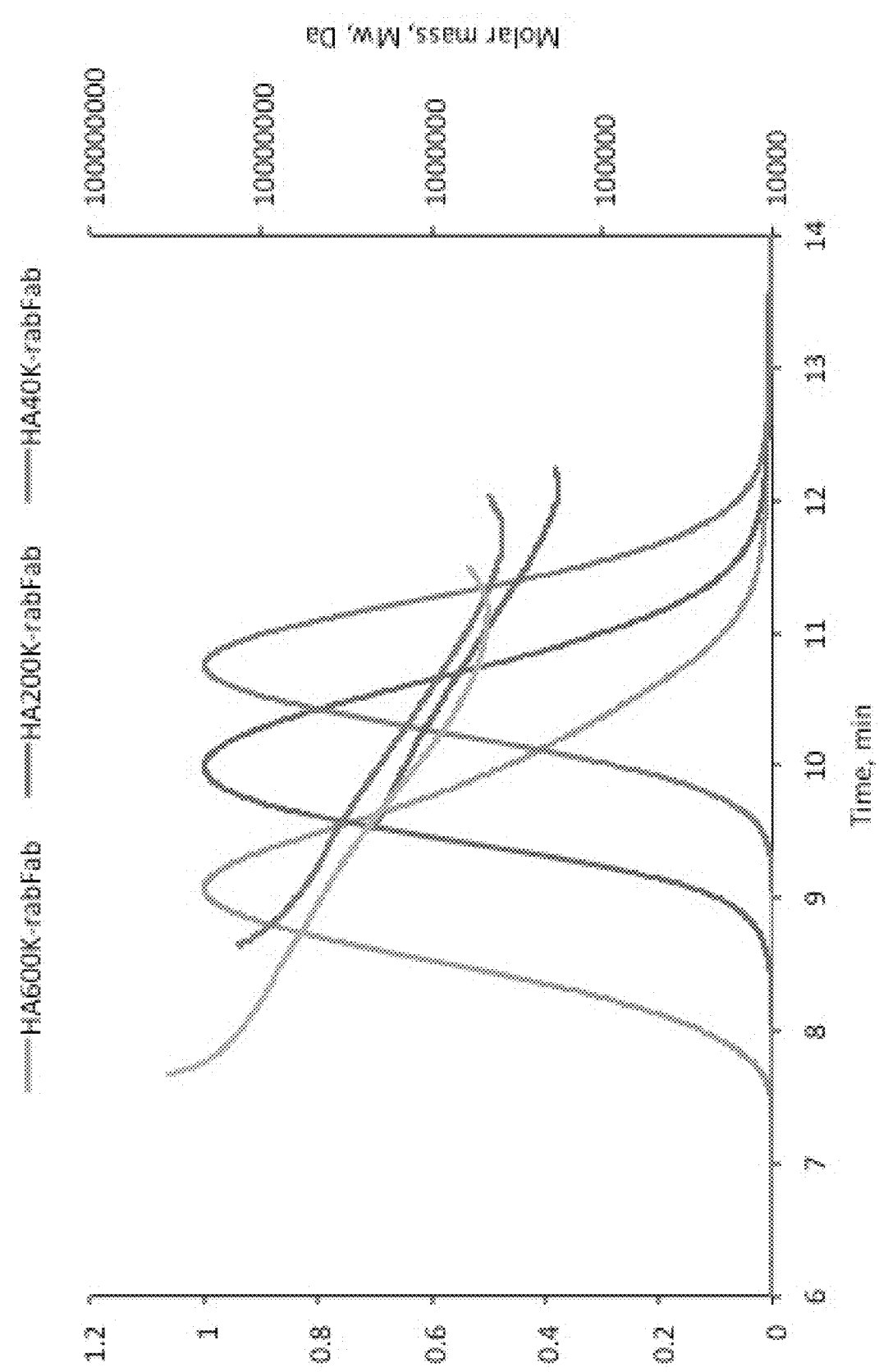
FIG. 14 is a graph showing size exclusion chromatography (SEC) and refractive index (RI) multi-angle light scattering (MALS) (SEC-RI-MALS) analysis of HA40K-rabFab, HA200K-rabFab, and HA600K-rabFab with weight-average molar mass (Mw) overlaid.
Figure 15:
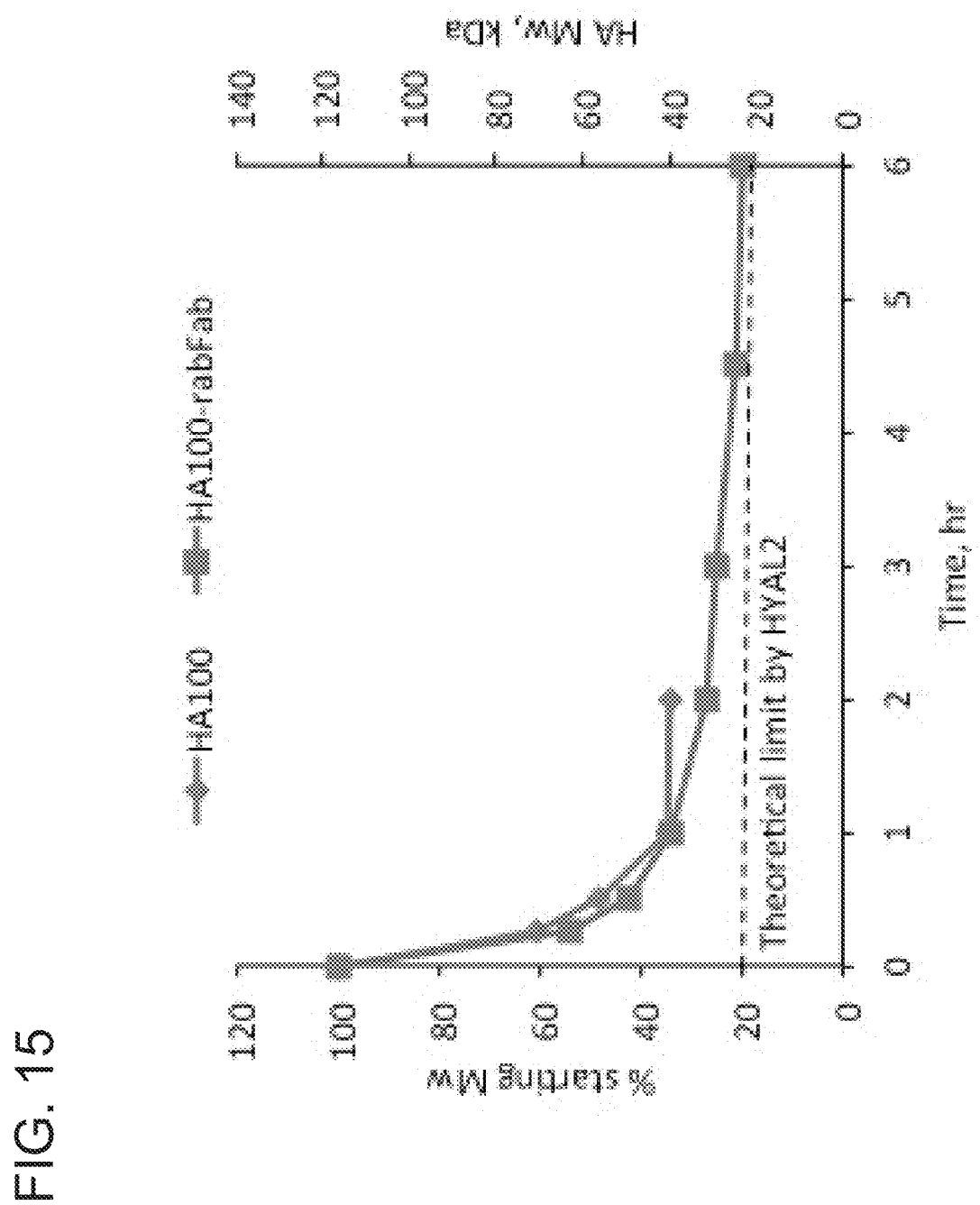
FIG. 15 is a graph showing that hyaluronic acid (HA) conjugated to rabFab retains enzymatic susceptibility to digestion by hyaluronidase-2 (HYAL2), as assessed by SEC-MALS analysis of HYAL-2-incubated HA and HA100K-rabFab. For HA-rabFab samples, the right Mw axis is expressed as Mw of the HA component of the conjugate only.
Figure 16:
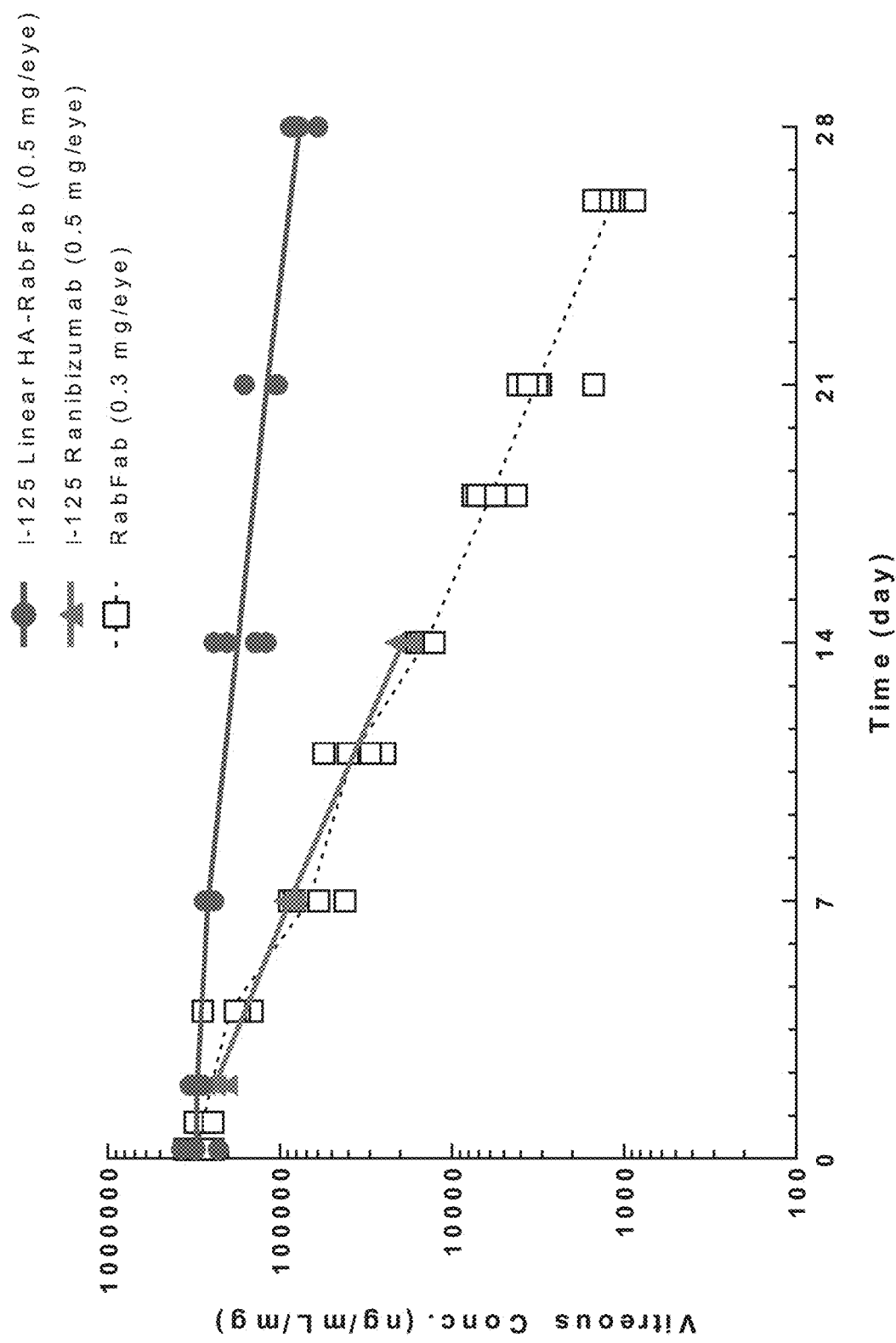
FIG. 16 is a graph showing clearance of ranibizumab, rabFab, and HA100K-rabFab ("linear HA-rabFab") from rabbit vitreous following intravitreal injection. HA100K-rabFab displayed a half-life of approximately 11.9 days, compared to approximately 2.5 days for rabFab.
Figure 17:
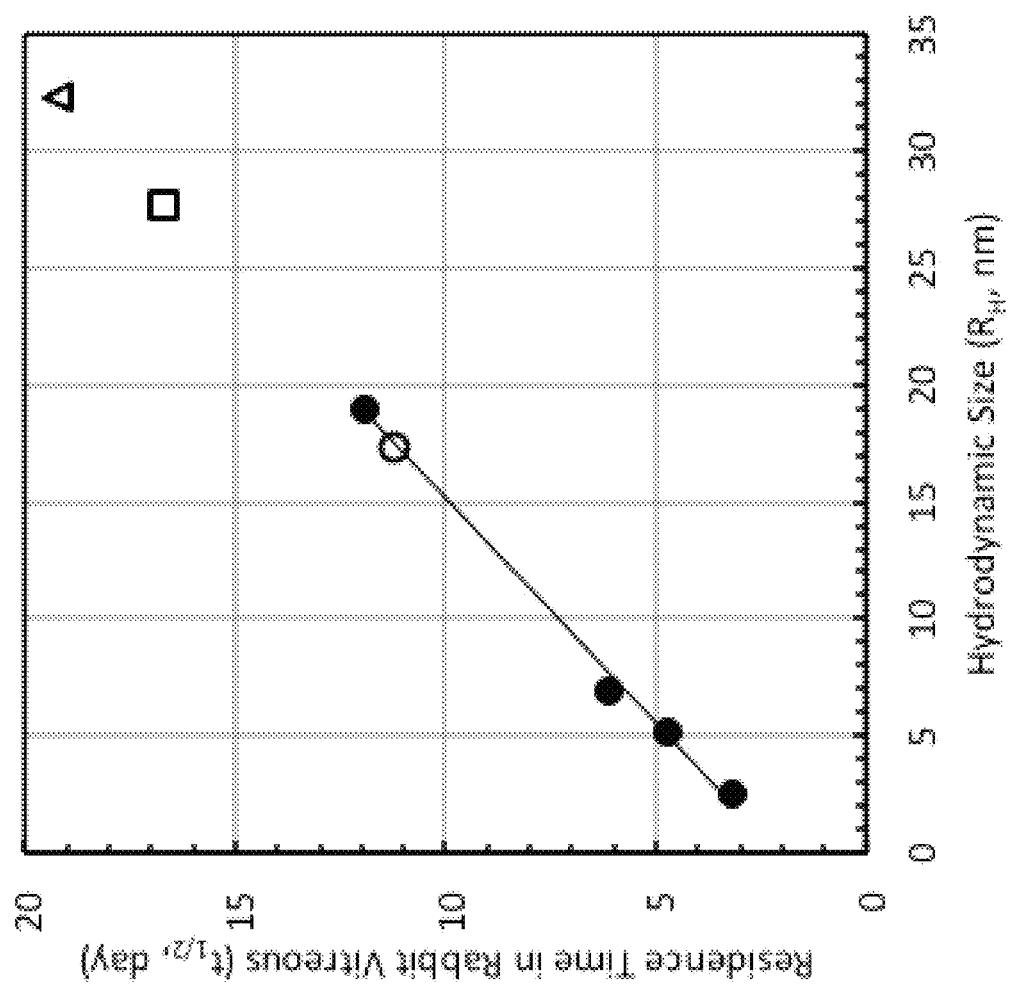
FIG. 17 is a graph showing that vitreal residence time is linearly correlated with hydrodynamic radius (Rh; indicated as "RH" in the graph) in rabbit vitreous. Historical data (filled circles) for rabFab, rabFab-20 kDa PEG, rabFab-40 kDa PEG and HA100K-rabFab can be used to predict half-lives for HA100K-G6.31 AARR (open circle), HA200K-G6.31 AARR (open square) and HA300K-G6.31 (open triangle) based on measured Rh values.

A combination of size exclusion chromatography (SEC), refractive index (RI) multi-angle light scattering (MALS), and quasi-elastic light scattering (QELS) (also referred to as SEC-RI-MALS-QELS) was used to assess HA Mw, conjugate Mw, percentage Fab loading (defined as the percentage of HA carboxylic acids groups which are occupied by a covalently-attached Fab molecule), hydrodynamic radius (Rh), free Fab (defined as the percentage of Fab molecules which are free in solution and not covalently attached to a HA molecule), and protein mass fraction (protein mass/(protein mass+HA mass) of selected HA-Fab conjugates (Table 16). FIG. 14 shows exemplary results of SEC-RI-MALS-QELS to assess the weight-average molar mass (Mw) of HA40K-rabFab, HA200K-rabFab, and HA600K-rabFab (note that the QELS data is not shown in FIG. 14).

TABLE 16

Properties of select HA-Fab conjugates as assessed by SEC-RI-MALS-QELS

| Sample | HA Mw (kDa) | Conjugate Mw (kDa) | % Fab loading | Rh (nm) | Free Fab | Protein mass fraction |
|---|---|---|---|---|---|---|
| HA40K-rabFab | 45.3 | 636.2 | 7.4 | ~10* | 0.45% | 0.929 |
| HA100K-rabFab** | 110.0 | 679.3 | 5.9 | 17.3 | 3.71% | 0.838 |
| HA200K-rabFab | 204.3 | 1805.3 | 8.6 | ~30* | 0.55% | 0.887 |
| HA600K-rabFab | 619.8 | 2569.2 | 3.2 | ~50* | 1.87% | 0.759 |
| HA200K-G6.31 AARR | 204.3 | 2478.0 | 11.0 | 27.7 | 0.63% | 0.918 |

*Approximated Rh values

**Sample investigated in rabbit PK study (see, e.g., FIG. 16 and below)

For treatment of ocular disorders such as AMD, a long ocular half-life but short systemic half-life may be desired, for example, to minimize systemic anti-VEGF exposure. HA clearance from systemic circulation is mediated by hyaluronidase-bearing hepatic cells. Previous reports indicate that hyaluronidase activity on native HA involves recognition through the glucuronic acid carboxylic acid groups. Since these carboxylic acid groups were modified to attach to the Fab-C molecules, the ability of the conjugated HA to be enzymatically digested by hyaluronidase was assessed. HA-conjugated rabFab retained enzymatic susceptibility to digestion by hyaluronidase-2 (HYAL2), as assessed by SEC-MALS analysis of HYAL2-incubated HA and HA100K-rabFab (FIG. 15).

The effect of HA conjugation of Fab fragments on ocular pharmacokinetic parameters (e.g., half-life and clearance) in rabbit vitreous following intravitreal administration was determined. Conjugation of rabFab to HA100K (HA100K-$I^{125}$-rabFab) resulted in a significant decrease in clearance and a significant increase in vitreal half-life compared to unconjugated rabFab or ranibizumab (FIG. 16 and Table 17). HA100K-conjugated rabFab had an approximate four-fold increase in vitreal half-life ($t_{1/2}$) compared to unconjugated rabFab from historical data (11.9 days versus 3.2 days, respectively) (FIG. 16 and Table 17). Table 17 also shows the Rh for rabFab and HA100K-$I^{125}$-rabFab. These data indicate that HA conjugation increased the hydrodynamic radius of Fabs and resulted in slowed vitreal clearance and increased vitreal half-life.

TABLE 17

Clearance of rabFab and HA100K-$^{125}I$-rabFab from rabbit vitreous after intravitreal administration

| Test Article | Rh (nm) | $t_{1/2}$ (days) | CL (mL/day) |
|---|---|---|---|
| HA100K-$I^{125}$-rabFab | 17.3 | 11.9 | 0.076 |
| rabFab (historical) | 2.5 | 3.2 | 0.32 |

The linear correlation between hydrodynamic size (e.g., in terms of hydrodynamic radius) and vitreal residence time (e.g., in terms of half-life), along with historical data for rabFab, rabFab conjugated to 20 KDa polyethylene glycol (PEG) (rabFab-20 kDa PEG), and rabFab conjugated to 40 kDa PEG (rabFab-40 kDa PEG) (Shatz et al. supra), coupled with the data described above for HA100K-rabFab, allowed prediction of the vitreal half-lives of G6.31 conjugated to HA100K or HA200K and G6.31 conjugated to HA300K (FIG. 17). HA100K-G6.31 has a predicted vitreal half-life of approximately 11 days, while HA200K-G6.31 has an even greater predicted vitreal half-life of approximately 17 days (FIG. 17). HA300K-G6.31 has a predicted vitreal half-life of approximately 19 days (FIG. 17). These results provide further evidence that conjugation of G6.31 AARR or other G6.31 variants described herein to linear, uncrosslinked HA results in increased ocular residence time (e.g., half-life) and decreased clearance following intravitreal injection.

The effect of HA conjugation on Fab thermodynamic stability was also evaluated (Table 18). Covalent attachment of rabFab to HA of three different molar masses did not alter the thermodynamic stability of the Fab, as demonstrated by the similar Tm onset and peak Tm for conjugates compared to the parent Fab (Table 18).

TABLE 18

Conjugation of Fabs to HA does not significantly alter Fab thermodynamic stability

| Sample | Tm Onset, ° C. | Tm, ° C. |
|---|---|---|
| rabFab | 66.8 | 85.6 |
| HA39K-rabFab | 69.5 | 84.1 |
| HA100K-rabFab | 69.8 | 84.0 |
| HA300K-rabFab | 69.7 | 83.8 |

Finally, the effect of HA conjugation on G6.31 AARR's VEGF inhibition potency was assessed. Surprisingly, conjugation of G6.31 AARR to linear, uncrosslinked HA resulted in significantly improved potency over the parent Fab when compared in a pKDR assay for VEGF inhibition (Table 19). The qAC50 values in Table 19 indicate the concentration required to elicit a 50% response in the activity assay format. The qAC50 values are equivalent to IC50 values. The HA-conjugated G6.31 AARR had an approximate 7-fold increase in potency compared to the unconjugated parent Fab (Table 19). Therefore, conjugation of G6.31 AARR and other G6.31 variants described herein can be useful both to improve vitreal pharmacokinetic parameters (including half-life and clearance) as well as VEGF inhibitory potency.

TABLE 19

Conjugation of G6.31 AARR to HA results in improved VEGF inhibition potency

| Test article | qAC50, nM |
|---|---|
| G6.31.AARR | 0.9325 |
| HA100K-G6.31 AARR | 0.1346 |

Based on the foregoing experimental data, HA-conjugated G6.31 AARR molecules have significantly improved characteristics for treatment of ocular disorders, including AMD (e.g., wet AMD), DME, DR, and RVO. These improved characteristics include increased potency and the opportunity for less-frequent dosing due to enhanced vitreal residence time.

Materials and Methods

A. Synthesis of Maleimide-Functionalized HA (HA-Mal)

Linear, uncrosslinked HA polymers of various molar masses were obtained from Lifecore Biomedical. HA was modified with maleimide groups using an aqueous reaction with the coupling reagent 4-(4,6-dimethoxy-1,3,5-triazin-2-yl)-4-methylmorpholinium chloride (DMTMM) and the linker N-(2-aminoethyl)maleimide trifluoroacetate salt (AEM). HA was dissolved in 100 mM 2-(N-morpholino) ethanesulfonic acid pH 5.5 at 2.5 mg/mL and to this solution was added 1.5 molar excess DMTMM and 3.75 molar excess AEM (molar excesses are calculated based on moles of carboxylic acid in HA) under stirring. The solution was heated to 70° C. for 2 hours.

Excess AEM and DMTMM were removed from the reaction via a desalting procedure. A HiPrep™ 26/10 desalting column was mounted on an ÄKTA™ purification system and equilibrated with 10 mM sodium acetate pH 4.0 150 mM NaCl. The reaction was injected neat onto the column, and the HA-mal peak was collected according to absorbance at 302 nm and concentrated to greater than 5 mg/mL using centrifugal ultrafiltration devices. The maleimide concentration in the HA-mal stock solution was measured by absorbance at 302 nm using a UV-visible spectrophotometer, and the molar ratio of maleimide groups per HA chain was assessed via size exclusion chromatography with multi-angle light scattering (SEC-MALS).

B. Conjugation of Fab-C to HA-Mal

A solution of Fab-C was pH adjusted to 6.5 using 1 M phosphate pH 6.5 to a final phosphate concentration of 50 mM. Ethylenediaminetetraacetic acid (EDTA) was spiked into the solution to a final concentration of 2.5 mM. The Fab-C solution was stirred and to it was added HA-mal diluted into reaction buffer (10 mM phosphate 150 mM NaCl 2.5 mM EDTA (pH 6.5)). The stoichiometry was set at 1.2 moles of Fab-C per mole of maleimide in the final reaction and the volume was set to give a final protein concentration of 1 mg/mL. The conjugation reaction was carried out at room temperature under stirring. At 3 hours, mercaptoethanol was added at 2 moles per mole of maleimide to cap unreacted maleimide groups. After 30 minutes following addition of mercaptoethanol, the reaction was diluted to less than 50 mM NaCl with 10 mM phosphate (pH 6.5) for purification.

Purification was carried out using anion exchange chromatography to separate free Fab-C and Fab dimer from the conjugate. A HiTrap™ Q FF 5 mL column was mounted on an AKTA™ purification system and equilibrated with 10 mM HisHCl (pH 5.5). The diluted reaction was flowed over the column, capturing the HA-Fab conjugate and simultaneously eluting free Fab-C and dimer. After washing with 10 mM HisHCl (pH 5.5) 100 mM NaCl, the conjugate was eluted by a step gradient to 10 mM HisHCl (pH 5.5) 500 mM NaCl. The eluted conjugate was pooled and diluted with 10 mM HisHCl (pH 5.5) to a final composition of 10 mM HisHCl (pH 5.5) 150 mM NaCl. The formulated conjugate was concentrated by centrifugal ultrafiltration.

C. Analysis of HA-Fab Conjugates

Residual free Fab content, total conjugate molar mass, and protein mass fraction were assessed by the combination of size exclusion chromatography (SEC) with refractive index (RI) multi-angle light scattering (MALS), and quasi-elastic light scattering (QELS) (also referred to as SEC-RI-MALS-QELS) on an Agilent 1200 high performance liquid chromatography (HPLC) System with a Wyatt Optilab T-rEX RI detector and Wyatt HELEOS-II MALS detector in-line. A Tosoh G6000 PWxl column was used for analysis with PBS (pH 7.4) as the running buffer. A BSA control was used to normalize MALS detectors and correct for band broadening between detectors. Free Fab content was measured by integrating the UV $A_{280}$ peaks corresponding with Fab and HA-Fab conjugate. Conjugate molar mass was taken as the weight-average molecular weight (Mw) (also referred to as weight-average molar mass) of the conjugate peak. Protein mass fraction was calculated using a protein conjugate analysis using the differential RI (dRI) and UV $A_{280}$ signals.

D. Dynamic Scanning Calorimetry (DSC) Studies of HA-rabFab Conjugates

Solutions of rabFab, rabFab conjugated to HA having a weight-average molar mass (Mw) of 39 kDa (HA39K-rabFab), rabFab conjugated to HA having a Mw of 100 kDa (HA100K-rabFab), and rabFab conjugated to HA having a Mw of 300 kDa (HA300K-rabFab) were prepared at 0.5 mg/mL (concentration given on protein basis) in 10 mM HisHCl (pH 5.5) 150 mM NaCl. DSC studies were carried out on a VP-DSC micocalorimeter (MicroCal, Inc.) from 15 to 105° C. with a 1° C./min ramp rate. A reference scan of buffer alone was subtracted from each sample scan. Melting temperature (Tm) and Tm onset were evaluated using the accompanying ORIGIN software suite.

E. Phosphorylated KDR (pKDR) Receptor Activation Assays

CHO cells engineered to overexpress KDR (KDR-CHO cells; see Binétruy-Tournaire et al. *EMBO J.* 19(7):1525-1533, 2000 and Benzinger et al. *BBA Biomembranes* 1466: 71-78, 2000, which are incorporated herein by reference in their entirety) were plated at 1×10$^4$ cells/well in 80 µl of cell plating medium (50:50 High Glucose DMEM/Ham's F-12, 0.2% BSA, 0.25% diafiltered fetal bovine serum (FBS), 25 mM HEPES, and 2 mM L-glutamax) in a flat-bottom 96-well tissue culture plate. The cells were incubated overnight at 37° C. In parallel, an NUNCO MAXISORB®384-well ELISA plate (Thermo Catalog No. 439454) was coated with 25 µl of anti-gD antibody (Genentech) diluted in PBS, and incubated at 4° C. overnight.

The next day, 2 hours before cell stimulation, the tissue culture plates were flicked and tamped, and the culture medium was changed into 40 µl of serum-free cell stimulation medium (50:50 High Glucose DMEM/Ham's F-12, 0.5% BSA, and 25 mM HEPES) and incubated for 2 h at 37° C. Three-fold serial dilutions of G6.31 AARR or HA100K-G6.31 AARR were made in cell stimulation medium. Dilutions of human VEGF$_{165}$ (100 ng/ml) were also prepared in cell stimulation medium. Using a deep well block plate, the samples from the serial dilutions of G6.31 AARR or HA100K-G6.31 AARR were mixed with the diluted VEGF samples and incubated for 1 h at 37° C. 40 µL of the resulting mixtures were added to each well of cells for a total culture volume of 80 µL. Wells having VEGF only or no VEGF added were also prepared as controls. The cells were incubated for 15 min at 37° C. The culture medium was flicked and tamped, and 25 µL of ice-cold cell lysis buffer (150 mM NaCl, 50 mM HEPES, 0.5% TRITON™ X-100, 1× HALT® protease and phosphatase inhibitor cocktail (Thermo Catalog No. 78444, added immediately before use from 100× stock), 5 mM EDTA) was added. The cells were lysed on ice for 15 min before proceeding with the ELISA.

The wells of the anti-gD coated ELISA plate were washed 3 times with washing buffer (PBS with 0.05% TWEEN® 20, pH 7.4). The wells were blocked with 80 µl blocking buffer (PBS with 0.5% BSA (R&D Systems, Catalog No. #DY995)) for 1 h at room temperature. The wells were then washed three times with washing buffer. Next, 25 µl of cell lysate per well was added to each well and incubated for 2 h at room temperature, followed by washing the wells four times with washing buffer. 25 µl of 1:2000 diluted anti-phosphotyrosine (Clone 4G10) biotin-conjugated antibody (0.5 µg/ml) (Millipore Catalog No. 16-103) was added in assay buffer (PBS with 0.5% BSA; same as blocking buffer) to each well and the resulting mixtures were incubated for 2 h at room temperature, followed by three washes with washing buffer. 25 µl of 1:10,000 diluted horseradish peroxidase (HRP)-Strepavidin (GE Health Care UK; Catalog No. RPN440IV) was added in assay buffer to each well and incubated for 30 min at room temperature, followed by three additional washes with washing buffer. 25 µl of TMB was then added to each well, and color was allowed to develop for 20 min prior to addition of 25 of H$_2$SO$_4$ to stop the reaction. Finally, the optical density of the wells were read on a plate reader at 450/620 nm.

F. Hyaluronidase Digestion of HA100K-rabFab

To confirm that Fab conjugation up to 10% (percent expressed on basis of available acid groups on HA) did not alter the hyaluronidase susceptibility of HA-Fab conjugates, HA with a Mw of 100 kDa (HA100K) and rabFab conjugated to HA100K (HA100K-rabFab) were incubated at 200 µg/mL HA (HA100K-rabFab concentration was adjusted to achieve 200 µg/mL concentration with respect to the HA backbone) with 4 µg/mL hyaluronidase-2 in 10 mM sodium acetate, pH 4.5. Samples were incubated at 37° C. and were immediately injected onto SEC-RI-MALS at 30-min intervals for Mw analysis, as described above.

G. PK Study to Assess Rate of HA-Fab Clearance from Rabbit Vitreous

An ocular pharmacokinetic profile of HA100K-rabFab in rabbit vitreous was compared to historical data for rabFab as described below.

HA100K-rabFab was labeled with $^{125}$I on the day prior to dosing. To prepare the dosing formulations, an appropriate amount of HA100K-rabFab was exchanged with Tris iodination buffer (25 mM Tris HCl, 0.4 M NaCl, pH 7.5) using Millipore AMICON®30K centrifugal filter tubes. A Pierce pre-coated iodination tube was wetted with Tris iodination buffer and decanted. An appropriate volume of Tris iodination buffer was added to the bottom of the tube followed by an appropriate amount of Na$^{125}$I (Perkin Elmer). The iodine was allowed to activate for 15 min with swirling every 30 sec. An appropriate volume of test sample, Tris iodination buffer, and activated iodine were added to a NUNC® microcentrifuge tube and mixed by gentle shaking for approximately 1 to 5 min. The iodination reaction was terminated by adding scavenging buffer (tyrosine, 2 mg/mL Tris buffer), and the formulation was mixed and incubated for 5 min with flick mixing at 1 and 4 min. For protein purification, an AMICON®30K centrifugal filter tube was prepared by centrifugation at 6,000 RPM for 15 min with PBS. The NUNCO tube contents were added to an AMICON®30K centrifugal filter tube and washed up to four times in PBS to achieve approximately 400 µL final radiolabeled test article volume. The radioactivity, protein concentration, and radiochemical purity of each test article were determined. Using a pipette, the contents of the AMICON® tube were transferred to a NUNC® tube and the formulation was brought to a final concentration of approximately 10 mg/mL.

HA100K-rabFab-$^{125}$I was injected intravitreally (500 µg/eye) into eyes of New Zealand White rabbits (n=24 eyes). For the intravitreal injections, rabbits were sedated/anesthetized to effect with isoflurane and placed in lateral recumbency. Tropicamide ophthalmic solution (two drops) and 2.5% phenylephrine HCl (one drop) were applied to both eyes. Topical proparacaine was applied to each eye immediately prior to preparation and dosing. The conjunctival fornices were flushed with a 1:50 dilution of betadine solution and the eyelid margins were swabbed with undiluted 5% betadine solution. The superotemporal bulbar conjunctiva was swabbed with undiluted betadine solution. A Jameson caliper was used to mark a spot 1.5 to 2.0 mm posterior to the limbus on the superotemporal bulbar conjunctiva. Conjunctival forceps were used to fix the globe position with the left hand while the needle affixed to the injection syringe was inserted with the right hand, at the marked spot, through the sclera and advanced 5 mm into the vitreous humor. The injection needle was positioned to face the posterior axis of the globe and the contents were delivered into the mid-vitreous by slowly depressing the syringe plunger. The needle affixed to the injection syringe was disinserted and the episcleral tissues approximated to the site of insertion grasped with the conjunctival forceps for 30 sec to lessen reflux of the injected material. The dose site was swabbed for residual radioactivity. Preparation and dose administration was repeated in the same manner for the second eye. The appropriate test article was maintained on wet ice for the duration of the procedure and was administered once at a dose volume of 50 μL per eye. Indirect ophthalmoscopic examinations were performed following injection to ensure no lens or retinal contact occurred. A dose wipe of each injection site was collected and was retained at room temperature prior to analysis by liquid scintillation counting (LSC) to determine residual radioactivity. The radioactivity recovered was subtracted from the administered amount to give the actual radioactive dose administered.

Blood samples were collected from the jugular vein of the animals into tubes containing no anticoagulant at room temperature pre-dose, 6 hours post-dose, and 1, 2, 4, 7, 11, 14, 21, and 28 days post-dose. An aliquot (approximately 0.1 mL) of whole blood was collected and processed for radioanalysis. The remaining blood was centrifuged at ambient temperature to obtain serum and processed for radioanalysis.

Two animals per time point were euthanized by intravenous injection of euthanasia solution followed by auscultation. The terminal time points were: 6 hours postdose, and 2, 7, 14, 21, and 28 days post-dose. Aqueous humor, lens, vitreous humor, retina/choroid, and sclera were collected from designated animals. The eyes were removed and any extraneous tissue was trimmed from the outside of the eyeball. The aqueous humor was removed via syringe with a tuberculin needle and collected into a pre-weighed gamma tube. The remaining eye was frozen in liquid nitrogen for approximately 30 sec. On a chilled cutting surface, the cornea, iris, and lens were removed. The lens was rinsed with a small amount of PBS and the rinse was collected into a gamma tube. The lens was blotted dry and placed in a pre-weighed gamma tube. The eye was re-frozen in liquid nitrogen as necessary. The sclera was cut and peeled back from the vitreous humor. The vitreous humor was removed and placed in a pre-weighed container for solubilization. The sclera with the retina/choroid attached was dipped into a 1-ml rinse of PBS, which was pooled with the previous rinse, and the tissue was gently blotted dry. The retina/choroid was removed from the sclera and placed into separate pre-weighed gamma tubes. The appropriate surfaces and tools were wiped with damp gauze and collected into a gamma tube for counting. All tissues, rinses, and wipes were collected into a plastic container and processed for radioanalysis.

One eye per time point from select animals (including animals from the time points 2, 14, and 28 days post-dose) was processed for radiochromatographic profiling of the vitreous humor. The right eye was removed and extraneous tissue was trimmed from the outside of the eyeball. The aqueous humor was removed via syringe with a tuberculin needle and placed into a pre-weighed gamma tube. The maximum amount of vitreous humor was collected using a 10-ml syringe with an 18-gauge needle. The contents were transferred to a pre-weighed container for analysis by HPLC-Gamma-RAM™. Vitreous humor samples were kept refrigerated or on wet ice for radiochromatographic profiling. The remaining right eye tissue was placed into a pre-weighed container for solubilization and processed for radioanalysis.

Single or duplicate aliquots of dosing formulations, serum, and whole blood were mixed well and sampled for direct analysis of radioactivity via the gamma counter. Ocular tissues were counted directly, diluted in PBS, or were solubilized in an incubating oven set at approximately 50° C. in a solution of 3N KOH/Methanol/TRITON™ X-100 and sampled in triplicate for analysis of radioactivity via the gamma counter. All radioactive samples collected were counted for at least 5 min or 100,000 counts in duplicate or triplicate, sample size allowing. All sample results (calculated at dpm/g sample) that had radioactivity greater than 200 dpm were within 15% of the mean value.

Radiochromatographic profiling was performed on right eye vitreous humor samples from one animal at 2, 14, and 28 hours post-dose. Samples were analyzed according to a fit-for-purpose method by HPLC-Gamma-RAM™. Peak areas and retention times were compared to assess test article integrity over time. To prepare the samples, a PRECELLYS® 24 homogenizer was pre-chilled to −10 to 0° C. with a cooled nitrogen stream. Zirconia beads were added to an appropriate tube. With a positive placement pipette, a sample of vitreous humor was added to the tube containing the Zirconia beads. The samples were placed in the pre-chilled PRECELLYS® 24 homogenizer and homogenized at 6,500 RPM for six 60-sec cycles. The tubes were centrifuged for 10 min at 14,000 RPM prior to analysis.

Pharmacokinetic parameters were estimated using PHOENIX® WinNonlin® version 6.2.1 (Certara USA, Inc., Princeton, NJ). A non-compartmental approach consistent with the intravitreal route of administration was used for parameter estimation. The half-life value for HA100K-rabFab-$^{125}$I in rabbit vitreous was 11.9 days, compared to 3.2 days for rabFab from historical data (Shatz et al. *Mol. Pharmaceutics* 2016; PubMed identifier (PMID) 27244474).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of identifying an amino acid residue alteration that confers enhanced binding of an antibody to a target molecule, the method comprising:
   (a) providing a display library comprising nucleic acids encoding candidate antibody variants, wherein each candidate antibody variant comprises an amino acid residue alteration in the VH or the VL compared to a reference antibody, and wherein amino acid residue alterations at every position of the VH or VL are present in the display library;
   (b) sorting the display library based on binding of the candidate antibody variants to the target molecule to form a sorted library, wherein the sorted library comprises candidate antibody variants with enhanced binding to the target molecule compared to the reference antibody; and
   (c) comparing the frequency at which each amino acid residue alteration is present in the display library and in the sorted library as determined by massively parallel sequencing, thereby determining whether each amino acid residue alteration is enriched in the sorted library compared to the display library,
   whereby the amino acid residue alteration is identified as conferring enhanced binding to the target molecule if it is enriched in the sorted library compared to the display library.

2. A method of identifying an amino acid residue alteration that confers enhanced stability to an antibody, the method comprising:
   (a) providing a display library comprising nucleic acids encoding candidate antibody variants, wherein each candidate antibody variant comprises an amino acid residue alteration in the VH or the VL compared to a reference antibody, and wherein amino acid residue alterations at every position of the VH or VL are present in the display library;
   (b) sorting the display library based on binding of the candidate antibody variants to the target molecule to form a sorted library, wherein the sorted library comprises candidate antibody variants with enhanced stability compared to the reference antibody; and
   (c) comparing the frequency at which each amino acid residue alteration is present in the display library and in the sorted library as determined by massively parallel sequencing, thereby determining whether each amino acid residue alteration is enriched in the sorted library compared to the display library,
   whereby the amino acid residue alteration is identified as conferring enhanced stability to the antibody if it is enriched in the sorted library compared to the display library.

3. The method of claim 1, further comprising determining the frequency at which each amino acid alteration is present in the display library and the sorted library by massively parallel sequencing following step (b).

4. The method of claim 1, wherein the amino acid residue alteration is enriched at least 2-fold in the sorted library compared to the display library.

5. The method of claim 1, wherein the display library is a phage display library, a bacterial display library, a yeast display library, a mammalian display library, a ribosome display library, or an mRNA display library.

6. The method of claim 1, wherein the amino acid residue alteration is encoded by a degenerate codon set.

7. The method of claim 6, wherein the degenerate codon set is an NNK or an NNS codon set, wherein N is A, C, G, or T; K is G or T; and S is C or G.

8. The method of claim 7, wherein the degenerate codon set is an NNK codon set.

9. The method of claim 1, wherein the sorting of step (b) comprises contacting the display library with an immobilized target molecule or epitope.

10. The method of claim 1, wherein the sorting of step (b) comprises contacting the display library with a soluble target molecule or epitope.

11. The method of claim 1, wherein the display library comprises at least $1 \times 10^6$ candidate antibody variants.

12. The method of claim 11, wherein the display library comprises at least $1 \times 10^8$ antibody variants.

13. The method of claim 12, wherein the display library comprises at least $1 \times 10^9$ antibody variants.

14. The method of claim 1, wherein the massively parallel sequencing comprises deep sequencing, ultra-deep sequencing, and/or next-generation sequencing.

15. The method of claim 1, wherein the antibody is a monoclonal antibody.

16. The method of claim 1, wherein the antibody is an IgG antibody.

17. The method of claim 1, wherein the antibody is an antibody fragment.

18. The method of claim 17, wherein the antibody fragment is an Fab, scFv, Fv, Fab', Fab-C, Fab'-SH, $F(ab')_2$, or diabody.

19. The method of claim 18, wherein the antibody fragment is an Fab.

20. The method of claim 1, wherein the method further comprises generating an antibody that comprises an amino acid residue alteration identified by the steps of the method.

* * * * *

SEQUENCE LISTING

```
<160> NUMBER OF SEQ ID NOS: 69

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asp Tyr Trp Ile His
```

1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Ile or His
<220> FEATURE:
<221> NAME/KEY: MISC_FEATURE
<222> LOCATION: (5)..(5)
<223> OTHER INFORMATION: Xaa is Ala or Arg
<220> FEATURE:
<221> NAME/KEY: MISC_FEATURE
<222> LOCATION: (8)..(8)
<223> OTHER INFORMATION: Xaa is Tyr or Lys
<220> FEATURE:
<221> NAME/KEY: MISC_FEATURE
<222> LOCATION: (9)..(9)
<223> OTHER INFORMATION: Xaa is Thr or Glu
<220> FEATURE:
<221> NAME/KEY: MISC_FEATURE
<222> LOCATION: (10)..(10)
<223> OTHER INFORMATION: Xaa is Arg, Tyr, Gln, or Glu
<220> FEATURE:
<221> NAME/KEY: MISC_FEATURE
<222> LOCATION: (12)..(12)
<223> OTHER INFORMATION: Xaa is Ala or Glu
<220> FEATURE:
<221> NAME/KEY: MISC_FEATURE
<222> LOCATION: (16)..(16)
<223> OTHER INFORMATION: Xaa is Lys or Glu
<220> FEATURE:
<221> NAME/KEY: MISC_FEATURE
<222> LOCATION: (17)..(17)
<223> OTHER INFORMATION: Xaa is Gly or Glu

<400> SEQUENCE: 2

Gly Xaa Thr Pro Xaa Gly Gly Xaa Xaa Xaa Tyr Xaa Asp Ser Val Xaa
1               5                   10                  15

Xaa

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Phe Val Phe Phe Leu Pro Tyr Ala Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Asp or Arg

<400> SEQUENCE: 4

Arg Ala Ser Gln Xaa Val Ser Thr Ala Val Ala
1               5                   10

```
<210> SEQ ID NO 5
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Ser or Met

<400> SEQUENCE: 5

Xaa Ala Ser Phe Leu Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Gln, Asn, or Thr
<220> FEATURE:
<221> NAME/KEY: MISC_FEATURE
<222> LOCATION: (6)..(6)
<223> OTHER INFORMATION: Xaa is Ala, Asn, Gln, or Arg

<400> SEQUENCE: 6

Xaa Gln Gly Tyr Gly Xaa Pro Phe Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic Construct

<400> SEQUENCE: 7

Gly Ile Thr Pro Ala Gly Gly Tyr Thr Arg Tyr Ala Asp Ser Val Lys
1               5                   10                  15

Gly

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Arg Ala Ser Gln Asp Val Ser Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Ser Ala Ser Phe Leu Tyr Ser
1               5
```

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Gln Gln Gly Tyr Gly Ala Pro Phe Thr
1               5

<210> SEQ ID NO 11
<211> LENGTH: 120
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Arg Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: Synthetic Construct

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

```
<210> SEQ ID NO 13
<211> LENGTH: 30
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser
            20                  25                  30

<210> SEQ ID NO 14
<211> LENGTH: 14
<212> TYPE: PRT
<213> ORGANISM: Artificial Sequence
<220> FEATURE:
<223> OTHER INFORMATION: Synthetic Construct

<400> SEQUENCE: 14

Trp Val Arg Gln Ala Pro Gly Lys Gly Leu Glu Trp Val Ala
1               5                   10

<210> SEQ ID NO 15
<211> LENGTH: 32
<212> TYPE: PRT
<213> ORGANISM: Artificial Sequence
<220> FEATURE:
<223> OTHER INFORMATION: Synthetic Construct

<400> SEQUENCE: 15

Arg Phe Thr Ile Ser Ala Asp Thr Ser Lys Asn Thr Ala Tyr Leu Gln
1               5                   10                  15

Met Arg Ser Leu Arg Ala Glu Asp Thr Ala Val Tyr Tyr Cys Ala Arg
            20                  25                  30

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Trp Gly Gln Gly Thr Leu Val Thr Val Ser Ser
1               5                   10

<210> SEQ ID NO 17
<211> LENGTH: 23
<212> TYPE: PRT
<213> ORGANISM: Artificial Sequence
<220> FEATURE:
<223> OTHER INFORMATION: Synthetic Construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 18
<211> LENGTH: 15
<212> TYPE: PRT
<213> ORGANISM: Artificial Sequence
<220> FEATURE:
```

<223> OTHER INFORMATION: Synthetic Construct

<400> SEQUENCE: 18

Trp Tyr Gln Gln Lys Pro Gly Lys Ala Pro Lys Leu Leu Ile Tyr
1               5                   10                  15

<210> SEQ ID NO 19
<211> LENGTH: 32
<212> TYPE: PRT
<213> ORGANISM: Artificial Sequence
<220> FEATURE:
<223> OTHER INFORMATION: Synthetic Construct

<400> SEQUENCE: 19

Gly Val Pro Ser Arg Phe Ser Gly Ser Gly Thr Asp Phe Thr
1               5                   10                  15

Leu Thr Ile Ser Ser Leu Gln Pro Glu Asp Ala Ala Thr Tyr Tyr Cys
            20                  25                  30

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Phe Gly Gln Gly Thr Lys Val Glu Ile Lys
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Gly Ile Thr Pro Ala Gly Gly Tyr Glu Tyr Tyr Ala Asp Ser Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Synthetic Construct

<400> SEQUENCE: 22

Gly Ile Thr Pro Ala Gly Gly Tyr Glu Tyr Tyr Ala Asp Ser Val Glu
1               5                   10                  15

Gly

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln Gly Tyr Gly Asn Pro Phe Thr
1               5

<210> SEQ ID NO 24
<211> LENGTH: 32
<212> TYPE: PRT
<213> ORGANISM: Artificial Sequence
<220> FEATURE:
<223> OTHER INFORMATION: Synthetic Construct

<400> SEQUENCE: 24

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 25
<211> LENGTH: 23
<212> TYPE: PRT
<213> ORGANISM: Artificial Sequence
<220> FEATURE:
<223> OTHER INFORMATION: Synthetic Construct

<400> SEQUENCE: 25

Asp Ile Gln Met Thr Gln Ser Pro Glu Ser Leu Ser Ala Ser Val Gly
1               5                   10                  15

Asp Glu Val Thr Ile Thr Cys
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Ser Leu Ser Ala Ser Val Gly
1               5                   10                  15

Asp Glu Val Thr Ile Thr Cys
            20

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Trp Tyr Gln Gln Lys Pro Gly Glu Ala Pro Lys Leu Leu Ile Tyr
1               5                   10                  15

<210> SEQ ID NO 28
<211> LENGTH: 32
<212> TYPE: PRT
<213> ORGANISM: Artificial Sequence
<220> FEATURE:
<223> OTHER INFORMATION: Synthetic Construct

<400> SEQUENCE: 28

Gly Val Pro Ser Arg Phe Ser Gly Ser Gly Ser Gly Thr Asp Phe Thr
1               5                   10                  15

Leu Thr Ile Glu Ser Leu Gln Pro Glu Asp Ala Ala Thr Tyr Tyr Cys
            20                  25                  30

<210> SEQ ID NO 29

```
<211> LENGTH: 30
<212> TYPE: PRT
<213> ORGANISM: Artificial Sequence
<220> FEATURE:
<223> OTHER INFORMATION: Synthetic Construct

<400> SEQUENCE: 29

Glu Glu Gln Leu Val Glu Gly Gly Gly Leu Val Gln Pro Gly Glu
1               5                   10                  15

Ser Leu Glu Leu Ser Cys Ala Ala Ser Gly Phe Glu Ile Ser
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Trp Val Arg Gln Glu Pro Gly Glu Gly Leu Glu Trp Val Ala
1               5                   10

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

Arg Phe Thr Ile Ser Ala Asp Thr Ser Glu Asn Thr Ala Tyr Leu Gln
1               5                   10                  15

Met Asn Glu Leu Arg Ala Glu Asp Thr Ala Val Tyr Tyr Cys Ala Arg
            20                  25                  30

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Trp Gly Gln Gly Glu Leu Val Thr Val Ser Ser
1               5                   10

<210> SEQ ID NO 33
<211> LENGTH: 120
<212> TYPE: PRT
<213> ORGANISM: Artificial Sequence
<220> FEATURE:
<223> OTHER INFORMATION: Synthetic Construct

<400> SEQUENCE: 33

Glu Glu Gln Leu Val Glu Gly Gly Gly Leu Val Gln Pro Gly Glu
1               5                   10                  15

Ser Leu Glu Leu Ser Cys Ala Ala Ser Gly Phe Glu Ile Ser Asp Tyr
            20                  25                  30

Trp Ile His Trp Val Arg Gln Glu Pro Gly Glu Gly Leu Glu Trp Val
        35                  40                  45

Ala Gly Ile Thr Pro Ala Gly Gly Tyr Glu Tyr Tyr Ala Asp Ser Val
    50                  55                  60

Glu Gly Arg Phe Thr Ile Ser Ala Asp Thr Ser Glu Asn Thr Ala Tyr
```

```
                65                  70                  75                  80
Leu Gln Met Asn Glu Leu Arg Ala Glu Asp Thr Ala Val Tyr Tyr Cys
                    85                  90                  95

Ala Arg Phe Val Phe Leu Pro Tyr Ala Met Asp Tyr Trp Gly Gln
                100                 105                 110

Gly Glu Leu Val Thr Val Ser Ser
            115                 120

<210> SEQ ID NO 34
<211> LENGTH: 107
<212> TYPE: PRT
<213> ORGANISM: Artificial Sequence
<220> FEATURE:
<223> OTHER INFORMATION: Synthetic Construct

<400> SEQUENCE: 34

Asp Ile Gln Met Thr Gln Ser Pro Glu Ser Leu Ser Ala Ser Val Gly
1               5                   10                  15

Asp Glu Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: Synthetic Construct

<400> SEQUENCE: 35

Asp Ile Gln Met Thr Gln Ser Pro Ser Ser Leu Ser Ala Ser Val Gly
1               5                   10                  15

Asp Glu Val Thr Ile Thr Cys Arg Ala Ser Gln Asp Val Ser Thr Ala
            20                  25                  30

Val Ala Trp Tyr Gln Gln Lys Pro Gly Glu Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Glu Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 36
<211> LENGTH: 107
<212> TYPE: PRT
<213> ORGANISM: Artificial Sequence
<220> FEATURE:
```

<223> OTHER INFORMATION: Synthetic Construct

<400> SEQUENCE: 36

Asp Ile Gln Met Thr Gln Ser Pro Glu Ser Leu Ser Ala Ser Val Gly
1               5                   10                  15

Asp Glu Val Thr Ile Thr Cys Arg Ala Ser Gln Asp Val Ser Thr Ala
            20                  25                  30

Val Ala Trp Tyr Gln Gln Lys Pro Gly Glu Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: Synthetic Construct

<400> SEQUENCE: 37

Asp Ile Gln Met Thr Gln Ser Pro Ser Ser Leu Ser Ala Ser Val Gly
1               5                   10                  15

Asp Glu Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: Synthetic Construct

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro

-continued

```
                65                  70                  75                  80
Glu Asp Phe Ala Thr Tyr Tyr Cys Gln Gln Gly Tyr Gly Asn Pro Phe
                    85                  90                  95

Thr Phe Gly Gln Gly Thr Lys Val Glu Ile Lys
            100                 105

<210> SEQ ID NO 39
<211> LENGTH: 14
<212> TYPE: PRT
<213> ORGANISM: Artificial Sequence
<220> FEATURE:
<223> OTHER INFORMATION: Synthetic Construct

<400> SEQUENCE: 39

Trp Val Arg Gln Glu Pro Gly Lys Gly Leu Glu Trp Val Ala
1               5                   10

<210> SEQ ID NO 40
<211> LENGTH: 120
<212> TYPE: PRT
<213> ORGANISM: Artificial Sequence
<220> FEATURE:
<223> OTHER INFORMATION: Synthetic Construct

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Glu Pro Gly Lys Gly Leu Glu Trp Val
        35                  40                  45

Ala Gly Ile Thr Pro Ala Gly Gly Tyr Glu Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 41
<211> LENGTH: 107
<212> TYPE: PRT
<213> ORGANISM: Artificial Sequence
<220> FEATURE:
<223> OTHER INFORMATION: Synthetic Construct

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 42
<211> LENGTH: 120
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 43
<211> LENGTH: 227
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
            145                 150                 155                 160
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His
225

<210> SEQ ID NO 44
<211> LENGTH: 32
<212> TYPE: PRT
<213> ORGANISM: Artificial Sequence
<220> FEATURE:
<223> OTHER INFORMATION: Synthetic Construct

<400> SEQUENCE: 44

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Ser Ala Thr Tyr Tyr Cys
                20                  25                  30

<210> SEQ ID NO 45
<211> LENGTH: 23
<212> TYPE: PRT
<213> ORGANISM: Artificial Sequence
<220> FEATURE:
<223> OTHER INFORMATION: Synthetic Construct

<400> SEQUENCE: 45

Asp Ile Gln Met Thr Gln Ser Pro Ser Ser Leu Ser Ala Ser Val Gly
1               5                   10                  15

Asp Arg Val Thr Ile Asp Cys
                20

<210> SEQ ID NO 46
<211> LENGTH: 107
<212> TYPE: PRT
<213> ORGANISM: Artificial Sequence
<220> FEATURE:
<223> OTHER INFORMATION: Synthetic Construct

<400> SEQUENCE: 46

Asp Ile Gln Met Thr Gln Ser Pro Ser Ser Leu Ser Ala Ser Val Gly
1               5                   10                  15

Asp Arg Val Thr Ile Asp Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
                100                 105
```

<210> SEQ ID NO 47
<211> LENGTH: 232
<212> TYPE: PRT
<213> ORGANISM: Homo sapiens

<400> SEQUENCE: 47

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 48
<211> LENGTH: 228
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

```
Leu Gln Met Arg Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr
225

<210> SEQ ID NO 49
<211> LENGTH: 228
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Arg Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205
```

Pro Ser Asn Thr Lys Val Asp Lys Lys Val Glu Pro Lys Ser Cys Asp
            210                 215                 220

Lys Thr His Leu
225

<210> SEQ ID NO 50
<211> LENGTH: 214
<212> TYPE: PRT
<213> ORGANISM: Artificial Sequence
<220> FEATURE:
<223> OTHER INFORMATION: Synthetic Construct

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 120
<212> TYPE: PRT
<213> ORGANISM: Artificial Sequence
<220> FEATURE:
<223> OTHER INFORMATION: Synthetic Construct

<400> SEQUENCE: 51

Glu Glu Gln Leu Val Glu Gly Gly Gly Leu Val Gln Pro Gly Glu
1               5                   10                  15

Ser Leu Arg Leu Ser Cys Ala Ala Ser Gly Phe Glu Ile Ser Asp Tyr
            20                  25                  30

Trp Ile His Trp Val Arg Gln Glu Pro Gly Glu Gly Leu Glu Trp Val
        35                  40                  45

Ala Gly Ile Thr Pro Ala Gly Gly Tyr Glu Tyr Tyr Ala Asp Ser Val
50                  55                  60

Glu Gly Arg Phe Thr Ile Ser Ala Asp Thr Ser Glu Asn Thr Ala Tyr
65                  70                  75                  80

Leu Gln Met Asn Glu Leu Arg Ala Glu Asp Thr Ala Val Tyr Tyr Cys
            85                  90                  95

Ala Arg Phe Val Phe Phe Leu Pro Tyr Ala Met Asp Tyr Trp Gly Gln
        100                 105                 110

Gly Glu Leu Val Thr Val Ser Ser
        115                 120

<210> SEQ ID NO 52
<211> LENGTH: 30
<212> TYPE: PRT
<213> ORGANISM: Artificial Sequence
<220> FEATURE:
<223> OTHER INFORMATION: Synthetic Construct

<400> SEQUENCE: 52

Glu Glu Gln Leu Val Glu Gly Gly Gly Leu Val Gln Pro Gly Glu
1               5                   10                  15

Ser Leu Arg Leu Ser Cys Ala Ala Ser Gly Phe Glu Ile Ser
            20                  25                  30

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct

<400> SEQUENCE: 53

Gly Ile Thr Pro Ala Gly Gly Tyr Thr Tyr Tyr Ala Asp Ser Val Lys
1               5                   10                  15

Gly

<210> SEQ ID NO 54
<211> LENGTH: 32
<212> TYPE: PRT
<213> ORGANISM: Artificial Sequence
<220> FEATURE:
<223> OTHER INFORMATION: Synthetic Construct

<400> SEQUENCE: 54

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Phe Gly Gln Gly Thr Lys Val Glu Val Lys
1               5                   10

<210> SEQ ID NO 56
<211> LENGTH: 34
<212> TYPE: DNA
<213> ORGANISM: Artificial Sequence
<220> FEATURE:

<223> OTHER INFORMATION: Synthetic Construct

<400> SEQUENCE: 56
catcagatgg cgggaagatg aagacagatg gtgc    34

<210> SEQ ID NO 57
<211> LENGTH: 23
<212> TYPE: DNA
<213> ORGANISM: Artificial Sequence
<220> FEATURE:
<223> OTHER INFORMATION: Synthetic Construct

<400> SEQUENCE: 57
gccatccaga tgacccagtc tcc    23

<210> SEQ ID NO 58
<211> LENGTH: 19
<212> TYPE: DNA
<213> ORGANISM: Artificial Sequence
<220> FEATURE:
<223> OTHER INFORMATION: Synthetic Construct

<400> SEQUENCE: 58
ggctgcacca tctgtcttc    19

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Tyr Gly Asn Pro Phe
                85                  90                  95

Thr Phe Gly Gln Gly Thr Lys Val Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Synthetic Construct

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Gly Ala Pro Phe
                 85                  90                  95

Thr Phe Gly Gln Gly Thr Lys Val Glu Ile Lys
            100                 105

<210> SEQ ID NO 61
<211> LENGTH: 5
<212> TYPE: PRT
<213> ORGANISM: Artificial Sequence
<220> FEATURE:
<223> OTHER INFORMATION: Synthetic construct

<400> SEQUENCE: 61

Gly Gly Gly Gly Ser
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic construct

<400> SEQUENCE: 62

Gly Tyr Tyr Met His
1               5

<210> SEQ ID NO 63
<211> LENGTH: 17
<212> TYPE: PRT
<213> ORGANISM: Artificial Sequence
<220> FEATURE:
<223> OTHER INFORMATION: Synthetic construct

<400> SEQUENCE: 63

Trp Ile Asn Pro Asn Ser Gly Gly Thr Asn Tyr Ala Gln Lys Phe Gln
1               5                   10                  15

Gly

<210> SEQ ID NO 64
<211> LENGTH: 20
<212> TYPE: PRT
<213> ORGANISM: Artificial Sequence
<220> FEATURE:
<223> OTHER INFORMATION: Synthetic construct

<400> SEQUENCE: 64

Ser Pro Asn Pro Tyr Tyr Tyr Asp Ser Ser Gly Tyr Tyr Tyr Pro Gly
1               5                   10                  15

Ala Phe Asp Ile
            20

<210> SEQ ID NO 65
<211> LENGTH: 11
<212> TYPE: PRT
<213> ORGANISM: Artificial Sequence
<220> FEATURE:
<223> OTHER INFORMATION: Synthetic construct

<400> SEQUENCE: 65

```
Gly Gly Asn Asn Ile Gly Ser Lys Ser Val His
1               5                   10
```

<210> SEQ ID NO 66
<211> LENGTH: 7
<212> TYPE: PRT
<213> ORGANISM: Artificial Sequence
<220> FEATURE:
<223> OTHER INFORMATION: Synthetic construct

<400> SEQUENCE: 66

```
Asp Asp Ser Asp Arg Pro Ser
1               5
```

<210> SEQ ID NO 67
<211> LENGTH: 11
<212> TYPE: PRT
<213> ORGANISM: Artificial Sequence
<220> FEATURE:
<223> OTHER INFORMATION: Synthetic construct

<400> SEQUENCE: 67

```
Gln Val Trp Asp Ser Ser Ser Asp His Trp Val
1               5                   10
```

<210> SEQ ID NO 68
<211> LENGTH: 129
<212> TYPE: PRT
<213> ORGANISM: Artificial Sequence
<220> FEATURE:
<223> OTHER INFORMATION: Synthetic construct

<400> SEQUENCE: 68

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser
```

<210> SEQ ID NO 69
<211> LENGTH: 110
<212> TYPE: PRT
<213> ORGANISM: Artificial Sequence
<220> FEATURE:
<223> OTHER INFORMATION: Synthetic construct

<400> SEQUENCE: 69

```
Ser Tyr Val Leu Thr Gln Pro Pro Ser Val Ser Val Ala Pro Gly Gln
1               5                   10                  15
```

-continued

```
Thr Ala Arg Ile Thr Cys Gly Gly Asn Asn Ile Gly Ser Lys Ser Val
            20              25              30

His Trp Tyr Gln Gln Lys Pro Gly Gln Ala Pro Val Leu Val Val Tyr
        35              40                      45

Asp Asp Ser Asp Arg Pro Ser Gly Ile Pro Glu Arg Phe Ser Gly Ser
    50              55              60

Asn Ser Gly Asn Thr Ala Thr Leu Thr Ile Ser Arg Val Glu Ala Gly
65              70              75                      80

Asp Glu Ala Asp Tyr Tyr Cys Gln Val Trp Asp Ser Ser Ser Asp His
                85              90              95

Trp Val Phe Gly Gly Gly Thr Lys Leu Thr Val Leu Gly Gln
            100             105             110
```